United States Patent
Zhu et al.

(10) Patent No.: US 6,872,728 B2
(45) Date of Patent: *Mar. 29, 2005

(54) GONADOTROPIN-RELEASING HORMONE RECEPTOR ANTAGONISTS AND METHODS RELATING THERETO

(75) Inventors: Yun-Fei Zhu, San Diego, CA (US); Chen Chen, San Diego, CA (US); Fabio C. Tucci, San Diego, CA (US); Zhiqiang Guo, San Diego, CA (US); Timothy D. Gross, San Diego, CA (US); Martin Rowbottom, La Jolla, CA (US); R. Scott Struthers, Encinitas, CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 29 days.

This patent is subject to a terminal disclaimer.

(21) Appl. No.: 10/361,144

(22) Filed: Feb. 6, 2003

(65) Prior Publication Data

US 2004/0048884 A1 Mar. 11, 2004

Related U.S. Application Data

(63) Continuation of application No. 09/771,107, filed on Jan. 25, 2001, now Pat. No. 6,608,197.
(60) Provisional application No. 60/239,683, filed on Oct. 11, 2000, and provisional application No. 60/177,933, filed on Jan. 25, 2000.

(51) Int. Cl.$^7$ ............... C07D 239/47; C07D 239/56; A61K 31/505; A61K 31/506; A61P 35/00
(52) U.S. Cl. ............ 514/269; 544/309; 544/310; 544/314; 544/311
(58) Field of Search ............... 544/309, 310, 544/314, 269

(56) References Cited

U.S. PATENT DOCUMENTS

| | | | |
|---|---|---|---|
| 4,950,670 A | 8/1990 | Frost et al. | 514/254 |
| 5,140,029 A | 8/1992 | Kennis et al. | 514/272 |
| 5,476,855 A | 12/1995 | el Kouni et al. | 514/269 |
| 5,744,479 A | 4/1998 | Furuya et al. | 514/301 |
| 5,780,437 A | 7/1998 | Goulet et al. | 514/19 |
| 5,849,764 A | 12/1998 | Goulet et al. | 514/337 |
| 5,859,014 A | 1/1999 | Bantle et al. | 514/255 |
| 6,232,318 B1 | 5/2001 | Nerenberg et al. | 514/274 |
| 6,608,197 B2 * | 8/2003 | Zhu et al. | 544/309 |

FOREIGN PATENT DOCUMENTS

| | | |
|---|---|---|
| EP | 0 748 800 A2 | 12/1996 |
| EP | 1 004 585 A1 | 5/2000 |
| WO | WO 96/24597 | 8/1996 |
| WO | WO 96/38438 | 12/1996 |
| WO | WO 97/14682 | 4/1997 |
| WO | WO 97/14697 | 4/1997 |
| WO | WO 97/21435 | 6/1997 |
| WO | WO 97/21703 | 6/1997 |
| WO | WO 97/21704 | 6/1997 |
| WO | WO 97/21707 | 6/1997 |
| WO | WO 97/44037 | 11/1997 |
| WO | WO 97/44041 | 11/1997 |
| WO | WO 97/44321 | 11/1997 |
| WO | WO 97/44339 | 11/1997 |
| WO | WO 98/55116 | 12/1998 |
| WO | WO 98/55119 | 12/1998 |
| WO | WO 98/55470 | 12/1998 |
| WO | WO 98/55479 | 12/1998 |
| WO | WO 99/09033 | 2/1999 |
| WO | WO 99/33831 | 7/1999 |
| WO | WO 99/51232 | 10/1999 |
| WO | WO 00/29386 | 5/2000 |
| WO | WO 00/69833 | 11/2000 |
| WO | WO 00/69859 | 11/2000 |
| WO | WO 01/29044 | 4/2001 |

OTHER PUBLICATIONS

Cho et al., "Discovery of a novel, potent, and orally active nonpeptide antagonist of the human luteinizing hormone–releasing hormone (LHRH) receptor," *J. Med. Chem.* 41(22):4190–4195, 1998.

Koerber et al., "Consensus Bioactive Conformation of Cyclic GnRH Antagonists Defined by NMR and Molecular Modeling," *J. Med. Chem.* 43(5):819–828, 2000.

Huirn and Lambalk, "Gonadotropin–releasing–hormone–receptor antagonists," *Lancet* 358(9295):1793–1803, 2001.

* cited by examiner

Primary Examiner—Venkataraman Balasubramanian
(74) Attorney, Agent, or Firm—Seed IP Law Group PLLC

(57) ABSTRACT

GnRH receptor antagonists are disclosed which have utility in the treatment of a variety of sex-hormone related conditions in both men and women. The compounds of this invention have the structure:

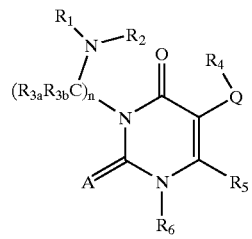

wherein A, Q, $R_1$, $R_2$, $R_{3a}$, $R_{3b}$, $R_4$, $R_5$, $R_6$ and n are as defined herein, including stereoisomers, prodrugs and pharmaceutically acceptable salts thereof. Also disclosed are compositions containing a compound of this invention in combination with a pharmaceutically acceptable carrier, as well as methods relating to the use thereof for antagonizing gonadotropin-releasing hormone in a subject in need thereof.

86 Claims, No Drawings

GONADOTROPIN-RELEASING HORMONE RECEPTOR ANTAGONISTS AND METHODS RELATING THERETO

CROSS-REFERENCE TO RELATED APPLICATIONS

This application is a continuation of U.S. application Ser. No. 09/771,107 filed Jan. 25, 2001, now U.S. Pat. No. 6,608,197, which claims the benefit of U.S. Provisional Patent Application No. 60/239,683 filed Oct. 11, 2000, and U.S. Provisional Patent Application No. 60/177,933 filed Jan. 25, 2000, all of which applications are hereby incorporated by reference in their entirety.

STATEMENT OF GOVERNMENT INTEREST

Partial funding of the work described herein was provided by the U.S. Government under Grant No. R43-HD38625 provided by the National Institutes of Health. The U.S. Government may have certain rights in this invention.

TECHNICAL FIELD

This invention relates generally to gonadotropin-releasing hormone (GnRH) receptor antagonists, and to methods of treating disorders by administration of such antagonists to a warm-blooded animal in need thereof.

BACKGROUND OF THE INVENTION

Gonadotropin-releasing hormone (GnRH) also known as luteinizing hormone-releasing hormone (LHRH), is a decapeptide (pGlu-His-Trp-Ser-Tyr-Gly-Leu-Arg-Pro-Gly-$NH_2$) that plays an important role in human reproduction. GnRH is released from the hypothalamus and acts on the pituitary gland to stimulate the biosynthesis and release of luteininzing hormone (LH) and follicle-stimulating hormone (FSH). LH released from the pituitary gland is responsible for the regulation of gonadal steroid production in both males and females, while FSH regulates spermatogenesis in makes and follicular development in females.

Due to its biological importance, synthetic and agonists to GnRH have been the focus of considerable attention, particularly in the context of prostate cancer, breast cancer, endometriosis, uterine leiomyoma, and precocious puberty. For example, peptidic GnRH agonists, such as leuprorelin (pGlu-His-Trp-Ser-Tyr-D-Leu-Leu-Arg-Pro-NHEt), have been used to treat such conditions. Such agonists appear to function by binding to the GnRH receptor in the pituitary gonadotropins, thereby inducing the synthesis and release of gonadotropins. Chronic administration of GnRH agonists depletes gonadotropins and subsequently down-regulates the receptor, resulting in suppression of steroidal hormones after some period of time (e.g., on the order of 2–3 weeks following initiation of chronic administration).

In contrast, GnRH antagonists are believed to suppress gonadotropins from the onset, and thus have received the most attention over the past two decades. To date, some of the primary obstacles to the clinical use of such antagonists have been their relatively low bioavailability and adverse side effects caused by histamine release. However, several peptidic antagonists with low histamine release properties have been reported, although they still must be delivered via sustained delivery routes (such as subcutaneous injection or intranasal spray) due to limited bioavailability.

In view of the limitations associated with peptidic GnRH antagonists, a number of nonpeptidic compounds have been proposed. For example, Cho et al. (*J. Med. Chem.* 41:4190–4195, 1998) discloses thieno[2,3-b]pyridin-4-ones for use as GnRH receptor antagonists; U.S. Pat. Nos. 5,780,437 and 5,849,764 teach substituted indoles as GnRH receptor antagonists (as do published PCTs WO 97/21704, 98/55479, 98/55470, 98/55116, 98/55119, 97/21707, 97/21703 and 97/21435); published PCT WO 96/38438 discloses tricyclic diazepines as GnRH receptor antagonists; published PCTs WO97/14682, 97/14697 and 99/09033 disclose quinoline and thienopyridine derivatives as GnRH antagonists; published PCTs WO 97/44037, 97/44041, 97/44321 and 97/44339 teach substituted quinolin-2-ones as GnRH receptor antagonists; and published PCT WO 99/33831 discloses certain phenyl-substituted fused nitrogen-containing bicyclic compounds as GnRH receptor antagonists.

While the significant strides have been made in this field, there remains a need in the art for effective small molecule GnRH receptor antagonists. There is also a need for pharmaceutical compositions containing such GnRH receptor antagonists, as well as methods relating to the use thereof to treat, for example, sex-hormone related conditions. The present invention fulfills these needs, and provides other related advantages.

SUMMARY OF THE INVENTION

In brief, this invention is generally directed to gonadotropin-releasing hormone (GnRH) receptor antagonists, as well as to methods for their preparation and use, and to pharmaceutical compositions containing the same. More specifically, the GnRH receptor antagonists of this invention are compounds having the following general structure (I):

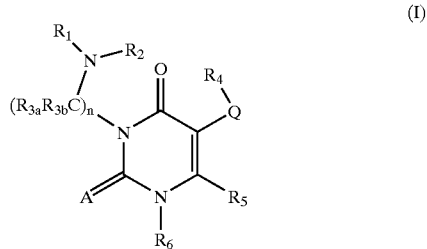

(I)

including stereoisomers, prodrugs and pharmaceutically acceptable salts thereof, wherein A, Q, $R_1$, $R_2$, $R_{3a}$, $R_{3b}$, $R_4$, $R_5$, $R_6$, and n are as defined below.

The GnRH receptor antagonists of this invention have utility over a wide range of therapeutic applications, and may be used to treat a variety of sex-hormone related conditions in both men and women, as well as mammal in general (also referred to herein as a "subject"). For example, such conditions include endometriosis, uterine fibroids, polycystic ovarian disease, hirsutism, precocious puberty, gonadal steroid-dependent neoplasia such as cancers of the prostate, breast and ovary, gonadotrophic pituitary adenomas, sleep apnea, irritable bowel syndrome, premenstrual syndrome, benign prostatic hypertrophy, contraception and infertility (e.g., assisted reproductive therapy such as in vitro fertilization). The compounds of this invention are also useful as an adjunct to treatment of growth hormone deficiency and short stature, and for the treatment of systemic lupus erythematosis. The compounds are also useful in combination with androgens, estrogens, progesterones, and antiestrogens and antiprogestogens for the treatment of endometriosis, fibroids, and in contraception, as well as in combination with an angiotensin-converting enzyme inhibitor, an angiotensin II-receptor antagonist, or a renin inhibitor for the treatment of uterine fibroids. In addition, the compounds may be used in combination with bisphosphonates and other agents for the treatment and/or prevention of disturbances of calcium, phosphate and bone metabolism, and in combination with estrogens, progesterones and/or androgens for the prevention or treatment of bone loss or hypogonadal symptoms such as hot flashes during therapy with a GnRH antagonist.

The methods of this invention include administering an effective amount of a GnRH receptor antagonist, preferably in the form of a pharmaceutical composition, to a mammal in need thereof. Thus, in still a further embodiment, pharmaceutical compositions are disclosed containing one or more GnRH receptor antagonists of this invention in combination with a pharmaceutically acceptable carrier and/or diluent.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION OF THE INVENTION

As mentioned above, the present invention is directed generally to compounds useful as gonadotropin-releasing hormone (GnRH) receptor antagonists. The compounds of this invention have the following structure (I):

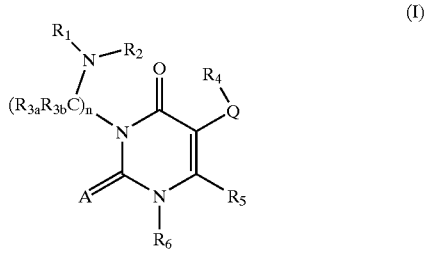

(I)

including stereoisomers, prodrugs and pharmaceutically acceptable salts thereof,
wherein:

Q is a direct bond or —$(CR_{8a}R_{8b})_r$—Z—$(CR_{10a}R_{10b})_s$—;

A is O, S, or $NR_7$;

r and s are the same or different and independently 0, 1, 2, 3, 4, 5 or 6;

n is 2, 3 or 4;

Z is a direct bond or —O—, —S—, —$NR_9$—, —SO—, —$SO_2$—, —$OSO_2$—, —$SO_2O$—, —$SO_2NR_9$—, —$NR_9SO_2$—, —CO—, —COO—, —OCO—, —$CONR_9$—, —$NR_9CO$—, —$NR_9CONR_{9a}$—, —$OCONR_9$— or —$NR_9COO$—;

$R_1$ and $R_2$ are the same or different and independently hydrogen, alkyl, substituted alkyl, aryl, substituted aryl, arylalkyl, substituted arylalkyl, heterocycle, substituted heterocycle, heterocyclealkyl, substituted heterocyclealkyl, —$C(R_{1a})(=NR_{1b})$ or —$C(NR_{1a}R_{1c})$ $(=NR_{1b})$;

or $R_1$ and $R_2$ taken together with the nitrogen atom to which they are unattached form a heterocycle ring or a substituted heterocycle ring;

$R_{3a}$ and $R_{3b}$ are the same or different and, at each occurrence, independently hydrogen, alkyl, substituted alkyl, alkoxy, alkylthio, alkylamino, aryl, substituted aryl, arylalkyl, substituted arylalkyl, heterocycle, substituted heterocycle, heterocyclealkyl, substituted heterocyclealkyl, —$COOR_{14}$ or —$CONR_{14}R_{15}$;

or $R_{3a}$ and $R_{3b}$ taken together with the carbon atom to which they are attached form a homocyclic ring, substituted homocyclic ring, heterocyclic ring or substituted heterocyclic ring;

or $R_{3a}$ and $R_{3b}$ taken together from $=NR_{3c}$;

or $R_{3a}$ and the carbon to which it is attached taken together with $R_1$ and the nitrogen to which it is attached form a heterocyclic ring or substituted heterocyclic ring;

$R_4$ is higher alkyl, substituted alkyl, aryl, substituted aryl, heterocycle, substituted heterocycle, —$COR_{11}$, —$COOR_{11}$, —$CONR_{12}R_{13}$, —$OR_{11}$, —$OCOR_{11}$, —$OSO_2R_{11}$, —$SR_{11}$, —$SO_2R_{11}$, —$NR_{12}R_{13}$, —$NR_{11}COR_{12}$, —$NR_{11}CONR_{12}R_{13}$, —$NR_{11}SO_2R_{12}$ or —$NR_{11}SO_2NR_{12}R_{13}$;

$R_5$ is hydrogen, halogen, lower alkyl, substituted lower alkyl, aryl, substituted aryl, arylalkyl, substituted arylalkyl, alkoxy, alkylthio, alkylamino, cyano or nitro;

$R_6$ is higher alkyl, substituted alkyl, aryl, substituted aryl, arylalkyl, substituted arylalkyl, heteroaryl, substituted heteroaryl, heteroarylalkyl or substituted heteroarylalkyl;

$R_7$ is hydrogen, —$SO_2R_{11}$, cyano, alkyl, substituted alkyl, aryl, substituted aryl, arylalkyl, substituted arylalkyl, heteroaryl, substituted heteroaryl, heteroarylalkyl or substituted heteroarylaklyl; and $R_{1a}$, $R_{1b}$, $R_{1c}$, $R_{3c}$, $R_{8a}$, $R_{8b}$, $R_9$, $R_{9a}$, $R_{10a}$, $R_{10b}$, $R_{11}$, $R_{12}$, $R_{13}$, $R_{14}$ and $R_{15}$ are the same or different and, at each occurrence, independently hydrogen acyl, alkyl, substituted alkyl, aryl, substituted aryl, arylalkyl, substituted arylalkyl, heterocycle, substituted heterocycle, heterocyclealkyl or substituted heterocyclealkyl;

or $R_{1a}$ and $R_{1b}$, $R_{8a}$ and $R_{8b}$, and $R_{10a}$ and $R_{10b}$, $R_{12}$ and $R_{13}$, or $R_{14}$ and $R_{15}$ taken together with the atom or atoms to which they are attached form a homocyclic ring, substituted homocyclic ring, heterocyclic ring or substituted heterocyclic ring.

As used herein, the above terms have the following meaning:

"Alkyl" means a straight chain or branched, noncyclic or cyclic, unsaturated or saturated aliphatic hydrocarbon containing from 1 to 10 carbon atoms, while the term "lower alkyl" has the same meaning as alkyl but contains from 1 to 6 carbon atoms. The term "higher alkyl" has the same meaning as alkyl but contains from 2 to 10 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cyclic alkyls are also referred to herein as a "homocycles" or "homocyclic rings." Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"Aryl" means an aromatic carbocyclic moiety such as phenyl or naphthyl.

"Arylalkyl" means an alkyl having at least one alkyl hydrogen atoms replaced with an aryl moiety, such as benzyl, —(CH$_2$)$_2$phenyl, —(CH$_2$)$_3$phenyl, —CH(phenyl)$_2$, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —CH$_2$pyridinyl, —CH$_2$pyrimidinyl, and the like.

"Heterocycle" (also referred to as a "heterocyclic ring") means a 4- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle, such as —CH$_2$morpholinyl, and the like.

"Homocycle" (also referred to herein as "homocyclic ring") means a saturated or unsaturated (but not aromatic) carbocyclic ring containing from 3–7 carbon atoms, such as cyclopropane, cyclobutane, cyclopentane, cyclohexane, cycloheptane, cyclohexene, and the like.

The term "substituted" as used herein means any of the above groups (i.e., alkyl, aryl, arylakyl, heteroaryl, heteroarylalkyl, homocycle, heterocycle and/or heterocyclealkyl) wherein at least one hydrogen atom is replaced with a substituent. In the case of a keto substituent ("—C(=O)—") two hydrogen atoms are replaced. When substituted one or more of the above groups are substituted, "substituents" within the context of this invention include halogen, hydroxy, cyano, nitro, amino, alkylamino, dialkylamino, alkyl, alkoxy, alkylthio, haloalkyl, aryl, arylalkyl, heteroaryl, heteroarylalkyl, heterocycle and heterocyclealkyl, as well as —NR$_a$R$_b$, —NR$_a$C(=O)R$_b$, —NR$_a$C(=O)NR$_a$NR$_b$, —NR$_a$C(=O)OR$_b$, —NR$_a$SO$_2$R$_b$, —C(=O)R$_a$, —C(=O)OR$_a$, —C(=O)NR$_a$R$_b$, —OC(=O) NR$_a$R$_b$, —OR$_a$, —SR$_a$, —SOR$_a$, —S(=O)$_2$R$_a$, —OS (=O)$_2$R$_a$ and —S(=O)$_2$OR$_a$. In addition, the above substituents may be further substituted with one or more of the above substituents, such that the substituent substituted alkyl, substituted aryl, substituted arylalkyl, substituted heterocycle or substituted heterocyclealkyl. R$_a$ and R$_b$ in this context may be the same or different and independently hydrogen, alkyl, haloalkyl, substituted aryl, aryl, substituted aryl, arylalkyl, substituted arylalkyl, heterocycle, substituted heterocycle, heterocyclealkyl or substituted heterocyclealkyl.

"Halogen" means fluoro, chloro, bromo and iodo.

"Haloalkyl" means an alkyl having at least one hydrogen atom replaced with halogen, such as trifluoromethyl and the like.

"Alkoxy" means an alkyl moiety attached through an oxygen bridge (i.e., —O—alkyl) such as methoxy, ethoxy, and the like.

"Alkylthio" means an alkyl moiety attached through a sulfur bridge (i.e., —S-alkyl) such as methylthio, ethylthio, and the like.

"Alkylsulfonyl" means an alkyl moiety attached through a sulfonyl bridge (i.e., —SO$_2$-alkyl) such as methylsulfonyl, ethylsulfonyl, and the like.

"Alkylamino" and "dialkylamino" mean one or two alkyl moiety attached through a nitrogen bridge (i.e., —N-alkyl) such as methylamino, ethylamino, dimethylamino, diethylamino, and the like.

In one embodiment of this invention, A is O and representative GnRH receptor antagonists of this invention include compounds having the following structure (II):

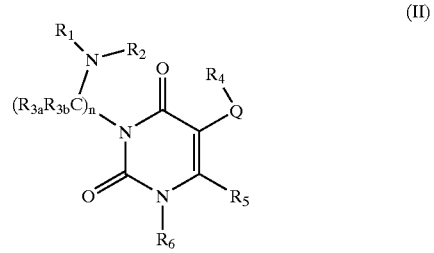

(II)

In another embodiment, Q is —(CR$_{8a}$R$_{8b}$)$_r$—Z— (CR$_{10a}$R$_{10b}$)$_s$—, r and s are both zero, and representative GnRH receptor antagonists of this invention include compounds having the following structure (III):

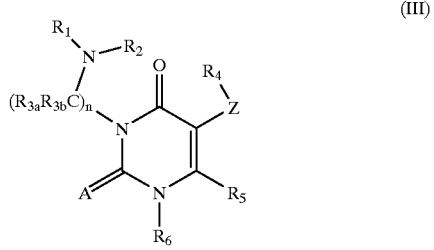

(III)

In another embodiment, A is S, as represented by the following structure (IV):

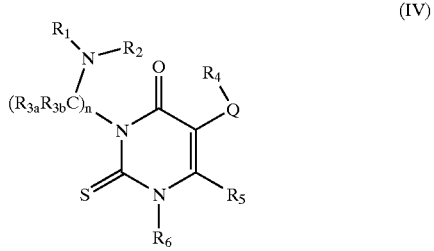

(IV)

Similarly, in another embodiment, A is NR$_7$, as represented by the following structure (V):

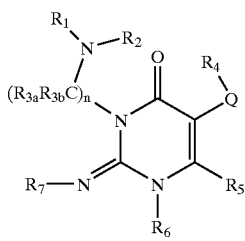

(V)

In further embodiments of this invention, R$_6$ is substituted or unsubstituted benzyl as represented by the following structure (VI) (wherein Y represents one or more optional substituents as defined above):

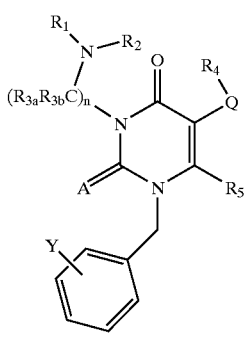

(VI)

In a more specific embodiment of structure (VI), A is O, n is 2, and each occurrence of R$_{3a}$ and R$_{3b}$ is H, as represented by the following structure (VII):

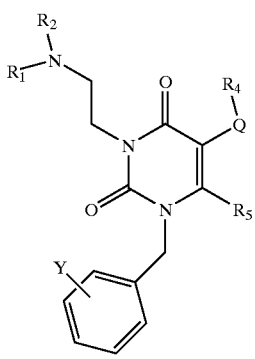

(VII)

With regard to the "R$_1$R$_2$N(CR$_{3a}$R$_{3b}$)$_n$—" moiety of structure (I), n may be 2, 3 or 4. Accordingly, this moiety may be represented by the following structure (i) when n is 2, structure (ii) when n is 3, and structure (iii) when n is 3:

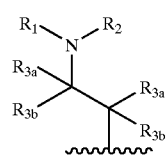

(i)

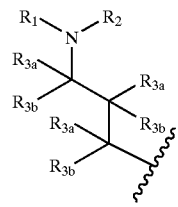

(ii)

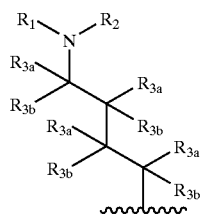

(iii)

wherein each occurrence of R$_{3a}$ and R$_{3b}$ above may be the same or different, and are as defined above. For example, when each occurrence of R$_{3a}$ and R$_{3b}$ in structure (i), (ii) and (iii) is hydrogen, the "R$_1$R$_2$N(CR$_{3a}$R$_{3b}$)$_n$—" moiety has the structure R$_1$R$_2$N(CH$_2$)$_2$—, R$_1$R$_2$N(CH$_2$)$_3$— and R$_1$R$_2$N(CH$_2$)$_4$—, respectively.

The compounds of the present invention may be prepared by known organic synthesis techniques, including the methods described in more detail in the Examples. However in general, the compounds of structure (I) above may be made by the following Reaction Schemes. Specifically, compounds of structure (I) wherein A is oxygen may be made by Reaction Schemes A to E. Reaction Schemes F to K are appropriate for compounds of structure (I) wherein A is sulfur or NR$_7$, as well as where A is oxygen. Reaction Scheme L shows conditions for the conversion of thiouracils (where A is sulfur) to embodiments wherein A is NR$_7$. All substituents in the following Reaction Schemes are as defined above unless indicated otherwise.

Reaction Scheme A

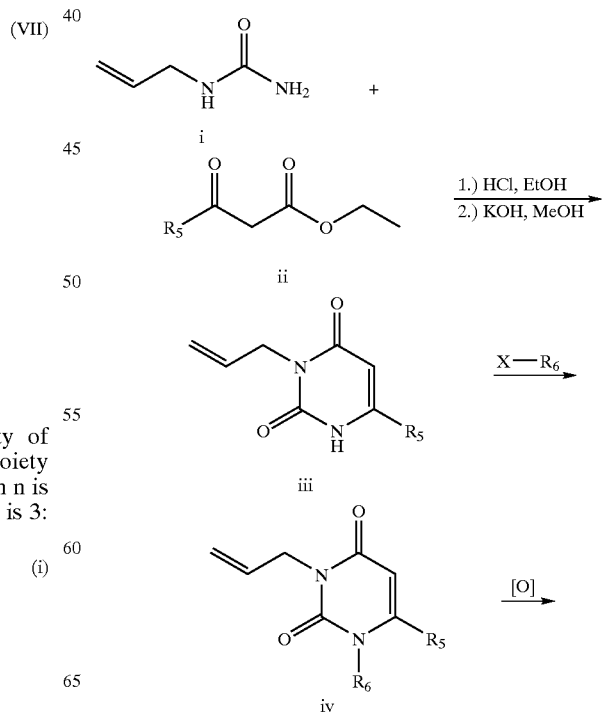

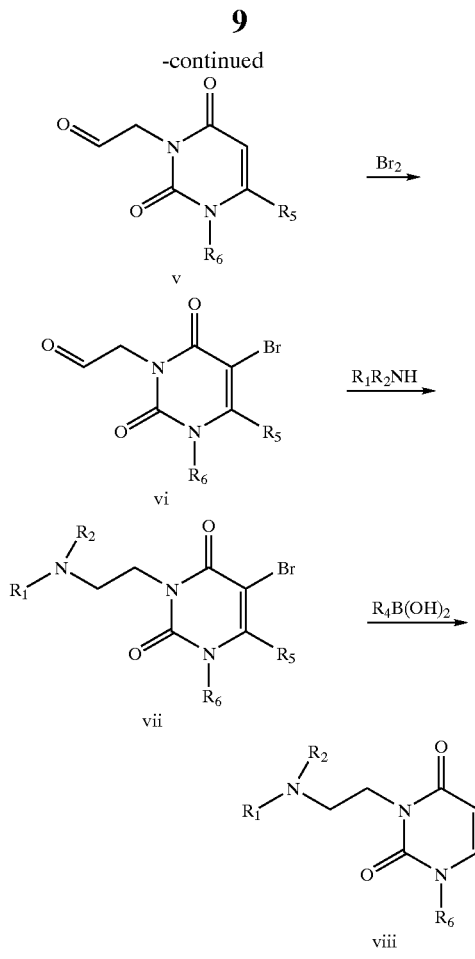

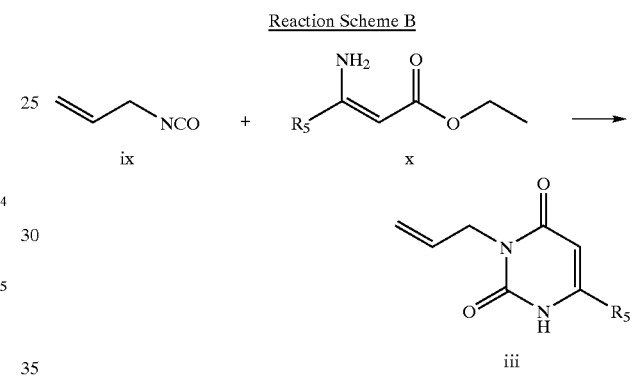

halogen) in a solvent such as DMF or ethanol for 1 hour to 2 days in the presence of a base such as sodium hydride or tetrabutylammonium fluoride to yield (iv). Oxidation of the allyl functionality, using osmium tetroxide and/or sodium periodate in solvent such as THF and/or water for 1–24 hours, gives aldehyde (v). Bromination of (v) using bromine or n-bromosuccinimide in a solvent such as acetic acid or chloroform for 1–24 hours resulted in brominated compound (vi). Reductive amination of (vi) with an appropriate amine using a reducing agent such as sodium triacetoxyborohydride in a solvent such as dichloroethane at 0 to 100° C. for 1–24 hours gives (vii) which when coupled with an appropriate boronic acid in a solvent such as ethanol or toluene at 25 to 150° C. for 1–24 hours in the presence of a Pd(0) catalyst gives (viii).

The final two steps of the above synthesis may also be reversed, the Suzuki coupling in that instance being the penultimate step and the reductive amination the final step. Alternatively, compound (iii) may be synthesized by the procedure in Example 2.

Allylurea (i) and substituted acetoacetate (ii) are condensed under acidic conditions in a solvent such as ethanol or DMF at 25 to 100° C. and then cyclized under strongly basic conditions to give the substituted 3-allyl-2,4-pyrimidinedione (iii). Compound (iii) can then be modified by alkylation with an appropriate alkyl halide (where X is Compound (iii) from Reaction Scheme A1 may also be synthesized by condensing and cyclizing allyl isocyanate (viii) and appropriate aminoalkene ester (ix) such as ethyl 3-aminocrotonate in a solvent such as toluene or DMF at 25 to 100° C. for 1–24 hours.

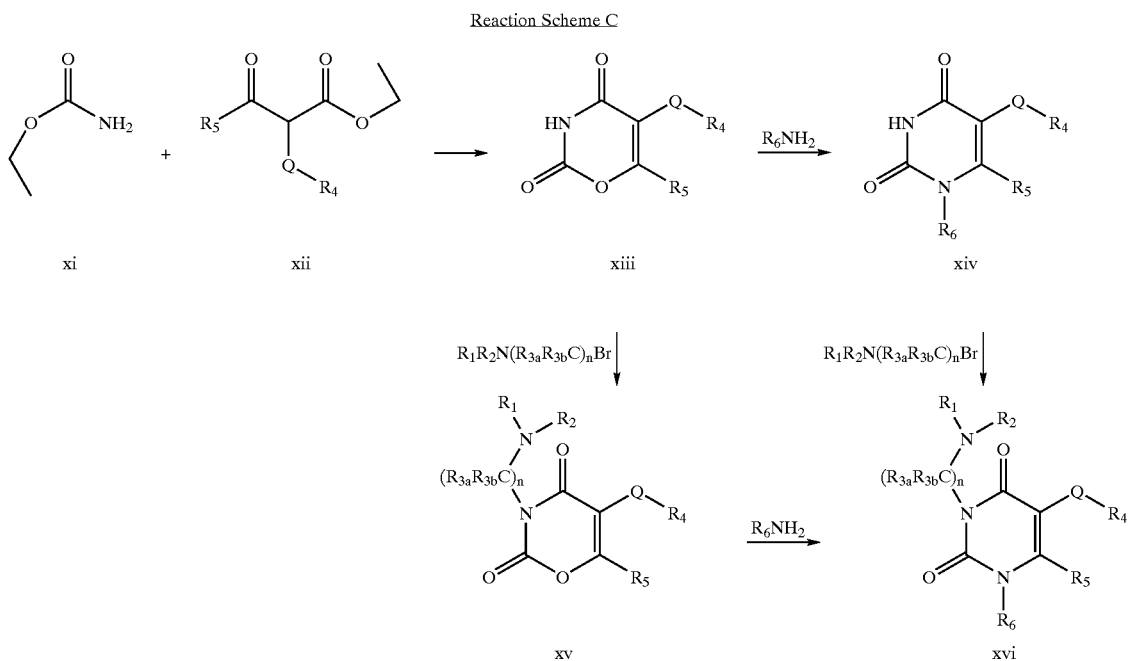

Cyclization of (xi) and (xii) in a solvent such as ethanol or DMF at 25 to 150° C. for 1 to 24 hours gives oxazime (xiii). Animation of (xiii) in a solvent such as DMF or ethanol at 25 to 150° C. for 1–24 hours yielded uracil derivative (xiv). Alkylation of (xiv) by an appropriate alkyl bromide in the presence of a base such as sodium hydride or sodium hydroxide in a solvent such as THF or DMF at 0 to 100° C. for 1–24 hours gives substituted uracil (xvi). The order of the reaction scheme may be changed allowing oxazine (xiii) to first be alkylated under conditions above to (xv) followed by amination to the product (xvi).

Reaction Scheme D

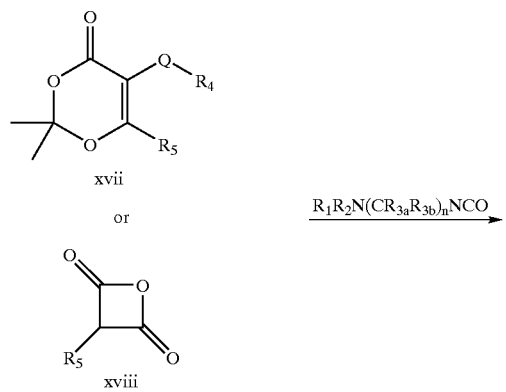

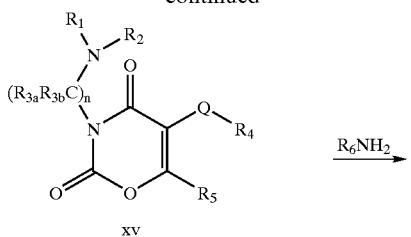

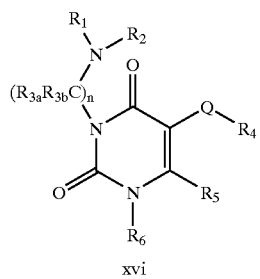

Compound (xvii) or (xviii) react with an appropriately substituted isocyante in a solvent such as toluene or chloroform at room temperature to 100° C. for 1–24 hours as an alternative synthesis to intermediate oxazine (xv). Animation with a substituted amine in a solvent such as DMF or ethanol at a temperature of 25 to 100° C. for a period of 1–24 hours results in product uracil (xvi).

Reaction Scheme E

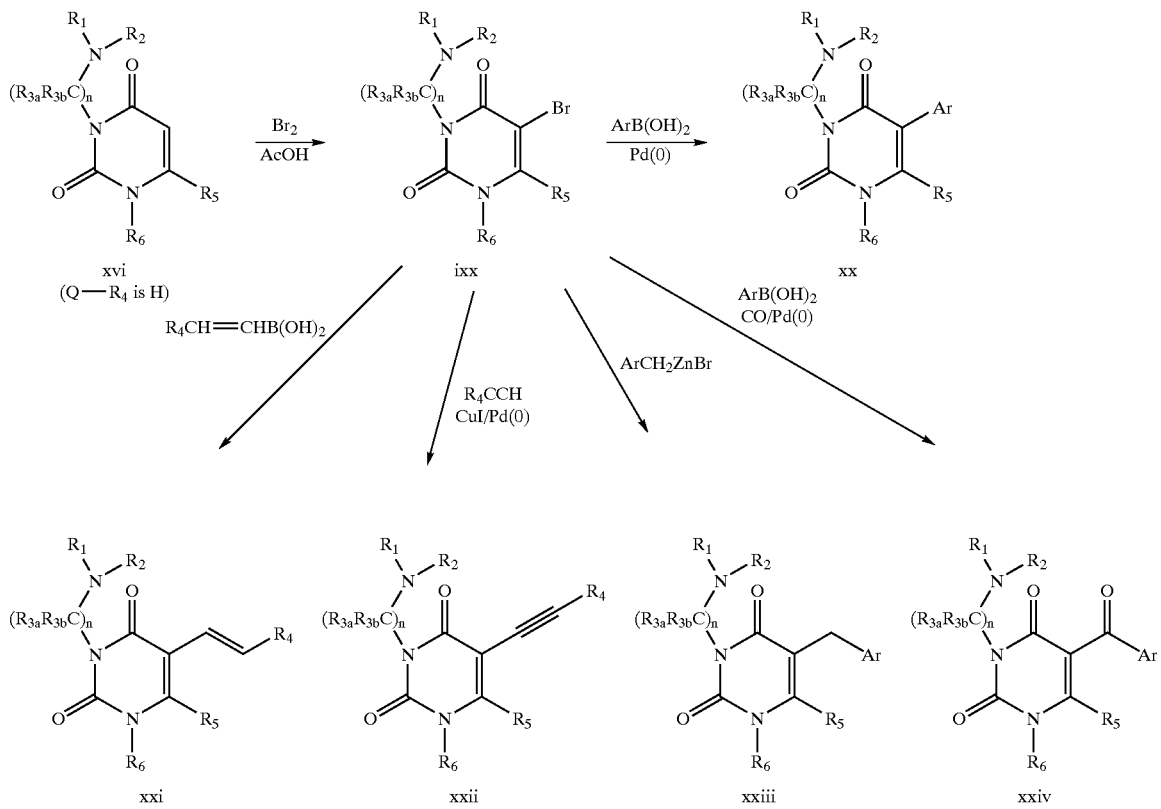

Intermediate (xvi) may be brominated using a brominating agent such as N-bromosuccinimide or bromine in a solvent such as acetic acid or chloroform at 0 to 100° C. for a period of 1–24 hours to yield bromo compound (ixx). The bromo compound can undergo various palladium catalyzed cross coupling reactions. Compound (ixx) taken in solvent such as ethanol or THF under nitrogen atmosphere using an appropriate Pd(0) catalyst such as tetrakis (triphenylphosphine)Pd(0), may be reacted for 1–24 hours at 25 to 150° C. with either an aryl bromic acid (ArB(OH)$_2$ where Ar is substituted aryl or heteroaryl) to yield product (xx) or with a substituted vinyl boronic acid to give compound (xxi). Compound (ixx) taken in solvent such as ethanol or THF using an appropriate Pd(0) catalyst in the presence of carbon monoxide and boronic acid yields (xxiv) after 1–24 hours at 0 to 150° C. Again using Pd(0) chemistry, compound (xxiii) is synthesized in a solvent such as THF or dioxane from the alkylation of (ixx) with an appropriate metal halide reagent for 1–24 hours at 0 to 150° C. Compound (ixx) in the presence of a substituted acetylene Pd(0) catalyst, metal halide such as CuI, and base such as triethylamine in an appropriate solvent such as acetonitrile or DMF at 25 to 150° C. for 1–24 hours gives alkyne (xxii). Alkynyl uracil (xxii) may be selectively reduced to the alkene using a catalyst such as palladium/BaSO$_4$ under hydrogen atmosphere in solvent such as ethyl acetate or methanol to give (xxi).

Vinyl ester (xxvi) and (xxv) can be cyclized in a solvent such as DMF or EtOH at 25 to 150° C. for 1–24 hours to give (xxvii). Alkylation of (xxvii) with an appropriate alkyl or aryl halide in a solvent such as DMF or THF in the presence of a base such as sodium hydride or sodium hydroxide for 1–24 hours at 0 to 150° C. gives (xxviii).

Reaction Scheme F

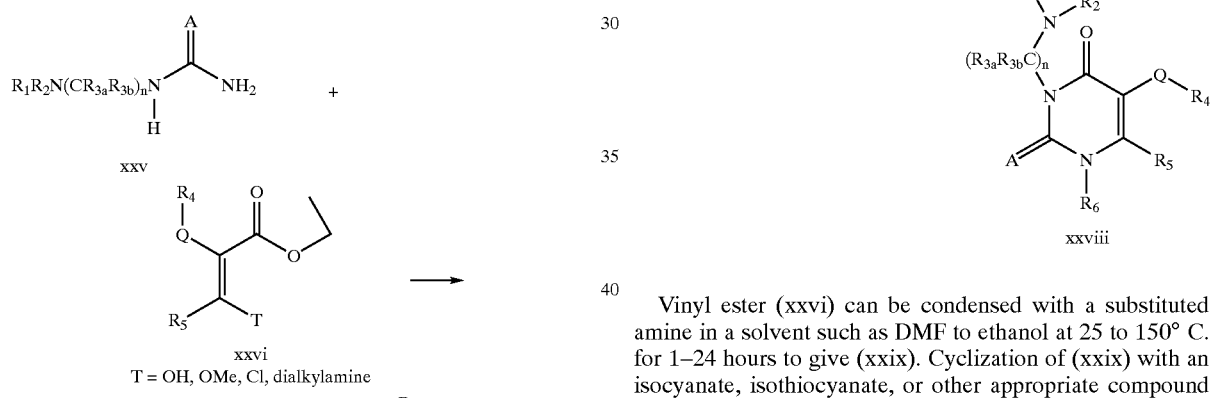

Reaction Scheme G

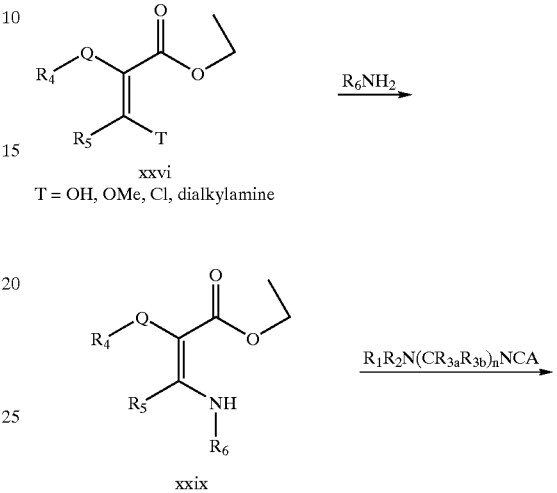

Vinyl ester (xxvi) can be condensed with a substituted amine in a solvent such as DMF to ethanol at 25 to 150° C. for 1–24 hours to give (xxix). Cyclization of (xxix) with an isocyanate, isothiocyanate, or other appropriate compound in a solvent such as DMF, THF or dioxane, with or without a base such as sodium ethoxide or sodium hydride at 0 to 100° C. for 1–24 hours gives product (xxviii).

Reaction Scheme H

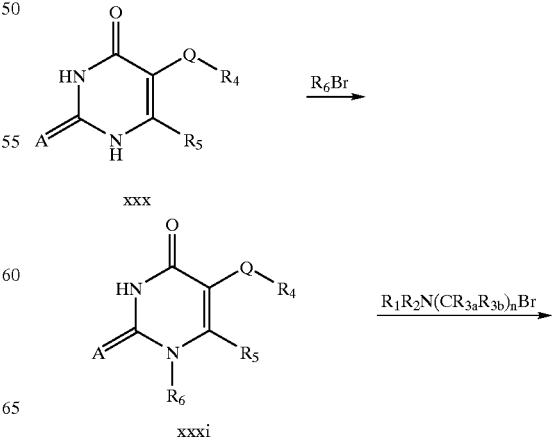

-continued

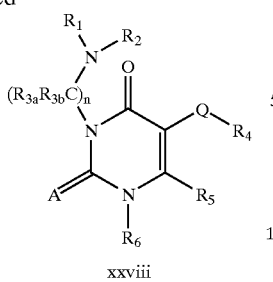

xxviii

Compound (xxx) may be alkylated by an appropriate alkyl halide in the presence of a base such as sodium hydride or sodium hydroxide in a solvent such as THF or DMF at 0 to 50° C. for 1–24 hours to give (xxxi), which under further alkylation by a second alkyl halide gives product (xxviii).

Reaction Scheme I

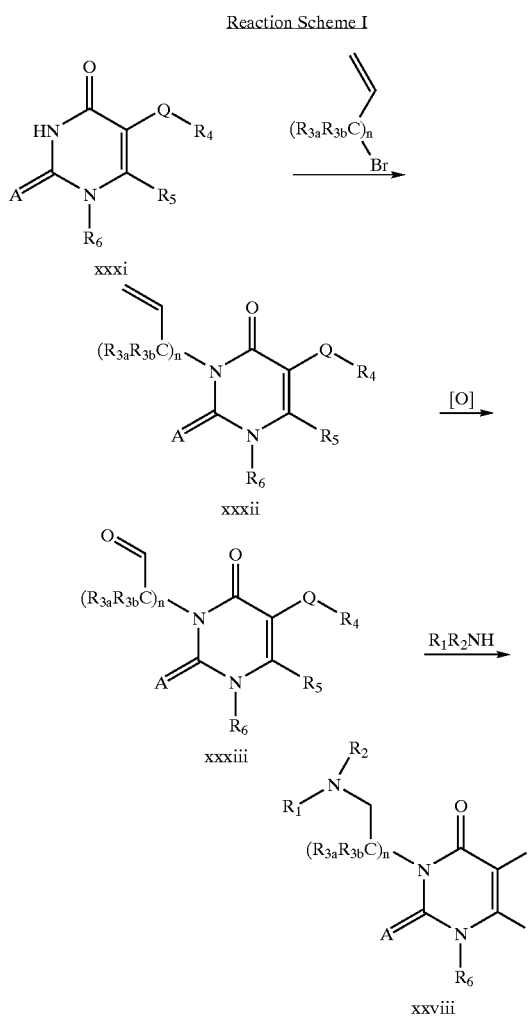

Compound (xxxi) may be alkylated by an appropriate alkyl halide in the presence of a base such as sodium hydride or sodium hydroxide in a solvent such as THF or DMF at 0 to 100° C. for 1–24 hours to give (xxxii). The terminal diode bond is oxidized using an appropriate oxidizing reagent such as osmium tetroxide or sodium periodate in solvent such as THF and/or water for 1–24 hours at 0 to 100° C. to give aldehyde (xxxiii). Reductive amination of (xxxiii) with an appropriate amine using a reducing agent such as sodium cyanoborohydride in a solvent such as dichloroethane or acetonitrile at 0 to 100° C. for 1–24 hours gives (xxviii).

Reaction Scheme J

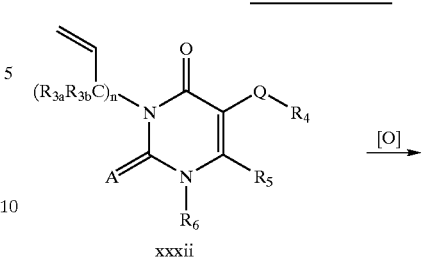

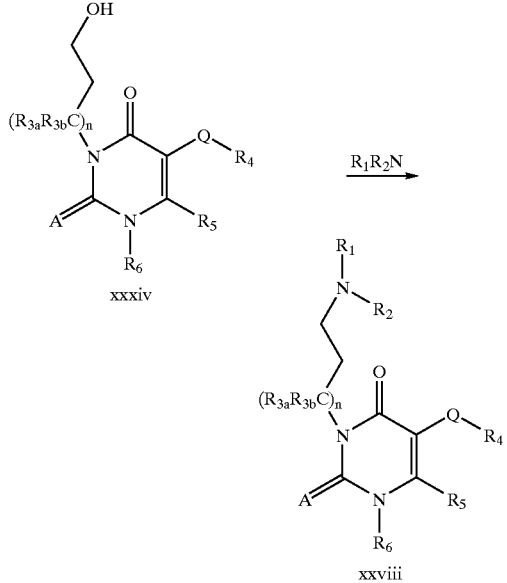

Compound (xxxii)) can be oxidized to the alcohol (xxxiv) first by hydroboration with a borane complex in a solvent such as THF followed by oxidation with ozone or hydrogen peroxide in a solvent such as methanol, ethanol and/or water at −25 to 100° C. for a period of 0.5–24 hours. Treatment of (xxxiv) with mesyl or tosyl chloride in methylene chloride with a base such as triethylamine or pyridine at 0 to 100° C. for 1–24 hours followed by reaction with an amine in a solvent such as DMF or toluene for 0.5–12 hours at 25 to 100° C. gives (xxviii).

Reaction Scheme K

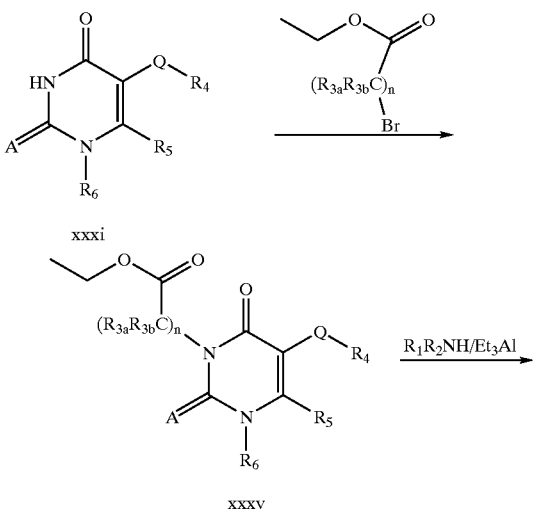

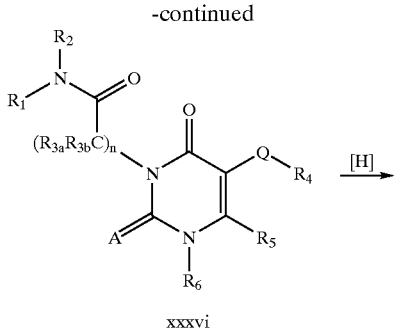

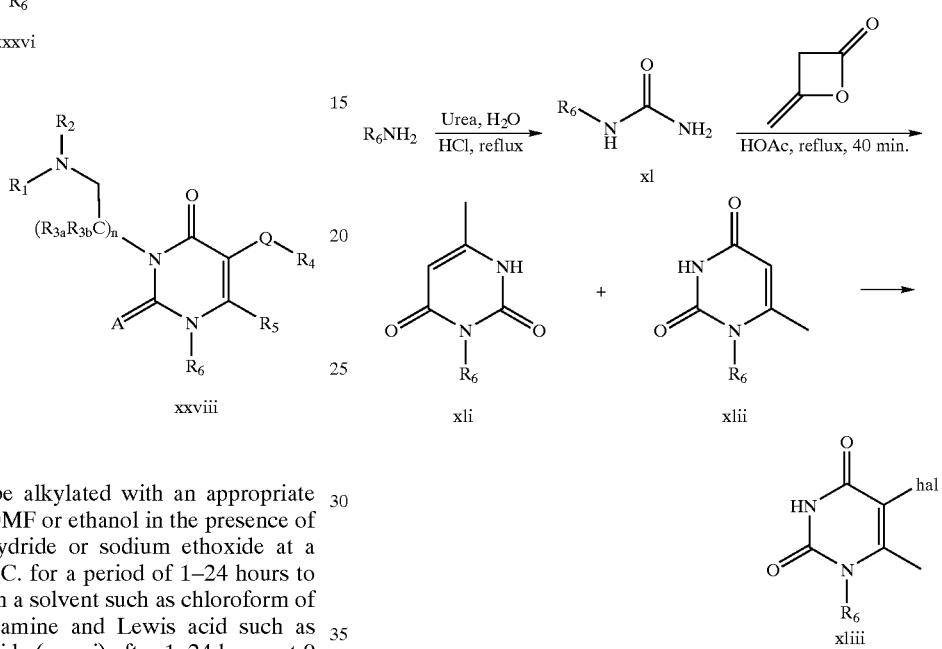

Compound (xxxi) can be alkylated with an appropriate ester in a solvent such as DMF or ethanol in the presence of a base such as sodium hydride or sodium ethoxide at a temperature of 25 to 150° C. for a period of 1–24 hours to give (xxxv). Ester (xxxv) in a solvent such as chloroform of benzene with substituted amine and Lewis acid such as triethylaluminum gives amide (xxxvi) after 1–24 hours at 0 to 100° C. Reduction of (xxxvi) with lithium aluminum hydride or borane complex in a solvent such as THF at ether at 0 to 100° C. for 1–12 hours gives product (xxviii).

Thiouracil compound (xxxvii) in the presence of a substituted sulfonylisocyanate in a solvent such as benzene or toluene for 1–48 hours at 25 to 125° C. gives sulfonamide (xxxviii). Thiouracil (xxxvii) chlorinated by thionyl chloride or phosphorous oxychloride at −25 to 100° C. for 1–24 hours followed by amination with an appropriate amine in a solvent such as benzene or toluene at 25 to 150° C. for 1–24 hours gives compound (xxxix).

Reaction Scheme M

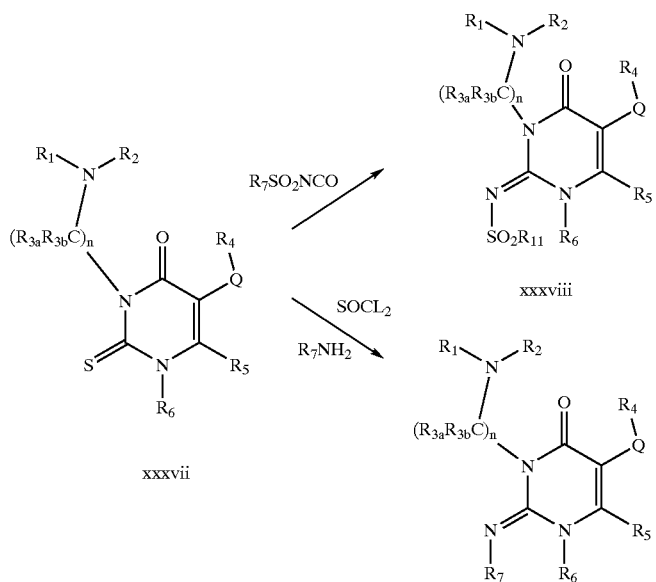

Substituted amine in the presence of urea or thiourea is heated at a temperature of 50–125° C. for 0.5 to 12 hours to Reaction Scheme L give (xi). Cyclization of (xi) with diketene at 50–150° C. in acidic media such as acetic or formic acid for 5 minutes to 4 hours gives a mixture of isomers (xli) and (xlii). Halogenation of (xlii) using a halogenating reagent such as N-halosuccinimide in chloroform or bromine in acetic acid for 5 minutes to 24 hours gives halogenated product (xliii).

Reaction Scheme N

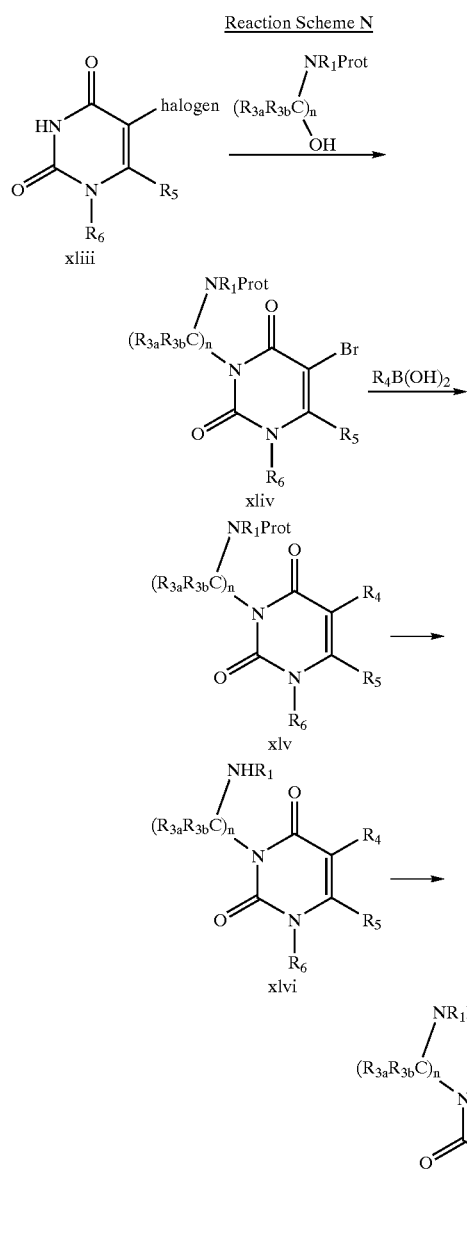

Uracil compound (xliii) and an appropriately substituted alcohol are condensed under Mitsonobu conditions such as diethyl or dibutyl axodicarboxylate and triphenylphosphine in a solvent such as THF at 0–100° C. for 0.5 to 10 hours to give compound (xliv). A Suzuki coupling of (xliv) and a boronic acid or boronic acid ester in a solvent such as ethanol or toluene at 25 to 150° C. for 1–24 hours in the presence of a Pd(0) catalyst gives (xlv). Deprotection of the protected amine gives (xlvi). Reductive amination of (xlvi) with an appropriate aldehyde in a solvent such as methylene chloride or acetonitrile using a reducing agent such as sodium triacetoxyborohydride or sodium borohydride at 0 to 100° C. for 1–24 hours gives (xlvii).

Reaction Scheme O

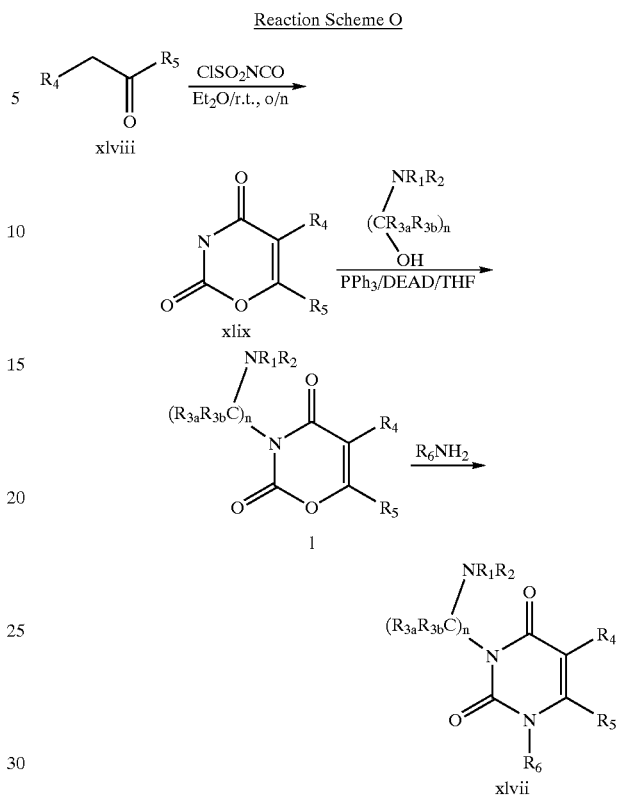

Keto or aldehyde xlviii in the presence of chlorosulfonylisocyanate or chlorocarbonylisocyanate yields oxaz-2,4-dione xlix after stirring for 1–24 hours at 0° C. to 75° C. in a solvent such as THF or ether. Mitsonobu condensation with an appropriate alcohol gives 1 which when in the presence of amine $R_6NH_2$ at room temperature to 125° C., with or without solvent such as DMF or catalyst such as acetic or hydrochloric acid, for ½ to 24 hours gives xlvii.

The compounds of the present invention may generally be utilized as the free acid or free base. Alternatively, the compounds of this invention may be used in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenyzylammonium, benzylammonium, 2-hydroxyethylammonium, and the like). Thus, the term "pharmaceutically acceptable salt" of structure (I) is intended to encompass any and all acceptable salt forms.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the compounds of structure (I). Further, in the case of a carboxylic acid (—COOH), esters may be employed, such as methyl esters, ethyl esters, and the like.

With regard to stereoisomers, the compounds of structure (I) may have chiral centers and may occur as racemates, racemic mixtures and as individual enantiomers or diastereomers. All such isomeric forms are included within the present invention, including mixtures thereof. Compounds of structure (I) may also posses axial chirality which may result in atropisomers. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

The effectiveness of a compound as a GnRH receptor antagonist may be determined by various assay methods. Suitable GnRH antagonists of this invention are capable of inhibiting the specific binding of GnRH to its receptor and antagonizing activities associated with GnRH. For example, inhibition of GnRH stimulated LH release in immature rats may be measured according to the method of Vilchez-Martinez (*Endocrinology* 96:1130–1134, 1975). Briefly, twenty-five day old male Sprague-Dawley rats are administered an GnRH antagonist in saline or other suitable formulation by oral gavage, sub-cutaneous injection, or intravenous injection. This is followed by sub-cutaneous injection of 200 ng GnRH in 0.2 ml saline. Thirty minutes after the last injection, the animals are decapitated and trunk blood collected. After centrifugation, the separated plasma is stored at −20° C. until determination of the LH and FSH by radioimmunoassay. Other techniques for determining the activity of GnRH receptor antagonists are well known in the field, such as the use of cultured pituitary cells for measuring GnRH activity (Vale et al., *Endocrinology* 91:562–572, 1972), and a technique for measuring radioligand binding to rat pituitary membranes (Perrin et al., *Mol. Pharmacol.* 23:44–51, 1983).

For example, effectiveness of a compound as a GnRH receptor antagonist may be determined by one or more of the following assays.

Rat Anterior Pituitary Cell Culture Assay of GnRH Antagonists

Anterior pituitary glands are collected from 7-week-old female Sprague-Dawley rats and the harvested glands digested with collagenase in a dispersion flask for 1.5 hr at 37° C. After collagenase digestion, the glands are further digested with neuramindase for 9 min at 37° C. The digested tissue is then washed with 0.1% BSA/McCoy's 5A medium, and the washed cells suspended in 3% FBS/0.1 BSA/McCoy's 5A medium and plated into 96-well tissue culture plates at a cell density of 40,000 cells per well in 200 $\mu$l medium. The cells are then incubated at 37° C. for 3 days. One pituitary gland normally yields one 96-well plate cells, which can be used for assaying three compounds. For assay of a GnRH antagonist, the incubated cells are first washed with 0.1% BSA/McCoy's 5A medium once, followed by addition of the test sample plus 1 nM GnRH in 200 $\mu$l 0.1% BSA/McCoy's 5A medium in triplicate wells. Each sample is assayed at 5-dose levels to generate a dose-response curve for determination of its potency on the inhibition of GnRH stimulated LH and/or FSH release. After 4-hr incubation at 37° C., the medium is harvested and the level of LH and/or FSH secreted into the medium determined by RIA.

RIA of LH and FSH

For determination of the LH levels, each sample medium is assayed in duplicates and all dilutions are done with RIA buffer (0.01M sodium phosphate buffer/0.15M NaCl/1% BSA/0.01% NaN3, pH 7.5) and the assay kit is obtained from the Nation Hormone and Pituitary Program supported by NIDDK. To a 12×75 mm polyethylene test tube is added 100 $\mu$l of sample medium diluted 1:5 or rLH standard in RIA buffer and 100 $\mu$l of [125I]-labeled rLH (~30,000 cpm) plus 100 $\mu$l of rabbit anti-rLH antibody diluted 1:187,500 and 100 $\mu$l RIA buffer. The mixture is incubated at room temperature over-night. In the next day, 100 $\mu$l of goat anti-rabbit IgG diluted 1:20 and 100 $\mu$l of normal rabbit serum diluted 1:1000 are added and the mixture incubated for another 3 hr at room temperature. The incubated tubes are then centrifuged at 3,000 rmp for 30 min and the supernatant removed by suction. The remaining pellet in the tubes is counted in a gamma-counter. RIA of FSH is done in a similar fashion as the assay for LH with substitution of the LH antibody by the FSH antibody diluted 1:30,000 and the labeled rLH by the labeled rFSH.

Radio-iodination of GnRH peptide

The GnRH analog is labeled by the chloramine-T method. To 10 $\mu$g of peptide in 20 $\mu$l of 0.5M sodium phosphate buffer, pH 7.6, is added 1 mCi of Na125I, followed by 22.5 $\mu$g chloramine-T and the mixture vortexed for 20 sec. The reaction is stopped by the addition of 60 $\mu$g sodium metabisulfite and the free iodine is removed by passing the iodinated mixture through a C-8 Sep-Pak cartridge (Millipore Corp., Milford, Mass.). The peptide is eluted with a small volume of 80% acetonitrile/water. The recovered labeled peptide is further purified by reverse phase HPLC on a Vydac C-18 analytical column (The Separations Group, Hesperia, Calif.) on a Beckman 334 gradient HPLC system using a gradient of acetonitrile in 0.1% TFA. The purified radioactive peptide is stored in 0.1% BSA/20% acetonitrile/0.1% TFA at −80° C. and can be used for up to 4 weeks.

GnRH receptor membrane binding assay

Cells stably, or transiently, transfected with GnRH receptor expression vectors are harvested, resuspended in 5% sucrose and homogenized using a polytron homogenizer (2×15 sec). Nucleii are removed by centrifugation (3000×g for 5 min.), and the supernatant centrifuged (20,000×g for 30 min, 4° C.) to collect the membrane fraction. The final membrane preparation is resuspended in binding buffer (10 mM Hepes (pH 7.5), 150 mM NaCl, and 0.1% BSA) and stored at −70° C. Binding reactions are performed in a Millipore MultiScreen 96-well filtration plate assembly with polyethylenimine coated GF/C membranes. The reaction is initiated by adding membranes (40 ug protein in 130 ul binding buffer) to 50 ul of [$^{125}$I]-labeled GnRH peptide (~100,000 cpm), and 20 ul of competitor at varying concentrations. The reaction is terminated after 90 minutes by application of vacuum and washing (2×) with phosphate buffered saline. Bound radioactivity is measured using 96-well scintillation counting (Packard Topcount) or by removing the filters from the plate and direct gamma counting $K_i$ values are calculated from competition binding data using non-linear least squares regression using the Prism software package (GraphPad Software).

Activity of GnRH receptor antagonists are typically calculated from the $IC_{50}$ as the concentration of a compound necessary to displace 50% of the radiolabeled ligand from the GnRH receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973). GnRH receptor antagonists of this invention have a $K_i$ of 100 μM or less. In a preferred embodiment of this invention, the GnRH receptor antagonists have a $K_i$ of less than 10 μM, and more preferably less than 1 μM, and even more preferably less than 0.1 μM (i.e., 100 nM). To this end, representative GnRH receptor antagonsists of this invention where have a $K_i$ of less than 100 nM when using the GnRH receptor membrane binding assay as described above include the following Compound Nos.

| Table No. | Compound No. |
|---|---|
| 1 | 3, 10, 11, 12, 13 |
| 3 | 1, 4 |
| 6 | 1, 2, 3, 8 |
| 7 | 2, 3, 4, 7, 9, 10, 11 |
| 8 | 2, 3, 4, 7, 12, 13, 14, 15, 16, 17, 19–21, 23, 25, 27–29, 31–36, 38–39, 42, 44, 51, 58, 59, 61, 63–66, 68, 70, 75, 77–97, 100, 106, 107, 109–113, 115–117, 124–135, 137–140 |
| 9 | 3, 4, 6, 7, 10, 14–16, 19, 24, 26, 32, 35, 37, 39, 40, 42, 46–49, 51–53, 55, 56, 58, 61, 63, 64, 66–68, 70, 72–78, 80–82, 85, 86, 89–93, 95, 96, 98–102, 107, 109, 110, 112, 138, 140, 142, 143, 145, 146, 149, 151–155, 157–162, 164, 166–168, 170–176, 178–188, 191, 194–197, 199, 200, 202–207, 210–212, 214, 215, 219, 224, 225, 227, 229, 232–234, 237, 240, 242, 244, 245, 247, 249, 251–256, 258–261, 263, 265–267, 270, 275, 277–279, 281, 286, 287, 295–301, 304, 305, 307–309, 312, 318, 320, 321, 325–329, 331–336, 338–346, 348–355, 357–359, 361, 362, 364–385, 387–397, 399, 402, 406, 409, 410, 413, 415, 417, 419–424, 427–434, 437–439, 441, 443, 446, 448, 454, 455, 470, 473, 477, 480–487, 490–493, 495, 502, 503, 509, 512, 514, 517, 519–524, 547–552, 554–560, 565–568, 570, 581–584, 589, 595, 596, 602, 606–609, 612, 613, 618, 621, 622, 624–627, 634, 636, 642–648, 652, 653, 655–658, 660–662, 664, 665, 668–672, 677, 678, 680, 681, 688, 694, 696, 698–702, 704, 706–708, 711, 712, 714, 718–726, 729–741, 745, 747–750, 755–756, 759–763, 774 |
| 10 | 1, 10, 14, 21–23, 25, 52, 54–56, 60, 61, 64, 65 |
| 12 | 1, 4, 5, 10, 20–22, 24, 27, 32 |
| 13 | 2, 4 |
| 15 | 1, 2 |

As mentioned above, the GnRH receptor antagonists of this invention have utility over a wide range of therapeutic applications, and may be used to treat variety of sex-hormone related conditions in both men and women, as well as mammals in general. For example, such conditions include endometriosis, uterine fibroids, polycystic ovarian disease, hirsutism, precocious puberty, gonadal steroid-dependent neoplasia such as cancers of the prostate, breast and ovary, gonadotrophe pituitary adenomas, sleep apnea, irritable bowel syndrome, premenstrual syndrome, benign prostatic hypertrophy, contraception and infertility (e.g., assisted reproductive therapy such as in vitro fertilization).

The compounds of this invention are also useful as an adjunct to treatment of growth hormone deficiency and short stature, and for the treatment of systemic lupus erythematosis.

In addition, the compounds are useful in combination with androgens, estrogens, progesterones, and antiestrogens and antiprogestogens for the treatment of endometriosis, fibroids, and in contraception, as well as in combination with an angiotensin-converting enzyme inhibitor, an angiotensin II-receptor antagonist, or a renin inhibitor for the treatment of uterine fibroids. The compounds may also be used in combination with bisphosphonates and other agents for the treatment and/or prevention of disturbances of calcium, phosphate and bone metabolism, and in combination with estrogens, progesterones and/or androgens for the prevention of treatment of bone loss or hypogonadal symptoms such as hot flashes during therapy with a GnRH antagonist.

In another embodiment of the invention, pharmaceutical compositions containing one or more GnRH receptor antagonists are disclosed. For the purpose of administration, the compounds of the present invention may be formulated as pharmaceutical compositions. Pharmaceutical compositions of the present invention comprise a GnRH receptor antagonist of the present invention and a pharmaceutically acceptable carrier and/or diluent. The GnRH receptor antagonist is present in the composition in an amount which is effective to treat a particular disorder—that is, in an amount sufficient to achieve GnRH receptor antagonist activity, and preferably with acceptable toxicity to the patient. Typically, the pharmaceutical compositions of the present invention may include a GnRH receptor antagonist in an amount from 0.1 mg to 250 mg per dosage depending upon the route of administration, and more typically from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tables which contain, in addition to a GnRH receptor antagonist, diluents, dispersing and surface active agents, binders, and lubricants. One skilled in this art may further formulate the GnRH receptor antagonist in an appropriate manner, and in accordance with accepted practices, such as those disclosed in *Remington's Pharmaceutical Sciences*, Gennaro, Ed., Mack Publishing Co., Easton, Pa. 1990.

In another embodiment, the present invention provides a method for treating sex-hormone related conditions as discussed above. Such methods include administering of a compound of the present invention to a warm-blooded animal in an amount sufficient to treat the condition. In this context, "treat" includes prophylactic administration. Such methods include systemic administration of a GnRH receptor antagonist of this invention, preferably in the form of a pharmaceutical composition as discussed above. As used herein, systemic administration includes oral and parenteral methods of administration. For oral administration, suitable pharmaceutical compositions of GnRH receptor antagonists include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain, in addition to the GnRH receptor antagonist, buffers, antioxidants, bacteriostats, and other additives commonly employed in such solutions.

The following example is provided for purposes of illustration, not limitation. In summary, the GnRH receptor antagonists of this invention may be assayed by the general methods disclosed above, while the following Examples disclose the synthesis of representative compounds of this invention.

EXAMPLE 1

Synthesis of 1-(2,6-difluorobenzyl)-5-(3-methoxyphenyl)-6-methyl-3-[N-methyl-N-(2-pyridylethyl)aminoethyl]uracil

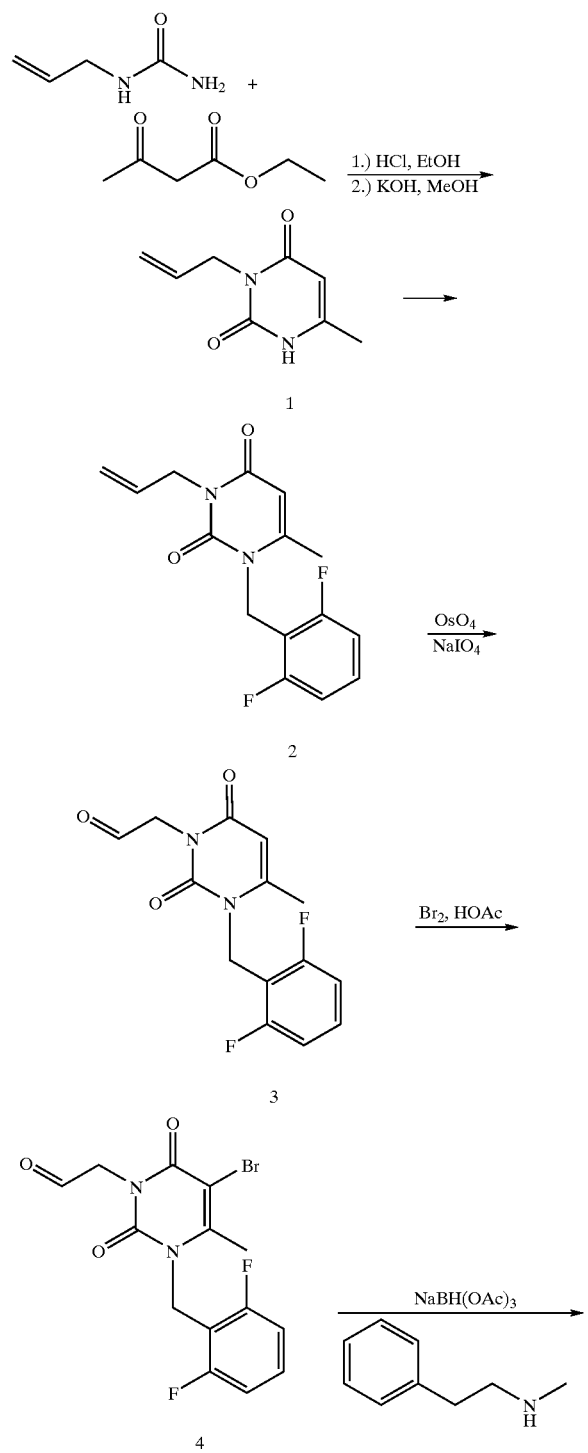

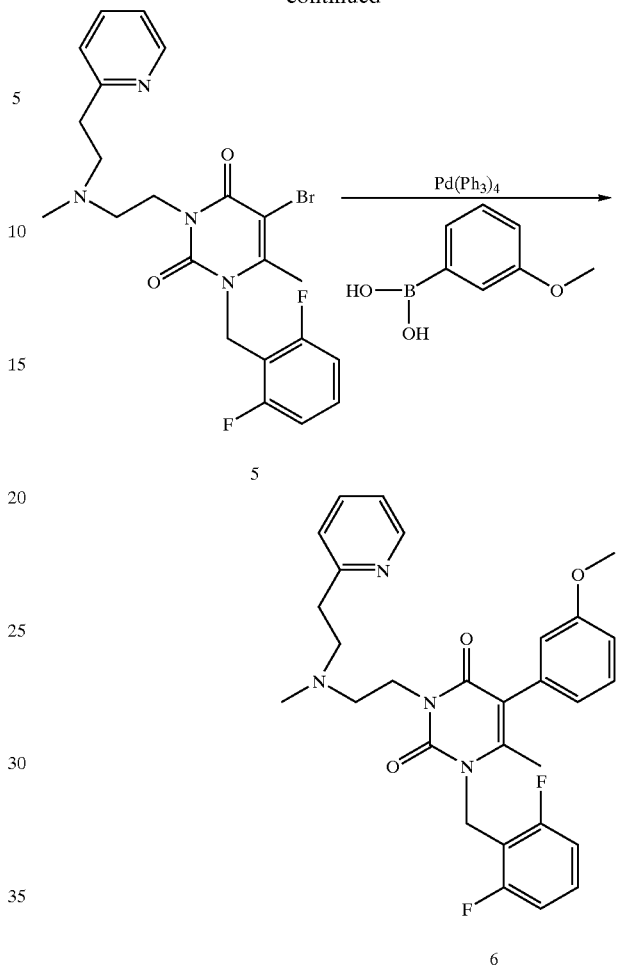

Step 1A 3-Allyl-6-methyluracil

To allylurea (25 g, 25 mol) in ethanol (10 mL) was added ethyl acetoacetate (31.86 mL, 25 mol) and 10 drops conc. HCl. After 12 days at room temperature, concentration gave an oil which was dissolved in MeOH. KOH (22.5 g, 0.34 mol) was added and the solution refluxed for 1 hour. After neutralization, the resulting solid 1 was collected. Yield 2.7 g (7%). NMR (CDCl$_3$) δ: 2.16 (3H, s), 4.52 (2H, d), 5.18 (1H, d), 5.23 (1H, d), 5.60 (1H, s), 5.82–5.93 (1H, m), 10.3 (1H, s).

Step 1B 3-Allyl-1-(2,6-difluorobenzyl)-6-methyluracil

To 1 (2.6 g, 15.7 mmol) in DMF (20 mL) was added tetrabutylammoniumfluoride (25 mmol) and 2,6-difluorobenzyl bromide (4.14 g, 20 mmol). After 2 days stirring at room temperature, column chromatography using ethyl acetate/hexane gave 2.7 g (59% yield) of 2. MS 293 (MH)$^+$.

Step 1C 3-Acetaldehyde-1-(2,6-difluorobenzyl)-6-methyluracil

To a solution of 2 (1.46 g, 5 mmol) in THF (20 mL) and H$_2$O (10 mL) was added osmium tetroxide (200 mg) and NaIO$_4$ (3.2 g, 15 mmol). After 2 hr, another 1 g of NaIO$_4$ was added. Ethyl acetate and H$_2$O were added and the layers separated. Evaporation of the organic layer gave 3 as a crude solid (1.0 g, 68%). MS 295 (MH)$^+$.

Step 1D 3-Acetaldehyde-5-bromo-1-(2,6-difluorobenzyl)-6-methyluracil 3 (294 mg, 1 mmol) was dissolved in acetic acid and bromine (1.2 eq) was added. The reaction mixture was stirred at room temperature for 1 hr, evaporated and the residue was dissolved in EtOAc, washed with 1N KOH solution and concentrated to give 4 as a crude oil (295 mg, 79%). Ms 373/375 (MH)+. NMR (CDCl$_3$) δ: 2.55 (3H, s), 4.87 (2H, d), 5.33 (2H, s), 7.26–7.33 (3H, 2m), 9.59 (1h, d).

Step 1E 5-Bromo-1-(2,6-difluorobenzyl)-6-methyl-3-[N-methyl-N-(2-pyridylethyl)aminoethyl]uracil To 4 (295 mg, 0.8 mmol) in dichlorethane was added 2-(methylaminoethyl)pyridine (200 mg, 1.5 mmol) and NaBH(OAc)$_3$ (636 mg, 3 mmol). After overnight stirring, the reaction mixture was concentrated, dissolved in EtOAc, washed with H$_2$O, and purified by prep TLC to give 190 mg of 5 (48%).

Step 1F 1-(2,6-Difluorobenzyl)-5-(3-methoxyphenyl)-6-methyl-3-[N-methyl-N-(2-pyridylethyl)aminoethyl]uracil ("Cpd. No. 1")

5 (150 mg, 0.3 mmol), 3-methoxyphenylboronic acid (92 mg, 0.6 mmol), K$_2$CO$_3$ (100 mg, 0.72 mmol), and Pd(PPh$_3$)$_4$ (20 mg) in H$_2$O (5 mL) and toluene (10 mL) was heated in a sealed tube at 100° C. for 12 hr. Purification by HPLC gave 40 mg of 6("Cpd No. 1") as the TFA salt (21% yield). MS 521 (MH)+ NMR (CDCl$_3$) δ: 2.14 (3H, s), 3.02 (3H, s), 3.50 (2H, m), 3.63 (2H, m), 3.71 (2H, m), 3.81 (3H, s), 4.37 (2H, m), 5.25 (2H, s), 6.81–6.83 (2H, m), 6.88–6.95 (3H, m), 7.28–7.34 (2H, m), 7.63 (1H, m), 7.89 (1H, d), 8.13 (1H, t), 8.62 (1H, br s).

EXAMPLE 2

Representative Compounds

Following the procedures as set forth in Example 1 above, the compounds of the following Table 1 were prepared.

TABLE 1

| Cpd. No. | R$_1$ | R$_2$ | MS (MH)+ |
|---|---|---|---|
| 1-1 | 2-PyCH$_2$CH$_2$ | H | 507 |
| 1-2 | 2-PyCH$_2$ | H | 493 |
| 1-3 | 2-PyCH$_2$ | Me | 507 |
| 1-4 | Bz | Me | 506 |
| 1-5 | PhCH$_2$CH$_2$ | Me | 520 |
| 1-6 | 2-PyCH$_2$CH$_2$ | Pr | 549 |
| 1-7 | PhCHCH$_3$ | Me | 520 |
| 1-8 | PhCHCH$_3$ | Me | 520 |
| 1-9 | Bz | (CH$_3$)$_2$N(CH$_2$)$_2$ | 563 |
| 1-10 | 2-PyCH$_2$CH$_2$ | Et | 535 |
| 1-11 | 2-(6-Cl—Py)CH$_2$CH$_2$ | Me | 416, 555 |
| 1-12 | 2-PyCH$_2$CH$_2$ | CyclopropylCH$_2$ | 561 |
| 1-13 | 1-Et-3-pyrrolidinyl | Et | 527 |

TABLE 1-continued

| Cpd. No. | R$_1$ | R$_2$ | MS (MH)+ |
|---|---|---|---|
| 1-14 | ethyl piperidine-1-carboxylate-4-yl | H | 557 |
| 1-15 | 2-methylpiperidin-1-yl | H | 541 |
| 1-16 | (CH$_3$)$_2$CHOCH$_2$CH$_2$CH$_2$ | H | 502 |
| 1-17 | Et$_2$NCH$_2$CH$_2$ | Me | 515 |
| 1-18 | pyrrolidin-1-yl (propyl linker) | H | 513 |
| 1-19 | CH$_3$OCH$_2$CH$_2$CH$_2$ | H | 474 |
| 1-20 | (EtO)$_2$CHCH$_2$CH$_2$ | H | 532 |
| 1-21 | CH$_3$OCH$_2$CH$_2$ | Me | 474 |
| 1-22 | 1-benzylpyrrolidin-3-yl | Me | 575 |
| 1-23 | 1-benzylpyrrolidin-3-yl | Me | 575 |
| 1-24 | 2,3-dihydrobenzo[1,4]dioxin-2-ylethyl | H | 550 |
| 1-25 | CH$_3$OCH$_2$CH$_2$CH$_2$ | Me | 488 |
| 1-26 | (EtO)$_2$CHCH$_2$CH$_2$ | Me | 546 |

TABLE 1-continued

| Cpd. No. | R₁ | R₂ | MS (MH)⁺ |
|---|---|---|---|
| 1-27 | benzo[1,4]dioxin-2-ylmethyl (ethyl linker) | Me | 564 |
| 1-28 | 1-(ethoxycarbonyl)piperidin-4-yl | Me | 571 |
| 1-29 | 3-(2-methylpiperidin-1-yl)propyl | Me | 555 |
| 1-30 | (CH₃)₂CHOCH₂CH₂CH₂ | Me | 516 |
| 1-31 | 3-(pyrrolidin-1-yl)propyl | Me | 527 |
| 1-32 | 1-methylpiperidin-4-yl | Me | 513 |
| 1-33 | (1,3-dioxolan-2-yl)methyl | Me | 502 |
| 1-34 | Et₂NCH₂CH₂ | Me | 487 |
| 1-35 | Me₂NCH₂CH₂CH₂ | Me | 501 |
| 1-36 | Et₂NCH₂CH₂CH₂ | Me | 529 |
| 1-37 | 1-methylpyrrolidin-3-yl | Me | 499 |
| 1-38 | EtOCH₂ | Me | 474 |
| 1-39 | 2-(1,3-dioxolan-2-yl)ethyl | Me | 516 |
| 1-40 | 1-phenyl-1-hydroxy-butyl | Me | 550 |
| 1-41 | 2-(1-methylpyrrolidin-2-yl)ethyl | H | 513 |
| 1-42 | 2-(1H-imidazol-4-yl)ethyl | H | 496 |
| 1-43 | 3-(morpholin-4-yl)propyl | H | 529 |
| 1-44 | Me₂NCH₂CH₂CH₂ | H | 487 |
| 1-45 | Et₂NCH₂CH₂CH₂ | H | 515 |

TABLE 1-continued

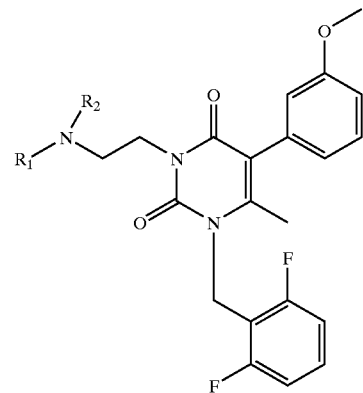

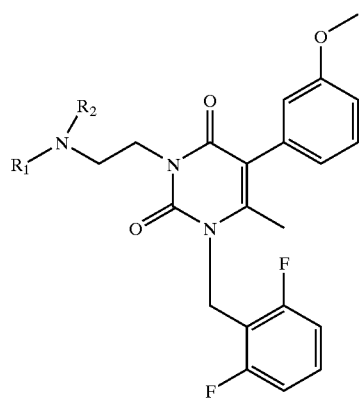

| Cpd. No. | R₁ | R₂ | MS (MH)⁺ |
|---|---|---|---|
| 1-46 | imidazol-1-yl-(CH₂)₃- | H | 510 |
| 1-47 | azepan-1-yl-(CH₂)₃- | H | 541 |
| 1-48 | Me₂CHCH₂OCH₂CH₂CH₂ | H | 516 |
| 1-49 | 1,3-dioxolan-2-yl-(CH₂)₂- | H | 502 |
| 1-50 | (R)-pyrrolidin-3-yl-CH₂- | H | 471 |
| 1-51 | (S)-pyrrolidin-3-yl-CH₂- | H | 471 |
| 1-52 | 3-phenyl-3-(2-hydroxyethyl)- (PhCH(CH₂CH₂OH)-) | H | 536 |
| 1-53 | (2,2-dimethyl-1,3-dioxolan-4-yl)-CH₂CH₂- | H | 516 |
| 1-54 | PyCH₂CH₂ | HOCH₂CH₂ | 551 |
| 1-55 | (1-methylpyrrolidin-2-yl)-(CH₂)₂- | Me | 527 |
| 1-56 | imidazol-4-yl-CH₂CH₂- | Me | 510 |
| 1-57 | morpholin-4-yl-(CH₂)₃- | Me | 543 |
| 1-58 | Me₂CHN(Me)CH₂CH₂CH₂ | Me | 529 |
| 1-59 | imidazol-1-yl-(CH₂)₃- | Me | 524 |
| 1-60 | azepan-1-yl-(CH₂)₃- | Me | 555 |
| 1-61 | Me₂CHCH₂OCH₂CH₂CH₂ | Me | 530 |

TABLE 1-continued

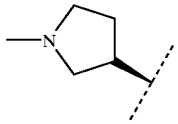

| Cpd. No. | R₁ | R₂ | MS (MH)+ |
|---|---|---|---|
| 1-62 | BuOCH$_2$CH$_2$CH$_2$ | Me | 530 |
| 1-63 |  | Me | 499 |
| 1-64 | 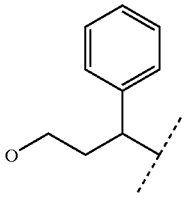 | Me | 499 |
| 1-65 | 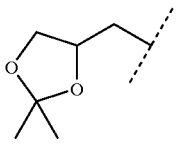 | Me | 550 |
| 1-66 | | Me | 530 |
| 1-67 | PhCH$_2$CH$_2$CH$_2$ | H | 506 |
| 1-68 | 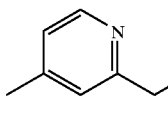 | Me | 535 |

EXAMPLE 3

Further Representative Compounds

By reversing Step 1E and Step 1F in Example 1, where the boronic acid coupling is performed followed by the reductive amination, the compounds of the following Tables 2–7 were also prepared.

TABLE 2

| Cpd. No. | R₁ | R₂ | MS (MH)+ |
|---|---|---|---|
| 2-1 | 2-PyCH$_2$CH$_2$ | Me | 519 |
| 2-2 | Bz | Me | 504 |
| 2-3 | 2-PyCH$_2$ | H | 491 |
| 2-4 | 2-PyCH$_2$CH$_2$ | H | 505 |
| 2-5 | PhCH$_2$CH$_2$ | Me | 518 |

TABLE 3

| Cpd. No. | R₁ | R₂ | MS (MH)+ |
|---|---|---|---|
| 3-1 | 2-PyCH$_2$CH$_2$ | Me | 535 |
| 3-2 | PhCH$_2$CH$_2$ | Me | 534 |
| 3-3 | 4-PyCH$_2$CH$_2$ | Me | 535 |
| 3-4 | 2-PyCH$_2$CH$_2$ | Et | 549 |

TABLE 4
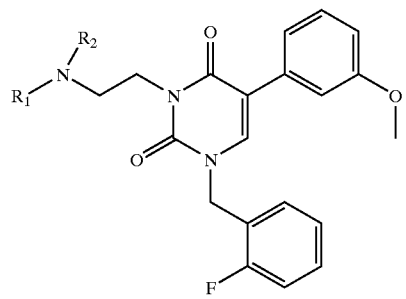
| Cpd. No. | R₁ | R₂ | MS (MH)⁺ |
|---|---|---|---|
| 4-1 | PhCH₂ | Me | 474 |
| 4-2 | 2-PyCH₂CH₂ | Me | 489 |
| 4-3 | 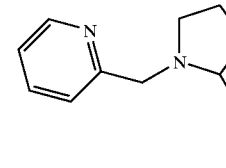 | 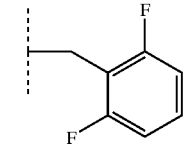 | 518 |
| 4-4 | 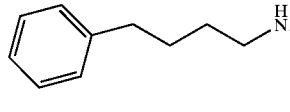 | 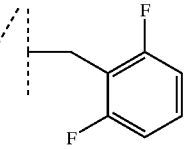 | 520 |
| 4-5 | 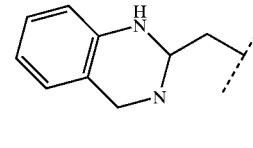 | 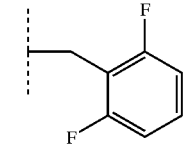 | 491 |
| 4-6 | 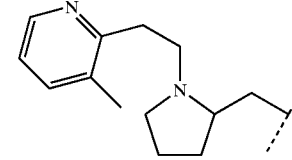 | 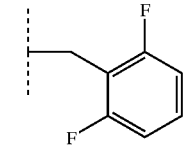 | 547 |

TABLE 5
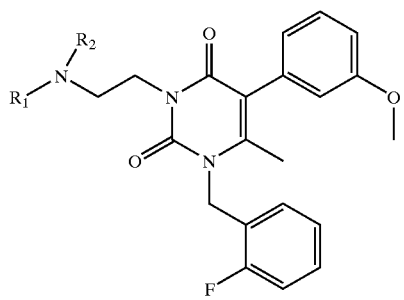
| Cpd. No. | R₁ | R₂ | MS (MH)⁺ |
|---|---|---|---|
| 5-1 | PhCH₂CH₂ | Me | 488 |
| 5-2 | 2-PyCH₂CH₂ | Me | 503 |
| 5-3 | 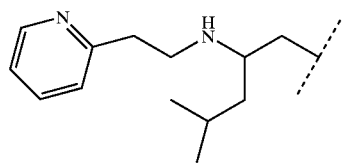 | | 545 |
| 5-4 | 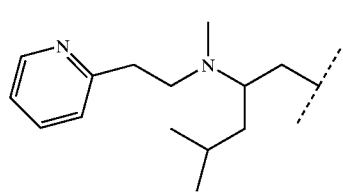 | | 559 |
TABLE 6
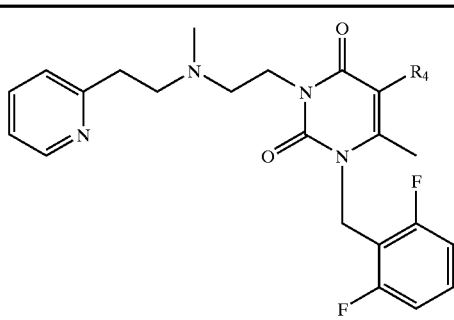
| Cpd. No. | R₄ | MS (MH)⁺ |
|---|---|---|
| 6-1 | 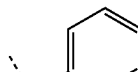 | 509 |
| 6-2 |  | 583 |
TABLE 6-continued
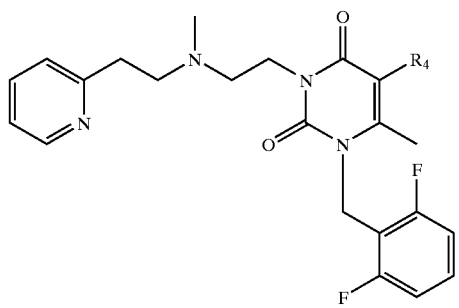
| Cpd. No. | R₄ | MS (MH)⁺ |
|---|---|---|
| 6-3 | 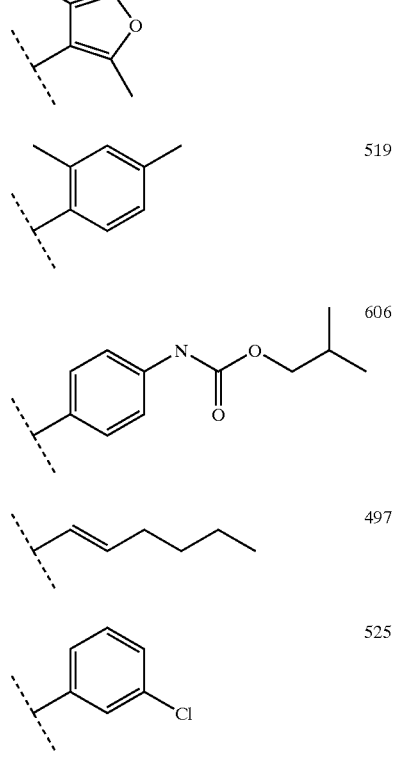 | 549 |
| 6-4 | | 481 |
| 6-5 | | 551 |
| 6-6 | | 495 |
| 6-7 | | 519 |
| 6-8 | | 606 |
| 6-9 | | 497 |
| 6-10 | | 525 |

TABLE 6-continued
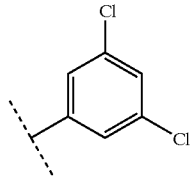
| Cpd. No. | R4 | MS (MH)+ |
|---|---|---|
| 6-11 | 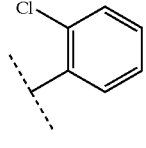 3,5-dichlorophenyl | 559/561 |
| 6-12 | 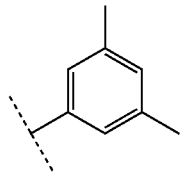 2-chlorophenyl | 525 |
| 6-13 | 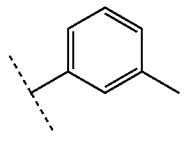 3,5-dimethylphenyl | 519 |
| 6-14 | 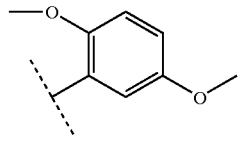 3-methylphenyl | 505 |
| 6-15 | 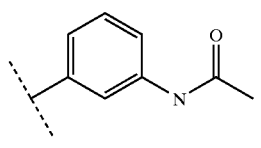 2,5-dimethoxyphenyl | 551 |
| 6-16 | 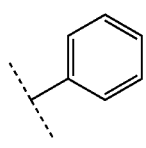 3-acetamidophenyl | 548 |
| 6-17 | 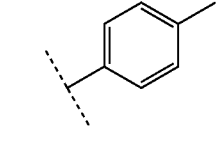 phenyl | 490 |
| 6-18 | 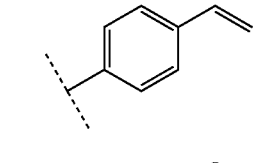 4-methylphenyl | 504 |
| 6-19 | 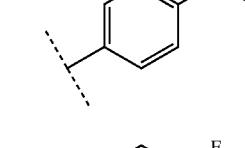 4-vinylphenyl | 516 |
| 6-20 | 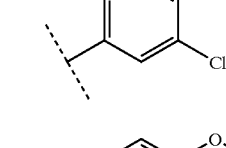 4-(trifluoromethoxy)phenyl | 575 |
| 6-21 | 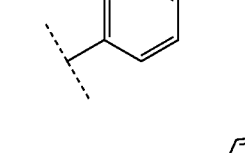 3-chloro-4-fluorophenyl | 543 |
| 6-22 | 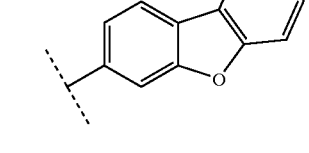 4-ethoxyphenyl | 535 |
| 6-23 | 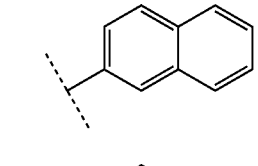 dibenzofuranyl | 581 |
| 6-24 | 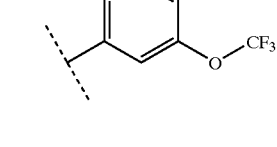 2-naphthyl | 541 |
| 6-25 | 3-(trifluoromethoxy)phenyl | 575 |

TABLE 6-continued

| Cpd. No. | R$_4$ | MS (MH)$^+$ |
|---|---|---|
| 6-26 | 3-(hydroxymethyl)phenyl | 521 |
| 6-27 | 3-ethylphenyl | 519 |
| 6-28 | benzofuran-2-yl | 531 |
| 6-29 | 3-isopropylphenyl | 533 |
| 6-30 | 4-biphenyl | 567 |
| 6-31 | 3-formylphenyl | 519 |
| 6-32 | 4-(methylthio)phenyl | 537 |
| 6-33 | 4-methoxyphenyl | 521 |
| 6-34 | 3,4,5-trimethoxyphenyl | 581 |
| 6-35 | 3-fluorophenyl | 509 |
| 6-36 | 4-fluorophenyl | 509 |
| 6-37 | 3-nitrophenyl | 536 |
| 6-38 | thiophen-2-yl | 497 |
| 6-39 | 3-ethoxyphenyl | 535 |
| 6-40 | 2,3-dimethylphenyl | 519 |

TABLE 6-continued

| Cpd. No. | R4 | MS (MH)+ |
|---|---|---|
| 6-41 | 3-biphenyl | 567 |
| 6-42 | 3-furyl | 481 |
| 6-43 | 3-thienyl | 497 |
| 6-44 | 3-hydroxyphenyl | 507 |
| 6-45 | 4-(NAc)phenyl | 548 |
| 6-46 | 4-(NC(O)cyclopropyl)phenyl | 573 |
| 6-47 | 4-(NHSO2Me)phenyl | 584 |
| 6-48 | 4-(NHSO2Ph)phenyl | 645 |
| 6-49 | 3-(NMe2)phenyl | 534 |
| 6-50 | 3-(CH2OMe)phenyl | 535 |
| 6-51 | 4-cyanophenyl (pyridyl) | 506 |
| 6-52 | 4-(NH-isobutyl)phenyl | 562 |
| 6-53 | 4-isopropylphenyl | 533 |
| 6-54 | 3-cyanophenyl | 516 |

TABLE 6-continued

| Cpd. No. | R₄ | MS (MH)⁺ |
|---|---|---|
| 6-55 | (2-methylphenyl) | 505 |

TABLE 7

| Cpd. No. | NR₁R₂ | MS (MH)⁺ |
|---|---|---|
| 7-1 | (2-hydroxymethyl-pyrrolidin-1-yl) | 486 |
| 7-2 | (4-pyrrolidin-1-yl-piperidin-1-yl) | 539 |
| 7-3 | (3-(trifluoroacetamido)-pyrrolidin-1-yl) | 567 |
| 7-4 | (3-(Boc-amino)-pyrrolidin-1-yl) | 571 |
| 7-5 | (2-benzyloxycarbonyl-pyrrolidin-1-yl) | 590 |
| 7-6 | (2-(ethylcarbamoyl)-pyrrolidin-1-yl) | 527 |
| 7-7 | (2-hydroxymethyl-pyrrolidin-1-yl) | 486 |
| 7-8 | (2-methoxycarbonyl-pyrrolidin-1-yl) | 514 |
| 7-9 | (4-hydroxy-2-methoxycarbonyl-pyrrolidin-1-yl) | 530 |
| 7-10 | (3-oxa-8-aza-bicyclic) | 484 |

TABLE 7-continued
| Cpd. No. | NR₁R₂ | MS (MH)⁺ |
|---|---|---|
| 7-11 | (acetamido-pyrrolidinyl) | 513 |
| 7-12 | (pyridinylmethyl-pyrrolidinyl) | 546 |
| 7-13 | (pyridin-3-yl-pyrrolidinyl) | 553 |
| 7-14 | (methylamino-pyrrolidinyl) | 485 |
| 7-15 | (methylamino-pyrrolidinyl) | 485 |
| 7-16 | (dimethylamino-pyrrolidinyl) | 499 |
| 7-17 | (dimethylamino-pyrrolidinyl) | 499 |
| 7-18 | (N-methyl-prolinamide) | 513 |
| 7-19 | (hydroxy-pyrrolidinyl) | 472 |
| 7-20 | (benzyl-pyrrolidinyl) | 546 |
EXAMPLE 4
Synthesis of 5-bromo-1-(2,6-difluorobenzyl)-6-methyl-uracil
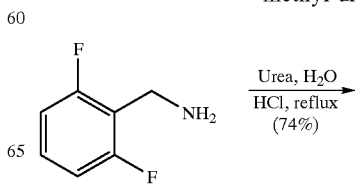

EXAMPLE 5

Further Representative Compounds

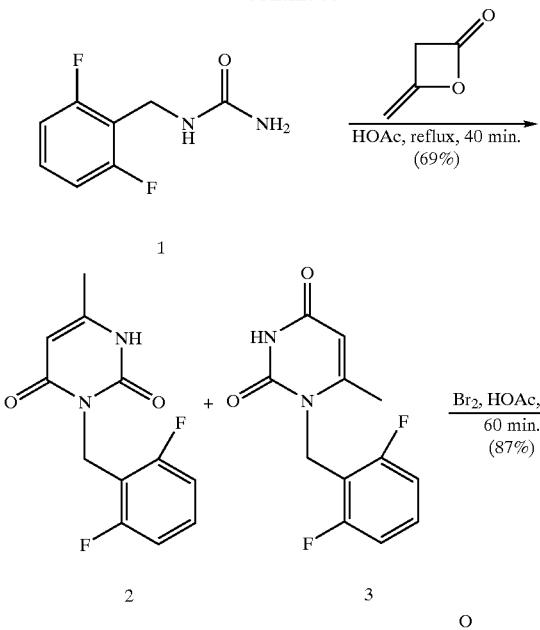

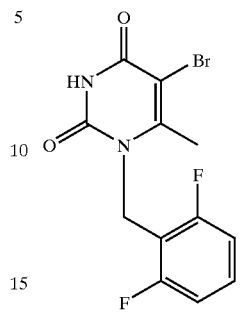

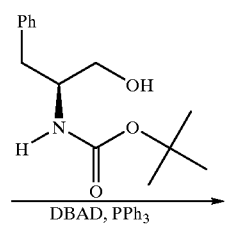

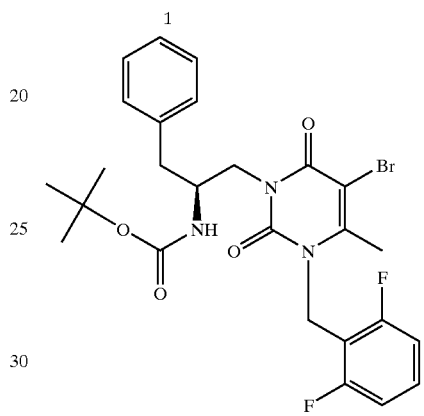

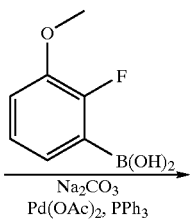

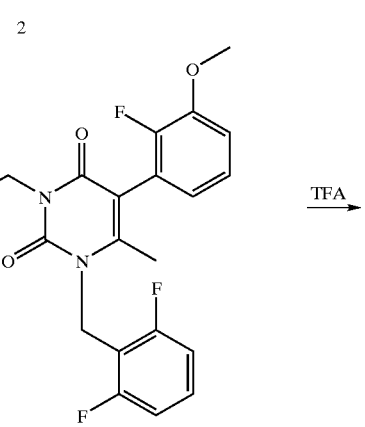

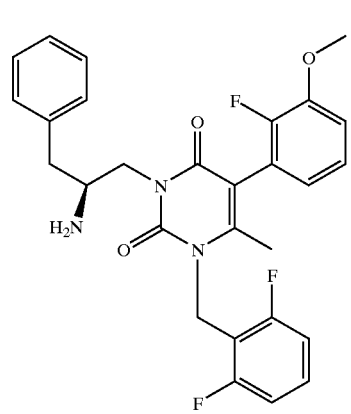

Step A 2,6-Difluorobenzyl urea 2,6-Difluorobenzylamine (25.0 g, 0.175 mol) was added dropwise to a stirring solution of urea (41.92 g, 0.699 mol) in water (70 mL) and concentrated HCl (20.3 mL). The resulting mixture was refluxed for 2.5 hours, after which time it was cooled to room temperature The solids that formed were filtered under vacuum, and were washed thoroughly with water. After drying under vacuum, the solids were recrystallized from EtOAc to yield the product 1 as light white needles (24.0 g, 0.129 mol, 74%).

Step B 1-(2,6-Difluorobenzyl)-6-methyl-uracil

Diketene (9.33 mL, 0.121 mol) was added in one portion to a refluxing solution of 2,6-difluorobenzyl urea 1 (20.46 g, 0.110 mol) and glacial acetic acid (110 mL). After 40 minutes at reflux, the mixture was cooled to room temperature and poured onto water (600 mL). The precipitate was collected by filtration, washed with water and dried under vacuum to yield a 1:3 mixture of isomers 2 and 3, respectively (19.07 g, 0.076 mol, 69%). The mixture was recrystallized from acetonitrile (~600 mL) to give the pure title compound 3 as white prisms ($1^{st}$ crop —7.85 g, 0.031 mol, 28%).

Step C 5-Bromo-1-(2,6-difluorobenzyl)-6-methyl-uracil 1-(2,6-Difluorobenzyl)-6-methyl-uracil 3 (7.56 g, 30 mmol) was suspended in glacial acetic acid (100 mL) and to that mixture, bromine (1.93 mL, 37.5 mmol) was added dropwise. The resulting range solution turned into a suspension in about 5 minutes. After stirring for 1 hour at room temperature, the precipitate was filtered under vacuum and washed with water. The solids were triturated with diethyl ether and dried under vacuum to give 4 (8.6 g, 0.026 mmol, 87%).

Step A-1 3-(1-[2-BOC-(S)-amino-3-phenylpropyl)-5-bromo-1-(2,6-difluorobenzyl)-6-methyl-uracil 2-BOC-(S)-amino-3-phenyl-1-propanol (2.51 g, 10 mmol) and triphenylphosphine (3.14 g, 12 mmol) were added to a solution of 5-bromo-1-(2,6-difluorobenzyl)-6-methyl-uracil 1 (3.31 g, 10 mmol) in THF (50 mL). Di-tert-butyl azodicarboxylate (2.76 g, 12 mmol) was added in several portions over 5 minutes. After 5 minutes the reaction mixture was clear. After 1 hour the reaction mixture was concentrated and the residue was purified by silica cartridge column (hexane/EtOAc as elutant). Concentration of like fractions gave 6.8 g of an oily material which was precipitated from hexane to yield product 2 (4.95 g, 88%).

Step B-1 3-(1-[2-BOC-(S)-amino-3-phenylpropyl)-1-(2,6-difluorobenzyl)-5-(2-fluoro-3-methoxyphenyl)-6-methyl-uracil Compound 2 (4.95 g, 8.78 mmol) and sodium carbonate (2.12 g, 20 mmol) were suspended in toluene (50 mL) and dimethoxyethane (10 mL). Water (20 mL) was added and $N_2$ was bubbled through the reaction mixture. After 5 minutes, both layers were clear and $Pd(OAc)_2$ (394 mg, 0.2 eq) and triphenylphosphine ((921 mg, 0.4 eq) were added. The boronic acid (1.7 g, 10 mmol) was added and the reaction vessel was sealed and heated overnight at 100° C. The organic layer was separated, evaporated and purified by silica chromatography. Product containing fractions were combined and evaporated to give 3 as a brown oil (1.5 g, 28% yield).

Step C-1 3-(1-[2-(S)-Amino-3-phenylpropyl)-1-(2,6-difluorobenzyl)-5-(2-fluoro-3-methoxyphenyl)-6-methyl-uracil Compound 3 (1.5 g, 2.5 mmol) in trifluoroacetic acid/dichloromethane (1:1, 50 mL) was heated for 4 hours. Evaporation gave a red oil which was purified by reverse phase prep HPLC using water/$CH_3CN$ with 0.05% trifluoroacetic acid as eluant. The product containing fractions were concentrated and lyophilized to give product 4 (0.56 g, 44%, $MH^+$=510).

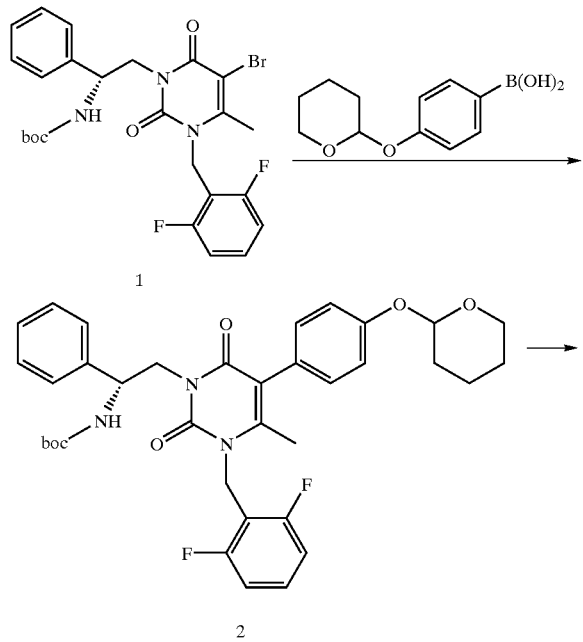

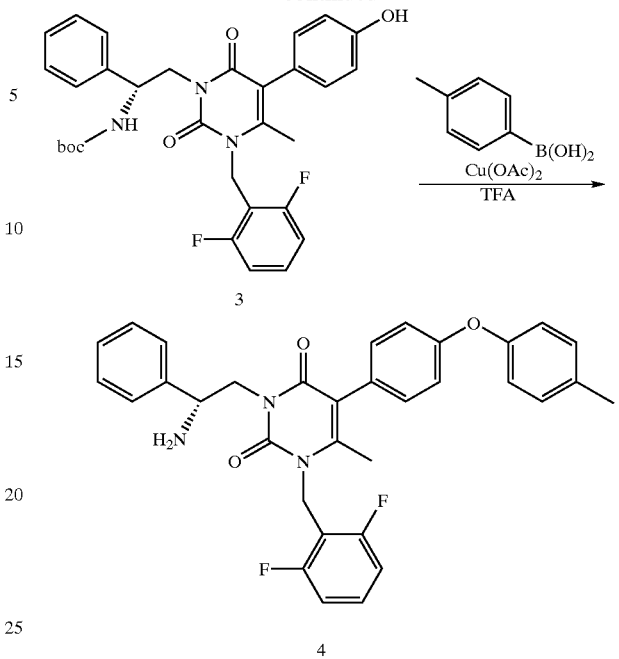

Step A-2 1-(2,6-Difluorobenzyl-3-[(2R)-tert-butoxycarbonylamino-2-phenyl]ethyl-6-methyl-5-(4-[tetrahydropyran-2-yloxy]phenyl)uracil 1-(2,6-Difluorobenzyl-3-[(2R)-tertbutylcarbonylamino-2-phenyl]ethyl-6-methyl-5-bromouracil 1 (2.58 g, 4.7 mmol), tetrakis(triphenylphosphine) palladium (0) (550 mg, 0.47 mmmol), 4-hydroxyphenyl boronic acid tetrahydropyran ether (1.25 g, 5.7 mmol) and barium hydroxide (38 mL of 0.14M solution, 5.2 mmol) in a benzene/ethanol/dimethoxyethane solution (10/1/11, 90 mL) was heated at 90° C. in a pressure vessel under $N_2$ atmosphere overnight. The organic layer was concentrated in vacuo and the residue was purified by silica gel chromatography (hexanes/ethyl acetate as elutant) to give 3.0 g of 2 as an off white foam.

Step B-2 1-(2,6-Difluorobenzyl-3-[(2R)-tert-butoxycarbonylamino-2-phenyl]ethyl-6-methyl-5-(4-hydroxyphenyl)uracil A mixture of 2 (3.0 g, 4.6 mmol) and pyridinium-p-toluenesulfonate (231 mg, 0.92 mmol) in ethanol (92 mL) was stirred at 45° C. for 5 hours. The reaction mixture was concentrated in vacuo and the residue was dissolved in methylene chloride and $H_2O$. The organic layer was concentrated and the residue purified by silica gel chromatography using hexanes/ethyl acetate as elutant to give 2.1 g of compound 3 as a yellow foam.

Step C-2 1-(2,6-Difluorobenzyl-3-[(2R)-amino-2-phenyl]ethyl-5-(4-[4-tolyloxy]phenyl)uracil Substituted uracil 3 (50 mg, 0.089 mmol), p-tolylboronic acid (18 mg, 0.133 mmol), copper (II) acetate (16 mg, 0.089 mmol) and triethylamine (0.06 mL, 0.445 mmol) in $CH_2Cl_2$ (1 mL) were stirred for 3 days at room temperature. The reaction mixture was purified by silica gel chromatography using 1% MeOH in $CH_2Cl_2$ to give 30 mg of protected product. This material was dissolved in $CH_2Cl_2$ (1 mL) with 5 drops of trifluoroacetic acid. Purification by reverse phase HPLC/MS gave 5.0 mg of product 4 m/z (CI) 554 ($MH^+$).

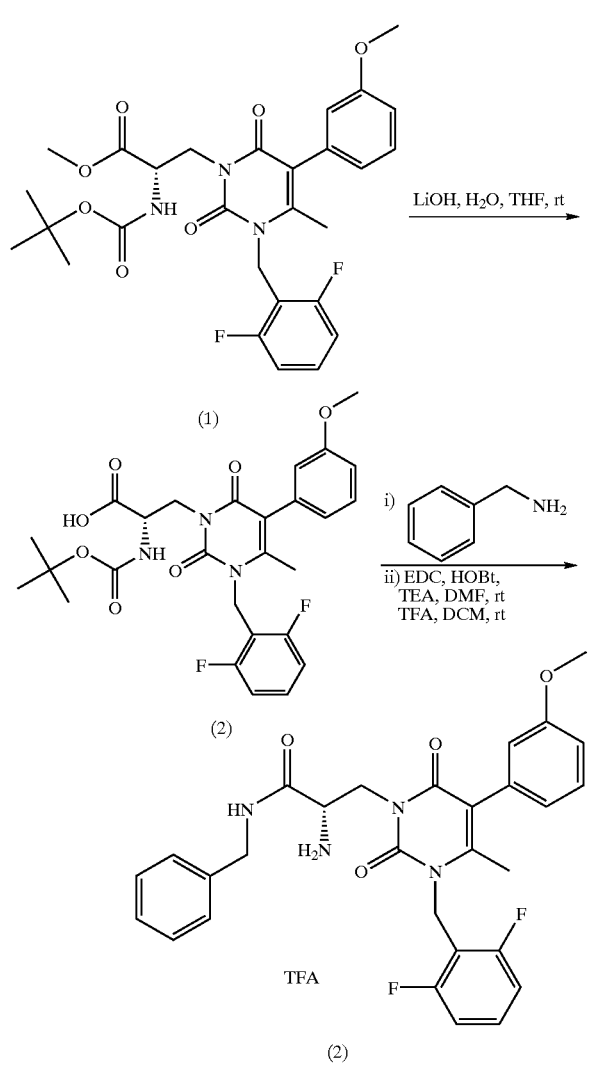

Step A-3 (S)-3-(1-N-tert-Butoxycarbonylamino-1-carboxylic acid ethyl)-1-(2,6-difluorobenzyl)-5-(3-methoxyphenyl)-6-methyluracil To a stirred solution of 1 (306 mg, 0.55 mmol) in tetrahydrofuran (15 mL) at room temperature, was added aqueous lithium hydroxide solution (15 mL of a 1 M solution, 15 mmol). After 2 h, most of the tetrahydrofuran was removed in vacuo and the resulting solution was acidified to pH 4 (with 10% aqueous citric acid solution). The resultant precipitate was extracted into ethyl acetate (2×15 mL) and the combined organic layer was washed with water, brine and dried (MgSO$_4$). The solvent was removed in vacuo to give 2 (283 mg, 94%) as a yellow oil which was not purified further, $\delta_H$ (300 MHz; CDCl$_3$) 7.26–7.34 (2H, m, Ar), 6.73–6.95 (5H, m, Ar), 5.74 (1H, brd, J 6, NH), 5.37 (1H, d, J 16, CHHAr), 5.22 (1H, d, J 16, CHHAr), 4.62 (1H, brs, CHN), 4.32–4.49 (2H, m, CH$_2$N), 3.80 (3H, s, OCH$_3$), 2.17 (3H, s, CH$_3$) and 1.42 (9H, s, 3×CH$_3$), m/z (CI) 446 (MH$^+$-Boc, 100%).

Step B-3 (S)-3-(1-Amino-1-NH-benzylcarboxamide ethyl)-1-(2,6-difluorobenzyl)-5-(3-methoxyphenyl)-6-methyluracil trifluoroacetic acid salt To a stirred solution of 2 (20 mg, 0.037 mmol), benzylamine (15 μL, 0.14 mmol), 1-(hydroxy)benzotriazole hydrate (9 mg, 0.066 mmol) and triethylamine (10 μL, 0.074 mmol) in anhydrous N,N-dimethylformamide (1 mL) at room temperature, was added 1-[3-(dimethylamino)propyl]-3-ethylcarbodiimide hydrochloride (11 mg, 0.056 mmol). After 10 h, the reaction mixture was poured into water (ca. 5 mL) and the resulting precipitate was extracted into ethyl acetate (ca. 5 mL). The organic layer was washed with brine and dried (MgSO$_4$). The solvent was removed in vacuo to give a yellow oil, which was redissolved in a mixture of dichloromethane (1 mL) and trifluoroacetic acid (0.5 mL, 6.5 mmol) and stirred at room temperature. After 1 h, the solvent was removed in vacuo to give a yellow oil, which was purified by reverse phase HPLC/MS to give 3 (6 mg, 30%) as a colorless solid, m/z (CI) 535.2 (MH$^+$, 100%).

By the above procedure, the compounds of the following Table 8 were also prepared.

TABLE 8

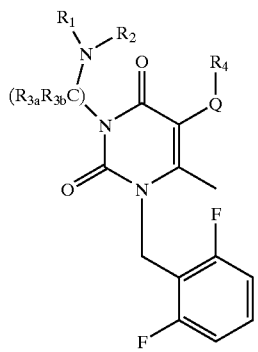

| Cpd. No. | R$_1$R$_2$N(CR$_{3a}$R$_{3b}$)$_n$- | -Q-R$_4$ | MS (calc) | MS Ion |
|---|---|---|---|---|
| 8-1 | (phenyl-CH$_2$-CH(NH$_2$)-CH$_2$-) | (3-methoxyphenyl) | 491.5 | 492 |

TABLE 8-continued

| Cpd. No. | R₁R₂N(CR₃ₐR₃ᵦ)ₙ- | -Q-R₄ | MS (calc) | MS Ion |
|---|---|---|---|---|
| 8-2 | (S)-PhCH₂CH(NH₂)CH₂- | 2-F-3-MeO-C₆H₃- | 509.5 | 510 |
| 8-3 | (R)-PhCH₂CH(NH₂)CH₂- | 2-F-3-MeO-C₆H₃- | 509.5 | 510 |
| 8-4 | (R)-PhCH₂CH(NH₂)CH₂- | H | 385.4 | 386 |
| 8-5 | H₂NCH₂CH(CH₃)CH₂- | 3-MeO-C₆H₄- | 415.4 | 416 |
| 8-6 | (R)-H₂NCH(CH₃)CH₂- | 2-F-3-MeO-C₆H₃- | 433.4 | 434 |
| 8-7 | (S)-PhCH₂CH(NH₂)CH₂- | H | 385.4 | 386 |
| 8-8 | (R)-H₂NCH(CH₃)CH₂- | 3-MeO-C₆H₄- | 415.4 | 416 |
| 8-9 | (S)-H₂NCH(CH₃)CH₂- | 3-MeO-C₆H₄- | 415.4 | 416 |

TABLE 8-continued

| Cpd. No. | R₁R₂N(CR₃ₐR₃ᵦ)ₙ- | -Q-R₄ | MS (calc) | MS Ion |
|---|---|---|---|---|
| 8-10 | H₂N-CH(CH₃)-CH₂- (S) | 2-F-3-methoxyphenyl | 433.4 | 434 |
| 8-11 | cyclohexyl-CH₂-CH(NH₂)-CH₂- | 2-F-3-methoxyphenyl | 515.6 | 516 |
| 8-12 | cyclohexyl-CH₂-CH(NH₂)-CH₂- | H | 391.5 | 392 |
| 8-13 | Ph-CH(NH₂)-CH₂- | 2-F-3-methoxyphenyl | 495.5 | 496 |
| 8-14 | Ph-CH(NH₂)-CH₂- | 2-F-3-methoxyphenyl | 495.5 | 496 |
| 8-15 | PhCH₂O-CH₂-CH(NH₂)-CH₂- | 2-F-3-methoxyphenyl | 539.6 | 540 |
| 8-16 | Ph-CH(NH₂)-CH₂- | 3-methoxyphenyl | 477.5 | 478 |

TABLE 8-continued

| Cpd. No. | R₁R₂N(CR₃ₐR₃ᵦ)ₙ- | -Q-R₄ | MS (calc) | MS Ion |
|---|---|---|---|---|
| 8-17 | | | 479.5 | 480 |
| 8-18 | | | 539.6 | 540 |
| 8-19 | | | 505.5 | 506 |
| 8-20 | | | 501.5 | 502.2 |
| 8-21 | | | 501.5 | 502.2 |
| 8-22 | | | 465.5 | 450 |
| 8-23 | | | 475.5 | 476.2 |

TABLE 8-continued

| Cpd. No. | R₁R₂N(CR₃ₐR₃ᵦ)ₙ- | -Q-R₄ | MS (calc) | MS Ion |
|---|---|---|---|---|
| 8-24 | H₂N—CH(iPr)CH₂— | 2-F-3-MeO-C₆H₃— | 461.5 | 462.2 |
| 8-25 | H₂N—CH(iPr)CH₂— | 2-F-3-MeO-C₆H₃— | 461.5 | 462.2 |
| 8-26 | H₂N—CH(cyclopentyl)CH₂— | 2-F-3-MeO-C₆H₃— | 487.5 | 488.2 |
| 8-27 | H₂N—CH(cyclopentyl)CH₂— | 2-F-3-MeO-C₆H₃— | 487.5 | 488.2 |
| 8-28 | 2-F-C₆H₄-CH₂-CH(NH₂)-CH₂— | 2-F-3-MeO-C₆H₃— | 527.5 | 528 |
| 8-29 | 2-Me-C₆H₄-CH₂-CH(NH₂)-CH₂— | 2-F-3-MeO-C₆H₃— | 523.6 | 524 |
| 8-30 | C₆H₅-CH₂CH₂-CH(NH₂)-CH₂— | 2-F-3-MeO-C₆H₃— | 523.6 | 524 |

TABLE 8-continued

| Cpd. No. | R₁R₂N(CR₃ₐR₃ᵦ)ₙ- | -Q-R₄ | MS (calc) | MS Ion |
|---|---|---|---|---|
| 8-31 | (S)-1-phenylpropyl-NH₂ | 2-fluoro-3-methoxyphenyl | 495.5 | 496 |
| 8-32 | (S)-4-methylpentyl-2-NH₂ | 2-fluoro-3-methoxyphenyl | 475.5 | 476.2 |
| 8-33 | (S)-1-phenylpropyl-NH₂ | 2,3-dihydrobenzo[1,4]dioxin-6-yl | 491.5 | 492 |
| 8-34 | (S)-1-phenylpropyl-NH₂ | 4-phenoxyphenyl | 539.6 | 540 |
| 8-35 | (S)-1-phenylpropyl-NH₂ | 2-chlorophenyl | 481.9 | 482 |
| 8-36 | (S)-1-phenylpropyl-NH₂ | 4-methylthiophenyl | 493.6 | 494 |
| 8-37 | (S)-1-phenylpropyl-NH₂ | 4-methylsulfonylphenyl | 525.6 | 526 |

TABLE 8-continued

| Cpd. No. | R₁R₂N(CR₃ₐR₃ᵦ)ₙ- | -Q-R₄ | MS (calc) | MS Ion |
|---|---|---|---|---|
| 8-38 | (tert-butyl-CH₂-CH(NH₂)-CH₂-) | 2-fluoro-3-methoxyphenyl | 489.5 | 490.2 |
| 8-39 | (isobutyl-CH(NH₂)-CH₂-) | 2-fluoro-3-methoxyphenyl | 475.5 | 476.2 |
| 8-40 | (HOCH₂-CH(NH₂)-CH₂-) | 2-fluoro-3-methoxyphenyl | 449.4 | 450 |
| 8-41 | (HOCH₂-CH(NH₂)-CH₂-) | 2,3-dihydro-1,4-benzodioxin-6-yl | 445.4 | 446 |
| 8-42 | (phenyl-CH(NH₂)-CH₂-) | 5-methylthiophen-2-yl | 467.5 | 469 |
| 8-43 | (phenyl-CH(NH₂)-CH₂-) | pyrazin-2-yl | 449.5 | 450 |
| 8-44 | (phenyl-CH(NH₂)-CH₂-) | 4-fluoro-3-methylphenyl | 479.5 | 480 |

TABLE 8-continued

| Cpd. No. | R₁R₂N(CR₃ₐR₃ᵦ)ₙ- | -Q-R₄ | MS (calc) | MS Ion |
|---|---|---|---|---|
| 8-45 | methyl 2-amino-butanoate ester | 3-methoxybenzyl | 459.4 | 460.2 |
| 8-46 | 2-amino-butanoic acid | 3-methoxybenzyl | 445.4 | 446.1 |
| 8-47 | N-benzyl-2-amino-butanamide | 3-methoxybenzyl | 534.6 | 535.2 |
| 8-48 | 2-amino-1-morpholinobutan-1-one | 3-methoxybenzyl | 514.5 | 515.2 |
| 8-49 | N-(pyridin-2-yl)-2-amino-butanamide | 3-methoxybenzyl | 521.5 | 522.2 |
| 8-50 | N-benzyl-N-methyl-2-amino-butanamide | 3-methoxybenzyl | 548.6 | 549.2 |
| 8-51 | N-phenyl-2-amino-butanamide | 3-methoxybenzyl | 520.3 | 521.2 |

TABLE 8-continued
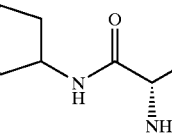
| Cpd. No. | R₁R₂N(CR₃ₐR₃ᵦ)ₙ- | -Q-R₄ | MS (calc) | MS Ion |
|---|---|---|---|---|
| 8-52 | 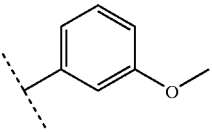 | 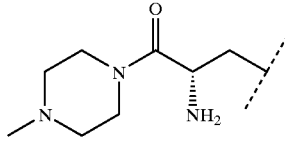 | 512.6 | 513.2 |
| 8-53 | 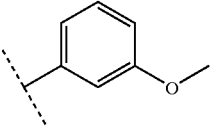 | 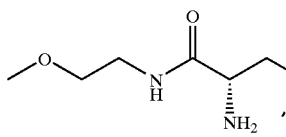 | 527.6 | 528.2 |
| 8-54 | 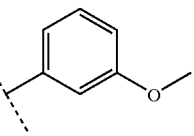 | 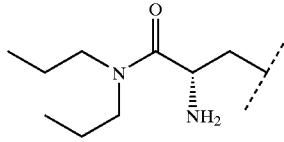 | 502.5 | 503.2 |
| 8-55 | 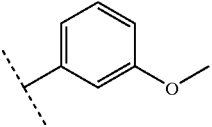 | 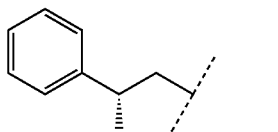 | 528.6 | 529.3 |
| 8-56 | 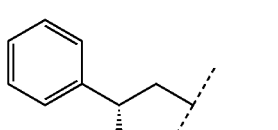 | H | 371.4 | 372.1 |
| 8-57 | 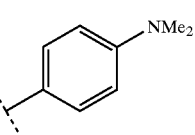 | 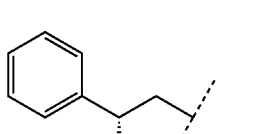 | 490.6 | 491.2 |
| 8-58 | 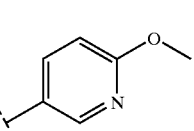 | 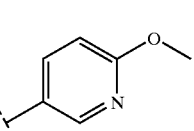 | 478.5 | 479.1 |

TABLE 8-continued

| Cpd. No. | R₁R₂N(CR₃ₐR₃ᵦ)ₙ- | -Q-R₄ | MS (calc) | MS Ion |
|---|---|---|---|---|
| 8-59 | (S)-1-phenylpropyl-NH₂ | 3-ethoxyphenyl | 491.5 | 492.2 |
| 8-60 | (S)-1-phenylpropyl-NH₂ | 3-(4-methylphenyl)-1,2,4-oxadiazol-5-yl | 515.5 | 516.2 |
| 8-61 | (S)-1-phenylpropyl-NH₂ | 3-(methylthio)phenyl | 493.6 | 494.1 |
| 8-62 | (S)-1-phenylpropyl-NH₂ | 4-(4-methylphenoxy)phenyl | 553.6 | 554.2 |
| 8-63 | (S)-1-phenylpropyl-NH₂ | 4-(2-methylphenoxy)phenyl | 553.6 | 554.2 |
| 8-64 | (S)-1-phenylpropyl-NH₂ | 4-(3-methylphenoxy)phenyl | 553.6 | 554.2 |
| 8-65 | (S)-1-phenylpropyl-NH₂ | 4-(4-fluorophenoxy)phenyl | 557.6 | 558.2 |

TABLE 8-continued

| Cpd. No. | R₁R₂N(CR₃ₐR₃ᵦ)ₙ- | -Q-R₄ | MS (calc) | MS Ion |
|---|---|---|---|---|
| 8-66 | (S)-1-phenylpropyl-3-amine | 4-(3-fluorophenoxy)phenyl | 557.6 | 558.2 |
| 8-67 | (S)-1-phenylpropyl-3-amine | 4-(4-methoxyphenoxy)phenyl | 569.6 | 570.2 |
| 8-68 | (S)-1-phenylpropyl-3-amine | 4-(3-methoxyphenoxy)phenyl | 569.6 | 570.2 |
| 8-69 | (S)-1-phenylpropyl-3-amine | 4-(4-chlorophenoxy)phenyl | 574.0 | 574.2 |
| 8-70 | (S)-1-phenylpropyl-3-amine | 4-(3-chlorophenoxy)phenyl | 574 | 574.2 |
| 8-71 | (S)-1-phenylpropyl-3-amine | 4-(4-isopropylphenoxy)phenyl | 581.7 | 582.3 |
| 8-72 | (S)-1-phenylpropyl-3-amine | 4-(4-tert-butylphenoxy)phenyl | 595.7 | 596.3 |

TABLE 8-continued

| Cpd. No. | R₁R₂N(CR₃ₐR₃ᵦ)ₙ- | -Q-R₄ | MS (calc) | MS Ion |
|---|---|---|---|---|
| 8-73 | phenyl-CH(NH₂)-CH₂- | -C₆H₄-O-C₆H₄-CF₃ | 607.6 | 608.2 |
| 8-74 | phenyl-CH(NH₂)-CH₂- | -C₆H₄-O-C₆H₃(Cl)₂ | 608.5 | 608.1 |
| 8-75 | phenyl-CH(NH₂)-CH₂- | 5-chlorothiophen-2-yl | 488 | 488.1 |
| 8-76 | phenyl-CH(NH₂)-CH₂- | 4-acetylphenyl | 489.5 | 490.2 |
| 8-77 | phenyl-CH(NH₂)-CH₂- | phenyl | 447.5 | 488.2 |
| 8-78 | 4-F-phenyl-CH(NH₂)-CH₂- | phenyl | 465.5 | 466.1 |
| 8-79 | 4-F-phenyl-CH(NH₂)-CH₂- | 2-F-3-methoxyphenyl | 513.5 | 514.1 |

TABLE 8-continued

| Cpd. No. | R₁R₂N(CR₃ₐR₃ᵦ)ₙ- | -Q-R₄ | MS (calc) | MS Ion |
|---|---|---|---|---|
| 8-80 | 4-F-phenyl-CH(NH₂)-CH₂- | 3-methoxyphenyl | 495.5 | 496.2 |
| 8-81 | 4-F-phenyl-CH(NH₂)-CH₂- | 2,3-dihydrobenzo[1,4]dioxin-6-yl | 509.5 | 510.1 |
| 8-82 | 2-F-phenyl-CH(NH₂)-CH₂- | phenyl | 465.5 | 466.2 |
| 8-83 | 2-F-phenyl-CH(NH₂)-CH₂- | 3-methoxyphenyl | 495.5 | 496.2 |
| 8-84 | 2-F-phenyl-CH(NH₂)-CH₂- | 2-F-3-methoxyphenyl | 513.5 | 514.2 |
| 8-85 | 2-F-phenyl-CH(NH₂)-CH₂- | 2,3-dihydrobenzo[1,4]dioxin-6-yl | 509.5 | 510.2 |
| 8-86 | phenyl-CH(NH₂)-CH₂- | 2-methylphenyl | 461.5 | 462 |

TABLE 8-continued

| Cpd. No. | R₁R₂N(CR₃ₐR₃ᵦ)ₙ- | -Q-R₄ | MS (calc) | MS Ion |
|---|---|---|---|---|
| 8-87 | (S)-1-phenylpropyl-NH₂ | 2-OMe-phenyl | 477.5 | 478 |
| 8-88 | (S)-1-phenylpropyl-NH₂ | 3-Cl-phenyl | 481.9 | 482 |
| 8-89 | (S)-1-phenylpropyl-NH₂ | 3-Me-phenyl | 461.5 | 462 |
| 8-90 | (S)-1-phenylpropyl-NH₂ | 3-CF₃-phenyl | 515.5 | 516 |
| 8-91 | (S)-1-phenylpropyl-NH₂ | 3-iPr-phenyl | 489.6 | 490 |
| 8-92 | (S)-1-phenylpropyl-NH₂ | 3-OCF₃-phenyl | 531.5 | 532 |
| 8-93 | (S)-1-phenylpropyl-NH₂ | 3-phenyl-phenyl | 523.6 | 524 |

TABLE 8-continued
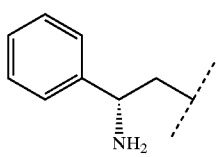
| Cpd. No. | R₁R₂N(CR₃ₐR₃ᵦ)ₙ- | -Q-R₄ | MS (calc) | MS Ion |
|---|---|---|---|---|
| 8-94 | 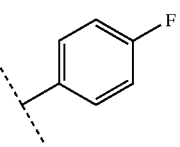 | 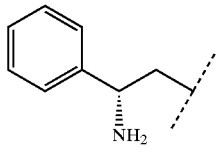 | 465.5 | 466 |
| 8-95 | 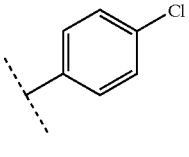 | 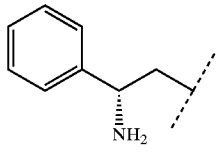 | 481.9 | 482 |
| 8-96 | 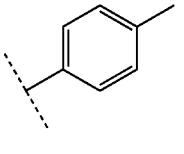 | 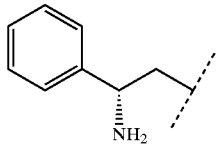 | 461.5 | 462 |
| 8-97 | 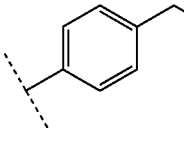 | 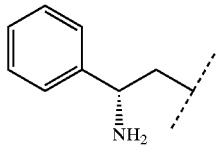 | 475.5 | 476 |
| 8-98 | 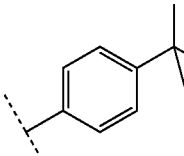 | 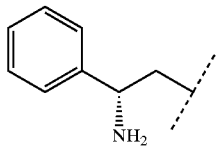 | 503.6 | 504 |
| 8-99 | 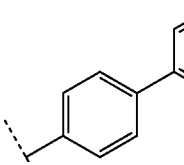 | 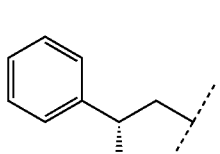 | 523.6 | 524 |
| 8-100 | 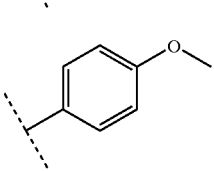 | | 477.5 | 478 |

TABLE 8-continued
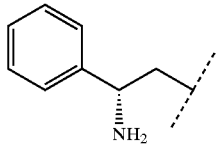
| Cpd. No. | R₁R₂N(CR₃ₐR₃ᵦ)ₙ- | -Q-R₄ | MS (calc) | MS Ion |
|---|---|---|---|---|
| 8-101 | 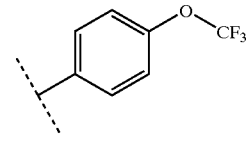 | 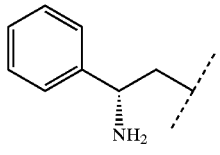 | 531.5 | 532 |
| 8-102 | 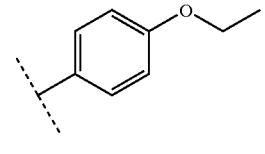 | 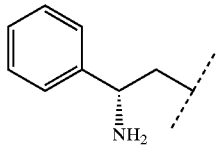 | 491.5 | 482 |
| 8-103 | 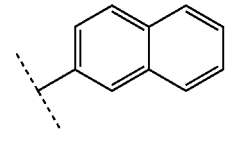 | 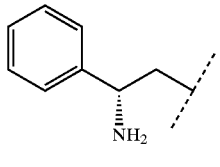 | 497.5 | 498 |
| 8-104 | 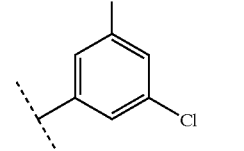 | 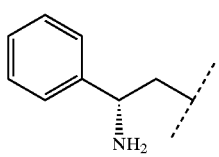 | 516.4 | 516 |
| 8-105 | 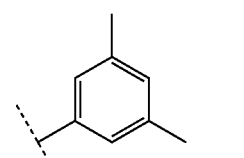 | 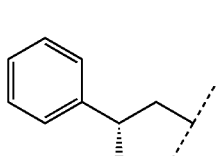 | 475.5 | 476 |
| 8-106 | 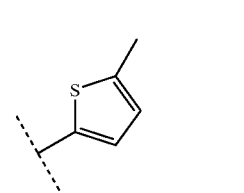 | | 467.5 | 468 |

TABLE 8-continued

| Cpd. No. | R₁R₂N(CR₃ₐR₃ᵦ)ₙ- | -Q-R₄ | MS (calc) | MS Ion |
|---|---|---|---|---|
| 8-107 | 1-phenyl-3-aminopropyl | 2-thienylmethyl | 453.5 | 454 |
| 8-108 | 1-phenyl-3-aminopropyl | 4-vinylbenzyl | 476.5 | 474 |
| 8-109 | 1-phenyl-3-aminopropyl | 4-isopropylbenzyl | 489.6 | 490 |
| 8-110 | 1-(3-fluorophenyl)-3-aminopropyl | benzyl | 465.5 | 466.1 |
| 8-111 | 1-(3-fluorophenyl)-3-aminopropyl | 3-methoxybenzyl | 495.5 | 496.2 |
| 8-112 | 1-(3-fluorophenyl)-3-aminopropyl | 2-fluoro-3-methoxybenzyl | 513.5 | 514.2 |
| 8-113 | 1-(3-fluorophenyl)-3-aminopropyl | 1,3-benzodioxol-5-ylmethyl | 509.5 | 510.1 |

TABLE 8-continued

| Cpd. No. | R₁R₂N(CR₃ₐR₃ᵦ)ₙ- | -Q-R₄ | MS (calc) | MS Ion |
|---|---|---|---|---|
| 8-114 | thiazol-5-ylmethyl-CH(NH₂)-CH₂-CH₂- | 3-methoxyphenyl | 498.6 | 498 |
| 8-115 | 3-(trifluoromethyl)phenyl-CH(NH₂)-CH₂-CH₂- | 3-methoxyphenyl | 545.5 | 546.2 |
| 8-116 | 3-(trifluoromethyl)phenyl-CH(NH₂)-CH₂-CH₂- | 2-fluoro-3-methoxyphenyl | 563.5 | 564.2 |
| 8-117 | 3-(trifluoromethyl)phenyl-CH(NH₂)-CH₂-CH₂- | benzo[1,3]dioxol-5-yl | 559.5 | 560.2 |
| 8-118 | 4-(trifluoromethoxy)phenyl-CH(NH₂)-CH₂-CH₂- | 3-methoxyphenyl | 561.5 | 562.2 |
| 8-119 | 4-(trifluoromethoxy)phenyl-CH(NH₂)-CH₂-CH₂- | 2-fluoro-3-methoxyphenyl | 579.5 | 580.2 |
| 8-120 | 4-(trifluoromethoxy)phenyl-CH(NH₂)-CH₂-CH₂- | benzo[1,3]dioxol-5-yl | 575.5 | 576.2 |

TABLE 8-continued

| Cpd. No. | R₁R₂N(CR₃ₐR₃ᵦ)ₙ- | -Q-R₄ | MS (calc) | MS Ion |
|---|---|---|---|---|
| 8-121 | 4-Cl-C₆H₄-CH(NH₂)-CH₂- | -O-C₆H₅ | 481.9 | 482.1 |
| 8-122 | 4-Cl-C₆H₄-CH(NH₂)-CH₂- | -O-CH₂-(3,4-methylenedioxyphenyl) | 525.9 | 526.1 |
| 8-123 | 4-Cl-C₆H₄-CH(NH₂)-CH₂- | -O-CH₂-(3-methoxyphenyl) | 512 | 512.1 |
| 8-124 | 4-Cl-C₆H₄-CH(NH₂)-CH₂- | -O-CH₂-(2-fluoro-3-methoxyphenyl) | 529.9 | 530.1 |
| 8-125 | 2,3-diF-C₆H₃-CH(NH₂)-CH₂- | -O-C₆H₅ | 483.5 | 484.1 |
| 8-126 | 2,3-diF-C₆H₃-CH(NH₂)-CH₂- | -O-CH₂-(3-methoxyphenyl) | 513.5 | 496.2 |
| 8-127 | 2,3-diF-C₆H₃-CH(NH₂)-CH₂- | -O-CH₂-(2-fluoro-3-methoxyphenyl) | 531.5 | 532.1 |

TABLE 8-continued

| Cpd. No. | R₁R₂N(CR₃ₐR₃ᵦ)ₙ- | -Q-R₄ | MS (calc) | MS Ion |
|---|---|---|---|---|
| 8-128 | | | 491.5 | 492.2 |
| 8-129 | | | 513.5 | 514.2 |
| 8-130 | | | 527.5 | 528.1 |
| 8-131 | | | 531.5 | 532.2 |
| 8-132 | | | 483.5 | 484.1 |
| 8-133 | | | 513.5 | 514.2 |

TABLE 8-continued
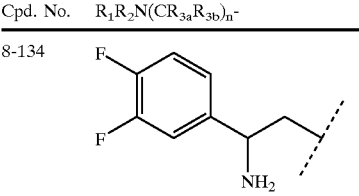
| Cpd. No. | R₁R₂N(CR₃ₐR₃ᵦ)ₙ- | -Q-R₄ | MS (calc) | MS Ion |
|---|---|---|---|---|
| 8-134 | 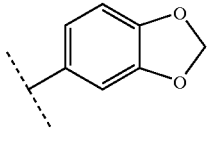 | 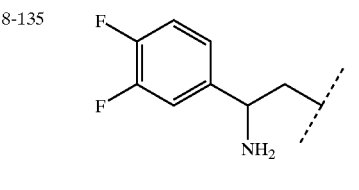 | 527.5 | 528.2 |
| 8-135 | 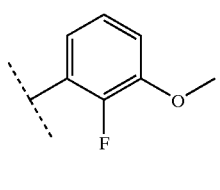 | 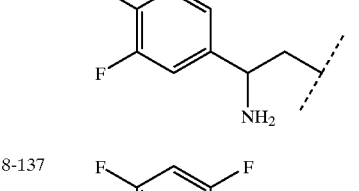 | 531.5 | 532.2 |
| 8-136 | 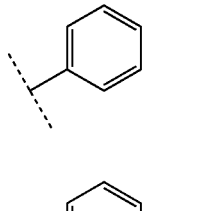 | 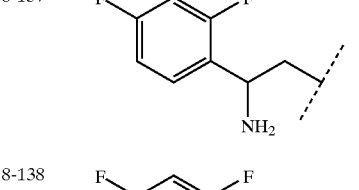 | 483.5 | 484.1 |
| 8-137 | 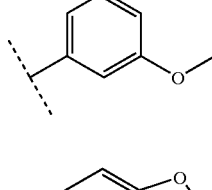 | 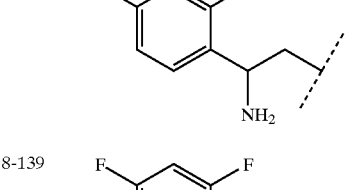 | 513.5 | 514.1 |
| 8-138 | 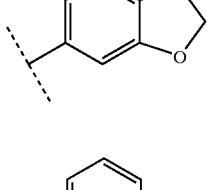 | 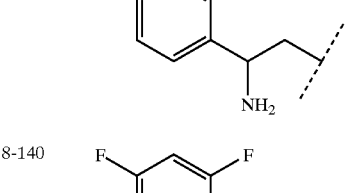 | 527.5 | 528.2 |
| 8-139 | 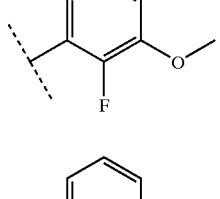 | 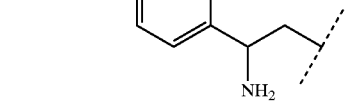 | 531.5 | 532.2 |
| 8-140 | 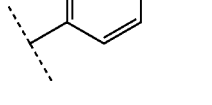 | | 483.5 | 484.1 |

EXAMPLE 6

Synthesis of Boronic Acids

Step A 2-Fluoro-3-methoxyphenylboronic acid n-Butyl lithium (20 mL, 2.5M) was added to a solution of tetramethylpiperidine (8.44 mL, 50 mmol) in THF (125 mL) at −78° C. The reaction mixture was stirred at −78° C. for 1.5 hours. 2-Fluoroanisole (6.31 g, 50 mmol) was added and the mixture was stirred for 8 hours at −78° C. Trimethyl borate (6.17 mL, 55 mmol) was added and the reaction mixture was allowed to warm slowly to room temperature overnight. The mixture was poured into 1N HCl (250 mL). Extraction with EtOAc followed by evaporation gave a sticky solid which was triturated with hexanes to give product (2.19 g, 26% yield).

EXAMPLE 7

Synthesis of Representative Compounds

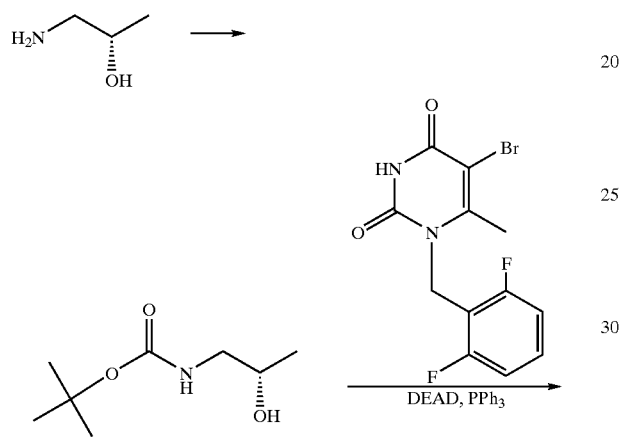

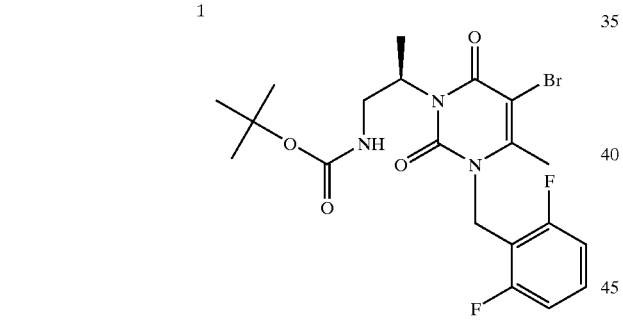

Step A BOC-(S)-1-amino-2-propanol

Di-t-butyl dicarbonate (6.76 g, 31 mmol) was added portionwise to a stirred solution of (S)-1-amino-2-propanol and triethylamine (4.4 mL, 31.5 mmol) in CH$_2$Cl$_2$ (75 mL) at 0° C. The reaction mixture was stirred for 1 hour at 0° C. and for 30 minutes at room temperature. Evaporation gave product 1 which was used without further purification.

Step B 3-(2-BOC-(R)-1-aminopropyl)-5-bromo-1-(2,6-difluorobenzyl)-6-methyl-uracil 5-Bromo-1-(2,6-difluorobenzyl)-6-methyluracil (3.31 g, 10 mmol) was suspended in THF (200 mL). Compound 1 (1.84 g, 10.5 mmol) and triphenylphosphine (3.93 g, 15 mmol) were added and the mixture was stirred. DEAD (2.36 mL, 15 mmol) was added and the reaction mixture became a solution. After stirring overnight, the volatiles were removed and the residue was chromatographed on silica using EtOAc/hexanes as elutant to give white solid 2 (4.57 g, 94% yield).

EXAMPLE 8

Synthesis of Representative Compounds

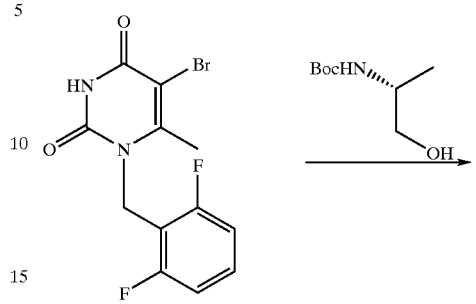

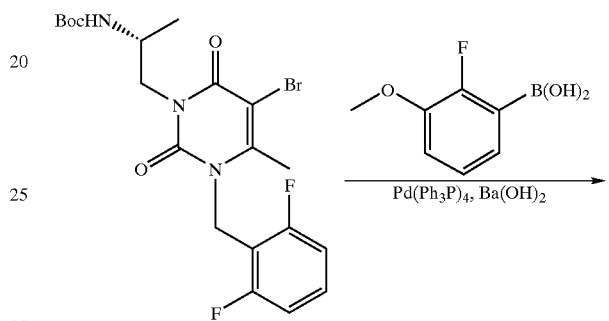

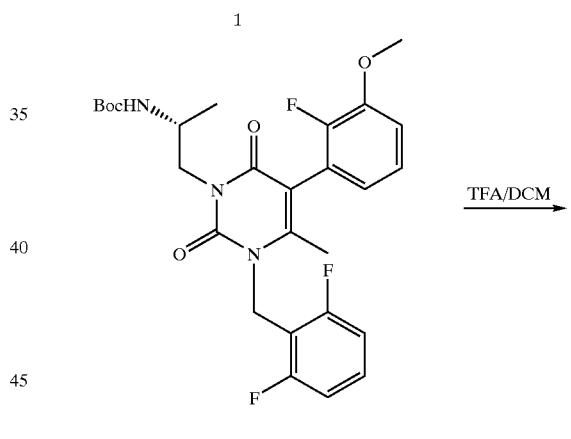

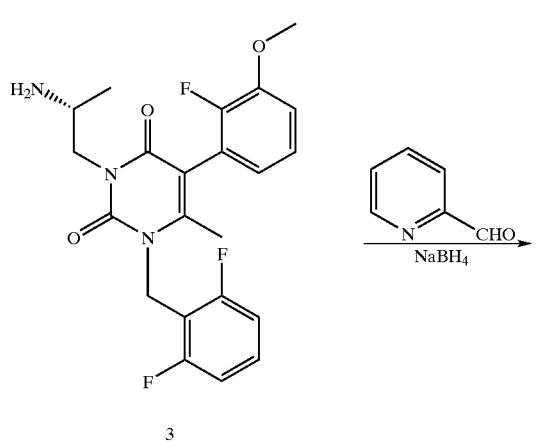

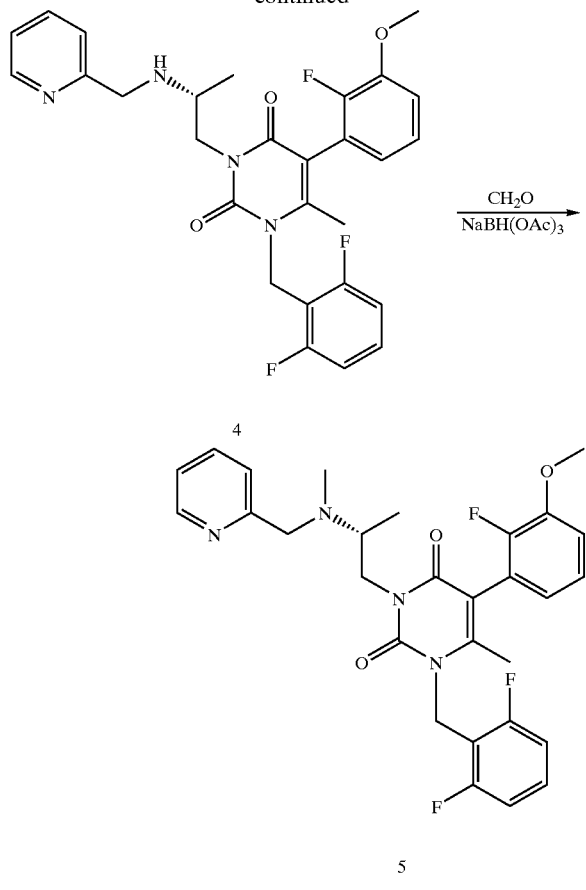

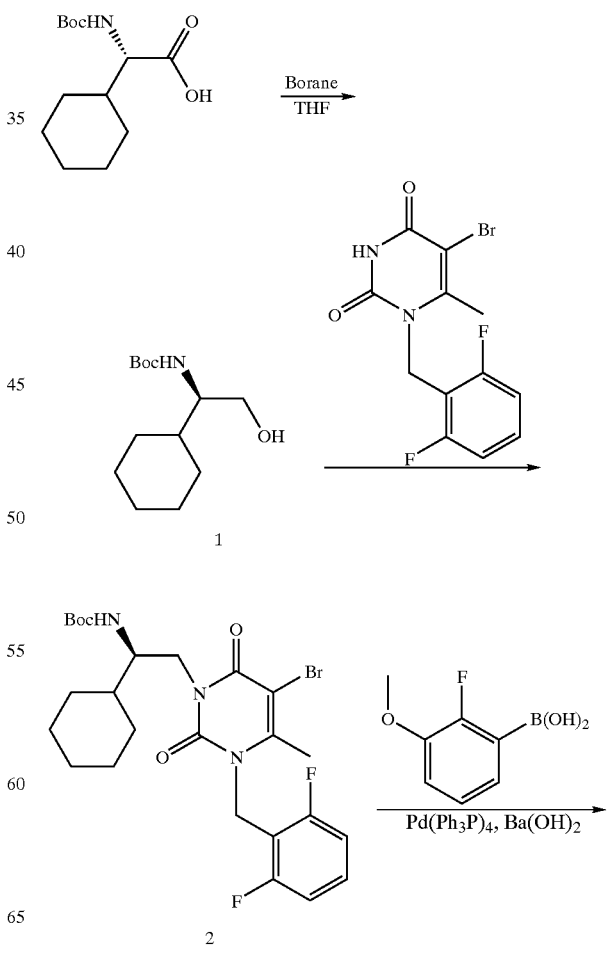

rated NaHCO₃/water and EtOAc. The organic layer was dried (sodium sulfate), evaporated, and purified by reverse phase HPLC (C-18 column, 15–75% acetonitrile/water) to give compound 3, MS (CI) m/z 434.2 (MH$^+$).

Step D

2-Pyridinecarboxyaldehyde (80 mg, 0.75 mmol) was added to a solution of 3 (267 mg, 0.5 mmol) in MeOH (5 mL) and the reaction mixture was stirred at ambient temperature for 10 hours. NaBH₄ (56 mg, 1.5 mmol) was added and the reaction mixture was kept at ambient temperature for 10 minutes. Volatiles were evaporated and the residue was partitioned between saturated NaHCO₃/water and dichloromethane. The organic layer was dried (sodium sulfate), evaporated, and purified by reverse phase HPLC (C-18 column, 15–75% acetonitrile/water) to give compound 4, MS (CI) m/z 525.20 (MH$^+$).

Step E

To a solution of 4 (20 mg, 0.04 mmol) in dichloromethane (2 mL) was added 1 drop of formaldehyde (37% solution in water) and NaBH(OAc)₃ (16 mg, 0.08 mmol). The reaction mixture was stirred at ambient temperature for 2 hours, volatiles were evaporated and the residue was partitioned between water and dichloromethane. The organic layer was dried (sodium sulfate), evaporated, and purified by reverse phase HPLC (C-18 column, 15–75% acetonitrile/water) to give compound 5, MS (CI) m/z 539.20 (MH$^+$).

Step A

A solution of N-(t-butyloxycarbonyl)-D-α-alaninol (1.75 g, 10 mmol) in anhydrous THF (15 mL) was treated with 5-bromo-1-(2,6-difluorobenzyl)-6-methyluracil (3.31 g, 10 mmol) and triphenylphosphine (3.15 g, 12 mmol) at ambient temperature, then di-tert-butylazodicarboxylate (2.76 g, 12 mmol) was introduced. The reaction mixture was stirred at ambient temperature for 16 hours and volatiles were evaporated. The residue was partitioned between saturated NaHCO₃/H₂O and EtOAc. The organic layer was dried (sodium sulfate), evaporated, and purified by flash chromatography (silica, 1:2 EtOAc/hexanes) to give compound 1 (4.69 g, 96.1%), MS (CI) m/z 388.0, 390.0 (MH$^+$-Boc).

Step B

To compound 1 (1.0 g, 2.05 mmol) in benzene/EtOH/ethylene glycol dimethyl ether (20/2/22 mL) was added 2-fluoro-3-methoxyphenylboronic acid (435 mg, 2.56 mmol) and saturated Ba(OH)₂/water (~0.5 M, 15 mL). The reaction mixture was deoxygenated with N₂ for 10 min, tetrakis(triphenylphosphine) palladium (0) (242 mg, 0.21 mmol) was added and the reaction mixture was heated at 80° C. overnight under the protection of N₂. The reaction mixture was partitioned between brine and EtOAc. The organic layer was dried (sodium sulfate), evaporated, purified by flash chromatography (silica, 40% EtOAc/hexanes) to give compound 2 (450 mg, 41.2%), MS (CI) m/z 434.2 (MH$^+$-Boc).

Step C

TFA (2 mL) was added to a solution of 2 (267 mg, 0.5 mmol) in dichloromethane (2 mL) and the reaction mixture was stirred at ambient temperature for 1 hour. Volatiles were evaporated and the residue was partitioned between satu-

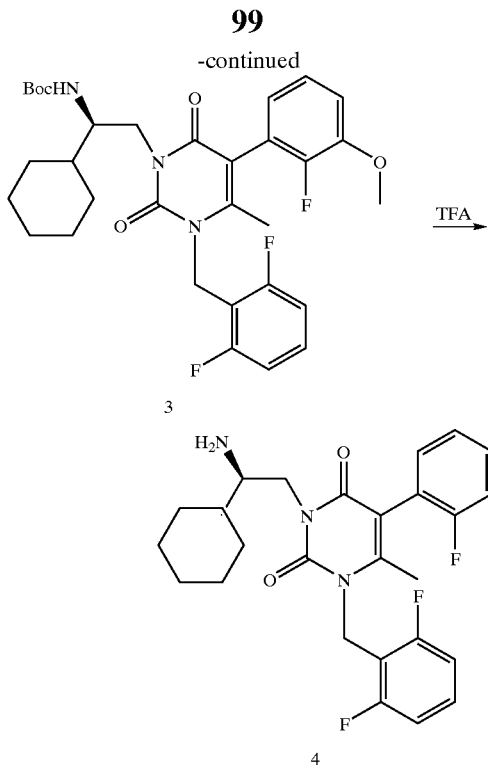

Step A

A solution of N$^\alpha$-(t-butyloxycarbonyl)-L-α-cyclohexylglycine (2.0 g, 7.77 mmol) in anhydrous THF (10 mL) was cooled down to 0° C. Borane solution (1 M in THF, 15.5 mL, 15.5 mmol) was added slowly and then warmed to ambient temperature, and the reaction mixture was stirred at ambient temperature for 2 h. The reaction was quenched with MeOH (5 mL), volatiles were evaporated and the residue was partitioned between water and EtOAc. The organic layer was washed with saturated NaHCO$_3$/water and brine, and then was dried (sodium sulfate) and evaporated to give compound 1 (1.26 g, 66.7%) MS (CI) m/z 144.20 (MH$^+$-Boc).

Step B

A solution of 1 (638 mg, 2.62 mmol) in THF (10 mL) was treated with 5-bromo-1-(2,6-difluorobenzyl)-6-methyluracil (869 mg, 2.62 mmol) and triphenylphosphine (1.03 g, 3.93 mmol) at ambient temperature, then di-tert-butylazodicarboxylate (906 mg, 3.93 mmol) was introduced. The reaction mixture was stirred at ambient temperature for 16 h and volatiles were evaporated. The residue was partitioned between saturated NaHCO$_3$/H$_2$O and EtOAc. The organic layer was dried (sodium sulfate), evaporated, and purified by flash chromatography (silica, 25% EtOAc/hexanes) to give compound 2 (1.39 g, 95.4%), MS (CI) m/z 456.10, 458.10 (MH$^+$-Boc).

Step C

Compound 2 (1.0 g, 1.79 mmol) in benzene/EtOH/ethylene glycol dimethyl ether (20/2/22 mL) was added 2-fluoro-3-methoxyphenylboronic acid (382 mg, 2.24 mmol) and saturated Ba(OH)$_2$/water (~0.5 M, 15 mL). The reaction mixture was deoxygenated with N$_2$ for 10 min, tetrakis(triphenylphosine) palladium (0) (208 mg, 0.18 mmol) was added and the reaction mixture was heated at 80° C. overnight under the protection of N$_2$. The reaction mixture was partitioned between brine and EtOAc. The organic layer was dried (sodium sulfate), evaporated, and purified by flash chromatography (silica, 30% EtOAc/hexanes) to give compound 3 (348 mg, 32.3%), MS (CI) m/z 502.20 (MH$^+$-Boc).

Step D

A solution of 3 (300 mg, 0.5 mmol) in dichloromethane (2 mL) was added TFA (2 mL) and the reaction mixture was stirred at ambient temperature for 1 h. Volatiles were evaporated and the residue was partitioned between saturated NaHCO$_3$/water and EtOAc. The organic layer was dried (sodium sulfate), evaporated, and purified by reverse phase HPLC (C-18 column, 15–75% ACN/water) to give compound 4, MS (CI) m/z 502.20 (MH$^+$).

By the above procedure, the compounds of the following Table 9 were also prepared.

TABLE 9

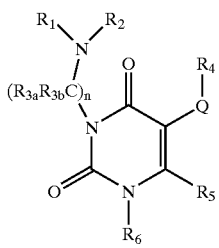

| Cpd. No. | R$_5$ | R$_6$ | NR$_1$R$_2$— (CR$_{3a}$CR$_{3b}$)$_n$— | —Q—R$_4$ | MW (calc.) | (obs.) |
|---|---|---|---|---|---|---|
| 9-1 | Me | [2,6-difluorobenzyl] | [pyrrolidinyl-CH$_2$OH group] | [3-methoxyphenyl-OMe] | 485.5 | 486 |

TABLE 9-continued

| | | | | | |
|---|---|---|---|---|---|
| 9-2 | Me | (2,6-difluorobenzyl)-(phenylpropanoyl-pyrrolidinyl-propyl) | | 3-OMe-phenyl | 589.6 590 |
| 9-3 | Me | (2,6-difluorobenzyl)-CH2NHC(O)-pyrrolidinyl-propyl | | 3-OMe-phenyl | 526.6 527 |
| 9-4 | Me | (2,6-difluorobenzyl)-(hydroxymethyl-pyrrolidinyl)-propyl | | 3-OMe-phenyl | 485.5 486 |
| 9-5 | Me | (2,6-difluorobenzyl)-(methoxycarbonyl-pyrrolidinyl)-propyl | | 3-OMe-phenyl | 513.5 514 |
| 9-6 | Me | (2,6-difluorobenzyl)-(hydroxy-methoxycarbonyl-pyrrolidinyl)-propyl | | 3-OMe-phenyl | 529.5 530 |
| 9-7 | Me | (2,6-difluorobenzyl)-acetamido-pyrrolidinyl-propyl | | 3-OMe-phenyl | 512.5 513 |
| 9-8 | Me | (2,6-difluorobenzyl)-(pyridin-2-yl-ethyl)-N-methyl-propyl | | 2,4-dimethylphenyl | 518.6 519 |
| 9-9 | Me | (2,6-difluorobenzyl)-(pyridin-2-yl-methyl)-pyrrolidinyl-methyl | | 3-OMe-phenyl | 532.6 533 |

TABLE 9-continued
| | | | | | |
|---|---|---|---|---|---|
| 9-10 | Me | 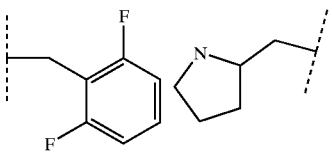 | 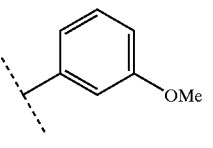 | 427 | 428 |
| 9-11 | Me | 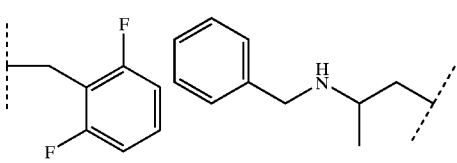 | 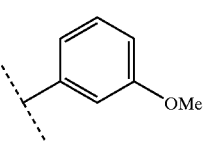 | 505.6 | 506 |
| 9-12 | Me | 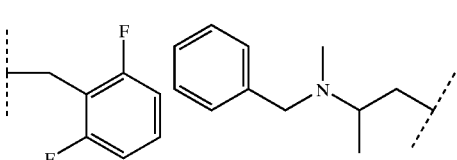 | 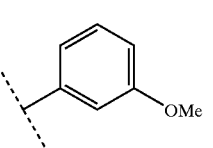 | 519.6 | 520 |
| 9-13 | Me | 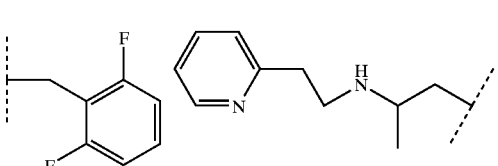 | 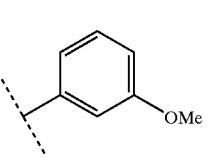 | 520.6 | 521 |
| 9-14 | Me | 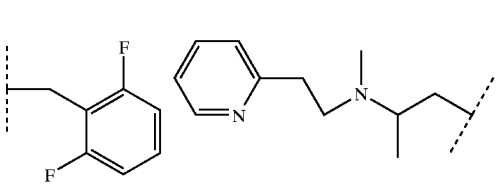 | 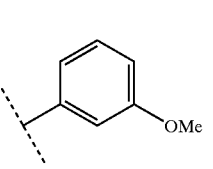 | 534.6 | 535 |
| 9-15 | Me |  | 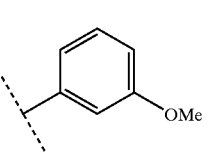 | 532.6 | 533 |
| 9-16 | Me | 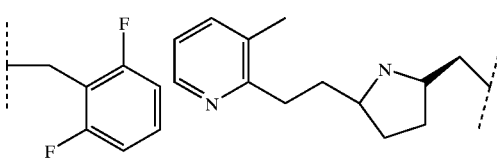 | 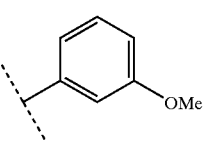 | 560.6 | 561 |
| 9-17 | Me | 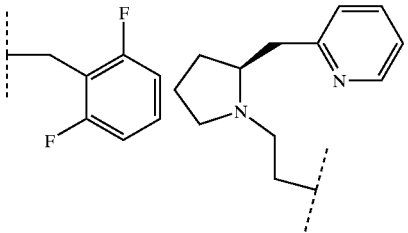 | 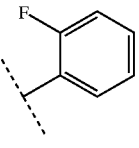 | 534.6 | 535 |

TABLE 9-continued

| | | | | | |
|---|---|---|---|---|---|
| 9-18 | Me | 2,6-difluorobenzyl; pyrrolidine with 3-pyridylmethyl | | 2-fluorophenyl | 534.6 535 |
| 9-19 | Me | 2,6-difluorobenzyl; isobutoxy-propyl-NH-CH(Me)- | | 3-methoxyphenyl | 529.6 530 |
| 9-20 | Me | 2,6-difluorobenzyl; 1-phenyl-3-hydroxypropyl-NH-CH(Me)- | | 3-methoxyphenyl | 549.6 550 |
| 9-21 | Me | 2,6-difluorobenzyl; pyrrolidine-2-C(O)N(H)-n-butyl | | 3-methoxyphenyl | 554.6 555 |
| 9-22 | Me | 2,6-difluorobenzyl; pyrrolidine-2-C(O)N(H)-isobutyl | | 3-methoxyphenyl | 554.6 555 |
| 9-23 | Me | 2,6-difluorobenzyl; pyrrolidine-2-C(O)N(H)-2-pyridyl | | 3-methoxyphenyl | 575.6 576 |
| 9-24 | Me | 2,6-difluorobenzyl; 2-(2-pyridyl)ethyl-N(Me)- | | 2-fluoro-3-methoxyphenyl | 538.6 539 |
| 9-25 | Me | 2,6-difluorobenzyl; pyrrolidine with cyclohexylmethyl | | 3-methoxyphenyl | 537.6 538 |

TABLE 9-continued

| # | R1 | Amine | Aryl | MW | MS |
|---|---|---|---|---|---|
| 9-26 | Me | 2,6-difluorobenzyl + (S)-2-ethylpyrrolidine | 3-OMe-phenyl | 441.5 | 442 |
| 9-27 | Me | 2,6-difluorobenzyl + 1-(2-(pyridin-2-yl)ethyl)-2-ethylpyrrolidine | 3-OMe-phenyl | 546.6 | 547 |
| 9-28 | Me | 2,6-difluorobenzyl + N-methyl-N-(2-(pyridin-2-yl)ethyl)propylamine | 2-F-5-OMe-phenyl | 538.6 | 539 |
| 9-29 | Me | 2,6-difluorobenzyl + indan-1-ylamine | 4-phenoxyphenyl | 579.6 | 447 |
| 9-30 | Me | 2,6-difluorobenzyl + 1-phenylethylamine | 4-phenoxyphenyl | 567.6 | 447 |
| 9-31 | Me | 2,6-difluorobenzyl + 3-methylbutan-2-ylamine | 4-phenoxyphenyl | 533.6 | 534 |
| 9-32 | Me | 2,6-difluorobenzyl + 3,5-bis(trifluoromethyl)benzylamine | 4-phenoxyphenyl | 689.6 | 690 |
| 9-33 | Me | 2,6-difluorobenzyl + N,N-diisopropylethylenediamine | 4-phenoxyphenyl | 590.7 | 591 |
| 9-34 | Me | 2,6-difluorobenzyl + 1-pyrrolidinyl-propyl | 4-phenoxyphenyl | 517.6 | 518 |

TABLE 9-continued
| | | | | | |
|---|---|---|---|---|---|
| 9-35 | Me | 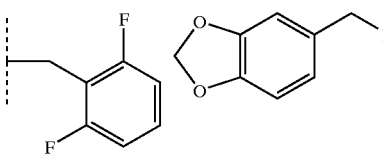 | 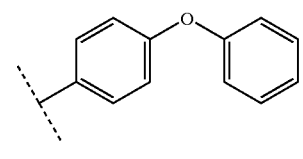 | 666.7 | 667 |
| 9-36 | Me | 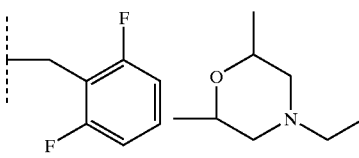 | 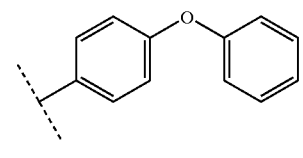 | 561.6 | 562 |
| 9-37 | Me | 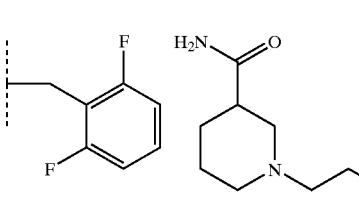 | 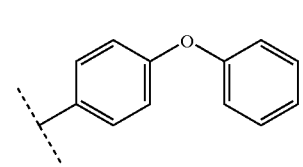 | 574.6 | 575 |
| 9-38 | Me | 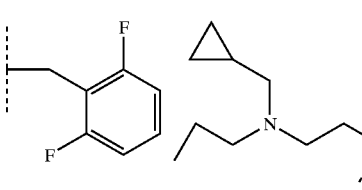 | 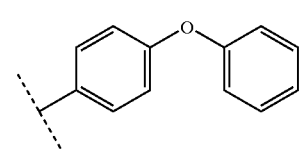 | 559.6 | 560 |
| 9-39 | Me | 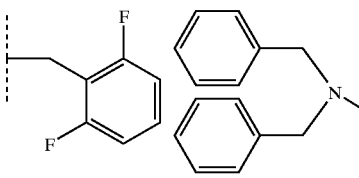 | 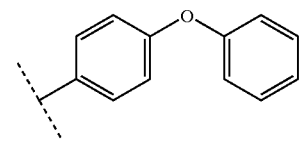 | 643.7 | 644 |
| 9-40 | Me | 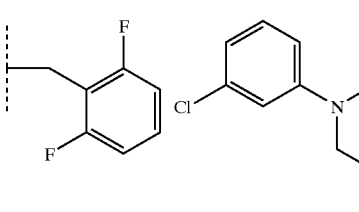 | 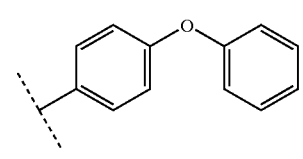 | 643.1 | 643 |
| 9-41 | Me | 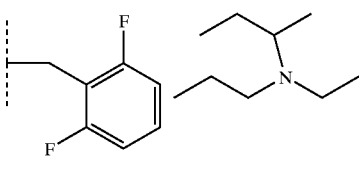 | 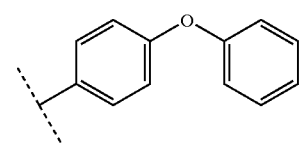 | 561.7 | 562 |
| 9-42 | Me | 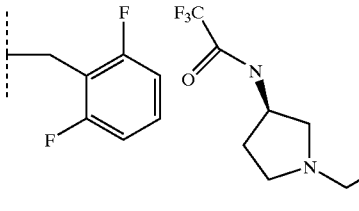 | 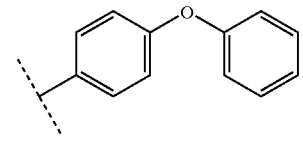 | 628.6 | 629 |

TABLE 9-continued

| | | | | | |
|---|---|---|---|---|---|
| 9-43 | Me | [2,6-difluorobenzyl] | [benzyl O-C(=O)-piperazine-N-propyl] | [4-phenoxyphenyl] | 666.7 667 |
| 9-44 | Me | [2,6-difluorobenzyl] | [furan-2-yl-CH2-NH-propyl] | [2-fluorophenyl] | 469.5 373 |
| 9-45 | Me | [2,6-difluorobenzyl] | [indan-1-yl-NH-propyl] | [2-fluorophenyl] | 505.5 373 |
| 9-46 | Me | [2,6-difluorobenzyl] | [1-phenylethyl-NH-propyl] | [2-fluorophenyl] | 493.5 373 |
| 9-47 | Me | [2,6-difluorobenzyl] | [3-methylbutan-2-yl-NH-propyl] | [2-fluorophenyl] | 459.5 373 |
| 9-48 | Me | [2,6-difluorobenzyl] | [3,5-bis(CF3)benzyl-NH-propyl] | [2-fluorophenyl] | 615.5 616 |
| 9-49 | Me | [2,6-difluorobenzyl] | [(iPr)2N-CH2CH2-NH-propyl] | [2-fluorophenyl] | 516.6 517 |
| 9-50 | Me | [2,6-difluorobenzyl] | [pyrrolidin-1-yl-propyl] | [2-fluorophenyl] | 443.5 373 |
| 9-51 | Me | [2,6-difluorobenzyl] | [benzo[1,3]dioxol-5-yl-CH2-piperazine-propyl] | [2-fluorophenyl] | 592.6 593 |

TABLE 9-continued

| | | | | | |
|---|---|---|---|---|---|
| 9-52 | Me | [2,6-difluorobenzyl with 2-methyl-morpholine-N-propyl] | | [2-fluorophenyl] | 487.5  373 |
| 9-53 | Me | [2,6-difluorobenzyl with piperidine-3-carboxamide-N-propyl] | | [2-fluorophenyl] | 500.5  501 |
| 9-54 | Me | [2,6-difluorobenzyl with N-(cyclopropylmethyl)-N-propyl-aminopropyl] | | [2-fluorophenyl] | 485.5  373 |
| 9-55 | Me | [2,6-difluorobenzyl with N,N-dibenzylaminopropyl] | | [2-fluorophenyl] | 569.6  372 |
| 9-56 | Me | [2,6-difluorobenzyl with 4-(3-chlorophenyl)piperazine-N-propyl] | | [2-fluorophenyl] | 569.0  569 |
| 9-57 | Me | [2,6-difluorobenzyl with N-sec-butyl-N-propyl-aminopropyl] | | [2-fluorophenyl] | 487.6  373 |
| 9-58 | Me | [2,6-difluorobenzyl with 4-(benzyloxycarbonyl)piperazine-N-propyl] | | [2-fluorophenyl] | 592.6  593 |
| 9-59 | Me | [2,6-difluorobenzyl with furan-2-ylmethylamino-propyl] | | [benzo[1,3]dioxol-5-yl] | 495.5  399 |

TABLE 9-continued
| | | | | | |
|---|---|---|---|---|---|
| 9-60 | Me | 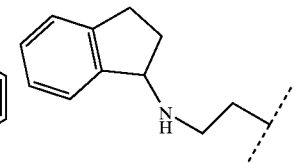 | 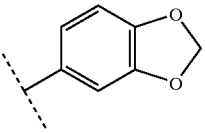 | 531.6 | 532 |
| 9-61 | Me | 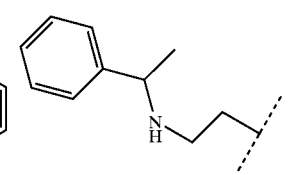 | 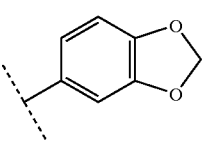 | 519.5 | 399 |
| 9-62 | Me | 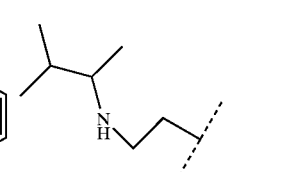 | 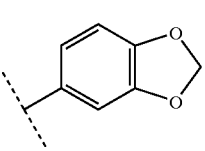 | 485.5 | 399 |
| 9-63 | Me | 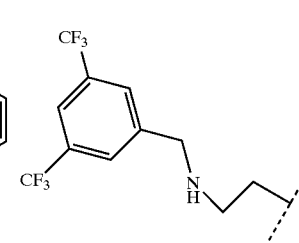 | 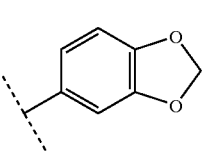 | 641.5 | 642 |
| 9-64 | Me | 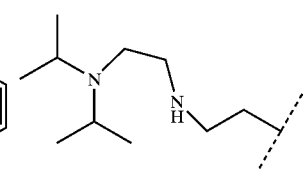 | 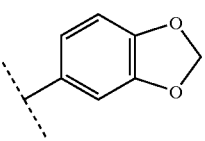 | 542.6 | 543 |
| 9-65 | Me | 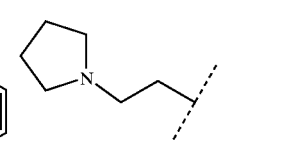 | 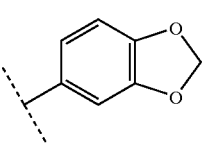 | 469.5 | 470 |
| 9-66 | Me | 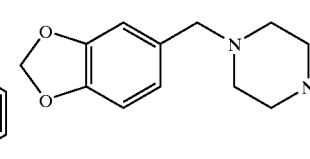 | 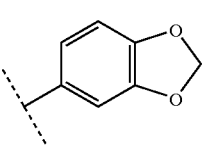 | 618.6 | 619 |
| 9-67 | Me | 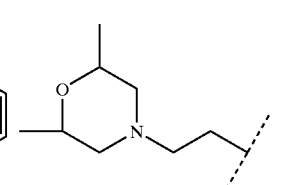 | 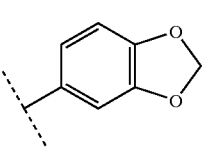 | 513.5 | 514 |

TABLE 9-continued
| | | | | | |
|---|---|---|---|---|---|
| 9-68 | Me |  |  |  | 526.5 527 |
| 9-69 | Me |  |  |  | 511.6 512 |
| 9-70 | Me |  |  |  | 595.0 595 |
| 9-71 | Me |  |  |  | 513.6 399 |
| 9-72 | Me |  |  |  | 618.6 619 |
| 9-73 | Me |  |  |  | 493.6 397 |
| 9-74 | Me |  |  |  | 529.6 397 |
| 9-75 | Me |  |  |  | 517.6 397 |

TABLE 9-continued

| # | R1 | R2 | R3 | MS1 | MS2 |
|---|----|----|----|-----|-----|
| 9-76 | Me | 2,6-difluorobenzyl | sec-butyl-NH-propyl | 4-isopropylphenyl | 483.6 | 397 |
| 9-77 | Me | 2,6-difluorobenzyl | 3,5-bis(trifluoromethyl)benzyl-NH-propyl | 4-isopropylphenyl | 639.6 | 640 |
| 9-78 | Me | 2,6-difluorobenzyl | diisopropylamino-ethyl-NH-propyl | 4-isopropylphenyl | 540.7 | 541 |
| 9-79 | Me | 2,6-difluorobenzyl | pyrrolidinyl-propyl | 4-isopropylphenyl | 467.6 | 468 |
| 9-80 | Me | 2,6-difluorobenzyl | 3,4-methylenedioxybenzyl-piperazinyl-propyl | 4-isopropylphenyl | 616.7 | 617 |
| 9-81 | Me | 2,6-difluorobenzyl | 2-methylmorpholinyl-propyl (via 6-aryl) | 4-isopropylphenyl | 511.6 | 512 |
| 9-82 | Me | 2,6-difluorobenzyl | 3-carbamoylpiperidinyl-propyl | 4-isopropylphenyl | 524.6 | 525 |
| 9-83 | Me | 2,6-difluorobenzyl | (cyclopropylmethyl)(propyl)amino-propyl | 4-isopropylphenyl | 509.6 | 510 |

TABLE 9-continued
| | | | | | |
|---|---|---|---|---|---|
| 9-84 | Me | 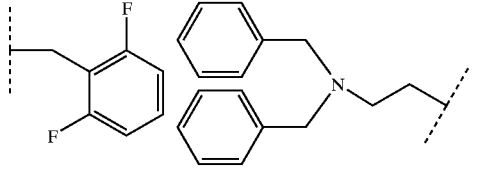 | 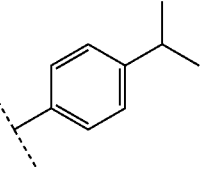 | 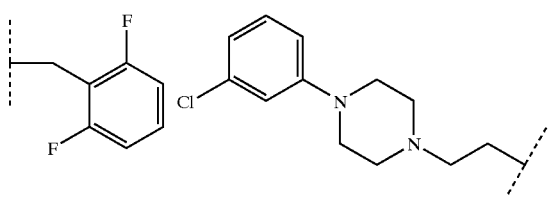 | 593.7 594 |
| 9-85 | Me | 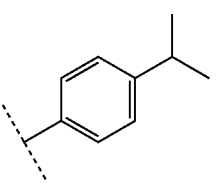 | 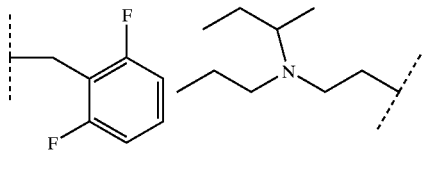 | | 593.1 593 |
| 9-86 | Me | 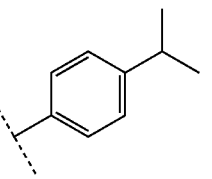 | 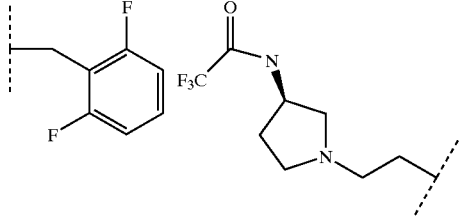 | | 511.7 512 |
| 9-87 | Me | 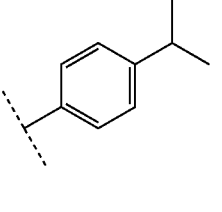 | 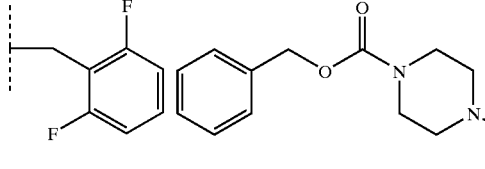 | | 578.6 579 |
| 9-88 | Me | 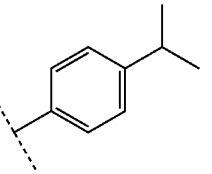 | 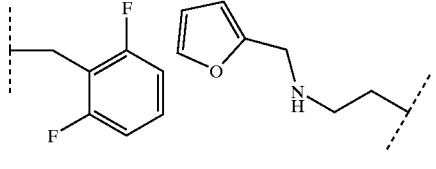 | | 616.7 617 |
| 9-89 | Me | 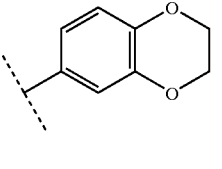 | 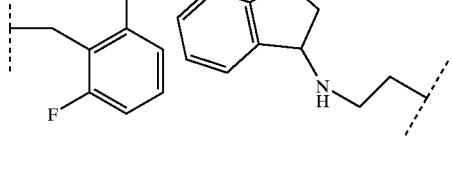 | | 509.5 413 |
| 9-90 | Me | 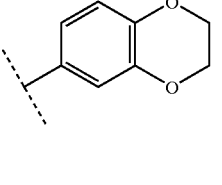 | | 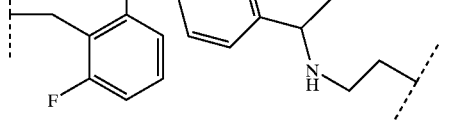 | 545.6 413 |
| 9-91 | Me | | 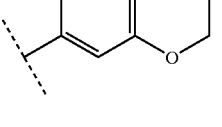 | | 533.6 413 |

TABLE 9-continued
| | | | | | |
|---|---|---|---|---|---|
| 9-92 | Me | 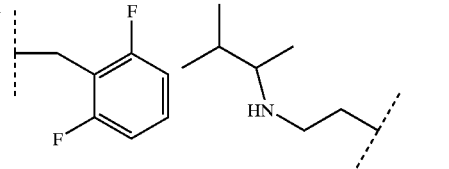 | 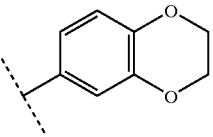 | 499.6 | 500 |
| 9-93 | Me | 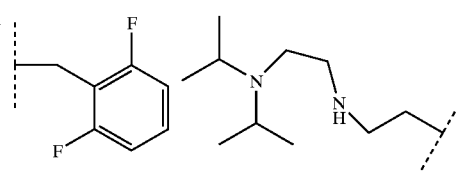 | 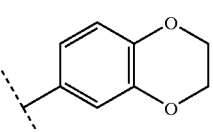 | 556.6 | 557 |
| 9-94 | Me | 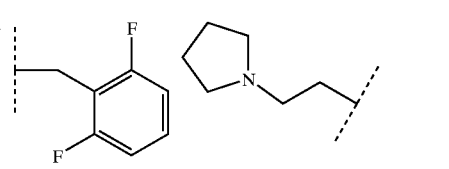 | 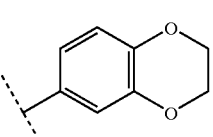 | 483.5 | 484 |
| 9-95 | Me | 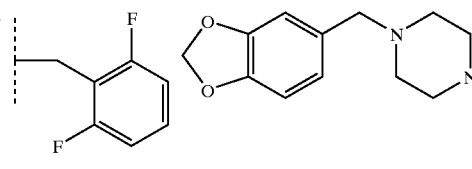 | 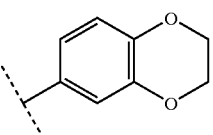 | 632.7 | 633 |
| 9-96 | Me | 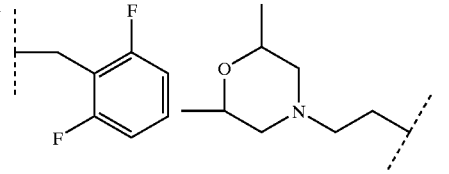 | 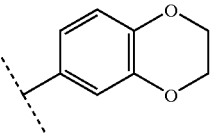 | 527.6 | 528 |
| 9-97 | Me | 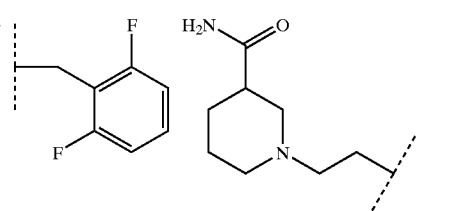 | 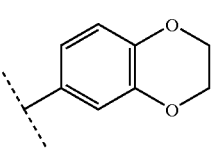 | 540.6 | 541 |
| 9-98 | Me | 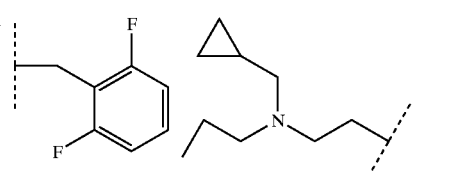 | 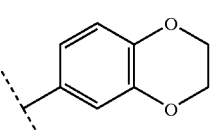 | 525.6 | 526 |
| 9-99 | Me | 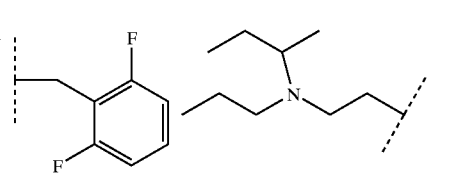 | 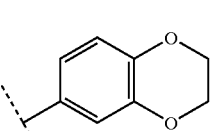 | 527.6 | 528 |
| 9-100 | Me | 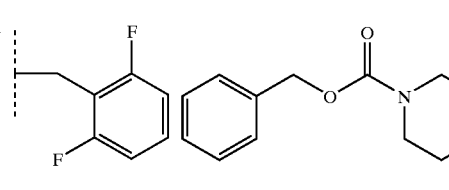 | 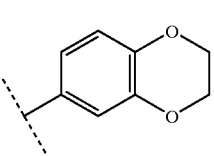 | 632.7 | 633 |

TABLE 9-continued

| | | | | | |
|---|---|---|---|---|---|
| 9-101 | Me | [2,6-difluorobenzyl with N-CO-CF3, 3-aminopyrrolidine] | | [2,3-dihydro-1,4-benzodioxine] | 554.5 555 |
| 9-102 | Me | [2,6-difluorobenzyl, 2-pyrrolidinyl] | | [1,3-benzodioxole] | 455.45 456 |
| 9-103 | Me | [2,6-difluorobenzyl, pyrrolidine-2-carbonyl-(4-methylpiperazine)] | | [3-OMe phenyl] | 581.66 |
| 9-104 | Me | [2,6-difluorobenzyl, N-benzyl-2-pyrrolidinyl] | | [1,3-benzodioxole] | 545.58 546 |
| 9-105 | Me | [2,6-difluorobenzyl, pyrrolidine-2-carboxamide-N-benzyl] | | [3-OMe phenyl] | 588.65 |
| 9-106 | Me | [2,6-difluorobenzyl, pyrrolidine-2-carboxamide-N-(pent-3-yl)] | | [3-OMe phenyl] | 568.66 |
| 9-107 | Me | [2,6-difluorobenzyl, pyrrolidine-2-carboxamide-N-isobutyl] | | [2-F-3-OMe phenyl] | 572.62 |
| 9-108 | Me | [2,6-difluorobenzyl, isobutoxypropyl-N-Me-N-(sec-butyl)amine] | | [3-OMe phenyl] | 543.65 544.3 |

TABLE 9-continued

| | | | | | |
|---|---|---|---|---|---|
| 9-109 | Me | 2,6-difluorobenzyl | pyridin-2-ylmethyl(sec-butyl)amine | 3-OMe-phenyl | 506.55 507.2 |
| 9-110 | Me | 2,6-difluorobenzyl | pyridin-2-ylmethyl-N-methyl(sec-butyl)amine | 3-OMe-phenyl | 520.57 521.2 |
| 9-111 | Me | 2,6-difluorobenzyl | prolyl-N-cyclopropylmethyl amide | 3-OMe-phenyl | 552.61 553.3 |
| 9-112 | Me | 2,6-difluorobenzyl | prolyl-N-sec-butyl amide | 3-OMe-phenyl | 554.63 555.3 |
| 9-113 | Me | 2,6-difluorobenzyl | prolyl-N-(1-methoxypropan-2-yl) amide | 3-OMe-phenyl | 570.63 571.3 |
| 9-114 | Me | 2,6-difluorobenzyl | 1,2-diphenylethylamine | 3-OMe-phenyl | 581.66 582.2 |
| 9-115 | Me | 2,6-difluorobenzyl | 2-chlorobenzylamine | 3-OMe-phenyl | 525.98 526.2 |
| 9-116 | Me | 2,6-difluorobenzyl | 4-chlorobenzylamine | 3-OMe-phenyl | 540.00 540.2 |

TABLE 9-continued

| | | | | | |
|---|---|---|---|---|---|
| 9-117 | Me | [3-Cl-benzyl-NH-propyl] | [3-OMe-phenyl] | 525.98 | 526.2 |
| 9-118 | Me | [4-F-2-Cl-benzyl-NH-propyl] | [3-OMe-phenyl] | 543.97 | 544.2 |
| 9-119 | Me | [2,3-diCl-benzyl-NH-propyl] | [3-OMe-phenyl] | 560.42 | 561.1 |
| 9-120 | Me | [3-Cl-phenethyl-NH-propyl] | [3-OMe-phenyl] | 540.00 | 540.2 |
| 9-121 | Me | [2,4-diCl-phenethyl-NH-propyl] | [3-OMe-phenyl] | 574.45 | 574.0 |
| 9-122 | Me | [benzyloxymethyl-butyl-NH-ethyl] | [3-OMe-phenyl] | 563.64 | 564.2 |
| 9-123 | Me | [cyclopropylmethyl-N-propyl-propyl] | [3-OMe-phenyl] | 497.58 | 498.2 |
| 9-124 | Me | [cyclohexyl-NH-propyl] | [3-OMe-phenyl] | 483.55 | 484.2 |
| 9-125 | Me | [cyclopentyl-NH-propyl] | [3-OMe-phenyl] | 469.52 | 470 |

TABLE 9-continued

| | | | | | |
|---|---|---|---|---|---|
| 9-126 | Me | [2,6-difluorobenzyl-N-ethyl-N-benzyl-propyl] | | [3-methoxyphenyl] | 519.58 520.2 |
| 9-127 | Me | [2,6-difluorobenzyl-N-ethyl-N-(pyridin-4-ylmethyl)-propyl] | | [3-methoxyphenyl] | 520.57 521.2 |
| 9-128 | Me | [2,6-difluorobenzyl-N,N-bis(pyridinylmethyl)-propyl] | | [3-methoxyphenyl] | 583.63 584.2 |
| 9-129 | Me | [2,6-difluorobenzyl-N-methyl-N-(2-hydroxy-2-phenylethyl)-propyl] | | [3-methoxyphenyl] | 535.58 536.2 |
| 9-130 | Me | [2,6-difluorobenzyl-N,N-bis(pyridin-2-ylmethyl)-propyl] | | [3-methoxyphenyl] | 583.63 584.2 |
| 9-131 | Me | [2,6-difluorobenzyl-N-isopropyl-N-(2-methoxyethyl)-propyl] | | [3-methoxyphenyl] | 501.57 502.2 |
| 9-132 | Me | [2,6-difluorobenzyl-N-isopropyl-N-(1-hydroxymethyl-2-methylpropyl)-propyl] | | [3-methoxyphenyl] | 529.62 528 |
| 9-133 | Me | [2,6-difluorobenzyl-pyrrolidine-2-carboxamide-N-(2-methoxyethyl)-propyl] | | [3-methoxyphenyl] | 556.60 557 |

TABLE 9-continued

| | | | | | |
|---|---|---|---|---|---|
| 9-134 | Me | [2,6-difluorobenzyl-pyrrolidine-N-(furan-2-ylmethyl)carboxamide] | | [3-methoxyphenyl] | 578.61 578 |
| 9-135 | Me | [2,6-difluorobenzyl-pyrrolidine-N-isopropylcarboxamide] | | [3-methoxyphenyl] | 540.60 541 |
| 9-136 | Me | [2,6-difluorobenzyl-(4-methylcyclohexyl)amino] | | [4-phenoxyphenyl] | 559.65 560.4 |
| 9-137 | Me | [2,6-difluorobenzyl-(3,3-dimethylbutan-2-yl)amino] | | [4-phenoxyphenyl] | 547.64 548.5 |
| 9-138 | Me | [2,6-difluorobenzyl-(2,2,2-trifluoroethyl)amino] | | [4-phenoxyphenyl] | 545.50 546.4 |
| 9-139 | Me | [2,6-difluorobenzyl-(4-fluorophenethyl)amino] | | [4-phenoxyphenyl] | 585.62 586.4 |
| 9-140 | Me | [2,6-difluorobenzyl-(3,3-diphenylpropyl)amino] | | [4-phenoxyphenyl] | 657.75 658.4 |
| 9-141 | Me | [2,6-difluorobenzyl-heptylamino] | | [4-phenoxyphenyl] | 561.66 562.6 |
| 9-142 | Me | [2,6-difluorobenzyl-(3-nitrobenzyl)amino] | | [4-phenoxyphenyl] | 598.60 599.3 |

TABLE 9-continued

| | | | | | |
|---|---|---|---|---|---|
| 9-143 | Me | [2,6-difluorobenzyl; 4-nitrobenzyl-NH-propyl] | | [4-phenoxyphenyl] | 598.60 599.3 |
| 9-144 | Me | [2,6-difluorobenzyl; methoxycarbonylethyl-NH-propyl] | | [4-phenoxyphenyl] | 549.57 550.4 |
| 9-145 | Me | [2,6-difluorobenzyl; 4-fluoro-2-trifluoromethylbenzyl-NH-propyl] | | [4-phenoxyphenyl] | 639.59 640.4 |
| 9-146 | Me | [2,6-difluorobenzyl; 4-phenylpiperazinyl-propyl] | | [4-phenoxyphenyl] | 608.68 609.4 |
| 9-147 | Me | [2,6-difluorobenzyl; pyridin-3-ylmethyl-N(cyanoethyl)-propyl] | | [4-phenoxyphenyl] | 607.65 608.2 |
| 9-148 | Me | [2,6-difluorobenzyl; methoxyethyl-N(ethyl)-propyl] | | [4-phenoxyphenyl] | 549.61 550.4 |
| 9-149 | Me | [2,6-difluorobenzyl; 4-methylcyclohexyl-NH-propyl] | | [2-fluorophenyl] | 485.54 486.4 |
| 9-150 | Me | [2,6-difluorobenzyl; tert-butyl-methyl-CH-NH-propyl] | | [2-fluorophenyl] | 473.53 474 |
| 9-151 | Me | [2,6-difluorobenzyl; trifluoroethyl-NH-propyl] | | [2-fluorophenyl] | 471.39 472.2 |

TABLE 9-continued

| | | | | | |
|---|---|---|---|---|---|
| 9-152 | Me | (2,6-difluorobenzyl) | 4-fluorophenethyl-NH-propyl | 2-fluorophenyl | 511.51 512.4 |
| 9-153 | Me | (2,6-difluorobenzyl) | 2,2-diphenylethyl-NH-propyl | 2-fluorophenyl | 583.65 584.2 |
| 9-154 | Me | (2,6-difluorobenzyl) | n-hexyl-NH-propyl | 2-fluorophenyl | 487.56 488.2 |
| 9-155 | Me | (2,6-difluorobenzyl) | 3-nitrobenzyl-NH-propyl | 2-fluorophenyl | 524.49 525.4 |
| 9-156 | Me | (2,6-difluorobenzyl) | 4-nitrobenzyl-NH-propyl | 2-fluorophenyl | 524.49 525.4 |
| 9-157 | Me | (2,6-difluorobenzyl) | 4-tert-butylcyclohexyl-NH-propyl | 2-fluorophenyl | 527.62 528.4 |
| 9-158 | Me | (2,6-difluorobenzyl) | methyl propanoate-NH-propyl | 2-fluorophenyl | 475.46 476.3 |
| 9-159 | Me | (2,6-difluorobenzyl) | 4-fluoro-2-trifluoromethylbenzyl-NH-propyl | 2-fluorophenyl | 565.48 566.4 |
| 9-160 | Me | (2,6-difluorobenzyl) | 4-phenylpiperazin-1-yl-propyl | 2-fluorophenyl | 534.57 535.4 |

TABLE 9-continued
| | | | | | |
|---|---|---|---|---|---|
| 9-161 | Me | 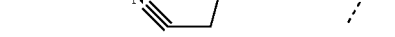 |  | 533.55 | 534.5 |
| 9-162 | Me | 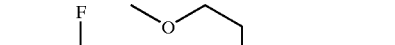 | 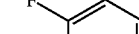 | 475.50 | 476.3 |
| 9-163 | Me |  |  | 499.55 | 500.4 |
| 9-164 | Me | 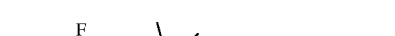 |  | 497.41 | 498.3 |
| 9-165 | Me |  | 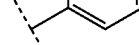 | 537.53 | 538.4 |
| 9-166 | Me |  |  | 609.67 | 610.3 |
| 9-167 | Me |  |  | 513.58 | 514.6 |
| 9-168 | Me |  |  | 550.51 | 551.3 |

TABLE 9-continued

| | | | | | |
|---|---|---|---|---|---|
| 9-169 | Me | [2,3-difluorobenzyl with 4-nitrobenzyl-NH-propyl linker] | | [benzo[1,3]dioxol-5-yl] | 550.51 551.2 |
| 9-170 | Me | [2,3-difluorobenzyl with 4-tert-butylcyclohexyl-NH-propyl linker] | | [benzo[1,3]dioxol-5-yl] | 553.64 554.3 |
| 9-171 | Me | [2,3-difluorobenzyl with methyl ester-NH-propyl linker] | | [benzo[1,3]dioxol-5-yl] | 501.48 502.3 |
| 9-172 | Me | [2,3-difluorobenzyl with 4-fluoro-2-CF₃-benzyl-NH-propyl linker] | | [benzo[1,3]dioxol-5-yl] | 591.50 592.4 |
| 9-173 | Me | [2,3-difluorobenzyl with 4-phenylpiperazinyl-propyl linker] | | [benzo[1,3]dioxol-5-yl] | 560.59 561.3 |
| 9-174 | Me | [2,3-difluorobenzyl with pyridin-3-ylmethyl-N(cyanoethyl)-propyl linker] | | [benzo[1,3]dioxol-5-yl] | 559.57 560.4 |
| 9-175 | Me | [2,3-difluorobenzyl with methoxyethyl-N(ethyl)-propyl linker] | | [benzo[1,3]dioxol-5-yl] | 501.52 502.3 |
| 9-176 | Me | [2,3-difluorobenzyl with 4-methylcyclohexyl-NH-propyl linker] | | [4-isopropylphenyl] | 509.63 510.6 |

TABLE 9-continued
| | | | | | |
|---|---|---|---|---|---|
| 9-177 | Me | 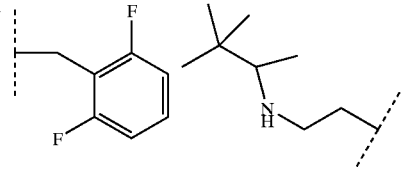 | 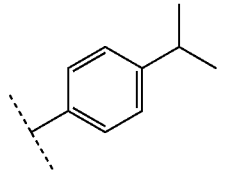 | 497.62 | 498.5 |
| 9-178 | Me | 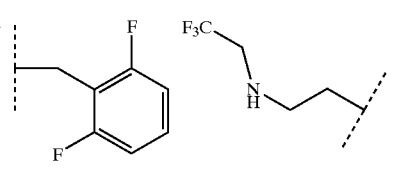 | 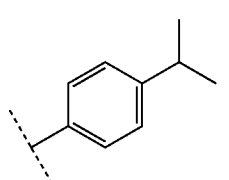 | 495.48 | 496.5 |
| 9-179 | Me | 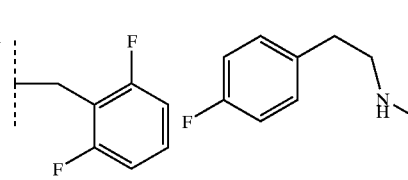 | 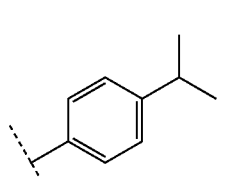 | 535.60 | 536.6 |
| 9-180 | Me | 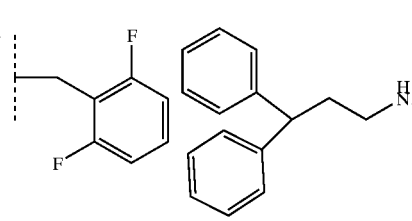 | 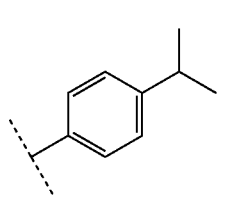 | 607.74 | 608.4 |
| 9-181 | Me | 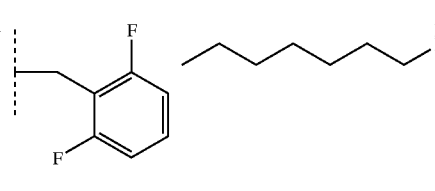 | 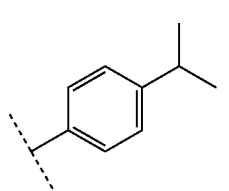 | 511.65 | 512.5 |
| 9-182 | Me | 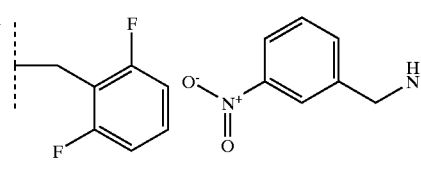 | 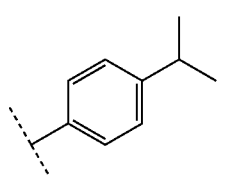 | 548.58 | 549.4 |
| 9-183 | Me | 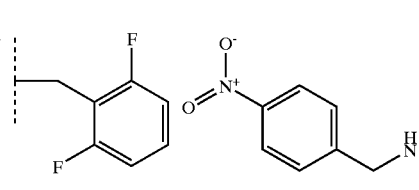 | 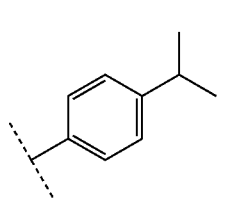 | 551.71 | 552.4 |
| 9-184 | Me | 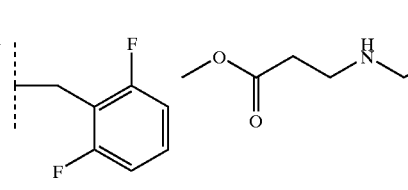 | 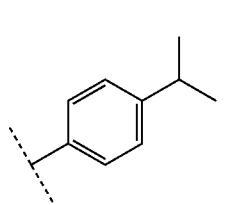 | 499.55 | 500.4 |

TABLE 9-continued
| | | | | | |
|---|---|---|---|---|---|
| 9-185 | Me | 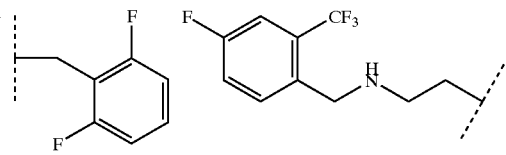 | 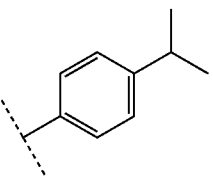 | 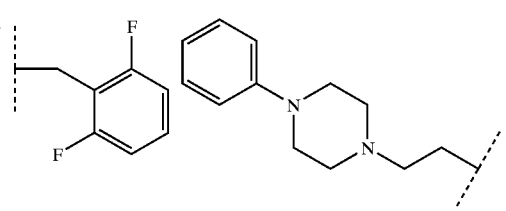 | 589.57 590.5 |
| 9-186 | Me | 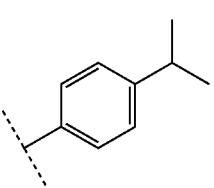 | 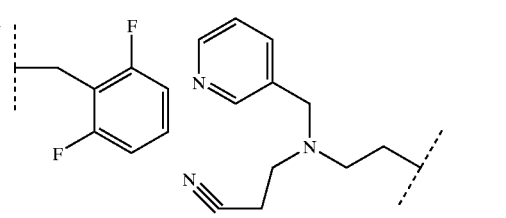 | 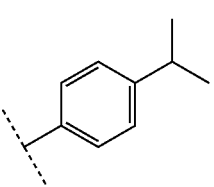 | 558.66 559.3 |
| 9-187 | Me | 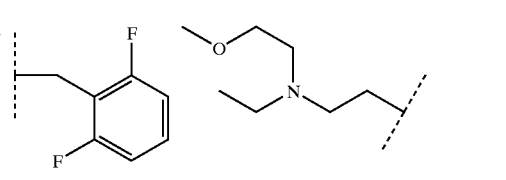 | 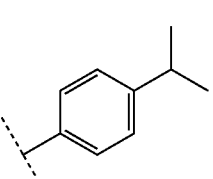 | 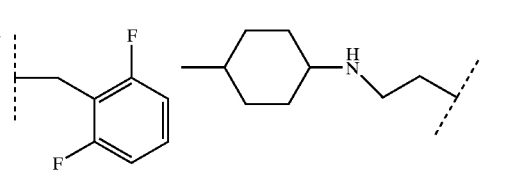 | 557.64 558.3 |
| 9-188 | Me | | 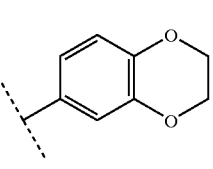 | | 499.59 500.4 |
| 9-189 | Me | | 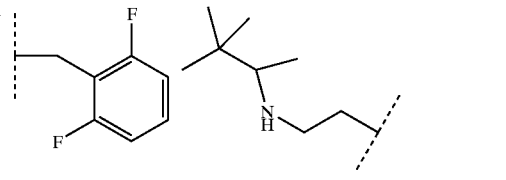 | 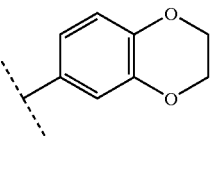 | 525.59 526.4 |
| 9-190 | Me | | 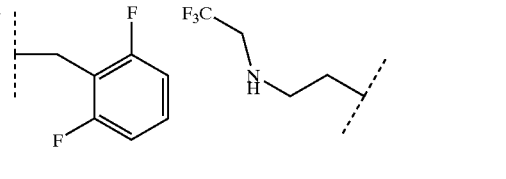 | | 513.58 514.2 |
| 9-191 | Me | | 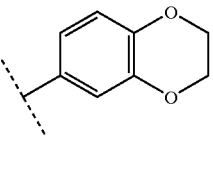 |  | 511.44 512.5 |
| 9-192 | Me | | 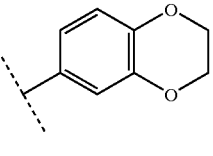 | | 551.56 552.3 |

TABLE 9-continued
| | | | | | |
|---|---|---|---|---|---|
| 9-193 | Me |  |  | 623.69 | 624.4 |
| 9-194 | Me |  | 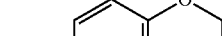 | 564.54 | 565.4 |
| 9-195 | Me |  |  | 564.54 | 565.4 |
| 9-196 | Me |  |  | 567.67 | 568.5 |
| 9-197 | Me |  | 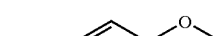 | 515.51 | 516.3 |
| 9-198 | Me |  |  | 605.53 | 606.4 |
| 9-199 | Me |  |  | 574.6 | 575.4 |
| 9-200 | Me | 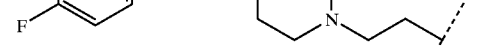 |  | 573.6 | 574.3 |

TABLE 9-continued

| | | | | | |
|---|---|---|---|---|---|
| 9-201 | Me | 2,6-difluorobenzyl | N-(2-methoxyethyl)-N-ethyl | 2,3-dihydrobenzo[1,4]dioxin-6-yl | 515.6 516.3 |
| 9-202 | Me | 2,6-difluorobenzyl | furan-2-ylmethylamino | 4-phenoxyphenyl | 543.56 544.2 |
| 9-203 | Me | 2,6-difluorobenzyl | 4-(3-chlorophenyl)piperazin-1-yl | 2,3-dihydrobenzo[1,4]dioxin-6-yl | 609.07 609.2 |
| 9-204 | Me | 2,6-difluorobenzyl | 3-(trifluoroacetylmethyl)pyrrolidin-1-yl | 2,3-dihydrobenzo[1,4]dioxin-6-yl | 593.54 595.2 |
| 9-205 | Me | 1-phenylethyl | N-methyl-N-(2-(pyridin-2-yl)ethyl) | 3-methoxyphenyl | 498.62 499.3 |
| 9-206 | Me | 1-phenylethyl | 2-(pyridin-2-yl)ethylamino | 3-methoxyphenyl | 484.59 485.2 |
| 9-207 | Me | 2,6-difluorobenzyl | N,N-dibenzyl | benzo[1,3]dioxol-5-yl | 595.64 596.4 |
| 9-208 | Me | 2,6-difluorobenzyl | 2-(pyridin-2-yl)pyrrolidin-1-yl | 3-methoxyphenyl | 532.58 533.2 |

TABLE 9-continued

| ID | | | | | |
|---|---|---|---|---|---|
| 9-209 | Me | (2,6-difluorobenzyl) | (3-(pyridin-2-yl)pyrrolidin-1-yl)propyl | (3-methoxyphenyl) | 532.58 533.2 |
| 9-210 | Me | (2,6-difluorobenzyl) | (2-(3-methylpyridin-2-yl)ethyl)-pyrrolidinyl | (benzo[d][1,3]dioxol-5-yl) | 574.62 575 |
| 9-211 | Me | (2,6-difluorobenzyl) | N-Boc-benzyl-aminopropyl | Br | 564.42 466/464 |
| 9-212 | Me | (2,6-difluorobenzyl) | N-Boc-benzyl-aminopropyl | Br | 564.42 464/466 |
| 9-213 | Me | (2,6-difluorobenzyl) | (2-ethylhexyl)aminopropyl | (4-phenoxyphenyl) | 575.69 576.3 |
| 9-214 | Me | (2,6-difluorobenzyl) | (2-(2-methoxyphenyl)ethyl)aminopropyl | (4-phenoxyphenyl) | 597.65 535.3 |
| 9-215 | Me | (2,6-difluorobenzyl) | (2-(2-methoxyphenyl)ethyl)aminopropyl | (4-phenoxyphenyl) | 597.65 598.2 |
| 9-216 | Me | (2,6-difluorobenzyl) | (2-(methoxy-phenoxyphenyl)ethyl)aminopropyl | (4-phenoxyphenyl) | 627.68 628.3 |

TABLE 9-continued
| | | | | | |
|---|---|---|---|---|---|
| 9-217 | Me | 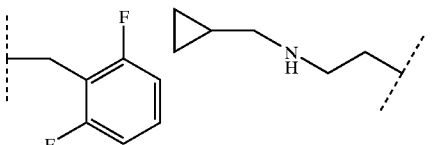 | 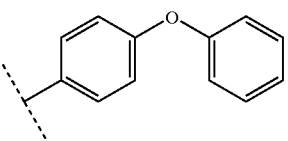 | 517.57 | 518.2 |
| 9-218 | Me | 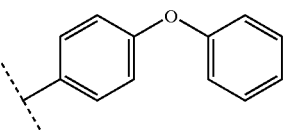 | 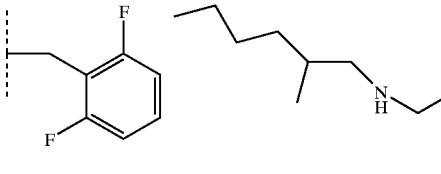 | 585.62 | 586.2 |
| 9-219 | Me | 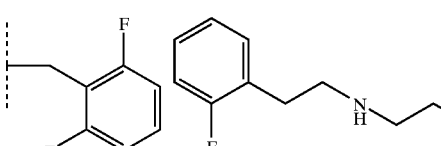 | 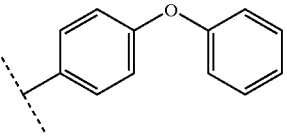 | 617.69 | 618.2 |
| 9-220 | Me | 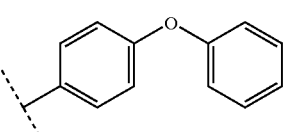 | 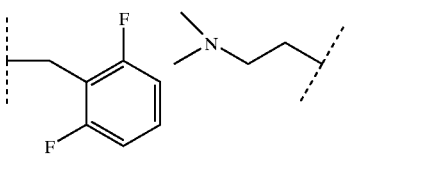 | 545.62 | 546.2 |
| 9-221 | Me | 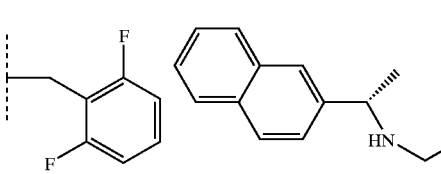 | 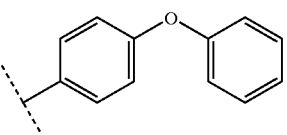 | 576.68 | 577.3 |
| 9-222 | Me | 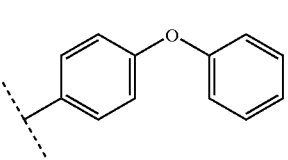 | 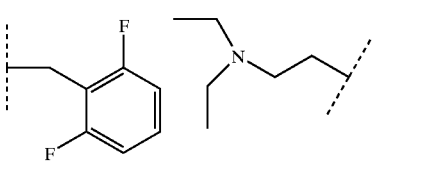 | 533.61 | 534.2 |
| 9-223 | Me | 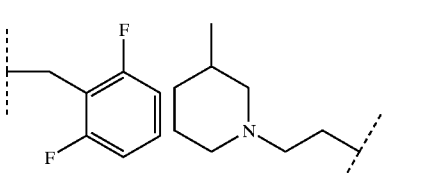 | 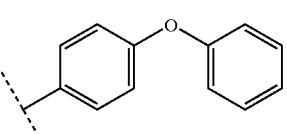 | 491.53 | 492.2 |
| 9-224 | Me | 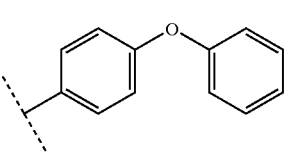 | 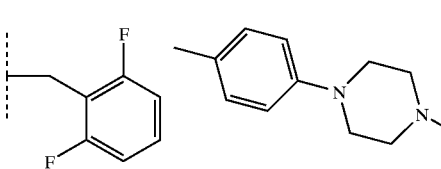 | 519.58 | 520.2 |
| 9-225 | Me | 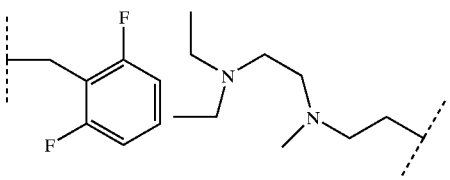 | 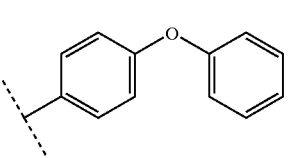 | 622.71 | 623.3 |

TABLE 9-continued

| | | | | | |
|---|---|---|---|---|---|
| 9-226 | Me | (2,6-difluorobenzyl); (2-ethylhexyl)aminopropyl | | (2-fluorophenyl) | 501.59 502.3 |
| 9-227 | Me | (2,6-difluorobenzyl); 2-(dimethylamino)ethylaminopropyl | | (2-fluorophenyl) | 460.49 461.2 |
| 9-228 | Me | (2,6-difluorobenzyl); 2-(2-methoxyphenyl)ethylaminopropyl | | (2-fluorophenyl) | 523.55 524.2 |
| 9-229 | Me | (2,6-difluorobenzyl); 2-(3,4-dimethoxyphenyl)ethylaminopropyl | | (2-fluorophenyl) | 553.57 554.2 |
| 9-230 | Me | (2,6-difluorobenzyl); cyclopropylmethylaminopropyl | | (2-fluorophenyl) | 443.46 444.2 |
| 9-231 | Me | (2,6-difluorobenzyl); 2-(2-fluorophenyl)ethylaminopropyl | | (2-fluorophenyl) | 511.51 512.2 |
| 9-232 | Me | (2,6-difluorobenzyl); (R)-1-(2-naphthyl)ethylaminopropyl | | (2-fluorophenyl) | 543.58 544.2 |
| 9-233 | Me | (2,6-difluorobenzyl); 2-methylaziridinylpropyl | | (2-fluorophenyl) | 429.44 430.1 |
| 9-234 | Me | (2,6-difluorobenzyl); 3-methylpiperidinylpropyl | | (2-fluorophenyl) | 471.52 472.2 |

TABLE 9-continued

| | | | | | |
|---|---|---|---|---|---|
| 9-235 | Me | 2,6-difluorobenzyl | N,N-diethyl-N'-methyl-ethylenediamine linker | 2-fluorophenyl | 502.57 503.3 |
| 9-236 | Me | 2,6-difluorobenzyl | 2-methylhexyl-NH linker | 2-fluorophenyl | 459.50 460.2 |
| 9-237 | Me | 2,6-difluorobenzyl | N,N-dimethylpropyl linker | 2-fluorophenyl | 417.42 418.1 |
| 9-238 | Me | 2,6-difluorobenzyl | N,N-diethylpropyl linker | 2-fluorophenyl | 445.48 446.1 |
| 9-239 | Me | 2,6-difluorobenzyl | 4-(4-methylphenyl)piperazinyl propyl | 2-fluorophenyl | 548.60 549.2 |
| 9-240 | Me | 2,6-difluorobenzyl | 4-propylpiperazinyl propyl | 2-fluorophenyl | 500.56 501.2 |
| 9-241 | Me | 2,6-difluorobenzyl | 2-ethylhexyl-NH linker | 1,3-benzodioxol-5-yl | 527.60 528.3 |
| 9-242 | Me | 2,6-difluorobenzyl | N,N-dimethyl-ethylenediamine-NH linker | 1,3-benzodioxol-5-yl | 486.51 487.2 |
| 9-243 | Me | 2,6-difluorobenzyl | 2-(2-methoxyphenyl)ethyl-NH linker | 1,3-benzodioxol-5-yl | 549.57 550.2 |

TABLE 9-continued
| | | | | | |
|---|---|---|---|---|---|
| 9-244 | Me | 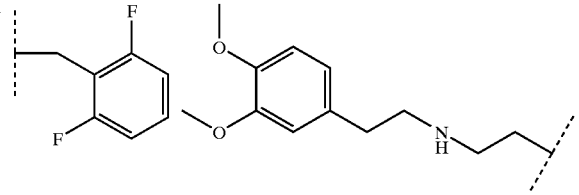 | 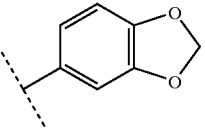 | 579.59 | 580.2 |
| 9-245 | Me | 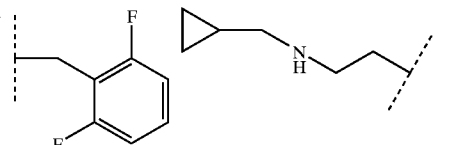 | 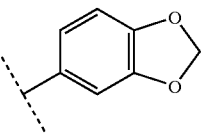 | 469.48 | 470.2 |
| 9-246 | Me | 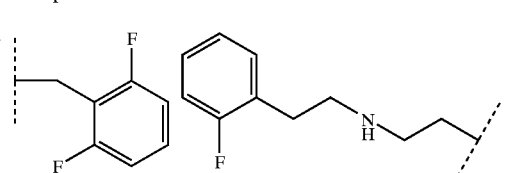 | 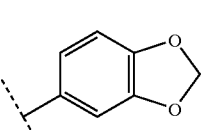 | 537.53 | 538.2 |
| 9-247 | Me | 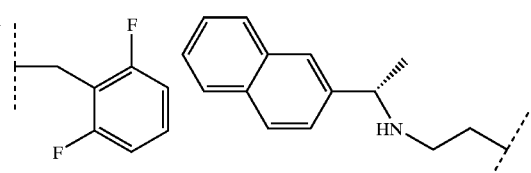 | 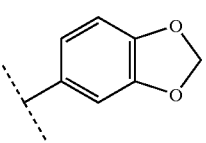 | 569.60 | 570.2 |
| 9-248 | Me | 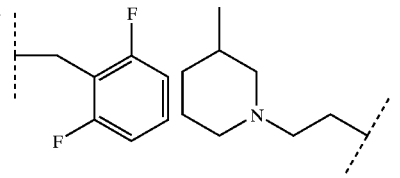 | 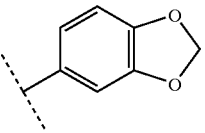 | 497.53 | 498.2 |
| 9-249 | Me | 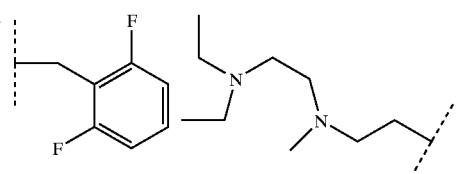 | 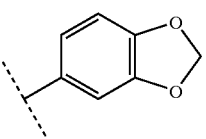 | 528.59 | 529.2 |
| 9-250 | Me | 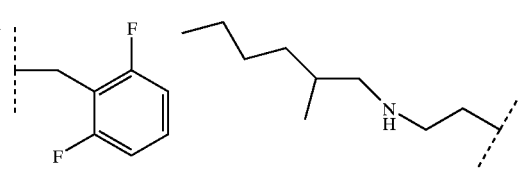 | 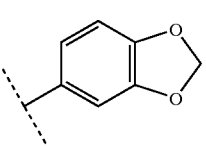 | 485.52 | 486.2 |
| 9-251 | Me | 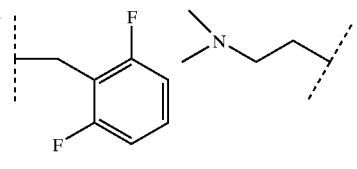 | 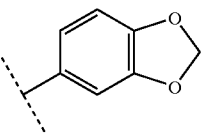 | 443.44 | 444.1 |
| 9-252 | Me | 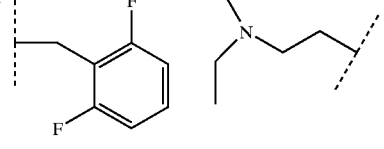 | 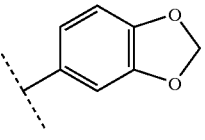 | 471.50 | 472.2 |

TABLE 9-continued

| ID | | | | | | |
|---|---|---|---|---|---|---|
| 9-253 | Me | | | | 574.62 | 575.2 |
| 9-254 | Me | | | | 526.58 | 527.2 |
| 9-255 | Me | | | | 525.68 | 526.3 |
| 9-256 | Me | | | | 484.58 | 485.2 |
| 9-257 | Me | | | | 547.64 | 548.3 |
| 9-258 | Me | | | | 577.66 | 578.3 |
| 9-259 | Me | | | | 467.55 | 468.2 |
| 9-260 | Me | | | | 535.60 | 536.2 |

TABLE 9-continued

| ID | R1 | R2 | R3 | MW calc | MW found |
|---|---|---|---|---|---|
| 9-261 | Me | 2,6-difluorobenzyl | (S)-1-(naphthalen-2-yl)ethyl-NH-propyl | 4-isopropylphenyl | 567.67 | 568.3 |
| 9-262 | Me | 2,6-difluorobenzyl | 3-methylpiperidin-1-yl-propyl | 4-isopropylphenyl | 495.61 | 496.2 |
| 9-263 | Me | 2,6-difluorobenzyl | N,N-diethylaminoethyl-N-methyl-propyl | 4-isopropylphenyl | 526.66 | 527.3 |
| 9-264 | Me | 2,6-difluorobenzyl | 2-methylhexyl-NH-propyl | 4-isopropylphenyl | 483.59 | 484.25 |
| 9-265 | Me | 2,6-difluorobenzyl | N,N-dimethylaminopropyl | 4-isopropylphenyl | 441.51 | 442.2 |
| 9-266 | Me | 2,6-difluorobenzyl | N,N-diethylaminopropyl | 4-isopropylphenyl | 469.57 | 470.3 |
| 9-267 | Me | 2,6-difluorobenzyl | 4-(p-tolyl)piperazin-1-yl-propyl | 4-isopropylphenyl | 572.69 | 573.3 |
| 9-268 | Me | 2,6-difluorobenzyl | 4-propylpiperazin-1-yl-propyl | 4-isopropylphenyl | 524.65 | 525.3 |

TABLE 9-continued
| | | | | | |
|---|---|---|---|---|---|
| 9-269 | Me | 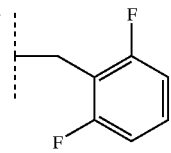 | 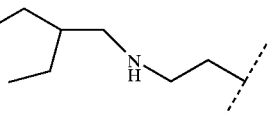 | 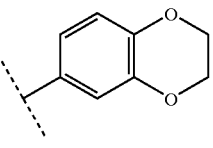 | 541.63 542.3 |
| 9-270 | Me | 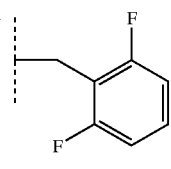 | 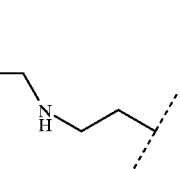 | 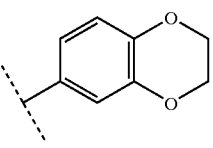 | 500.54 501.2 |
| 9-271 | Me | 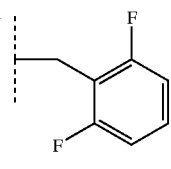 | 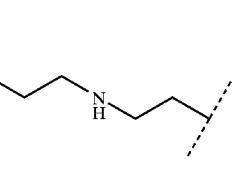 | 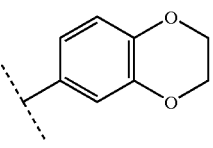 | 563.59 564.2 |
| 9-272 | Me | 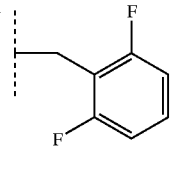 | 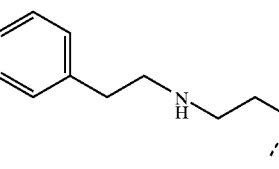 | 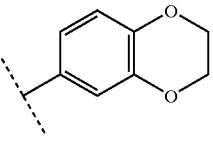 | 593.62 594.2 |
| 9-273 | Me | 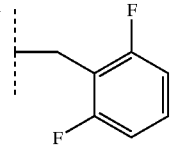 | 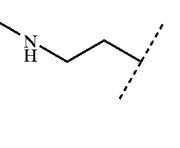 | 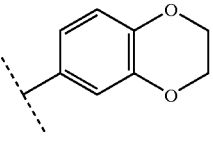 | 483.51 484.2 |
| 9-274 | Me | 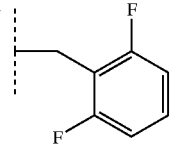 | 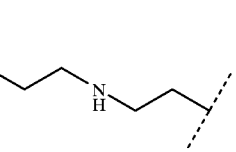 | 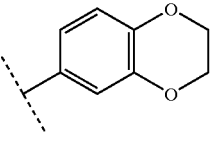 | 551.56 552.2 |
| 9-275 | Me | 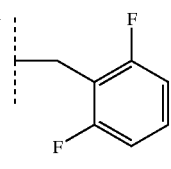 | 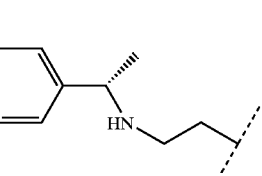 | 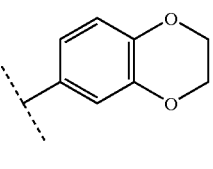 | 583.63 584.2 |
| 9-276 | Me | 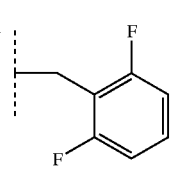 | 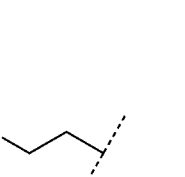 | 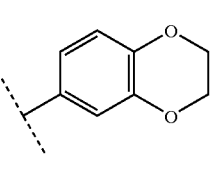 | 511.56 512.2 |
| 9-277 | Me | 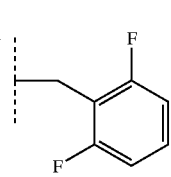 | 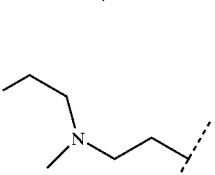 | 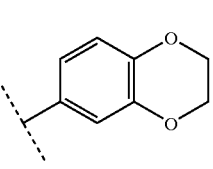 | 542.62 543.3 |

TABLE 9-continued
| | | | | | |
|---|---|---|---|---|---|
| 9-278 | Me | 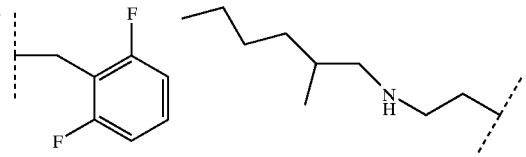 | 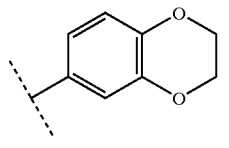 | 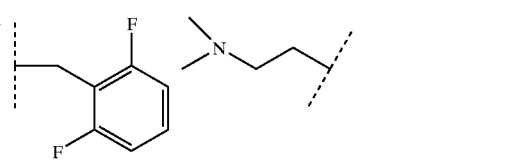 | 499.55 500.3 |
| 9-279 | Me | 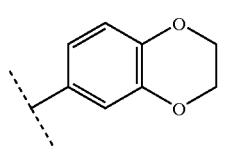 | 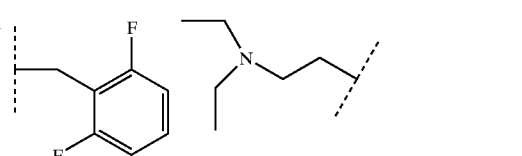 | 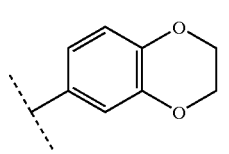 | 457.47 458.2 |
| 9-280 | Me | 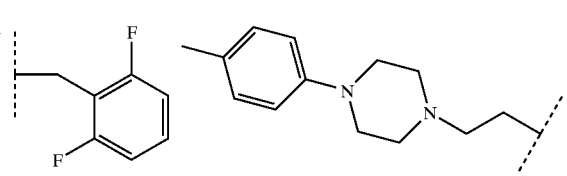 | 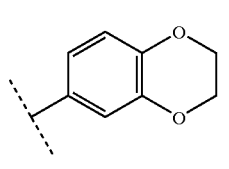 | 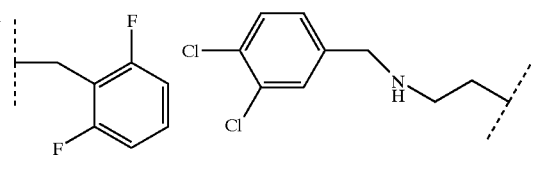 | 485.52 486.2 |
| 9-281 | Me | 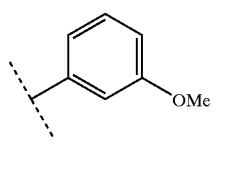 | 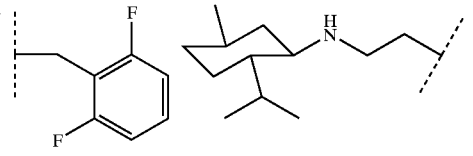 | 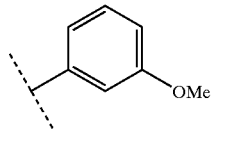 | 588.65 589.3 |
| 9-282 | Me | 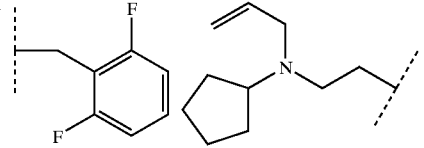 | 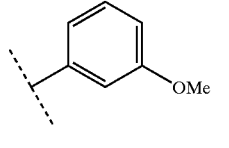 | 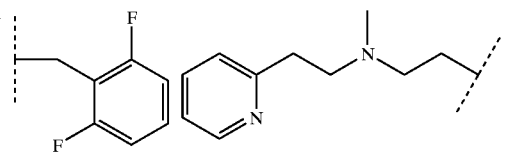 | 560.42 560 |
| 9-283 | Me | 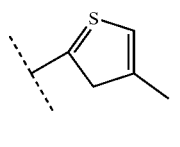 | 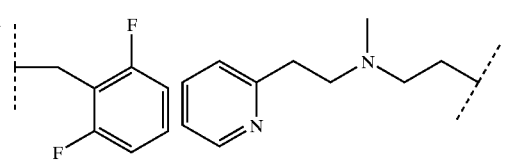 | 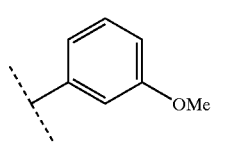 | 539.66 540 |
| 9-284 | Me | | | | 509.59 510 |
| 9-285 | Me | | | | 510.60 511.5 |
| 9-286 | Me | | | | 538.56 539.5 |

TABLE 9-continued

| | | | | | |
|---|---|---|---|---|---|
| 9-287 | Me | (2,6-difluorobenzyl) | (pyridin-2-yl-ethyl-N-methyl-propyl) | styryl | 516.58 517.4 |
| 9-288 | Me | (2,6-difluorobenzyl) | (phenyl-N-butyl-propyl) | 3-OMe-phenyl | 547.64 547 |
| 9-289 | Me | (2,6-difluorobenzyl) | (isobutoxyethyl-NH-propyl) | 2-F-3-OMe-phenyl | 519.56 534 |
| 9-290 | Me | (2,6-difluorobenzyl) | (benzyl-NH-(S)-methylpropyl) | 2-F-3-OMe-phenyl | 523.55 524.2 |
| 9-291 | Me | (2,6-difluorobenzyl) | (bis-(pyridin-2-ylmethyl)-N-propyl) | 2-F-3-OMe-phenyl | 615.65 616.3 |
| 9-292 | Me | (2,6-difluorobenzyl) | (benzyl-N-methyl-methylpropyl) | 2-F-phenyl | 507.55 508.2 |
| 9-293 | Me | (2,6-difluorobenzyl) | (pyridin-2-yl-ethyl-N-methyl-methylpropyl) | 2-F-phenyl | 522.56 523.6 |
| 9-294 | Me | (2,6-difluorobenzyl) | (pyridin-2-yl-ethyl-NH-methylpropyl) | 2-F-phenyl | 508.54 509.5 |
| 9-295 | Me | (2,6-difluorobenzyl) | (benzyl-N-methyl-methylpropyl) | 2-F-3-OMe-phenyl | 537.57 538.7 |

TABLE 9-continued

| | | | | | |
|---|---|---|---|---|---|
| 9-296 | Me | (2,6-difluorobenzyl) | (pyridin-2-yl-ethyl-N(Me)-CH(Me)CH2-) | (2-fluoro-3-methoxyphenyl) | 552.59 553.2 |
| 9-297 | Me | (2,6-difluorobenzyl) | (pyridin-2-yl-ethyl-NH-CH(Me)CH2-) | (2-fluoro-3-methoxyphenyl) | 538.56 539.5 |
| 9-298 | Me | (benzyl) | (benzyl-N(Me)-CH2CH2-) | (3-methoxyphenyl) | 469.58 470.3 |
| 9-299 | Me | (benzyl) | (pyridin-2-yl-ethyl-N(Me)-CH2CH2-) | (3-methoxyphenyl) | 484.59 485.3 |
| 9-300 | Me | (benzyl) | (pyridin-2-yl-ethyl-NH-CH2CH2-) | (3-methoxyphenyl) | 470.57 471.3 |
| 9-301 | Me | (2,6-difluorobenzyl) | (pyridin-2-yl-ethyl-N(Me)-CH2CH2-) | (4-tert-butylphenyl) | 546.65 547 |
| 9-302 | Me | (2,6-difluorobenzyl) | (N-propyl proline methyl ester) | (3-methoxyphenyl) | 513.53 514 |
| 9-303 | Me | (2,6-difluorobenzyl) | (N-cyclopropylmethyl-2-ethyl-pyrrolidine) | (3-methoxyphenyl) | 495.56 496 |
| 9-304 | Me | (2,6-difluorobenzyl) | (benzyl-NH-CH(Me)CH2-) | (2-fluoro-3-methoxyphenyl) | 523.55 524 |

TABLE 9-continued

| ID | | | | | MW | MS |
|---|---|---|---|---|---|---|
| 9-305 | Me | 2,6-difluorobenzyl | N-benzyl-N-methyl-(S)-butyl | | 2-fluoro-3-methoxyphenyl | 537.57 538 |
| 9-306 | Me | 2,6-difluorobenzyl | (S)-1-(propyl)-N-(sec-butyl)pyrrolidine-2-carboxamide | | 2-fluoro-3-methoxyphenyl | 572.62 573 |
| 9-307 | Me | 2,6-difluorobenzyl | N-benzyl-N-methyl-(R)-butyl | | 2-fluoro-3-methoxyphenyl | 537.57 538.3 |
| 9-308 | Me | 2,6-difluorobenzyl | 1-(cyclopropylmethyl)-2-ethylpyrrolidine | | Br | 505.36 505/507 |
| 9-309 | Me | 2,6-difluorobenzyl | 2-(pyridin-2-yl)ethyl-N-methyl-propyl | | 2-fluoro-3-methylphenyl | 522.56 523 |
| 9-310 | Me | 2,6-difluorobenzyl | N-benzyl-2-methylpropyl | | 3-methoxyphenyl | 505.56 506 |
| 9-311 | Me | 2,6-difluorobenzyl | N-(cyclopropylmethyl)-2-methylpropyl | | 3-methoxyphenyl | 469.52 470 |
| 9-312 | Me | 2,6-difluorobenzyl | N-benzyl-2-methylpropyl | | 3-methoxyphenyl | 505.56 506 |
| 9-313 | Me | 2,6-difluorobenzyl | N-(cyclopropylmethyl)-2-methylpropyl | | 3-methoxyphenyl | 469.52 470 |

TABLE 9-continued
| | | | | | |
|---|---|---|---|---|---|
| 9-314 | Me | 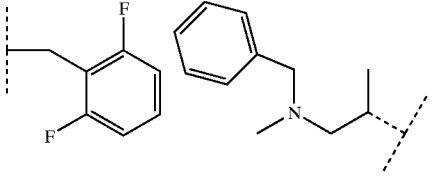 | 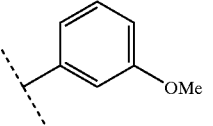 | 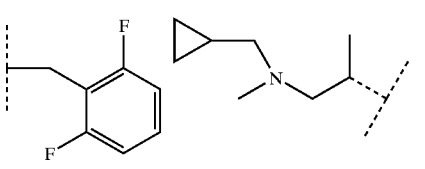 | 519.58 520 |
| 9-315 | Me | 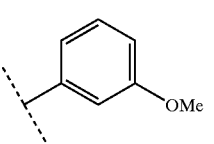 | | 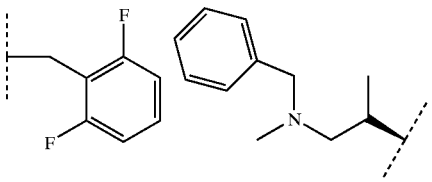 | 483.55 484 |
| 9-316 | Me | 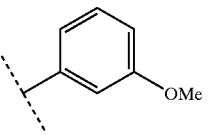 | | 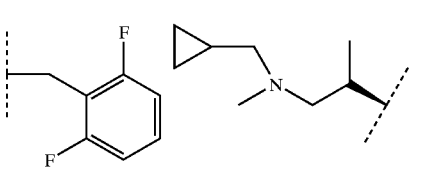 | 519.58 520 |
| 9-317 | Me | 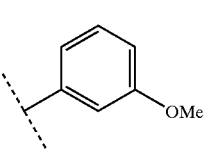 | | 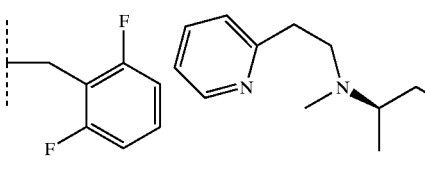 | 483.55 484 |
| 9-318 | Me | 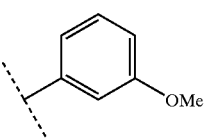 | | 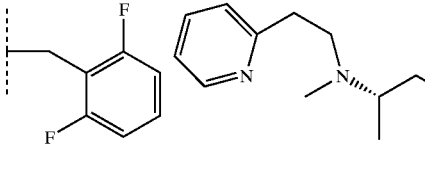 | 534.60 535.3 |
| 9-319 | Me | 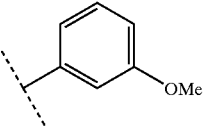 | | 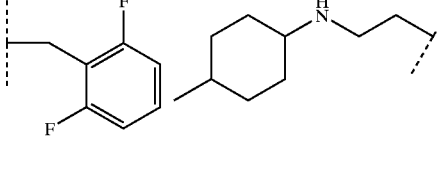 | 534.60 535.3 |
| 9-320 | Me | 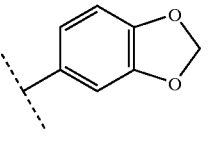 | | 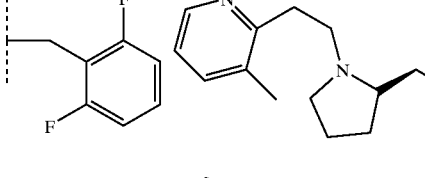 | 511.56 512.5 |
| 9-321 | Me | 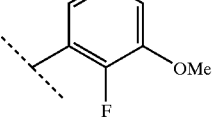 | | 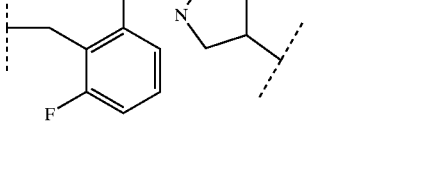 | 578.63 598 |
| 9-322 | Me | 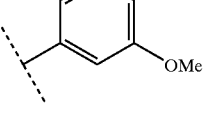 | | | 427.44 428.1 |

TABLE 9-continued

| | | | | | |
|---|---|---|---|---|---|
| 9-323 | Me | 2,6-difluorobenzyl / 1-benzylpyrrolidin-3-yl | | 3-MeO-phenyl | 517.57  518.2 |
| 9-324 | Me | 2,6-difluorobenzyl / 1-(pyridin-2-ylmethyl)pyrrolidin-3-yl | | 3-MeO-phenyl | 518.56  519.2 |
| 9-325 | Me | 2,6-difluorobenzyl / N-acetyl-lysine methyl ester derivative | | 4-phenoxyphenyl | 648.70  649.5 |
| 9-326 | Me | 2,6-difluorobenzyl / (5-methylhexan-2-yl)aminopropyl | | 4-phenoxyphenyl | 561.66  562.5 |
| 9-327 | Me | 2,6-difluorobenzyl / 1-(p-tolyl)ethylaminopropyl | | 4-phenoxyphenyl | 602.07  447.3 |
| 9-328 | Me | 2,6-difluorobenzyl / ethylaminopropyl | | 4-phenoxyphenyl | 491.53  447.4 |
| 9-329 | Me | 2,6-difluorobenzyl / allylaminopropyl | | 4-phenoxyphenyl | 503.54  447.3 |
| 9-330 | Me | 2,6-difluorobenzyl / isobutylaminopropyl | | 4-phenoxyphenyl | 519.58  447.2 |
| 9-331 | Me | 2,6-difluorobenzyl / 3-[4-(3-trifluoromethylphenyl)piperazin-1-yl]propyl | | 4-phenoxyphenyl | 676.68  677.5 |

TABLE 9-continued
| | | | | | |
|---|---|---|---|---|---|
| 9-332 | Me |  | 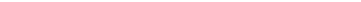 | 604.65 | 605.3 |
| 9-333 | Me | 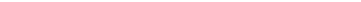 |  | 595.68 | 596.4 |
| 9-334 | Me |  |  | 632.70 | 633.4 |
| 9-335 | Me |  | 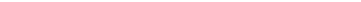 | 698.81 | 699.5 |
| 9-336 | Me | 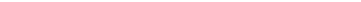 |  | 574.62 | 575.4 |
| 9-337 | Me | 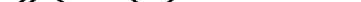 |  | 636.73 | 637.5 |
| 9-338 | Me |  | 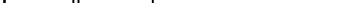 | 574.59 | 575.4 |
| 9-339 | Me | 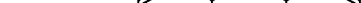 |  | 558.60 | 559.3 |

TABLE 9-continued
| | | | | | |
|---|---|---|---|---|---|
| 9-340 | Me | 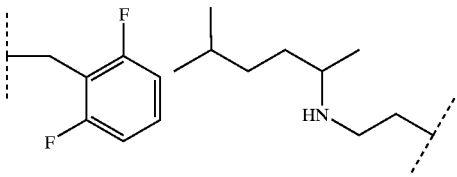 | 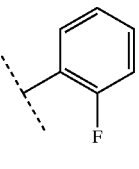 | 487.56 | 488.3 |
| 9-341 | Me | 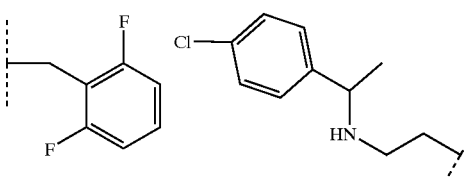 | 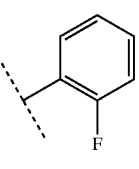 | 527.97 | 373.3 |
| 9-342 | Me | 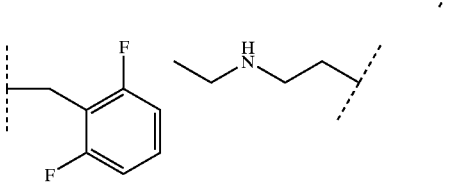 | 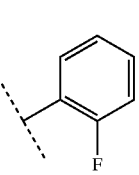 | 417.42 | 373.1 |
| 9-343 | Me | 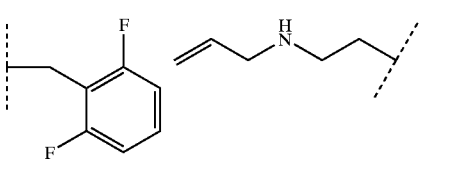 | 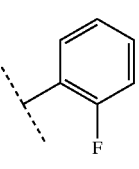 | 429.44 | 373.3 |
| 9-344 | Me | 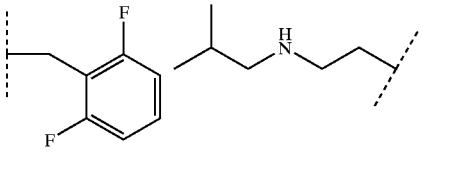 | 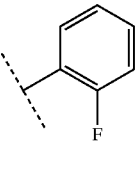 | 445.48 | 373.2 |
| 9-345 | Me | 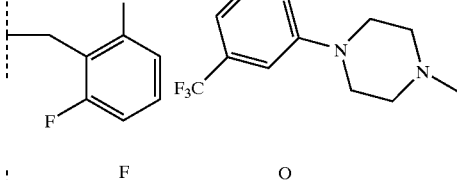 | 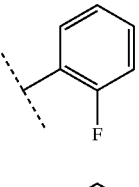 | 602.57 | 603.5 |
| 9-346 | Me | 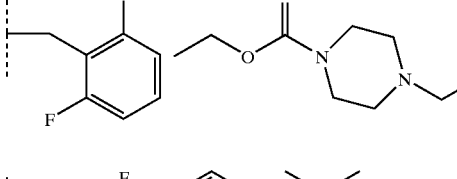 | 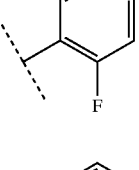 | 530.54 | 531.3 |
| 9-347 | Me | 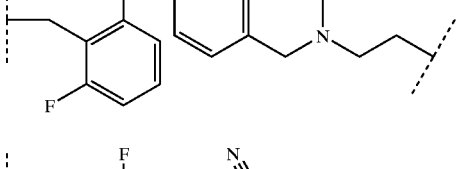 | 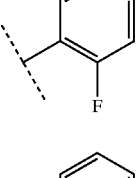 | 521.58 | 373.1 |
| 9-348 | Me | 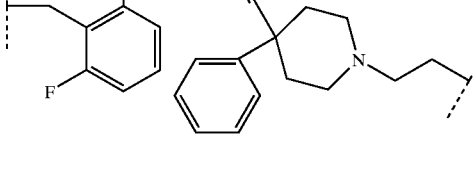 | 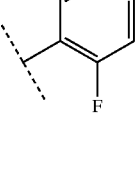 | 558.60 | 559.3 |

TABLE 9-continued

| ID | | | | | |
|---|---|---|---|---|---|
| 9-349 | Me | (2,6-difluorobenzyl) | (4-benzhydrylpiperazin-1-yl)propyl | (2-fluorophenyl) | 624.70 625.3 |
| 9-350 | Me | (2,6-difluorobenzyl) | N-(cyanomethyl)-N-methylaminopropyl | (2-fluorophenyl) | 442.43 373.3 |
| 9-351 | Me | (2,6-difluorobenzyl) | 3-acetamidopyrrolidin-1-yl propyl | (2-fluorophenyl) | 500.51 501.4 |
| 9-352 | Me | (2,6-difluorobenzyl) | 1-benzyl-3-(methylamino)pyrrolidinyl propyl | (2-fluorophenyl) | 562.63 563.4 |
| 9-353 | Me | (2,6-difluorobenzyl) | N-acetyl-lysine methyl ester | (benzo[d][1,3]dioxol-5-yl) | 600.61 601.3 |
| 9-354 | Me | (2,6-difluorobenzyl) | naphthalen-1-ylaminoethylaminopropyl | (benzo[d][1,3]dioxol-5-yl) | 584.62 585.2 |
| 9-355 | Me | (2,6-difluorobenzyl) | (4-chlorophenyl)(phenyl)methylaminopropyl | (benzo[d][1,3]dioxol-5-yl) | 616.06 201.3 |
| 9-356 | Me | (2,6-difluorobenzyl) | (5-methylhexan-2-yl)aminopropyl | (benzo[d][1,3]dioxol-5-yl) | 513.58 399.2 |

TABLE 9-continued
| | | | | | |
|---|---|---|---|---|---|
| 9-357 | Me | 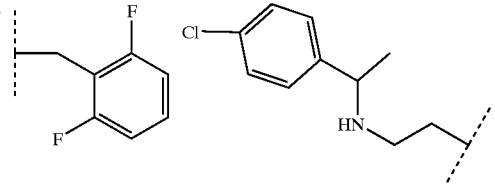 | 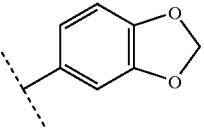 | 553.99 | 399.2 |
| 9-358 | Me | 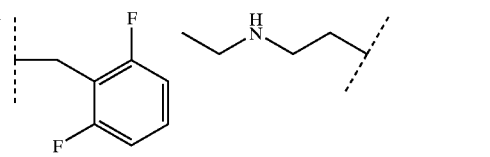 | 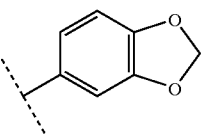 | 443.44 | 399.3 |
| 9-359 | Me | 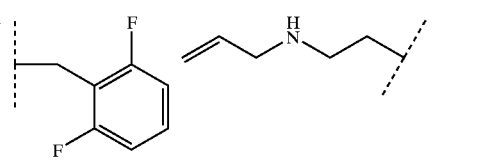 | 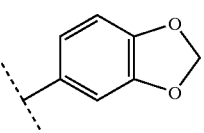 | 455.45 | 399.2 |
| 9-360 | Me | 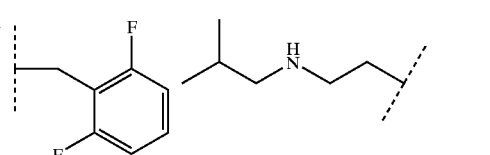 | 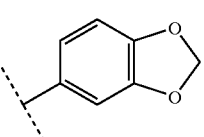 | 471.50 | 399.3 |
| 9-361 | Me | 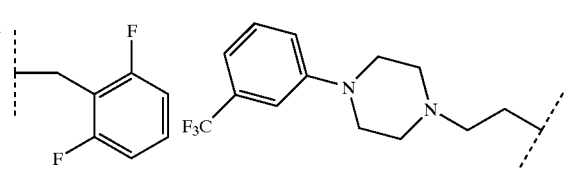 | 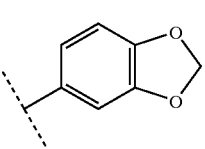 | 628.59 | 629.6 |
| 9-362 | Me | 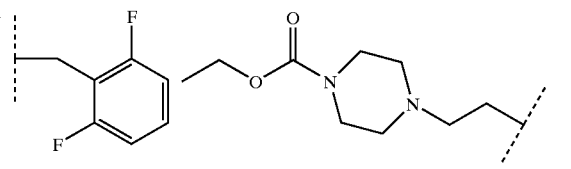 | 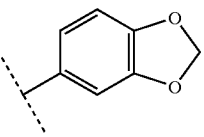 | 556.56 | 557.3 |
| 9-363 | Me | 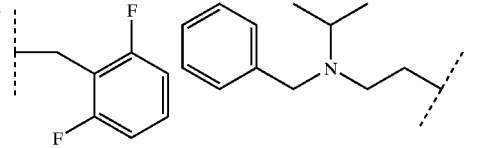 | 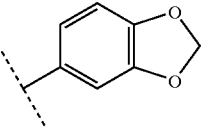 | 547.59 | 548.5 |
| 9-364 | Me | 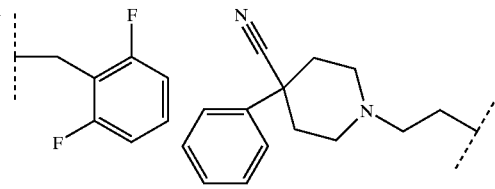 | 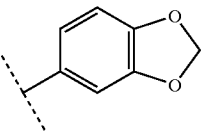 | 584.62 | 585.2 |
| 9-365 | Me | 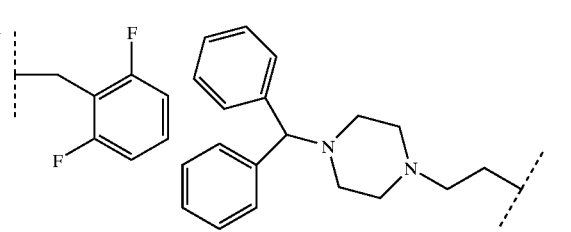 | 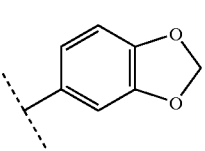 | 650.72 | 651.2 |

TABLE 9-continued
| | | | | | |
|---|---|---|---|---|---|
| 9-366 | Me | 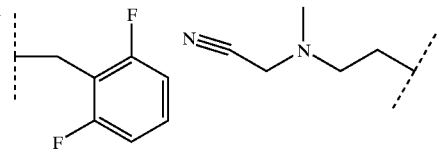 | 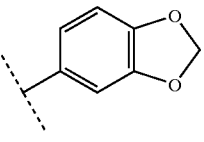 | 468.45 | 399.1 |
| 9-367 | Me | 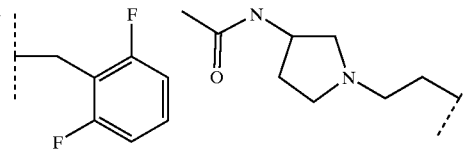 | 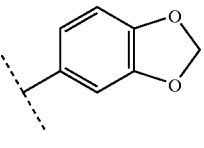 | 526.53 | 527.3 |
| 9-368 | Me | 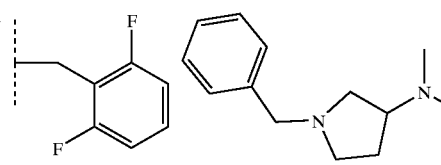 | 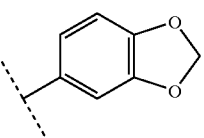 | 588.65 | 589.5 |
| 9-369 | Me | 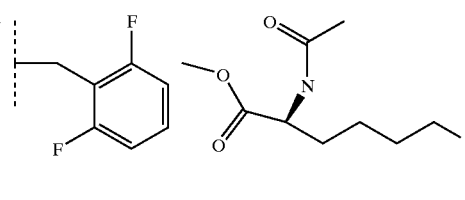 | 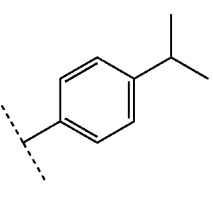 | 598.68 | 599.4 |
| 9-370 | Me | 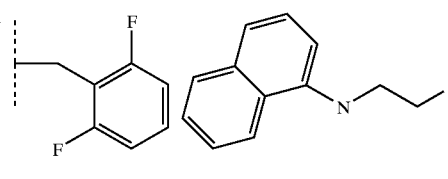 | 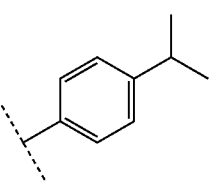 | 582.69 | 583.4 |
| 9-371 | Me | 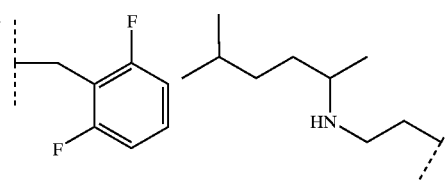 | 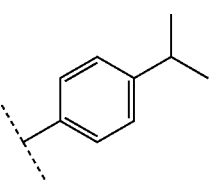 | 511.65 | 512.5 |
| 9-372 | Me | 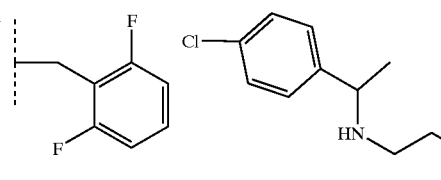 | 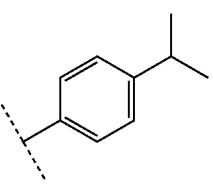 | 552.06 | 397 |
| 9-373 | Me | 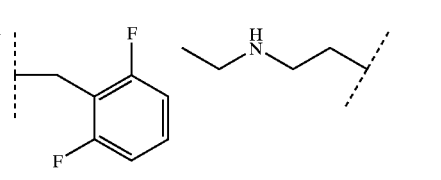 | 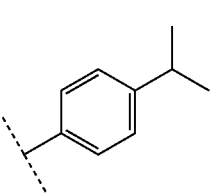 | 441.51 | 397.1 |

TABLE 9-continued

| | | | | | |
|---|---|---|---|---|---|
| 9-374 | Me | (2,6-difluorobenzyl with allyl-NH-propyl) | | (4-isopropylphenyl) | 453.53  397 |
| 9-375 | Me | (2,6-difluorobenzyl with isobutyl-NH-propyl) | | (4-isopropylphenyl) | 469.57  397.1 |
| 9-376 | Me | (2-F, 3-CF3 benzyl with 3-CF3-phenyl piperazinyl propyl) | | (4-isopropylphenyl) | 626.66  627.6 |
| 9-377 | Me | (2,6-difluorobenzyl-O-C(O)-piperazinyl propyl) | | (4-isopropylphenyl) | 554.63  555.5 |
| 9-378 | Me | (2,6-difluorobenzyl with N-benzyl-N-isopropyl propyl) | | (4-isopropylphenyl) | 545.67  546.4 |
| 9-379 | Me | (2,6-difluorobenzyl with 4-cyano-4-phenyl piperidinyl propyl) | | (4-isopropylphenyl) | 582.69  583.3 |
| 9-380 | Me | (2,6-difluorobenzyl with 4-benzhydryl piperazinyl propyl) | | (4-isopropylphenyl) | 648.79  649.6 |
| 9-381 | Me | (2,6-difluorobenzyl with 3-acetamido pyrrolidinyl propyl) | | (4-isopropylphenyl) | 524.60  525.5 |

TABLE 9-continued
| | | | | | |
|---|---|---|---|---|---|
| 9-382 | Me | 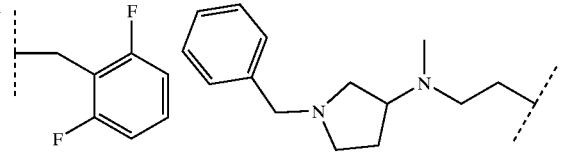 | 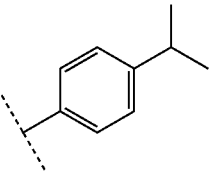 | 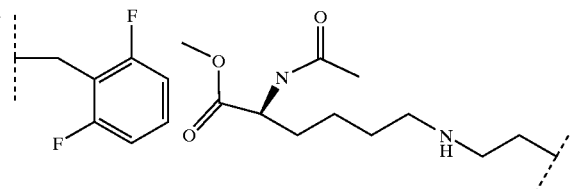 | 586.72 587.5 |
| 9-383 | Me | 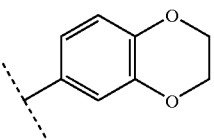 | 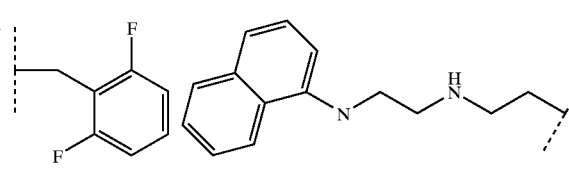 | 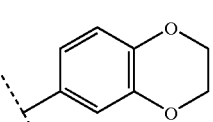 | 614.64 615.5 |
| 9-384 | Me | 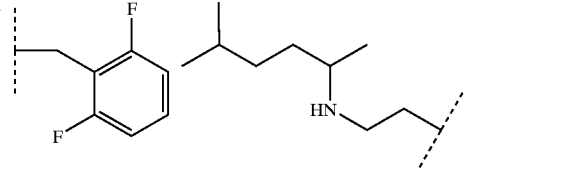 | 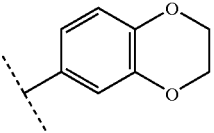 | 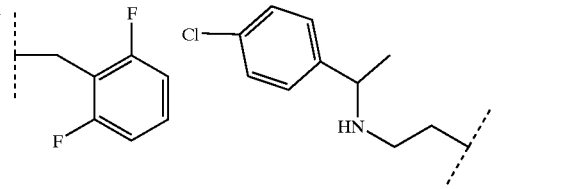 | 598.64 599.4 |
| 9-385 | Me | 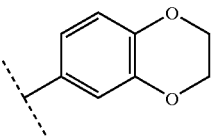 | 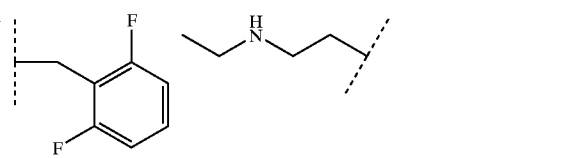 | 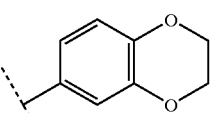 | 527.60 528.2 |
| 9-386 | Me | 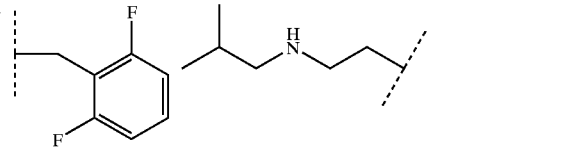 | 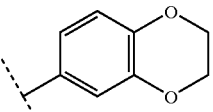 | 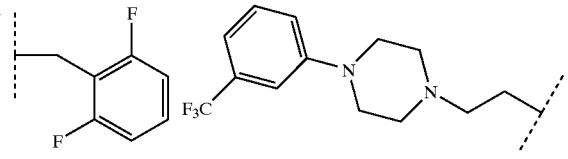 | 568.01 568.5 |
| 9-387 | Me | 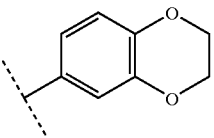 | | 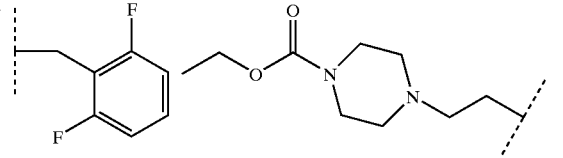 | 457.47 458 |
| 9-388 | Me | | | | 485.52 486.3 |
| 9-389 | Me | | | | 642.62 643.7 |
| 9-390 | Me | | | | 570.59 571 |

TABLE 9-continued

| | | | | | |
|---|---|---|---|---|---|
| 9-391 | Me | (2,6-difluorobenzyl) | (N-benzyl-N-isopropyl-aminopropyl) | | (2,3-dihydrobenzo[1,4]dioxin-6-yl) | 561.62 | 562.5 |
| 9-392 | Me | (2,6-difluorobenzyl) | (4-cyano-4-phenylpiperidin-1-yl-propyl) | | (2,3-dihydrobenzo[1,4]dioxin-6-yl) | 598.64 | 599.4 |
| 9-393 | Me | (2,6-difluorobenzyl) | (4-benzhydrylpiperazin-1-yl-propyl) | | (2,3-dihydrobenzo[1,4]dioxin-6-yl) | 664.74 | 665.5 |
| 9-394 | Me | (2,6-difluorobenzyl) | (3-acetamidopyrrolidin-1-yl-propyl) | | (2,3-dihydrobenzo[1,4]dioxin-6-yl) | 540.56 | 541.6 |
| 9-395 | Me | (2,6-difluorobenzyl) | (1-benzyl-3-(N-methylamino)pyrrolidinyl-propyl) | | (2,3-dihydrobenzo[1,4]dioxin-6-yl) | 602.67 | 603.6 |
| 9-396 | Me | (2,6-difluorobenzyl) | (N-cyanomethyl-N-methyl-aminopropyl) | | (2-fluorophenyl) | 442.43 | 373.3 |
| 9-397 | Me | (2,6-difluorobenzyl) | (pyridin-2-yl-ethylaminopropyl) | | (3-methoxyphenyl) | 520.57 | 521.3 |
| 9-398 | Me | (2,6-difluorobenzyl) | (pyridin-2-yl-ethylaminopropyl) | | (3-methoxyphenyl) | 520.57 | 521.2 |
| 9-399 | Me | (2,6-difluorobenzyl) | (sec-butylaminopropyl) | | (2-fluoro-3-methoxyphenyl) | 503.56 | 504.2 |

TABLE 9-continued

| | | | | | |
|---|---|---|---|---|---|
| 9-400 | Me | 2,6-difluorobenzyl | 2-(pyridin-2-yl)ethyl-pyrrolidin-3-yl | 3-MeO-phenyl | 532.58 533.2 |
| 9-401 | Me | 2,6-difluorobenzyl | (pyridin-2-ylmethyl)amino-isobutyl | 3-MeO-phenyl | 506.55 507 |
| 9-402 | Me | 2,6-difluorobenzyl | (pyridin-2-ylmethyl)amino-isobutyl | 3-MeO-phenyl | 506.55 507 |
| 9-403 | Me | 2,6-difluorobenzyl | Boc-amino-isobutyl | 3-MeO-phenyl | 515.55 416 |
| 9-404 | Me | 2,6-difluorobenzyl | N-benzylpyrrolidin-2-yl-ethyl | 3-MeO-phenyl | 531.6 532 |
| 9-405 | Me | 2,6-difluorobenzyl | N-benzylpyrrolidin-2-yl-ethyl | 3-MeO-phenyl | 549.5 550 |
| 9-406 | Me | 2,6-difluorobenzyl | N-(pyridin-2-ylmethyl)pyrrolidin-2-yl-ethyl | 3-MeO-phenyl | 550.57 550 |
| 9-407 | Me | 2,6-difluorobenzyl | N-methyl-N-(2-(pyridin-2-yl)ethyl)amino-isobutyl | 3-MeO-phenyl | 534.60 535 |
| 9-408 | Me | 2,6-difluorobenzyl | N-methyl-N-(2-(pyridin-2-yl)ethyl)amino-isobutyl | 3-MeO-phenyl | 534.60 535 |

TABLE 9-continued

| | | | | | |
|---|---|---|---|---|---|
| 9-409 | Me | 2,6-difluorobenzyl; N-methyl-N-((pyridin-2-yl)methyl)-propan-2-yl | | 2-fluoro-3-methoxyphenyl | 538.56 539 |
| 9-410 | Me | 2,6-difluorobenzyl; N-((pyridin-2-yl)methyl)amino-propan-2-yl | | 2-fluoro-3-methoxyphenyl | 524.54 525 |
| 9-411 | Me | 2,6-difluorobenzyl; prolyl-N-sec-butylamide | | 3-methoxyphenyl | 554.63 555 |
| 9-412 | Me | 2,6-difluorobenzyl; pyrrolidin-2-yl | | H | 335.35 336 |
| 9-413 | Me | 2,6-difluorobenzyl; 3-methylpyridin-2-yl-ethyl-pyrrolidinyl | | Br | 533.41 533/535 |
| 9-414 | Me | 2,6-difluorobenzyl; pyrrolidin-2-yl | | 2-fluoro-3-methoxyphenyl | 459.46 460 |
| 9-415 | Me | 2,6-difluorobenzyl; 3-methylpyridin-2-yl-ethyl-pyrrolidinyl | | H | 454.51 455 |
| 9-416 | Me | 2,6-difluorobenzyl; (pyridin-2-yl)ethyl-N-methylamino | | 4-methoxymethylphenyl | 534.60 535.5 |
| 9-417 | Me | 2,6-difluorobenzyl; (pyridin-2-yl)ethyl-N-methylamino | | 3-methoxyphenyl | 520.57 521.5 |

TABLE 9-continued

| | | | | | |
|---|---|---|---|---|---|
| 9-418 | Me | [2,6-difluorobenzyl] | [3-chlorobenzyl-NH-CH(Me)-CH2-] | [2-fluoro-3-methoxyphenyl] | 557.99 558 |
| 9-419 | Me | [2,6-difluorobenzyl] | [4-hydroxybenzyl-NH-CH(Me)-CH2-] | [2-fluoro-3-methoxyphenyl] | 539.55 540 |
| 9-420 | Me | [2,6-difluorobenzyl] | [2-methoxybenzyl-NH-CH(Me)-CH2-] | [2-fluoro-3-methoxyphenyl] | 553.57 554 |
| 9-421 | Me | [2,6-difluorobenzyl] | [2-methylbenzyl-NH-CH(Me)-CH2-] | [2-fluoro-3-methoxyphenyl] | 537.57 538 |
| 9-422 | Me | [2,6-difluorobenzyl] | [3-hydroxybenzyl-NH-CH(Me)-CH2-] | [2-fluoro-3-methoxyphenyl] | 539.55 540 |
| 9-423 | Me | [2,6-difluorobenzyl] | [4-methoxybenzyl-NH-CH(Me)-CH2-] | [2-fluoro-3-methoxyphenyl] | 553.57 554 |
| 9-424 | Me | [2,6-difluorobenzyl] | [2-fluorobenzyl-NH-CH(Me)-CH2-] | [2-fluoro-3-methoxyphenyl] | 541.54 542 |
| 9-425 | Me | [2,6-difluorobenzyl] | [4-fluorobenzyl-NH-CH(Me)-CH2-] | [2-fluoro-3-methoxyphenyl] | 541.54 542 |
| 9-426 | Me | [2,6-difluorobenzyl] | [N-propyl-prolinamide-isopropyl] | [3-methoxyphenyl] | 568.66 569 |

TABLE 9-continued

| | | | | | |
|---|---|---|---|---|---|
| 9-427 | Me | (2,6-difluorobenzyl); N-(4-chlorophenyl)(phenyl)methyl-N-propyl | | 4-phenoxyphenyl | 664.14 664.2 |
| 9-428 | Me | (2,6-difluorobenzyl); N-(4-chlorophenyl)(phenyl)methyl-N-propyl | | 4-isopropylphenyl | 614.13 614.2 |
| 9-429 | Me | (2,6-difluorobenzyl); N-(4-chlorophenyl)(phenyl)methyl-N-propyl | | 2-fluorophenyl | 590.04 590.2 |
| 9-430 | Me | (2,6-difluorobenzyl); N-(4-chlorophenyl)(phenyl)methyl-N-propyl | | 2,3-dihydrobenzo[1,4]dioxin-6-yl | 630.08 630.2 |
| 9-431 | Me | (2,6-difluorobenzyl); N-allyl-N-propyl | | 2,3-dihydrobenzo[1,4]dioxin-6-yl | 469.48 470.2 |
| 9-432 | Me | (2,6-difluorobenzyl); N-(cyanomethyl)-N-methyl-N-propyl | | 2,3-dihydrobenzo[1,4]dioxin-6-yl | 482.48 483.1 |
| 9-433 | Me | (2,6-difluorobenzyl); N-(cyanomethyl)-N-methyl-N-propyl | | 4-isopropylphenyl | 466.52 467.2 |

TABLE 9-continued

| | | | | | |
|---|---|---|---|---|---|
| 9-434 | Me | (2,6-difluorobenzyl)-N(Me)-CH2-CN group | | 4-phenoxyphenyl | 516.54 517.2 |
| 9-435 | Me | (2,6-difluorobenzyl)-N(CH2Ph)2 with (S)-methyl | | 3-OMe phenyl | 595.68 596.3 |
| 9-436 | Me | (2,6-difluorobenzyl)-N(CH2Ph)2 with (R)-methyl | | 3-OMe phenyl | 595.68 596.3 |
| 9-437 | Me | (2,6-difluorobenzyl)-NH-CH2CH2-(2-pyridyl) (S)-Me | | 2-F-3-OMe phenyl | 538.56 539.2 |
| 9-438 | Me | (2,6-difluorobenzyl)-N(Me)-CH2CH2-(2-pyridyl) (S)-Me | | 2-F-3-OMe phenyl | 552.59 553.3 |
| 9-439 | Me | (2,6-difluorobenzyl)-NH-CH2CH2-(2-pyridyl) (S)-Me | | 3-OMe phenyl | 506.55 507.2 |
| 9-440 | Me | (2,6-difluorobenzyl)-NH-CH2CH2-(2-pyridyl) (R)-Me | | 3-OMe phenyl | 506.55 507.2 |
| 9-441 | Me | (2,6-difluorobenzyl)-N(Me)-CH2-(2-pyridyl) (S)-Me | | 3-OMe phenyl | 520.57 521.2 |
| 9-442 | Me | (2,6-difluorobenzyl)-N(Me)-CH2-(2-pyridyl) (R)-Me | | 3-OMe phenyl | 520.57 521.2 |

TABLE 9-continued

| | | | | | |
|---|---|---|---|---|---|
| 9-443 | Me | [2,6-difluorobenzyl] | [N,N-dimethyl-benzyl-substituted chain] | [2-fluoro-3-methoxyphenyl] | 537.57 538 |
| 9-444 | Me | [2,6-difluorobenzyl] | [4-hydroxybenzyl-NH-chain] | [3-methoxyphenyl] | 521.56 522.2 |
| 9-445 | Me | [2,6-difluorobenzyl] | [3-hydroxybenzyl-NH-chain] | [3-methoxyphenyl] | 521.56 522.2 |
| 9-446 | Me | [2,6-difluorobenzyl] | [2-fluorobenzyl-NH-chain] | [3-methoxyphenyl] | 523.55 524.2 |
| 9-447 | Me | [2,6-difluorobenzyl] | [4-fluorobenzyl-NH-chain] | [3-methoxyphenyl] | 523.55 524.2 |
| 9-448 | Me | [2,6-difluorobenzyl] | [3-fluorobenzyl-NH-chain] | [3-methoxyphenyl] | 523.55 524.2 |
| 9-449 | Me | [2,6-difluorobenzyl] | [2-cyanobenzyl-NH-chain] | [3-methoxyphenyl] | 530.57 531.2 |
| 9-450 | Me | [2,6-difluorobenzyl] | [3-cyanobenzyl-NH-chain] | [3-methoxyphenyl] | 530.57 531.2 |
| 9-451 | Me | [2,6-difluorobenzyl] | [4-cyanobenzyl-NH-chain] | [3-methoxyphenyl] | 530.57 531.2 |

TABLE 9-continued

| ID | R | Group 2 | Group 3 | MW | MS |
|---|---|---|---|---|---|
| 9-452 | Me | 2,6-difluorobenzyl–(4-methyl-3-methylphenyl)-CH2-NH-CH2-CH(Me)- | 3-MeO-phenyl | 533.61 | 534.3 |
| 9-453 | Me | 2,6-difluorobenzyl–(2,5-dimethylphenyl)-CH2-NH-CH2-CH(Me)- | 3-MeO-phenyl | 533.61 | 534.3 |
| 9-454 | Me | 2,6-difluorobenzyl–(3,5-dimethylphenyl)-CH2-NH-CH2-CH(Me)- | 3-MeO-phenyl | 533.61 | 534.2 |
| 9-455 | Me | 2,6-difluorobenzyl–(2-methoxyphenyl)-CH2-NH-CH2-CH(Me)- | 3-MeO-phenyl | 535.58 | 536.2 |
| 9-456 | Me | 2,6-difluorobenzyl–(2,6-dimethylphenyl)-CH2-NH-CH2-CH(Me)- | 3-MeO-phenyl | 547.64 | 548.3 |
| 9-457 | Me | 2,6-difluorobenzyl–(4-dimethylaminophenyl)-CH2-NH-CH2-CH(Me)- | 3-MeO-phenyl | 548.63 | 549.3 |
| 9-458 | Me | 2,6-difluorobenzyl–(benzo[1,3]dioxol-5-yl)-CH2-NH-CH2-CH(Me)- | 3-MeO-phenyl | 549.57 | 550.2 |
| 9-459 | Me | 2,6-difluorobenzyl–O–(4-phenyl)-CH2-NH-CH2-CH(Me)- | 3-MeO-phenyl | 535.58 | 536.2 |

TABLE 9-continued

| | | | | | |
|---|---|---|---|---|---|
| 9-460 | Me | [2,6-difluorobenzyl; 2,3-dihydrobenzofuran-5-ylmethyl-NH-CH2-CH(Me)-] | | [3-methoxyphenyl] | 547.59 548.3 |
| 9-461 | Me | [2,6-difluorobenzyl; 2-hydroxy-5-chlorobenzyl-NH-CH2-CH(Me)-] | | [3-methoxyphenyl] | 556.00 556.2 |
| 9-462 | Me | [2,6-difluorobenzyl; 4-hydroxy-3-chlorobenzyl-NH-CH2-CH(Me)-] | | [3-methoxyphenyl] | 556.00 556.2 |
| 9-463 | Me | [2,6-difluorobenzyl; 4-hydroxy-2-chlorobenzyl-NH-CH2-CH(Me)-] | | [3-methoxyphenyl] | 556.00 556.2 |
| 9-464 | Me | [2,6-difluorobenzyl; 4-fluoro-3-chlorobenzyl-NH-CH2-CH(Me)-] | | [3-methoxyphenyl] | 557.99 558.2 |
| 9-465 | Me | [2,6-difluorobenzyl; 2-chloro-4-fluorobenzyl-NH-CH2-CH(Me)-] | | [3-methoxyphenyl] | 557.99 558.2 |
| 9-466 | Me | [2,6-difluorobenzyl; 4-trifluoromethylbenzyl-NH-CH2-CH(Me)-] | | [3-methoxyphenyl] | 573.55 574.2 |
| 9-467 | Me | [2,6-difluorobenzyl; indol-3-ylmethyl-NH-CH2-CH(Me)-] | | [3-methoxyphenyl] | 544.59 545.2 |

TABLE 9-continued

| | | | | | |
|---|---|---|---|---|---|
| 9-468 | Me | [2,6-difluorobenzyl-indol-1-yl-CH2-NH-CH(Me)-] | | [3-methoxyphenyl] | 558.62 559.2 |
| 9-469 | Me | [2,6-difluorobenzyl-imidazol-2-yl-CH2-NH-CH(Me)-] | | [3-methoxyphenyl] | 495.52 496.2 |
| 9-470 | Me | [2,6-difluorobenzyl-pyridin-2-yl-CH2CH2-NH-CH(Me)-] | | [2-fluoro-3-methoxyphenyl] | 538.56 539 |
| 9-471 | Me | [2,6-difluorobenzyl-imidazol-4-yl-CH2-NH-CH(Me)-] | | [3-methoxyphenyl] | 495.52 496.2 |
| 9-472 | Me | [2,6-difluorobenzyl-(2-methylphenyl)-CH2-NH-CH(Me)-] | | [3-methoxyphenyl] | 519.58 520.2 |
| 9-473 | Me | [2,6-difluorobenzyl-(3-methylphenyl)-CH2-NH-CH(Me)-] | | [3-methoxyphenyl] | 519.58 520.2 |
| 9-474 | Me | [2,6-difluorobenzyl-(4-methylphenyl)-CH2-NH-CH(Me)-] | | [3-methoxyphenyl] | 519.58 520.2 |
| 9-475 | Me | [2,6-difluorobenzyl-(2-hydroxypyridin-3-yl)-CH2-NH-CH(Me)-] | | [3-methoxyphenyl] | 521.56 535.2 |
| 9-476 | Me | [2,6-difluorobenzyl-(3-methylphenyl)-CH2-NH-CH(Me)-] | | [3-methoxyphenyl] | 533.61 534.2 |

TABLE 9-continued

| | | | | | |
|---|---|---|---|---|---|
| 9-477 | Me | 2,6-difluorobenzyl | 3-methoxybenzyl-NH-CH(Me)CH2- | | 3-OMe-phenyl | 535.58 | 536.2 |
| 9-478 | Me | 2,6-difluorobenzyl | 4-methoxy-3-methylbenzyl-NH-CH(Me)CH2- | | 3-OMe-phenyl | 549.61 | 550.2 |
| 9-479 | Me | 2,6-difluorobenzyl | 4-methylthiobenzyl-NH-CH(Me)CH2- | | 3-OMe-phenyl | 551.65 | 552.2 |
| 9-480 | Me | 2,6-difluorobenzyl | 1-naphthylmethyl-NH-CH(Me)CH2- | | 3-OMe-phenyl | 555.62 | 556.3 |
| 9-481 | Me | 2,6-difluorobenzyl | 2-(pyridin-2-yl)ethyl-N(Me)-CH(Me)CH2- | | 2-F-3-OMe-phenyl | 552.59 | 553 |
| 9-482 | Me | 2,6-difluorobenzyl | 2-methylbenzyl-NH-CH(Me)CH2- | | 2-F-3-OMe-phenyl | 537.57 | 538.2 |
| 9-483 | Me | 2,6-difluorobenzyl | 3-hydroxybenzyl-NH-CH(Me)CH2- | | 2-F-3-OMe-phenyl | 539.55 | 540.2 |
| 9-484 | Me | 2,6-difluorobenzyl | 4-hydroxybenzyl-NH-CH(Me)CH2- | | 2-F-3-OMe-phenyl | 539.55 | 540.2 |
| 9-485 | Me | 2,6-difluorobenzyl | 2-fluorobenzyl-NH-CH(Me)CH2- | | 2-F-3-OMe-phenyl | 541.54 | 542.2 |

TABLE 9-continued

| | | | | | |
|---|---|---|---|---|---|
| 9-486 | Me | 2,6-difluorobenzyl | 4-fluorobenzyl-NH-CH(Me)- | 2-fluoro-3-methoxyphenyl | 541.54 542.2 |
| 9-487 | Me | 2,6-difluorobenzyl | 3-fluorobenzyl-NH-CH(Me)- | 2-fluoro-3-methoxyphenyl | 541.54 542.2 |
| 9-488 | Me | 2,6-difluorobenzyl | 3-cyanobenzyl-NH-CH(Me)- | 2-fluoro-3-methoxyphenyl | 548.56 549.2 |
| 9-489 | Me | 2,6-difluorobenzyl | 4-cyanobenzyl-NH-CH(Me)- | 2-fluoro-3-methoxyphenyl | 548.56 549.3 |
| 9-490 | Me | 2,6-difluorobenzyl | 2,5-dimethylbenzyl-NH-CH(Me)- | 2-fluoro-3-methoxyphenyl | 551.60 552.3 |
| 9-491 | Me | 2,6-difluorobenzyl | 3,5-dimethylbenzyl-NH-CH(Me)- | 2-fluoro-3-methoxyphenyl | 551.60 552.2 |
| 9-492 | Me | 2,6-difluorobenzyl | 2-methoxybenzyl-NH-CH(Me)- | 2-fluoro-3-methoxyphenyl | 553.57 554.2 |
| 9-493 | Me | 2,6-difluorobenzyl | 3-methoxybenzyl-NH-CH(Me)- | 2-fluoro-3-methoxyphenyl | 553.57 554.2 |

TABLE 9-continued

| | | | | | |
|---|---|---|---|---|---|
| 9-494 | Me | [2,6-difluorobenzyl; 4-methoxybenzyl-NH-CH(Me)-] | | [2-fluoro-3-methoxyphenyl] | 553.57 554.2 |
| 9-495 | Me | [2,6-difluorobenzyl; 2,3-dihydrobenzofuran-5-ylmethyl-NH-CH(Me)-] | | [2-fluoro-3-methoxyphenyl] | 565.58 566.2 |
| 9-496 | Me | [2,6-difluorobenzyl; 2,4,6-trimethylbenzyl-NH-CH(Me)-] | | [2-fluoro-3-methoxyphenyl] | 565.63 566.3 |
| 9-497 | Me | [2,6-difluorobenzyl; 4-isopropylbenzyl-NH-CH(Me)-] | | [2-fluoro-3-methoxyphenyl] | 565.63 566.3 |
| 9-498 | Me | [2,6-difluorobenzyl; 4-dimethylaminobenzyl-NH-CH(Me)-] | | [2-fluoro-3-methoxyphenyl] | 566.62 566.2 |
| 9-499 | Me | [2,6-difluorobenzyl; benzo[d][1,3]dioxol-5-ylmethyl-NH-CH(Me)-] | | [2-fluoro-3-methoxyphenyl] | 567.56 567.3 |
| 9-500 | Me | [2,6-difluorobenzyl; 4-methoxy-3-methylbenzyl-NH-CH(Me)-] | | [2-fluoro-3-methoxyphenyl] | 567.60 568.2 |
| 9-501 | Me | [2,6-difluorobenzyl; 4-methylthiobenzyl-NH-CH(Me)-] | | [2-fluoro-3-methoxyphenyl] | 569.64 568.2 |
| 9-502 | Me | [2,6-difluorobenzyl; naphthalen-1-ylmethyl-NH-CH(Me)-] | | [2-fluoro-3-methoxyphenyl] | 573.61 570.2 |

TABLE 9-continued

| | | | | | |
|---|---|---|---|---|---|
| 9-503 | Me | 2,6-difluorobenzyl | 5-chloro-2-hydroxy-benzylamine derivative | | 2-fluoro-3-methoxyphenyl | 573.99 | 574.2 |
| 9-504 | Me | 2,6-difluorobenzyl | 3-chloro-4-hydroxy-benzylamine derivative | | 2-fluoro-3-methoxyphenyl | 573.99 | 574.2 |
| 9-505 | Me | 2,6-difluorobenzyl | 2-chloro-4-hydroxy-benzylamine derivative | | 2-fluoro-3-methoxyphenyl | 573.99 | 574.2 |
| 9-506 | Me | 2,6-difluorobenzyl | 3-chloro-4-fluoro-benzylamine derivative | | 2-fluoro-3-methoxyphenyl | 575.98 | 574.2 |
| 9-507 | Me | 2,6-difluorobenzyl | 2-chloro-4-fluoro-benzylamine derivative | | 2-fluoro-3-methoxyphenyl | 575.98 | 576.2 |
| 9-508 | Me | 2,6-difluorobenzyl | 4-trifluoromethylbenzylamine derivative | | 2-fluoro-3-methoxyphenyl | 591.54 | 592.2 |
| 9-509 | Me | 2,6-difluorobenzyl | indol-3-yl-methylamine derivative | | 2-fluoro-3-methoxyphenyl | 562.58 | 563.2 |
| 9-510 | Me | 2,6-difluorobenzyl | imidazol-2-yl-methylamine derivative | | 2-fluoro-3-methoxyphenyl | 513.51 | 514.2 |
| 9-511 | Me | 2,6-difluorobenzyl | imidazol-4-yl-methylamine derivative | | 2-fluoro-3-methoxyphenyl | 513.51 | 514.2 |

TABLE 9-continued

| | | | | | |
|---|---|---|---|---|---|
| 9-512 | Me | 2,6-difluorobenzyl | pyridin-2-ylmethyl-NH-CH2-CH(Me)- | 2-fluoro-3-methoxyphenyl | 524.54 525.2 |
| 9-513 | Me | 2,6-difluorobenzyl | 4-isopropylbenzyl-NH-CH2-CH(Me)- | 3-methoxyphenyl | 547.64 548.3 |
| 9-514 | Me | 2,6-difluorobenzyl | (2-fluoro-6-chloropyridin-3-yl)methyl-NH-CH2-CH(Me)- | 3-methoxyphenyl | 557.99 558.2 |
| 9-515 | Me | 2,6-difluorobenzyl | cyclohexylmethyl-N(Me)-CH2-CH(Me)- | 3-methoxyphenyl | 525.63 526.3 |
| 9-516 | Me | 2,6-difluorobenzyl | cyclohexylmethyl-NH-CH2-CH(Me)- | 3-methoxyphenyl | 511.60 512.3 |
| 9-517 | Me | 2,6-difluorobenzyl | benzyl-CH(NHMe)-CH2- | 2-fluoro-3-methoxyphenyl | 523.55 524 |
| 9-518 | Me | 2,6-difluorobenzyl | 1,2,3,4-tetrahydroisoquinolin-3-ylmethyl | 2-fluoro-3-methoxyphenyl | 521.53 522 |
| 9-519 | Me | 2,6-difluorobenzyl | 1-(cyclohexylmethyl)pyrrolidin-2-ylmethyl | 2-fluoro-3-methoxyphenyl | 555.63 556 |

TABLE 9-continued

| | | | | | |
|---|---|---|---|---|---|
| 9-520 | Me | [2,6-difluorobenzyl] | [N-Boc-N-methyl, benzyl, (S)-pentyl] | H | 499.55 400 (MH − BOC)+ |
| 9-521 | Me | [2,6-difluorobenzyl] | [N-methyl, benzyl, pentyl] | H | 399.43 400 |
| 9-522 | Me | [2,6-difluorobenzyl] | [tetrahydroisoquinoline-propyl] | H | 397.42 398 |
| 9-523 | Me | [2,6-difluorobenzyl] | [N-methyl, benzyl, pentyl] | Br | 478.33 478/480 |
| 9-524 | Me | [2,6-difluorobenzyl] | [tetrahydroisoquinoline-propyl] | Br | 476.31 476/478 |
| 9-525 | Me | [2,6-difluorobenzyl] | [N-benzyl, (S)-methyl-butyl] | [3-OMe-phenyl] | 505.56 506.3 |
| 9-526 | Me | [2,6-difluorobenzyl] | [N-benzyl-N-methyl, (S)-methyl-butyl] | [3-OMe-phenyl] | 519.58 520.3 |
| 9-527 | Me | [2,6-difluorobenzyl] | [N-benzyl, (R)-methyl-butyl] | [3-OMe-phenyl] | 505.56 506.2 |
| 9-528 | Me | [2,6-difluorobenzyl] | [N-benzyl-N-methyl, (R)-methyl-butyl] | [3-OMe-phenyl] | 519.58 520.2 |

TABLE 9-continued
| | | | | | |
|---|---|---|---|---|---|
| 9-529 | Me | 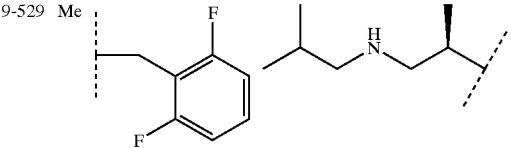 | 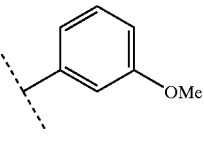 | 471.54 | 472.2 |
| 9-530 | Me | 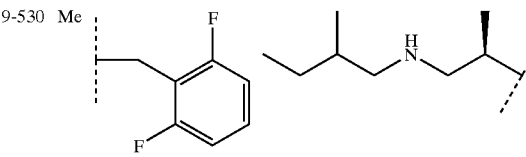 | 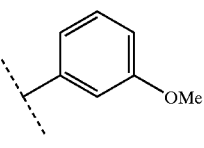 | 485.57 | 486.3 |
| 9-531 | Me | 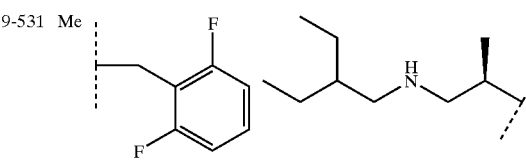 | 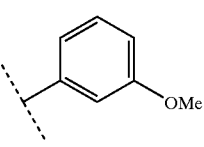 | 499.59 | 500.3 |
| 9-532 | Me | 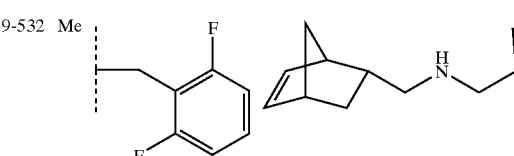 | 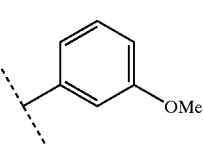 | 521.60 | 522.2 |
| 9-533 | Me | 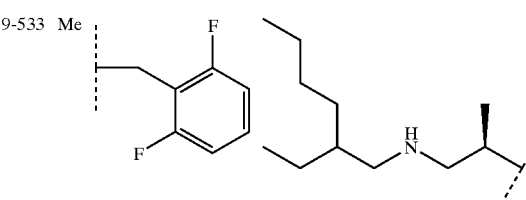 | 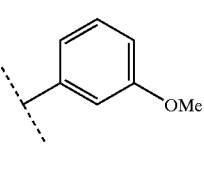 | 527.65 | 528.3 |
| 9-534 | Me | 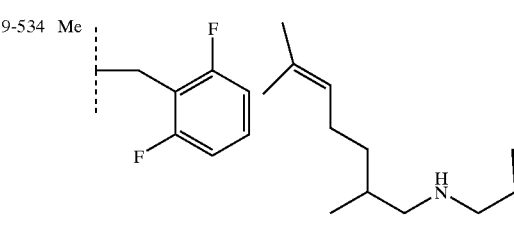 | 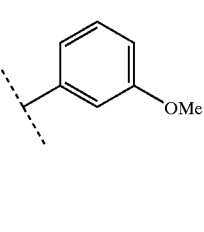 | 539.66 | 540.3 |
| 9-535 | Me | 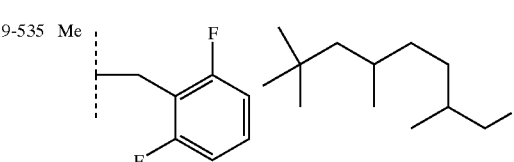 | 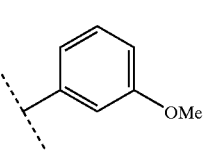 | 583.75 | 584.4 |
| 9-536 | Me | 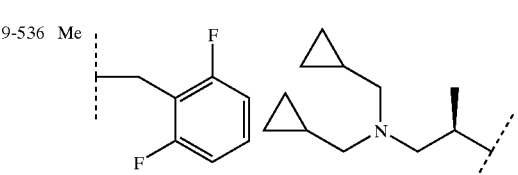 | 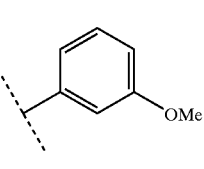 | 523.62 | 524.3 |

TABLE 9-continued

| ID | R | Structure | Ar | MW | MS |
|---|---|---|---|---|---|
| 9-537 | Me | 2,6-diF-C6H3-CH2- / isoalkyl chain with NH-CH(Me)- | | 3-OMe-C6H4- | 555.70 556.3 |
| 9-538 | Me | 2,6-diF-C6H3-CH2- / cyclopropyl-CH(Me)-NH-CH2-CH(Me)- | | 3-OMe-C6H4- | 483.55 484.2 |
| 9-539 | Me | 2,6-diF-C6H3-CH2- / cyclopentyl-NH-CH2-CH(Me)- | | 3-OMe-C6H4- | 483.55 484.2 |
| 9-540 | Me | 2,6-diF-C6H3-CH2- / cyclohexyl-NH-CH2-CH(Me)- | | 3-OMe-C6H4- | 497.58 498.3 |
| 9-541 | Me | 2,6-diF-C6H3-CH2- / iPr-CH(Me)-NH-CH2-CH(Me)- | | 3-OMe-C6H4- | 485.57 486.3 |
| 9-542 | Me | 2,6-diF-C6H3-CH2- / Et-CH(Me)-CH(Me)-NH-CH2-CH(Me)- | | 3-OMe-C6H4- | 499.59 500.3 |
| 9-543 | Me | 2,6-diF-C6H3- with NC-(CH2)3-CH(Me)-NH-CH2-CH(Me)- | | 3-OMe-C6H4- | 510.58 511.2 |
| 9-544 | Me | 2,6-diF-C6H3-CH2- / alkyl-CH(Et)-NH-CH2-CH(Me)- | | 3-OMe-C6H4- | 513.62 514.3 |
| 9-545 | Me | 2,6-diF-C6H3-CH2- / cyclohexyl-CH(Me)-NH-CH2-CH(Me)- | | 3-OMe-C6H4- | 525.63 526.3 |

TABLE 9-continued

| | | | | | |
|---|---|---|---|---|---|
| 9-546 | Me | 2,6-difluorobenzyl; cyclopentyl-NH-CH(Me)- | | 2-fluoro-3-methoxyphenyl | 501.54 502.2 |
| 9-547 | Me | 2,6-difluorobenzyl; methyl 2-(NH-CH(Me)-)cyclopentanecarboxylate | | 2-fluoro-3-methoxyphenyl | 559.58 560.2 |
| 9-548 | Me | 2,6-difluorobenzyl; cyclohexyl-NH-CH(Me)- | | 2-fluoro-3-methoxyphenyl | 515.57 516.2 |
| 9-549 | Me | 2,6-difluorobenzyl; HO-(CH2)3-CH(Me)-NH-CH(Me)- | | 2-fluoro-3-methoxyphenyl | 519.56 520.2 |
| 9-550 | Me | 2,6-difluorobenzyl; 2-Cl-benzyl-NH-CH(Me)- | | 2-fluoro-3-methoxyphenyl | 557.99 558.2 |
| 9-551 | Me | 2,6-difluorobenzyl; 3-CN-benzyl-NH-CH(Me)- | | 2-fluoro-3-methoxyphenyl | 548.56 549.2 |
| 9-552 | Me | 2,6-difluorobenzyl; 3-F-benzyl-NH-CH(Me)- | | 2-fluoro-3-methoxyphenyl | 541.54 542.2 |
| 9-553 | Me | 2,6-difluorobenzyl; imidazol-2-yl-CH2-NH-CH(Me)- | | 2-fluoro-3-methoxyphenyl | 513.51 514.2 |
| 9-554 | Me | 2,6-difluorobenzyl; 3-methylthien-2-yl-CH2-NH-CH(Me)- | | 2-fluoro-3-methoxyphenyl | 543.60 544.2 |

TABLE 9-continued

| ID | R | | | MW | MS |
|---|---|---|---|---|---|
| 9-555 | Me | 2,6-difluorobenzyl / 5-methylthiophen-2-ylmethyl-NH-CH(Me)CH2- | | 2-fluoro-3-methoxyphenyl | 543.60 544.2 |
| 9-556 | Me | 2,6-difluorobenzyl / thiophen-3-ylmethyl-NH-CH(Me)CH2- | | 2-fluoro-3-methoxyphenyl | 529.58 530.1 |
| 9-557 | Me | 2,6-difluorobenzyl / isobutyl-NH-CH(Me)CH2- | | 2-fluoro-3-methoxyphenyl | 489.53 490.2 |
| 9-558 | Me | 2,6-difluorobenzyl / geranyl-like-NH-CH(Me)CH2- | | 2-fluoro-3-methoxyphenyl | 557.65 558.2 |
| 9-559 | Me | 2,6-difluorobenzyl / 2-methylbutyl-NH-CH(Me)CH2- | | 2-fluoro-3-methoxyphenyl | 503.56 504.2 |
| 9-560 | Me | 2,6-difluorobenzyl / 2-ethylhexyl-NH-CH(Me)CH2- | | 2-fluoro-3-methoxyphenyl | 545.64 546.2 |
| 9-561 | Me | 2,6-difluorobenzyl / MeS-CH2CH2CH2-NH-CH(Me)CH2- | | 2-fluoro-3-methoxyphenyl | 521.60 522.2 |
| 9-562 | Me | 2,6-difluorobenzyl / 1-phenylethyl-NH-CH(Me)CH2- | | 2-fluoro-3-methoxyphenyl | 537.57 538.2 |
| 9-563 | Me | 2,6-difluorobenzyl / 3-methylpentan-2-yl-NH-CH(Me)CH2- | | 2-fluoro-3-methoxyphenyl | 517.58 518.2 |

TABLE 9-continued

| | | | | | |
|---|---|---|---|---|---|
| 9-564 | Me | [2,6-difluorobenzyl] | [4,4,2-trimethyl chain with NH and (R)-methyl] | [2-fluoro-3-methoxyphenyl] | 559.66 560.2 |
| 9-565 | Me | [2,6-difluorobenzyl] | [2-cyanobenzyl NH (R)-methyl] | [2-fluoro-3-methoxyphenyl] | 548.56 549.2 |
| 9-566 | Me | [2,6-difluorobenzyl] | [cyclobutyl-CH(Me)-NH-(R)-methyl] | [2-fluoro-3-methoxyphenyl] | 515.57 516.2 |
| 9-567 | Me | [2,6-difluorobenzyl] | [cyclopentyl-NH-(R)-methyl] | [2-fluoro-3-methoxyphenyl] | 501.54 502.2 |
| 9-568 | Me | [2,6-difluorobenzyl] | [cyclohexyl-NH-(R)-methyl] | [2-fluoro-3-methoxyphenyl] | 515.57 516.2 |
| 9-569 | Me | [2,6-difluorobenzyl] | [imidazol-2-yl-CH2-NH-(R)-methyl] | [2-fluoro-3-methoxyphenyl] | 513.51 514.2 |
| 9-570 | Me | [2,6-difluorobenzyl] | [thien-3-yl-CH2-NH-(R)-methyl] | [2-fluoro-3-methoxyphenyl] | 529.58 530.2 |
| 9-571 | Me | [2,6-difluorobenzyl] | [4-hydroxybenzyl-NH-(R)-methyl] | [2-fluoro-3-methoxyphenyl] | 539.55 540.2 |
| 9-572 | Me | [2,6-difluorobenzyl] | [geranyl-type chain NH (R)-methyl] | [2-fluoro-3-methoxyphenyl] | 557.65 558.3 |

TABLE 9-continued

| | | | | | |
|---|---|---|---|---|---|
| 9-573 | Me | [2,6-difluorobenzyl] | [2-ethyl-hexyl-NH-CH(Me)CH2-] | [3-methoxy-2-fluorophenyl] | 545.64 546.3 |
| 9-574 | Me | [2,6-difluorobenzyl] | [isopentyl-NH-CH(Me)CH2-] | [3-methoxy-2-fluorophenyl] | 503.56 504.3 |
| 9-575 | Me | [2,6-difluorobenzyl] | [2-(pyridin-2-yl)ethyl-N(Me)-CH2CH2-] | [4-isobutylphenyl] | 546.65 547.3 |
| 9-576 | Me | [2,6-difluorobenzyl] | [3,5,5-trimethylhexyl-NH-CH(Me)CH2-] | [3-methoxy-2-fluorophenyl] | 559.66 560.3 |
| 9-577 | Me | [2,6-difluorobenzyl] | [3-phenylbutyl-NH-CH(Me)CH2-] | [3-methoxy-2-fluorophenyl] | 565.63 566.3 |
| 9-578 | Me | [2,6-difluorobenzyl] | [2-cyanobenzyl-NH-CH(Me)CH2-] | [3-methoxy-2-fluorophenyl] | 548.56 549.2 |
| 9-579 | Me | [2,6-difluorobenzyl] | [4-isopropylphenyl-CH2CH(Me)CH2-NH-CH(Me)CH2-] | [3-methoxy-2-fluorophenyl] | 607.71 608.4 |
| 9-580 | Me | [2,6-difluorobenzyl] | [3-hydroxybutyl-NH-CH(Me)CH2-] | [3-methoxy-2-fluorophenyl] | 505.53 506.2 |
| 9-581 | Me | [2,6-difluorobenzyl] | [pyridin-2-yl-CH2-NH-CH(Me)CH2-] | [3-methoxy-2-fluorophenyl] | 524.54 525.2 |

TABLE 9-continued

| | | | | | |
|---|---|---|---|---|---|
| 9-582 | Me | [2,6-difluorobenzyl] | [N-methyl-N-((R)-1-methylpropyl)-pyridin-2-ylmethylamine] | [2-fluoro-3-methoxybenzyl] | 538.56 539.2 |
| 9-583 | Me | [2,6-difluorobenzyl] | [(S)-N,N-dimethyl-1-phenylpropylamine] | [2-fluoro-3-methoxybenzyl] | 523.55 524.2 |
| 9-584 | Me | [2,6-difluorobenzyl] | [(R)-N,N-dimethyl-1-phenylpropylamine] | [2-fluoro-3-methoxybenzyl] | 523.55 524.2 |
| 9-585 | Me | [2,6-difluorobenzyl] | [(R)-N-(2-methylbenzyl)-2-methylpropylamine] | [3-methoxybenzyl] | 519.58 520.2 |
| 9-586 | Me | [2,6-difluorobenzyl] | [(R)-N-(2-methoxybenzyl)-2-methylpropylamine] | [3-methoxybenzyl] | 535.58 536.2 |
| 9-587 | Me | [2,6-difluorobenzyl] | [(R)-N-(2-fluorobenzyl)-2-methylpropylamine] | [3-methoxybenzyl] | 523.55 524.2 |
| 9-588 | Me | [2,6-difluorobenzyl] | [(R)-N-(2-hydroxybenzyl)-2-methylpropylamine] | [3-methoxybenzyl] | 521.56 522.2 |
| 9-589 | Me | [2,6-difluorobenzyl] | [N-(cyclohexylmethyl)-2-methylpropylamine] | [2-fluoro-3-methoxybenzyl] | 529.6 530.2 |
| 9-590 | Me | [2,6-difluorobenzyl] | [N-(2-methylbutyl)-2-methylpropylamine] | [2-fluoro-3-methoxybenzyl] | 531.61 532.3 |

TABLE 9-continued

| | | | | | |
|---|---|---|---|---|---|
| 9-591 | Me | [structure] | [structure] | 541.56 | 542.3 |
| 9-592 | Me | [structure] | [structure] | 513.51 | 514.2 |
| 9-593 | Me | [structure] | [structure] | 527.54 | 528.2 |
| 9-594 | Me | [structure] | [structure] | 601.74 | 602.4 |
| 9-595 | Me | [structure] | [structure] | 541.56 | 542.2 |
| 9-596 | Me | [structure] | [structure] | 543.62 | 542.2 |
| 9-597 | Me | [structure] | [structure] | 483.55 | 484.2 |
| 9-598 | Me | [structure] | [structure] | 471.54 | 472.1 |
| 9-599 | Me | [structure] | [structure] | 485.57 | 486.3 |

TABLE 9-continued

| | | | | | |
|---|---|---|---|---|---|
| 9-600 | Me | [2,6-difluorobenzyl group] | [branched alkyl chain with NH, stereochemistry] | [3-methoxyphenyl] | 499.59 500.3 |
| 9-601 | Me | [2,6-difluorobenzyl group] | [branched alkyl chain with NH, stereochemistry] | [2-fluoro-3-methoxyphenyl] | 601.74 602.4 |
| 9-602 | Me | [2,6-difluorobenzyl group] | [4-methylimidazol-5-yl-methyl-NH chain with stereochemistry] | [2-fluoro-3-methoxyphenyl] | 527.54 528.2 |
| 9-603 | Me | [2,6-difluorobenzyl group] | [imidazol-4-yl-methyl-NH chain with stereochemistry] | [2-fluoro-3-methoxyphenyl] | 513.51 514.2 |
| 9-604 | Me | [2,6-difluorobenzyl group] | [pyridin-2-yl-ethyl-N(Me) chain] | [benzothiophen-2-yl] | 546.63 547 |
| 9-605 | Me | [2,6-difluorobenzyl group] | [pyridin-2-yl-ethyl-N(Me) chain] | [4-chlorophenyl] | 524.99 525 |
| 9-606 | Me | [2,6-difluorobenzyl group] | [cyclopropyl-methyl-NH chain with stereochemistry] | [2-fluoro-3-methoxyphenyl] | 501.54 502.2 |
| 9-607 | Me | [2,6-difluorobenzyl group] | [3-chlorobenzyl-NH chain with stereochemistry] | [2-fluoro-3-methoxyphenyl] | 557.99 558.2 |
| 9-608 | Me | [2,6-difluorobenzyl group] | [4-fluorobenzyl-NH chain with stereochemistry] | [2-fluoro-3-methoxyphenyl] | 541.54 542.2 |

TABLE 9-continued

| | | | | | |
|---|---|---|---|---|---|
| 9-609 | Me | [2,6-difluorobenzyl structure] | [2-hydroxybenzyl-NH-CH(Me)- structure] | [2-fluoro-3-methoxyphenyl structure] | 539.55 540.3 |
| 9-610 | Me | [2,6-difluorobenzyl structure] | [bis(2-methylbutyl)N-CH(Me)- structure] | [2-fluoro-3-methoxyphenyl structure] | 601.74 602.4 |
| 9-611 | Me | [2,6-difluorobenzyl structure] | [bis(isobutyl)N-CH(Me)- structure] | [2-fluoro-3-methoxyphenyl structure] | 573.69 574.3 |
| 9-612 | Me | [2,6-difluorobenzyl structure] | [di-n-butyl-N-CH(Me)- structure] | [2-fluoro-3-methoxyphenyl structure] | 545.64 546.3 |
| 9-613 | Me | [2,6-difluorobenzyl structure] | [isopropyl-CH(Me)-NH-CH(Me)- structure] | [2-fluoro-3-methoxyphenyl structure] | 503.56 504.2 |
| 9-614 | Me | [2,6-difluorobenzyl structure] | [bis(cyclopropylmethyl)N-CH(Me)- structure] | [2-fluoro-3-methoxyphenyl structure] | 541.61 542.3 |
| 9-615 | Me | [2,6-difluorobenzyl structure] | [isopropyl-NH-CH(Me)- structure] | [2-fluoro-3-methoxyphenyl structure] | 475.50 476.2 |
| 9-616 | Me | [2,6-difluorobenzyl structure] | [sec-butyl-NH-CH(Me)- structure] | [2-fluoro-3-methoxyphenyl structure] | 489.53 490.3 |
| 9-617 | Me | [2,6-difluorobenzyl structure] | [CH(OH)CH(Me)NH-CH(Me)- structure] | [2-fluoro-3-methoxyphenyl structure] | 505.53 506.30 |

TABLE 9-continued

| | | | | | |
|---|---|---|---|---|---|
| 9-618 | Me | [2,6-difluorobenzyl] | [(1-methylpyrrol-2-yl)methyl-NH-CH(Me)CH2-] | [2-fluoro-3-methoxyphenyl] | 526.55 527.2 |
| 9-619 | Me | [2,6-difluorobenzyl] | [(furan-2-yl)-CH=CH-CH2-NH-CH(Me)CH2-] | [2-fluoro-3-methoxyphenyl] | 539.55 540.2 |
| 9-620 | Me | [2,6-difluorobenzyl] | [(furan-2-yl)-CH=CH-CH2-NH-CH(Me)CH2-] | [2-fluoro-3-methoxyphenyl] | 539.55 540.2 |
| 9-621 | Me | [2,6-difluorobenzyl] | [(thien-2-yl)methyl-NH-CH(Me)CH2-] | [2-fluoro-3-methoxyphenyl] | 529.58 530.2 |
| 9-622 | Me | [2,6-difluorobenzyl] | [(4-bromothien-2-yl)methyl-NH-CH(Me)CH2-] | [2-fluoro-3-methoxyphenyl] | 608.47 608.1 |
| 9-623 | Me | [2,6-difluorobenzyl] | [(pyridin-3-yl)methyl-NH-CH(Me)CH2-] | [2-fluoro-3-methoxyphenyl] | 524.54 525.2 |
| 9-624 | Me | [2,6-difluorobenzyl] | [(3,5-difluorophenyl)methyl-NH-CH(Me)CH2-] | [2-fluoro-3-methoxyphenyl] | 559.53 560.2 |

TABLE 9-continued
| | | | | | |
|---|---|---|---|---|---|
| 9-625 | Me | 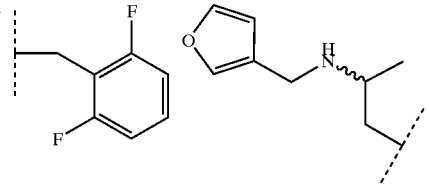 | | 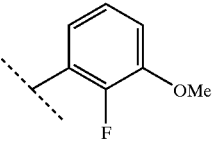 | 513.51 514.2 |
| 9-626 | Me | 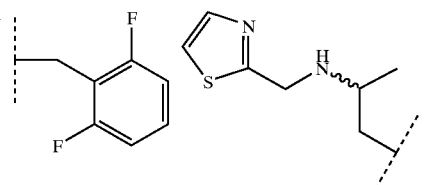 | | 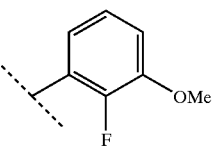 | 530.56 531.2 |
| 9-627 | Me | 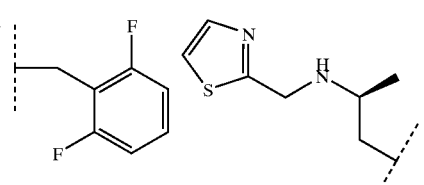 | | 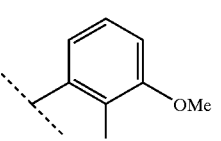 | 530.56 531.2 |
| 9-628 | Me | 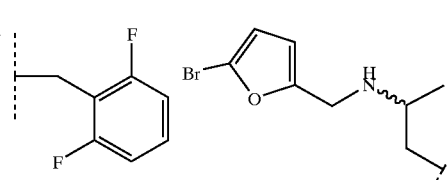 | | 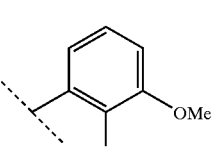 | 592.40 594.1 |
| 9-629 | Me | 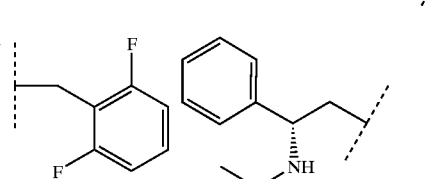 | | 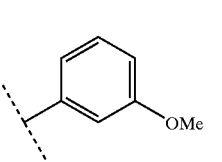 | 519.58 520.2 |
| 9-630 | Me | 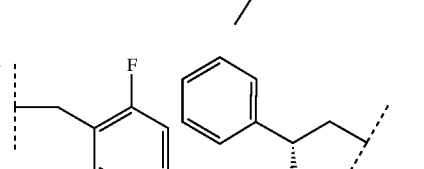 | | 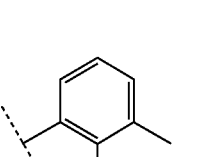 | 521.58 522.2 |
| 9-631 | Me | 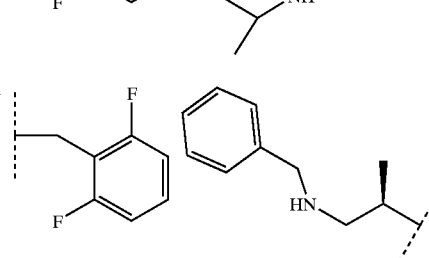 | | 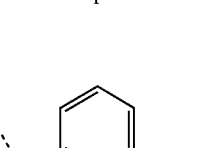 | 507.55 508.3 |
| 9-632 | Me | 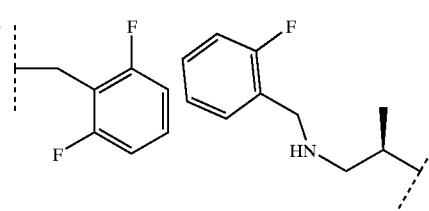 | | 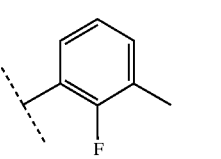 | 525.54 526.2 |

TABLE 9-continued

| ID | | | | | MW calc | MW obs |
|---|---|---|---|---|---|---|
| 9-633 | Me | 2,6-difluorobenzyl | 2-Cl-benzyl-NH-CH2-CH(Me)- | 2-F-3-Me-phenyl | 541.99 | 542.2 |
| 9-634 | Me | 2,6-difluorobenzyl | 2-OMe-benzyl-NH-CH2-CH(Me)- | 2-F-3-Me-phenyl | 537.57 | 538.3 |
| 9-635 | Me | 2,6-difluorobenzyl | 2-(OCH2COOH)-benzyl-NH-CH2-CH(Me)- | 2-F-3-Me-phenyl | 581.58 | 582.2 |
| 9-636 | Me | 2,6-difluorobenzyl | 2-OEt-benzyl-NH-CH2-CH(Me)- | 2-F-3-Me-phenyl | 551.60 | 552.3 |
| 9-637 | Me | 2,6-difluorobenzyl | 2-OH-benzyl-NH-CH2-CH(Me)- | 2-F-3-Me-phenyl | 523.55 | 524.2 |
| 9-638 | Me | 2,6-difluorobenzyl | 2-CF3-benzyl-NH-CH2-CH(Me)- | 2-F-3-Me-phenyl | 575.55 | 576.2 |
| 9-639 | Me | 2,6-difluorobenzyl | 2-Me-benzyl-NH-CH2-CH(Me)- | 2-F-3-Me-phenyl | 521.58 | 522.2 |

TABLE 9-continued

| ID | R | Structure 1 | Structure 2 | MW | MS |
|---|---|---|---|---|---|
| 9-640 | Me | 2,6-difluorobenzyl-N(CH2)-CH(Me)-CH2- with 2-(OCF3)benzyl | 2-fluoro-3-methylphenyl | 573.55 | 574.2 |
| 9-641 | Me | 2,6-difluorobenzyl-N(CH2)-CH(Me)-CH2- with 2-(OCF3)benzyl | 2-fluoro-3-methylphenyl | 591.54 | 592.2 |
| 9-642 | Me | 2,6-difluorobenzyl group with OBn, NH-benzyl | 2-fluoro-3-methoxyphenyl | 629.67 | 630 |
| 9-643 | Me | 2,6-difluorobenzyl group with OBn, NH-cyclopentyl | 2-fluoro-3-methoxyphenyl | 607.66 | 608 |
| 9-644 | Me | 2,6-difluorobenzyl group with OBn, NH-(2-methylbenzyl) | 2-fluoro-3-methoxyphenyl | 643.70 | 644 |
| 9-645 | Me | 2,6-difluorobenzyl group with OBn, NH-(3-methylthien-2-ylmethyl) | 2-fluoro-3-methoxyphenyl | 649.73 | 650 |
| 9-646 | Me | 2,6-difluorobenzyl group with OBn, NH-(4-fluorobenzyl) | 2-fluoro-3-methoxyphenyl | 647.66 | 648 |
| 9-647 | Me | 2,6-difluorobenzyl group with OBn, NH-(2-chlorobenzyl) | 2-fluoro-3-methoxyphenyl | 664.12 | 664 |

TABLE 9-continued
| | | | | | |
|---|---|---|---|---|---|
| 9-648 | Me | 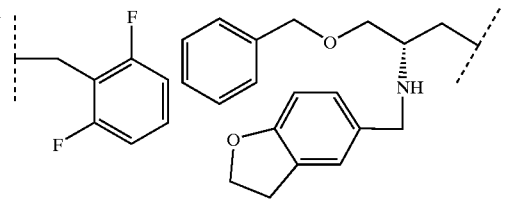 | | 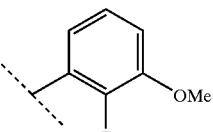 | 671.71 672 |
| 9-649 | Me | 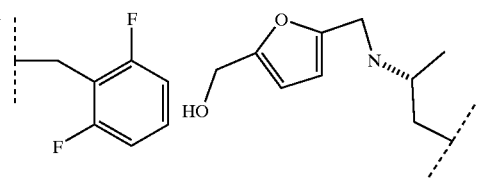 | | 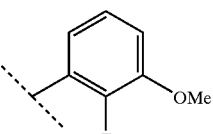 | 543.53 544.2 |
| 9-650 | Me | 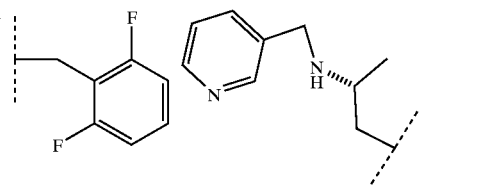 | | 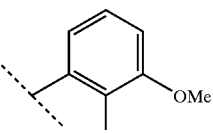 | 524.54 525.2 |
| 9-651 | Me | 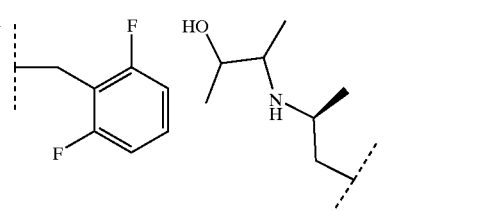 | | 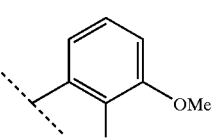 | 505.53 506.2 |
| 9-652 | Me | 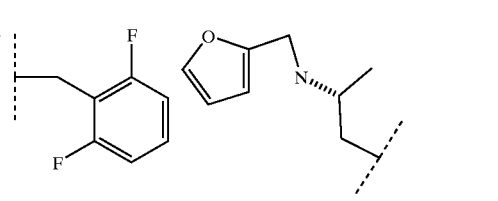 | | 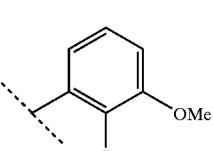 | 513.51 514.2 |
| 9-653 | Me | 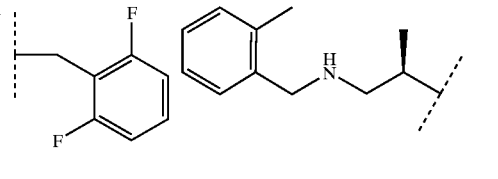 | | 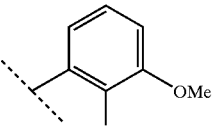 | 537.57 538.3 |
| 9-654 | Me | 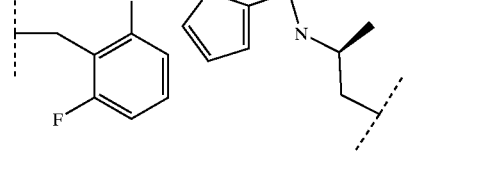 | | 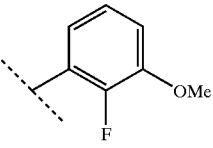 | 513.51 514.2 |
| 9-655 | Me | 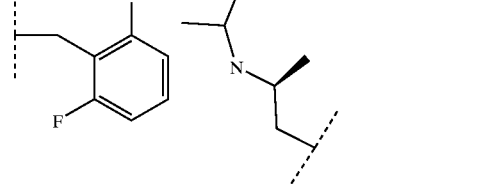 | | 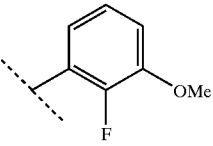 | 475.50 476.2 |

TABLE 9-continued

| ID | R | | | | MW | MS |
|---|---|---|---|---|---|---|
| 9-656 | Me | (2,6-difluorobenzyl) | (sec-butyl-N-(R)-methylpropyl) | | (2-fluoro-3-methoxyphenyl) | 503.56 504.3 |
| 9-657 | Me | (2,6-difluorobenzyl) | (cyclobutyl-N-(R)-methylpropyl) | | (2-fluoro-3-methoxyphenyl) | 487.51 488.3 |
| 9-658 | Me | (2,6-difluorobenzyl) | (cyclopropylethyl-N-(R)-methylpropyl) | | (2-fluoro-3-methoxyphenyl) | 501.54 502.2 |
| 9-659 | Me | (2,6-difluorobenzyl) | (pyridin-3-ylmethyl-N-(R)-methylpropyl) | | (2-fluoro-3-methoxyphenyl) | 524.54 525.2 |
| 9-660 | Me | (2,6-difluorobenzyl) | (5-(hydroxymethyl)furan-2-ylmethyl-N-(R)-methylpropyl) | | (2-fluoro-3-methoxyphenyl) | 543.53 544.2 |
| 9-661 | Me | (2,6-difluorobenzyl) | (sec-butyl-N-(R)-methylpropyl) | | (2-fluoro-3-methoxyphenyl) | 489.53 490.3 |
| 9-662 | Me | (2,6-difluorobenzyl) | (5-ethylfuran-2-ylmethyl-N-(R)-methylpropyl) | | (2-fluoro-3-methoxyphenyl) | 541.56 542.3 |

TABLE 9-continued

| ID | | | | | |
|---|---|---|---|---|---|
| 9-663 | Me | | | | 557.99 558.2 |
| 9-664 | Me | | | | 526.55 527.2 |
| 9-665 | Me | | | | 541.56 542.3 |
| 9-666 | Me | | | | 559.53 560.2 |
| 9-667 | Me | | | | 524.54 525.2 |
| 9-668 | Me | | | | 513.51 514.2 |
| 9-669 | Me | | | | 517.58 518.2 |
| 9-670 | Me | | | | 524.54 525.2 |

TABLE 9-continued

| | | | | | |
|---|---|---|---|---|---|
| 9-671 | Me | 2,6-difluorobenzyl | cyclopentyl-NH-CH(Me)- | 2-fluoro-3-methoxyphenyl | 501.54 502 |
| 9-672 | Me | 2,6-difluorobenzyl | BnO-CH2-CH(NHBoc)- | 2-fluoro-3-methoxyphenyl | 639.66 540 |
| 9-673 | Me | 2,6-difluorobenzyl | BnO-CH2-CH(NH-1-naphthyl)- | 2-fluoro-3-methoxyphenyl | 679.73 680 |
| 9-674 | Me | 2,6-difluorobenzyl | BnO-CH2-CH(NH-CH2-2-MeOC6H4)- | 2-fluoro-3-methoxyphenyl | 659.70 660 |
| 9-675 | Me | 2,6-difluorobenzyl | Cy-CH(Me)-N(Me)- | 2-fluoro-3-methoxyphenyl | 543.62 544.3 |
| 9-676 | Me | 2,6-difluorobenzyl | Cy-CH(Me)-N(Me)- | 2-fluoro-3-methoxyphenyl | 543.62 544.3 |
| 9-677 | Me | 2,6-difluorobenzyl | (5-chlorothien-2-yl)methyl-N(Me)- | 2-fluoro-3-methoxyphenyl | 564.02 564.2 |
| 9-678 | Me | 2,6-difluorobenzyl | 2,3-dimethylpentyl-N(Me)- | 2-fluoro-3-methoxyphenyl | 531.61 532.3 |

TABLE 9-continued

| | | | | | |
|---|---|---|---|---|---|
| 9-679 | Me | [2,6-difluorobenzyl; N(cyclohexylmethyl)(R-methyl)] | | [2-F-3-OMe-phenyl] | 529.6 530.2 |
| 9-680 | Me | [2,6-difluorobenzyl; NH-CH2-(4-hydroxyphenyl)(R-methyl)] | | [2-F-3-OMe-phenyl] | 539.55 540.2 |
| 9-681 | Me | [2,6-difluorobenzyl; N(n-propyl)2(R-methyl)] | | [2-F-3-OMe-phenyl] | 517.58 518.3 |
| 9-682 | Me | [2,6-difluorobenzyl; NH-CH2CH2-phenyl(R-methyl)] | | [2-F-3-OMe-phenyl] | 537.57 538.2 |
| 9-683 | Me | [2,6-difluorobenzyl; N(n-butyl)2(R-methyl)] | | [2-F-3-OMe-phenyl] | 545.64 544.3 |
| 9-684 | Me | [2,6-difluorobenzyl; NH-CH2-(2-hydroxyphenyl)(R-methyl)] | | [2-F-3-OMe-phenyl] | 539.55 540.2 |
| 9-685 | Me | [2,6-difluorobenzyl; N(cyclobutyl)(R-methyl)] | | [2-F-3-OMe-phenyl] | 487.51 488.2 |
| 9-686 | Me | [2,6-difluorobenzyl; N(CH2CH2CH2SMe)2(R-methyl)] | | [2-F-3-OMe-phenyl] | 609.77 610.3 |

TABLE 9-continued

| | | | | | |
|---|---|---|---|---|---|
| 9-687 | Me | [2,6-difluorobenzyl-S-phenyl-CH2-N(R-Me)-CH2-] | | [2-F-3-OMe-phenyl] | 569.64 570.2 |
| 9-688 | Me | [2,6-difluorobenzyl-CH(iBu)(Et)-NH-CH(Me)-CH2-] | | [2-F-3-OMe-phenyl] | 531.61 532.3 |
| 9-689 | Me | [2,6-difluorobenzyl-(bis-2-methylbutyl)N-CH(Me)-CH2-] | | [2-F-3-OMe-phenyl] | 601.74 602.4 |
| 9-690 | Me | [2,6-difluorobenzyl-4-Cl-phenyl-CH2-NH-CH(Me)-CH2-] | | [2-F-3-OMe-phenyl] | 557.99 558.2 |
| 9-691 | Me | [2,6-difluorobenzyl-cinnamyl-NH-CH(Me)-CH2-] | | [2-F-3-OMe-phenyl] | 549.59 550.2 |
| 9-692 | Me | [2,6-difluorobenzyl-CH(iBu)(Me)-NH-CH(Me)-CH2-] | | [2-F-3-OMe-phenyl] | 517.58 518.2 |
| 9-693 | Me | [2,6-difluorobenzyl-CH(Et)2-NH-CH(Me)-CH2-] | | [2-F-3-OMe-phenyl] | 503.56 504.3 |
| 9-694 | Me | [2,6-difluorobenzyl-CH(Et)2-NH-CH(Me)-CH2-] | | [2-F-3-OMe-phenyl] | 503.56 504.3 |

TABLE 9-continued
| | | | | | |
|---|---|---|---|---|---|
| 9-695 | Me | 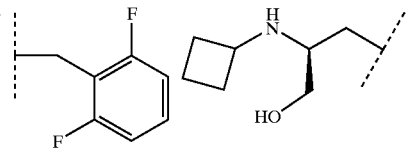 | | 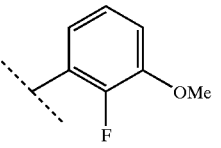 | 503.51 504 |
| 9-696 | Me | 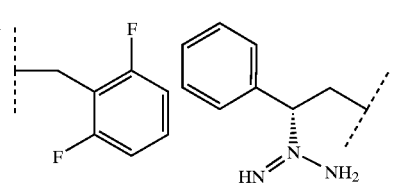 | | 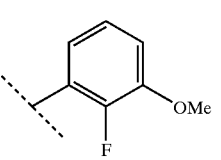 | 537.53 538.2 |
| 9-697 | Me | 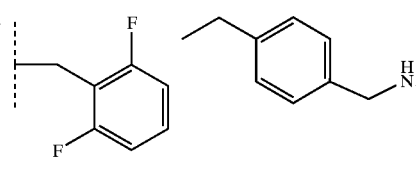 | | 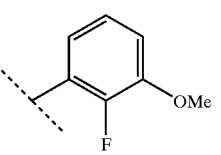 | 551.60 552.3 |
| 9-698 | Me | 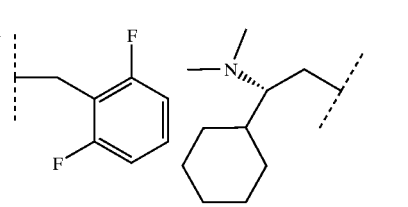 | | 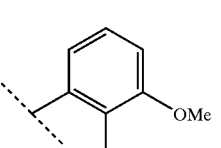 | 529.6 530.2 |
| 9-699 | Me | 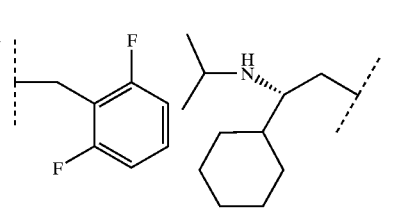 | | 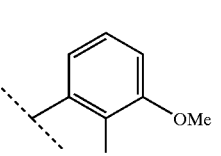 | 543.62 544.3 |
| 9-700 | Me | 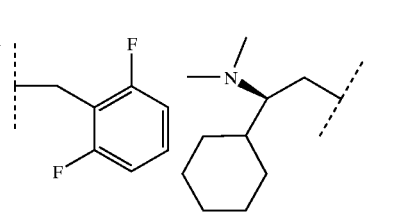 | | 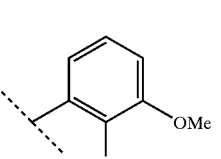 | 529.6 530.2 |
| 9-701 | Me | 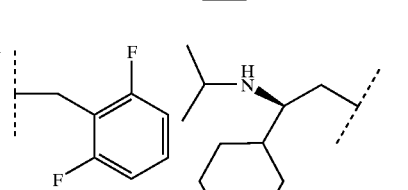 | | 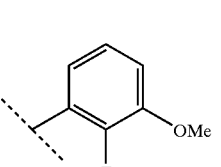 | 543.62 544.3 |
| 9-702 | Me | 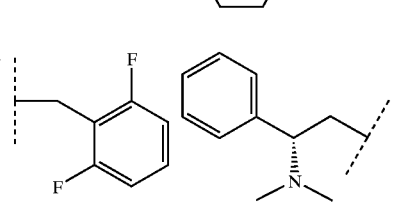 | | 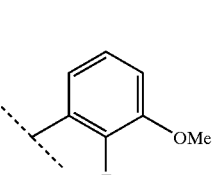 | 523.55 524.2 |

TABLE 9-continued

| | | | | | |
|---|---|---|---|---|---|
| 9-703 | Me | 2,6-difluorobenzyl | HOCH2-C(NHBoc)- | | 3-OMe-2-F-phenyl | 549.54 | 450 |
| 9-704 | Me | 2,6-difluorobenzyl | iBu-CH(NMe2)- | 3-OMe-2-F-phenyl | 503.56 | 504.3 |
| 9-705 | Me | 2,6-difluorobenzyl | (4-Br-thien-2-yl)CH2NH-CH(Me)- | 3-OMe-2-F-phenyl | 608.47 | 610.1 |
| 9-706 | Me | 2,6-difluorobenzyl | (thien-2-yl)CH2NH-CH(Me)- | 3-OMe-2-F-phenyl | 529.58 | 530.2 |
| 9-707 | Me | 2,6-difluorobenzyl | iBu-CH(NHiPr)- | 3-OMe-2-F-phenyl | 517.58 | 518.2 |
| 9-708 | Me | 2,6-difluorobenzyl | iBu-CH(NHEt)- | 3-OMe-2-F-phenyl | 503.56 | 504.3 |
| 9-709 | Me | 2,6-difluorobenzyl | 2-phenyl-5-ethyl-pyrrolidinyl | 3-OMe-2-F-phenyl | 535.56 | 536.2 |
| 9-710 | Me | 2,6-difluorobenzyl | iPr-CH(NMe2)- | 3-OMe-2-F-phenyl | 489.53 | 490.2 |

TABLE 9-continued

| | | | | | |
|---|---|---|---|---|---|
| 9-711 | Me | [structure: 2,6-difluorobenzyl with N(Me)-CH(iPr)-CH2] | | [structure: 2-fluoro-3-methoxyphenyl] | 489.53  490.2 |
| 9-712 | Me | [structure: 2,6-difluorobenzyl with NH-CH(iPr)-CH(iPr)-CH2] | | [structure: 2-fluoro-3-methoxyphenyl] | 503.56  504.2 |
| 9-713 | Me | [structure: 2,6-difluorobenzyl with NH-CH(iPr)-CH(iPr)-CH2] | | [structure: 2-fluoro-3-methoxyphenyl] | 503.56  504.2 |
| 9-714 | Me | [structure: 2,6-difluorobenzyl with NH-Et, CH(iPr)-CH2] | | [structure: 2-fluoro-3-methoxyphenyl] | 489.53  490.2 |
| 9-715 | Me | [structure: 2,6-difluorobenzyl with NH-Et, CH(iPr)-CH2] | | [structure: 2-fluoro-3-methoxyphenyl] | 489.53  490.2 |
| 9-716 | Me | [structure: 2,6-difluorophenyl-phenyl-NH-CH(Me)-CH2] | | [structure: 2-fluoro-3-methoxyphenyl] | 523.55  524.2 |
| 9-717 | Me | [structure: 2,6-difluorobenzyl with iBu-CH(N=N-NH2)-CH2] | | [structure: 2-fluoro-3-methoxyphenyl] | 517.54  518.2 |
| 9-718 | Me | [structure: 2,6-difluorobenzyl with Ph-CH(N=N-NH2)-CH2] | | [structure: 2-fluoro-3-methoxyphenyl] | 523.55  524 |
| 9-719 | Me | [structure: 2,6-difluorobenzyl with iBu-CH(NH-iPr)-CH2] | | [structure: 2-fluoro-3-methoxyphenyl] | 517.58  518.3 |

TABLE 9-continued
| | | | | | |
|---|---|---|---|---|---|
| 9-720 | Me | 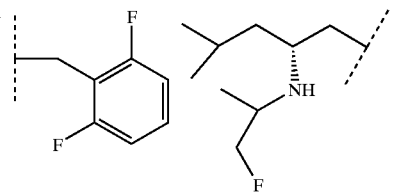 | 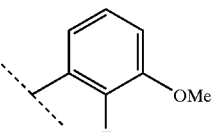 | 535.57 | 536.3 |
| 9-721 | Me | 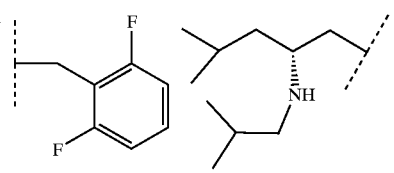 | 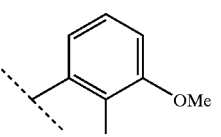 | 531.61 | 532.3 |
| 9-722 | Me | 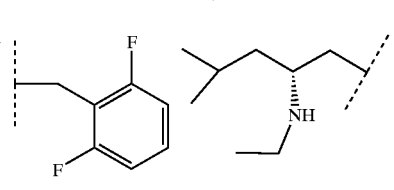 | 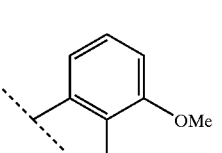 | 503.56 | 504.3 |
| 9-723 | Me | 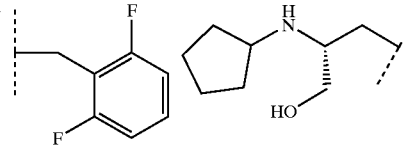 | 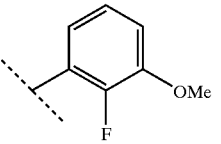 | 517.54 | 518 |
| 9-724 | Me | 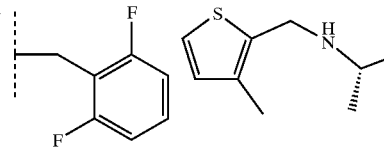 | 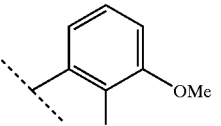 | 543.60 | 544 |
| 9-725 | Me | 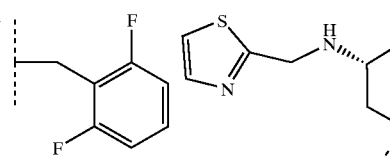 | 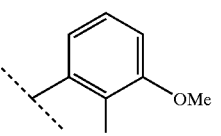 | 530.56 | 531 |
| 9-726 | Me | 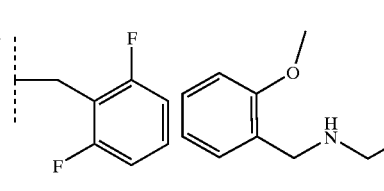 | 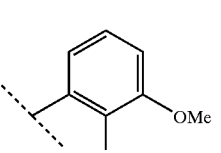 | 553.57 | 554 |
| 9-727 | Me | 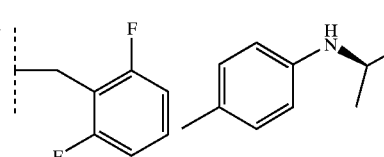 | 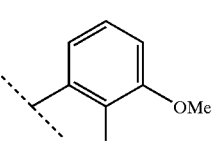 | 523.55 | 524.2 |
| 9-728 | Me | 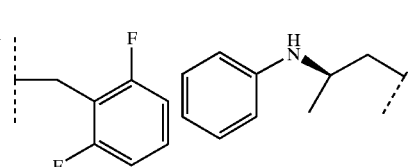 | 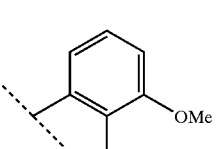 | 509.52 | 510.2 |

TABLE 9-continued
| | | | | | |
|---|---|---|---|---|---|
| 9-729 | Me | 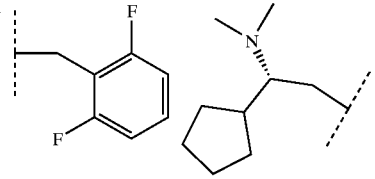 | 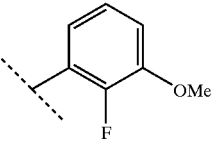 | 515.57 | 516.3 |
| 9-730 | Me | 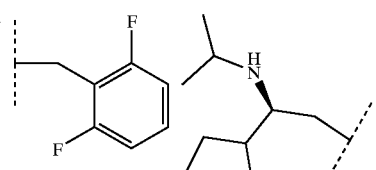 | 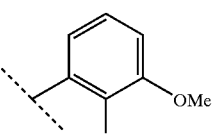 | 529.6 | 530.3 |
| 9-731 | Me | 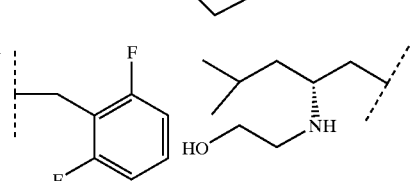 | 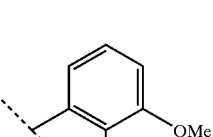 | 519.56 | 520.2 |
| 9-732 | Me | 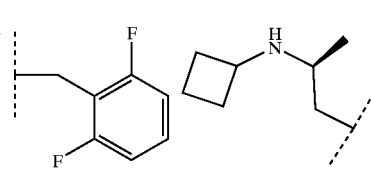 | 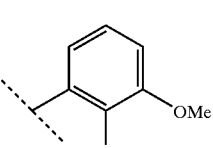 | 487.519 | 488 |
| 9-733 | Me | 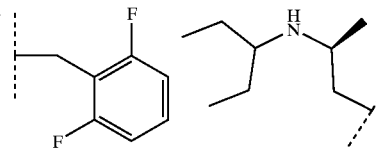 | 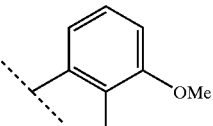 | 503.562 | 504 |
| 9-734 | Me | 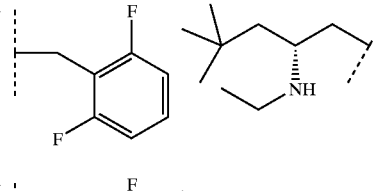 | 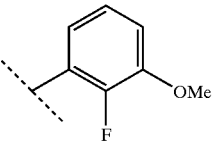 | 517.6 | 518.2 |
| 9-735 | Me | 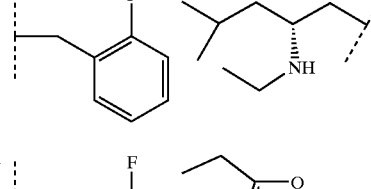 | 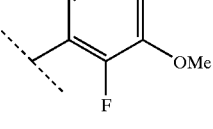 | 485.6 | 486.2 |
| 9-736 | Me | 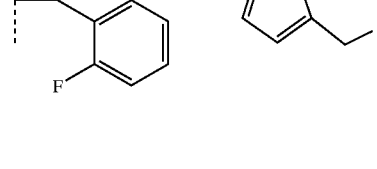 | 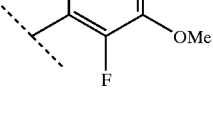 | 541.6 | 542 |
| 9-737 | Me | 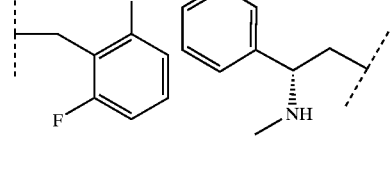 | 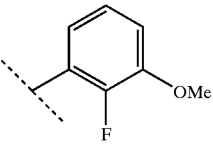 | 509.5 | 510.2 |

TABLE 9-continued

| | | | | | |
|---|---|---|---|---|---|
| 9-738 | Me | 2,6-difluorobenzyl; CH(Ph)CH2 with NHMe | | 2-F-3-OMe-phenyl | 491.5 492.2 |
| 9-739 | Me | 2,6-difluorobenzyl; CH(cyclopentyl)CH2 with NEt2 | | 2-F-3-OMe-phenyl | 543.6 544.3 |
| 9-740 | Me | 2,6-difluorobenzyl; CH(cyclopentyl)CH2 with NMe2 | | 2-F-3-OMe-phenyl | 515.6 516.3 |
| 9-741 | Me | 2,6-difluorobenzyl; CH(CH2OH)CH2 with NH-cyclopentyl | | 2-F-3-OMe-phenyl | 513.5 514 |
| 9-742 | Me | 2,6-difluorobenzyl; CH(CH2OH)CH2 with N(CH2-cyclohexyl)2 | | 3,4-methylenedioxyphenyl | 637.8 638 |
| 9-743 | Me | 2,6-difluorobenzyl; CH(CH2OH)CH2 with N(CH2-2-thienyl)2 | | 3,4-methylenedioxyphenyl | 637.7 638 |
| 9-744 | Me | 2,6-difluorobenzyl; CH(CH2OH)CH2 with N(CH2Ph)2 | | 3,4-methylenedioxyphenyl | 625.7 626 |
| 9-745 | Me | 2,6-difluorobenzyl; CH(CH2OH)CH2 with N(CH2-cyclopropyl)2 | | 3,4-methylenedioxyphenyl | 553.6 554 |

TABLE 9-continued

| | | | | | |
|---|---|---|---|---|---|
| 9-746 | Me | (2,6-difluorobenzyl)(N,N-bis(3-fluorobenzyl))-CH(CH2OH)- | | benzo[1,3]dioxol-5-yl | 661.6 662 |
| 9-747 | Me | (2,6-difluorobenzyl), (S)-CH(Ph)CH2- with NHMe | | benzo[1,3]dioxol-5-yl | 505.5 506.2 |
| 9-748 | Me | (2,6-difluorobenzyl), (S)-CH(Ph)CH2- with NHMe | | 2,3-dihydrobenzo[1,4]dioxin-6-yl | 519.5 520.2 |
| 9-749 | Me | (2,6-difluorobenzyl), cyclopentyl-NH-CH(CH2OH)- | | 2-fluoro-3-methoxyphenyl | 517.5 518 |
| 9-750 | Me | (2,6-difluorobenzyl), isobutyl-CH(NHMe)- | | 2-fluoro-3-methoxyphenyl | 489.5 490.2 |
| 9-751 | Me | (2,6-difluorobenzyl), thien-2-ylmethyl-NH-CH(CH2OH)- | | benzo[1,3]dioxol-5-yl | 541.6 542 |
| 9-752 | Me | (2,6-difluorobenzyl), pyridin-2-ylmethyl-NH-CH(CH2OH)- | | benzo[1,3]dioxol-5-yl | 536.5 537 |
| 9-753 | Me | (2,6-difluorobenzyl), tetrahydropyran-4-yl-NH-CH(CH2OH)- | | benzo[1,3]dioxol-5-yl | 529.5 530 |
| 9-754 | Me | (2,6-difluorobenzyl), 1-methylpiperidin-4-yl-NH-CH(CH2OH)- | | benzo[1,3]dioxol-5-yl | 542.6 543 |

TABLE 9-continued

| | | | | | |
|---|---|---|---|---|---|
| 9-755 | Me | 2,6-difluorobenzyl | isobutyl-CH(NHMe)-CH2- | | 3-methoxyphenyl | 471.5 | 472.2 |
| 9-756 | Me | 2,6-difluorobenzyl | isobutyl-CH(NHMe)-CH2- | | 3,4-methylenedioxyphenyl | 485.5 | 486.2 |
| 9-757 | Me | 2,6-difluorobenzyl | MeO2C-CH(NHBoc)-CH2- | | 3-methoxyphenyl | 559.6 | 460.2 |
| 9-758 | Me | 2,6-difluorobenzyl | Ph-CH(NHBoc)-CH2- | | 3-methoxyphenyl | 527.6 | 428.2 |
| 9-759 | Me | 2,6-difluorobenzyl | cyclopentyl-CH(NHMe)-CH2- | | 3-methoxyphenyl | 483.6 | 484.2 |
| 9-760 | Me | 2,6-difluorobenzyl | cyclopentyl-CH(NHMe)-CH2- | | 2,3-dihydrobenzo[1,4]dioxin-6-yl | 511.6 | 512.2 |
| 9-761 | Me | 2,6-difluorobenzyl | isobutyl-CH(NHMe)-CH2- | | 2,3-dihydrobenzo[1,4]dioxin-6-yl | 49.6 | 500.2 |
| 9-762 | Me | 2,6-difluorobenzyl | cyclopentyl-CH(NMe2)-CH2- | | 3-methoxyphenyl | 497.6 | 498.2 |
| 9-763 | Me | 2,6-difluorobenzyl | cyclopentyl-CH(NMe2)-CH2- | | 2,3-dihydrobenzo[1,4]dioxin-6-yl | 525.6 | 526.2 |

TABLE 9-continued

| | | | | | |
|---|---|---|---|---|---|
| 9-764 | Me | [2,6-difluorobenzyl]; [(S)-1-phenyl-1-(acetamido)propyl] | | [benzo[1,3]dioxol-5-yl] | 533.5 534.2 |
| 9-765 | Me | [2,6-difluorobenzyl]; [(piperidin-2-yl)ethyl] | | [3-methoxyphenyl] | 455.5 456.2 |
| 9-766 | Me | [2,6-difluorobenzyl]; [(piperidin-2-yl)ethyl] | | [3-methoxyphenyl] | 455.5 456.2 |
| 9-767 | Me | [2,6-difluorobenzyl]; [(thiazolidin-4-yl)ethyl] | | [3-methoxyphenyl] | 459.5 460.1 |
| 9-768 | Me | [2,6-difluorobenzyl]; [(thiazolidin-4-yl)ethyl] | | [3-methoxyphenyl] | 459.5 459 |
| 9-769 | Me | [2,6-difluorobenzyl]; [(indolin-2-yl)ethyl] | | [3-methoxyphenyl] | 489.5 489 |
| 9-770 | Me | [2,6-difluorobenzyl]; [(piperidin-2-yl)ethyl] | | [3-methoxy-2-fluorophenyl] | 487.5 488 |
| 9-771 | Me | [2,6-difluorobenzyl]; [(piperidin-2-yl)ethyl] | | Br | 442.3 442 |
| 9-772 | Me | [2,6-difluorobenzyl]; [(piperidin-2-yl)ethyl] | | H | 363.4 364 |

TABLE 9-continued

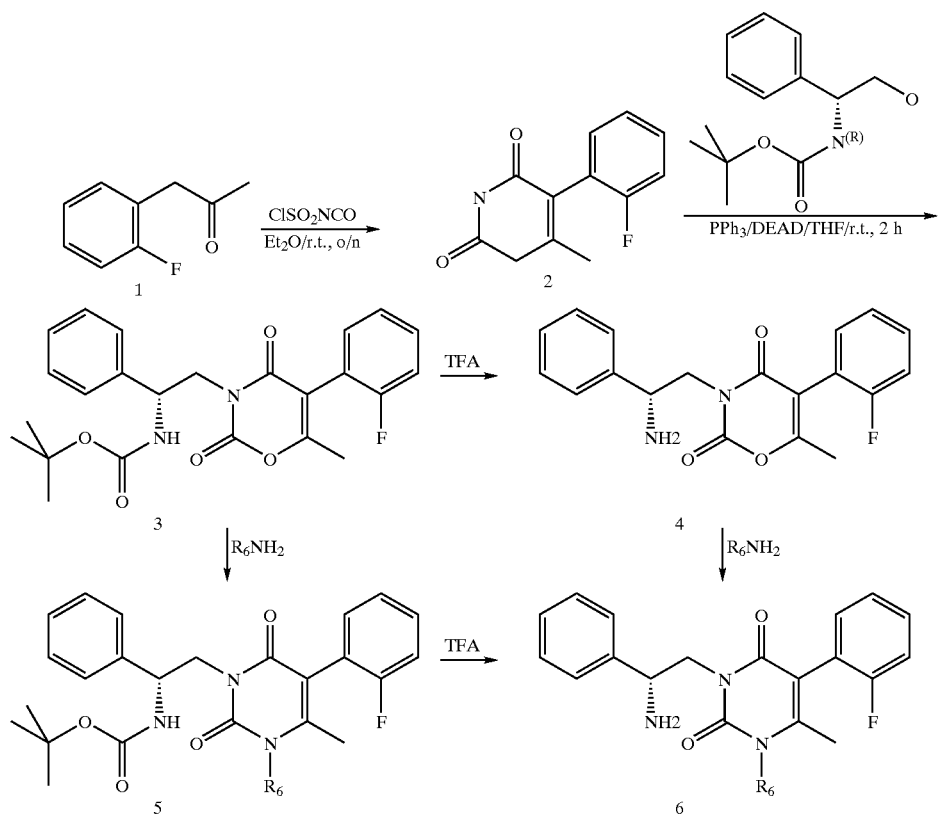

EXAMPLE 10

Synthesis of Representative Compounds

Step A 6-Methyl-5-(2-fluorophenyl)-oxaz-2,4-dione

To a stirred solution of 2'-fluorophenylacetone 1 (7.6 g, 50 mmol) in ether (50 mL) was added dropwise chlorosulfonylisocyanate (CSI, 16.2 g, 115 mmol) at room temperature. The yellow solution was stirred overnight, poured into ice (100 g) and basified with sodium carbonate. The product was extracted with ethyl acetate (2×200 mL) and the extract was washed with water and brine, dried over magnesium sulfate and concentrated in vacuo to give a yellow residue (9.5 g, proton NMR, about 70% product). The crude product was crystallized from ether-hexanes to give compound 2 as a yellow solid (3.6 g, 33% yield); $^1$H NMR (CDCl$_3$): 2.14 (s, 3H), 7.16 (t, J=9.0 Hz, 1H), 7.24 (m, 2H), 7.41 (m, 1H), 9.20 (brs, 1H).

Step B 6-Methyl-5-(2-fluorophenyl)-3-[2(R)-tert-butoxycarbonylamino-2-phenylethyl]oxaz-2,4-dione DEAD (348 mg, 1.2 mmol) was added into a solution of oxazine 2 (221 mg, 1.0 mmol), triphenylphosphine (314 mg, 1.2 mmol) and N-Boc-(R)-phenylglysinol (249 mg, 1.05 mmol) in dry THF (5 mL). The mixture was stirred at room temperature for 2 hours, concentrated, and purified by chromatography on silica gel with 1:3 ethyl acetate/hexanes to give the product 3 (380 mg, 87%) as a white solid; $^1$H NMR (CDCl$_3$): 1.39 (s, 9H), 2.14 (s, 3H), 4.02 (m, 1H), 4.28 (m, 1H), 5.21 (brs, 1H), 5.30 (m, 1H), 7.38 (m, 9H); MS (341, MH$^+$-BuOCO).

Step C 6-Methyl-5-(2-fluorophenyl)-3-[2(R)-amino-2-phenylethyl]oxaz-2,4-dione trifluoroacetic acid salt 6-Methyl-5-(2-fluorophenyl)-3-[2(R)-tert-butoxycarbonylamino-2-phenylethyl]oxaz-2,4-dione 3 (30 mg) was treated with trifluoroacetic acid (1 mL) at room temperature for 30 minutes. Concentration in vacuo gave the title compound 4 as a colorless oil in quantitative yield; $^1$H NMR (CDCl$_3$): 2.05 & 2.08 (s, 3H), 4.10 (m, 1H), 4.45 (m, 1H), 4.62 (m, 1H), 7.15 (m, 3H), 7.40 (m, 6H), 8.20 (brs, 3H); MS: 341 (MH$^+$).

Step D 6-Methyl-5-(2-fluorophenyl)-3-[2(R)-tert-butoxycarbonylamino-2-phenylethyl]-1-(2-methoxybenzyl)uracil A mixture of 6-methyl-5-(2-fluorophenyl)-3-[2(R)-tert-butoxycarbonylamino-2-phenylethyl]oxaz-2,4-dione 3 (29 mg) and 2-methoxybenzylamine (0.15 mL) was heated in a sealed reacti-vial at 100° C. for 1 hour. Chromatography on silica gel with 1:2 ethyl acetate-hexanes gave compound 5 as a colorless oil; $^1$H NMR (CDCl$_3$): 1.40 (s, 9H), 2.04 (s, 3H), 3.87 (s, 3H), 4.18 (m, 1H), 4.44 (m, 1H), 5.22 (m, 2H), 5.65 (brs, 1H), 5.78 (m, 1H), 6.85–7.42 (m, 13H); MS: 460 (MH$^+$-BuOCO).

The following protected intermediates were made using the same procedure but substituting different amines for 2-methoxybenzylamine. Acetic acid may be used to catalyze the reaction.

6-Methyl-5-(2-fluorophenyl)-3-[2(R)-tert-butoxycarbonylamino-2-phenylethyl]-1-(2,6-difluorobenzyl)uracil $^1$H NMR (CDCl$_3$): 1.39 (s, 9H), 2.18 (s, 3H), 4.10 (m, 1H), 4.38 (m, 1H), 4.90–5.80 (m, 4H), 6.92 (m, 2H), 7.10–7.42 (m, 10H); MS: 466 (MH$^+$-BuOCO).

6-Methyl-5-(2-fluorophenyl)-3-[2(R)-tert-butoxycarbonylamino-2-phenylethyl]-1-(2-chlorobenzyl)uracil $^1$H NMR (CDCl$_3$): 1.40 (s, 9H), 2.02 (s, 3H), 4.15 (m, 1H), 4.50 (m, 1H), 5.35 (m, 3H), 5.62 (m, 1H), 6.95 (m, 13H); MS: 464 (MH$^+$-BuOCO).

6-Methyl-5-(2-fluorophenyl)-3-[2(R)-tert-butoxycarbonylamino-2-phenylethyl]-1-(2-methylbenzyl)uracil $^1$H NMR (CDCl$_3$): 1.40 (s, 9H), 2.02 (s, 3H), 2.37 (s, 3H), 4.15 (m, 1H), 4.42 (m, 1H), 5.72 (m, 1H), 6.80–7.42 (m, 13H); MS: 444 (MH$^+$-BuOCO).

Step E 6-Methyl-5-(2-fluorophenyl)-3-[2(R)-amino-2-phenylethyl]-1-(2-methoxybenzyl)uracil trifluoroacetic acid salt 6-Methyl-5-(2-fluorophenyl)-3-[2(R)-tert-butoxycarbonylamino-2-phenylethyl]-1-(2-methoxybenzyl)uracil 5 (20 mg) was treated with trifluoroacetic acid (1 mL) at room temperature for 30 minutes. Concentration in vacuo gave the product 6 as a colorless oil in quantitative yield; $^1$H NMR (CDCl$_3$): 2.04 (s, 3H), 3.82 & 3.85 (s, 3H), 4.20 (m, 1H), 4.62 (m, 2H), 5.10 (m, 2H), 6.82–7.40 (m, 13H), 8.05 (brs, 3H); MS: 460 (MH$^+$).

The following products were also prepared using the same procedure.

6-Methyl-5-(2-fluorophenyl)-3-[2(R)-amino-2-phenylethyl]-1-(2-chlorobenzyl)uracil trifluoroacetic acid salt $^1$H NMR (CDCl$_3$): 2.01 (s, 3H), 4.20 (m, 1H), 4.70 (m, 2H), 5.25 (m, 2H), 6.90–7.45 (m, 13H), 8.20 (brs, 3H); MS: 464 (MH$^+$).

6-Methyl-5-(2-fluorophenyl)-3-[2(R)-amino-2-phenylethyl]-1-(2-methylbenzyl)uracil trifluoroacetic acid salt $^1$H NMR (CDCl$_3$): 2.00 (s, 3H), 2.27 & 2.34 (s, 3H), 4.15 (m, 4H), 4.62 (m, 2H), 5.15 (m, 2H), 6.80–7.40 (m, 13H); MS: 444 (MH$^+$).

6-Methyl-5-(2-fluorophenyl)-3-[2(R)-amino-2-phenylethyl]-1-(2,6-difluorobenzyl)uracil trifluoroacetic acid salt $^1$H NMR (CDCl$_3$): 2.14 (s, 3H), 4.18 (m, 1H), 4.62 (m, 2H), 5.20 (m, 2H), 5.62 (brs, 3H), 6.85–7.40 (m, 13H); MS: 466 (MH$^+$).

By the above procedure, the compounds of the following Table 10 were also prepared.

TABLE 10

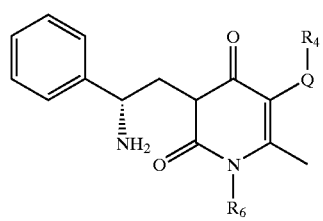

| Cpd. No. | R$_6$ | —Q—R$_4$ | MW (calc.) | (obs.) |
|---|---|---|---|---|
| 10-1 | 2,6-difluorobenzyl | 2-fluorophenyl | 465.5 | 466 |

TABLE 10-continued
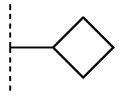
| Cpd. No. | R_6 | —Q—R_4 | MW (calc.) | MW (obs.) |
|---|---|---|---|---|
| 10-2 | cyclobutylmethyl | 2-fluorophenyl | 393.5 | 394.2 |
| 10-3 | cyclopropylmethyl | 2-fluorophenyl | 379.4 | 363 |
| 10-4 | cyclopentyl | 2-fluorophenyl | 407.5 | 323.3 |
| 10-5 | cyclohexyl | 2-fluorophenyl | 421.5 | 405.4 |
| 10-6 | cyclohexylmethyl | 2-fluorophenyl | 435.5 | 436.2 |
| 10-7 | (1-methylpyrrolidin-2-yl)ethyl | 2-fluorophenyl | 450.6 | 451.3 |
| 10-8 | 2-(imidazol-4-yl)ethyl | 2-fluorophenyl | 433.5 | 417.3 |
| 10-9 | (tetrahydrofuran-2-yl)methyl | 2-fluorophenyl | 423.5 | 407.2 |

TABLE 10-continued
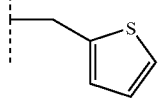
| Cpd. No. | R$_6$ | —Q—R$_4$ | MW (calc.) | (obs.) |
|---|---|---|---|---|
| 10-10 | 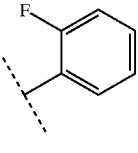 | 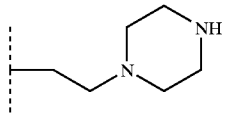 | 435.5 | 419.2 |
| 10-11 | 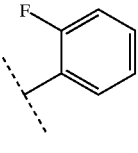 | 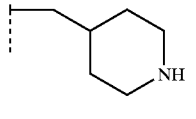 | 451.5 | 452.3 |
| 10-12 | 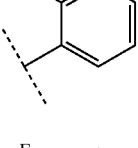 | 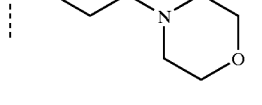 | 436.5 | 323.3 |
| 10-13 | 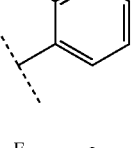 | 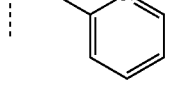 | 466.6 | 450.3 |
| 10-14 | 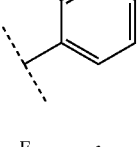 | 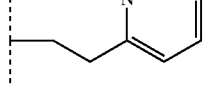 | 430.5 | 414.4 |
| 10-15 | 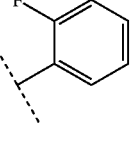 | 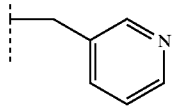 | 444.5 | 428.4 |
| 10-16 | 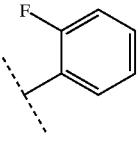 | 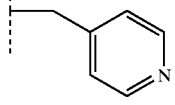 | 430.5 | 414.4 |
| 10-17 | 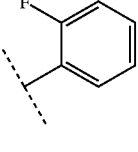 | | 430.5 | 414.4 |

TABLE 10-continued
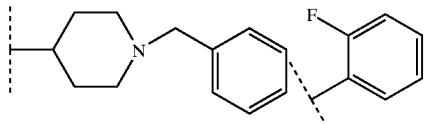
| Cpd. No. | R₆ | —Q—R₄ | MW (calc.) | MW (obs.) |
|---|---|---|---|---|
| 10-18 | 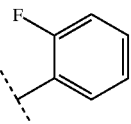 |  | 512.6 | 513.3 |
| 10-19 | 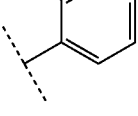 |  | 410.5 | 323.3 |
| 10-20 | 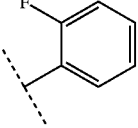 |  | 381.4 | 382.2 |
| 10-21 | 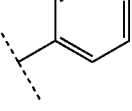 | 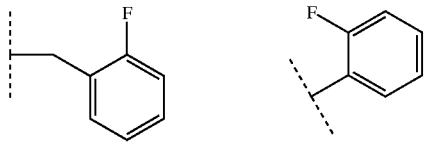 | 429.5 | 413.2 |
| 10-22 | 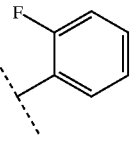 | 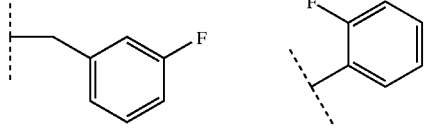 | 447.5 | 431.4 |
| 10-23 | 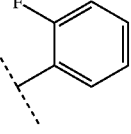 | 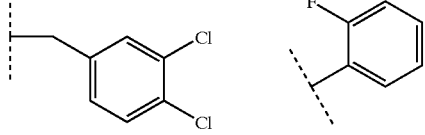 | 447.5 | 431.3 |
| 10-24 | 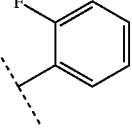 | 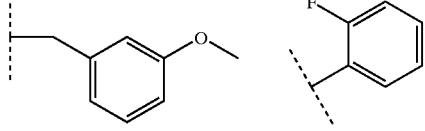 | 498.4 | 481.4 |
| 10-25 | 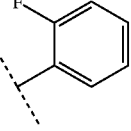 | | 459.5 | 443.3 |

TABLE 10-continued

| Cpd. No. | R$_6$ | —Q—R$_4$ | MW (calc.) | MW (obs.) |
|---|---|---|---|---|
| 10-26 | 3-methylbenzyl | 2-fluorophenyl | 443.5 | 427.2 |
| 10-27 | 4-chlorobenzyl | 2-fluorophenyl | 463.9 | 447.1 |
| 10-28 | 4-methylbenzyl | 2-fluorophenyl | 443.5 | 427.2 |
| 10-29 | 2-hydroxypropyl | 2-fluorophenyl | 397.4 | 398.2 |
| 10-30 | isobutyl | 2-fluorophenyl | 395.5 | 379.2 |
| 10-31 | 2-methylbutyl | 2-fluorophenyl | 409.5 | 393.3 |
| 10-32 | 2-(methylamino)ethyl | 2-fluorophenyl | 396.5 | 380.3 |
| 10-33 | 2-(dimethylamino)ethyl | 2-fluorophenyl | 410.5 | 394.1 |

TABLE 10-continued
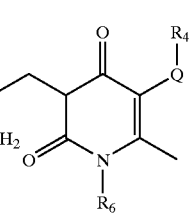
| Cpd. No. | R$_6$ | —Q—R$_4$ | MW (calc.) | (obs.) |
|---|---|---|---|---|
| 10-34 | 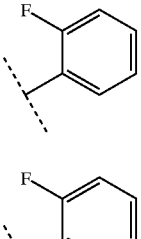 | 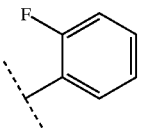 | 397.4 | 381.2 |
| 10-35 | 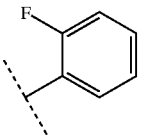 | 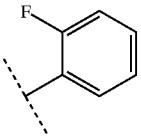 | 383.4 | 367.1 |
| 10-36 | 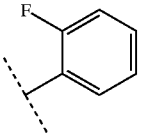 | 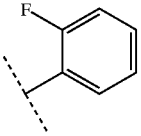 | 443.5 | 427.2 |
| 10-37 | 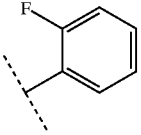 | | 379.4 | 363.3 |
| 10-38 | | | 409.5 | 393.3 |
| 10-39 | | | 382.4 | 366.2 |
| 10-40 | | | 381.4 | 365.2 |
| 10-41 | | | 424.5 | 408.5 |

TABLE 10-continued

| Cpd. No. | R₆ | —Q—R₄ | MW (calc.) | MW (obs.) |
|---|---|---|---|---|
| 10-42 | -(CH₂)₃-OH | 2-F-C₆H₄ | 397.4 | 381.2 |
| 10-43 | -(CH₂)₃-NH₂ | 2-F-C₆H₄ | 396.5 | 380.3 |
| 10-44 | -(CH₂)₄-CH₃ | 2-F-C₆H₄ | 409.5 | 393.3 |
| 10-45 | -CH₂-(3,4-diF-C₆H₃) | 2-F-C₆H₄ | 465.5 | 449.4 |
| 10-46 | -CH₂-(4-CF₃-C₆H₄) | 2-F-C₆H₄ | 497.5 | 481.4 |
| 10-47 | -(CH₂)₃-CH₃ | 2-F-C₆H₄ | 395.5 | 379.3 |
| 10-48 | -(CH₂)₃-(1-pyrrolidinyl) | 2-F-C₆H₄ | 450.6 | 451.3 |
| 10-49 | -(CH₂)₃-OCH₃ | 2-F-C₆H₄ | 411.5 | 395.2 |

TABLE 10-continued

| Cpd. No. | R6 | —Q—R4 | MW (calc.) | MW (obs.) |
|---|---|---|---|---|
| 10-50 | cyclopropylmethyl | 2-fluorophenyl | 393.5 | 377.3 |
| 10-51 | 2-(pyridin-4-yl)ethyl | 2-fluorophenyl | 444.5 | 428.4 |
| 10-52 | 3-chlorobenzyl | 2-fluorophenyl | 463.9 | 447.1 |
| 10-53 | 3,5-dimethylbenzyl | 2-fluorophenyl | 457.5 | 441.3 |
| 10-54 | 2-chloro-4-fluorobenzyl | 2-fluorophenyl | 481.9 | 465.4 |
| 10-55 | 2,3-dichlorobenzyl | 2-fluorophenyl | 498.4 | 481.2 |
| 10-56 | 2-hydroxy-1-(hydroxymethyl)ethyl | 2-fluorophenyl | 413.4 | 397.1 |
| 10-57 | 2,5-dichlorobenzyl | 2-fluorophenyl | 498.4 | 481.2 |

TABLE 10-continued

| Cpd. No. | R_6 | —Q—R_4 | MW (calc.) | MW (obs.) |
|---|---|---|---|---|
| 10-58 | pyrrolidin-3-ylmethyl | 2-fluorophenyl | 408.5 | 409.2 |
| 10-59 | 2-isopropoxyethyl | 2-fluorophenyl | 425.5 | 409.2 |
| 10-60 | (pyridin-3-yl)methyl | 2-fluorophenyl | 444.5 | 428.4 |
| 10-61 | (pyrrolidin-2-yl)methyl | 2-fluorophenyl | 422.5 | 323.4 |
| 10-62 | (2,3-dihydro-1,4-benzodioxin-2-yl)methyl | 2-fluorophenyl | 487.5 | 471.3 |
| 10-63 | (1,3-benzodioxol-5-yl)methyl | 2-fluorophenyl | 473.5 | 474.2 |
| 10-64 | (2,4-dichlorophenyl)methyl | 2-fluorophenyl | 498.4 | 498.1 |
| 10-65 | (4-fluorophenyl)methyl | 2-fluorophenyl | 447.5 | 448.2 |

TABLE 10-continued
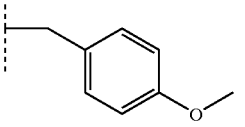
| Cpd. No. | R6 | —Q—R4 | MW (calc.) | (obs.) |
|---|---|---|---|---|
| 10-66 | 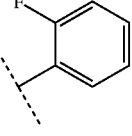 | 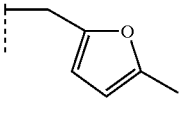 | 459.5 | 460.2 |
| 10-67 | 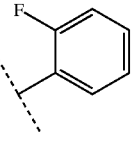 | 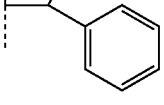 | 443.5 | 434.2 |
| 10-68 | 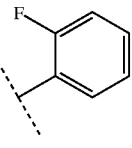 | 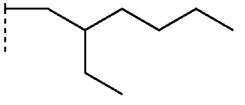 | 443.5 | 444.2 |
| 10-69 | 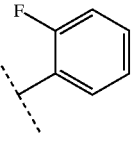 | 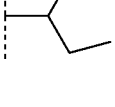 | 451.6 | 452.3 |
| 10-70 | 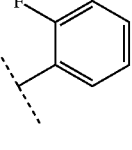 |  | 409.5 | 410.2 |
| 10-71 | 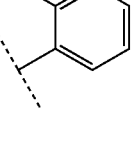 | 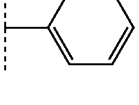 | 409.5 | 410.2 |
| 10-72 | 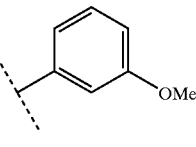 |  | 427.5 | 428.2 |

EXAMPLE 11

Synthesis of Representative Compounds

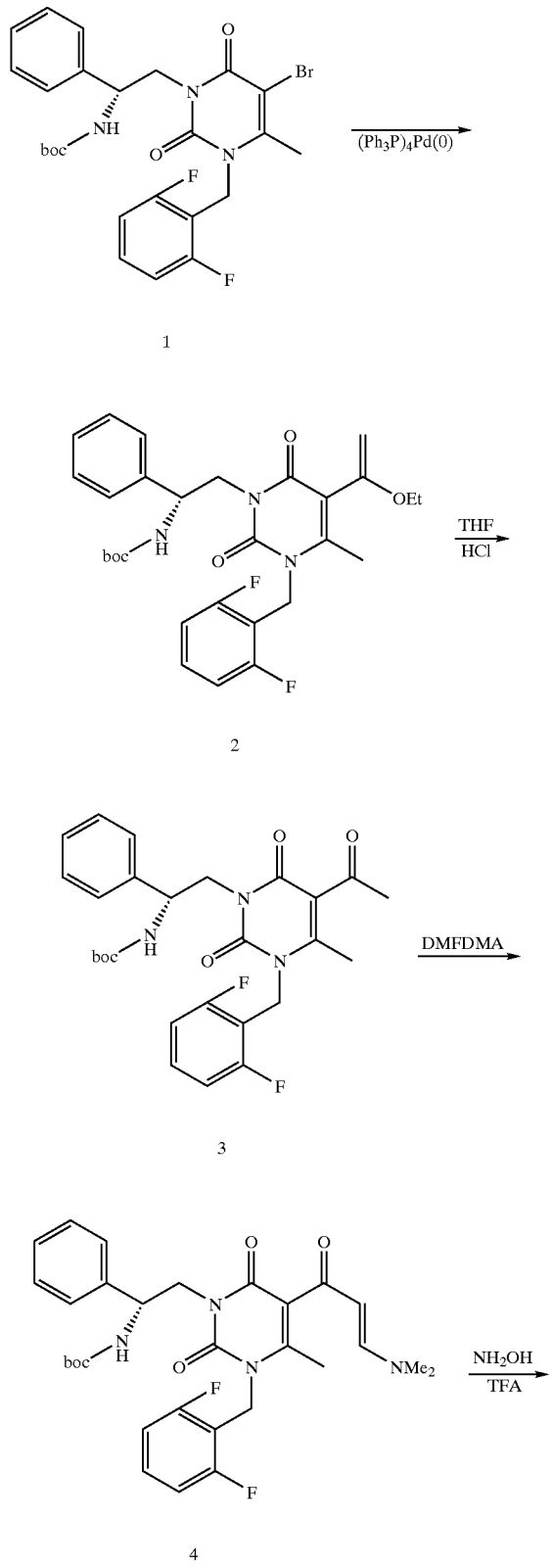

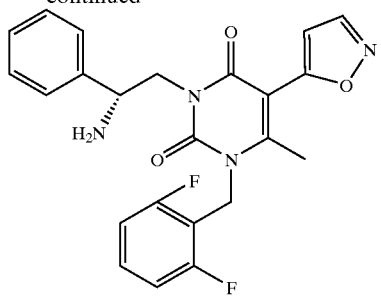

Step A 1-(2,6-difluorobenzyl-3-[(2R)-tertbutylcarbonylamino-2-phenyl]ethyl-5-(1-ethoxyvinyl)-6-methyluracil A solution of 1-(2,6-difluorobenzyl-3-[(2R)-tertbutylcarbonylamino-2-phenyl]ethyl-5-bromo-6-methyluracil 1 (500 mg, 0.91 mmol), tributyl(ethoxyvinyl) tin (0.39 mL) and (Ph$_3$P)$_4$Pd(0) (105 mg) in dioxane (5 mL) was heated at 100° C. under nitrogen for 2 hours. The reaction mixture was concentrated in vacuo and the crude product 2 was used for next step. MS: 442 (MH+-Boc).

Step B 1-(2,6-Difluorobenzyl-3-[(2R)-tertbutyloxycarbonylamino-2-phenyl]ethyl-5-acetyl-6-methyluracil A solution of 1-(2,6-difluorobenzyl-3-[(2R)-tertbutylcarbonylamino-2-phenyl]ethyl-5-(1-ethoxyvinyl)-6-methyluracil 2 (490 mg) in THF (10 mL) was treated with 2.5M aqueous HCl (3 mL) and stirred at r.t. for one hour. The reaction mixture was neutralized with NaHCO$_3$ and concentrated in vacuo to remove THF. The product was extracted with ethyl acetate. The extract was washed with water and brine, dried over MgSO$_4$ and concentrated in vacuo to give a brown solid. Chromatography on silica gel with 1:2 to 1:1 ethyl acetate/hexanes gave compound 3 as a white solid (227 mg, 50% yield); 1H NMR: 1.37 (s, 9H), 2.38 (s, 3H), 2.58 (s, 3H), 4.12 (dd, J=4.2, 10.0 Hz, 1H), 4.65 (dd, J=6.5, 10.0 Hz, 1H), 5.20 (m, 1H), 5.40 (d, J=12.0 Hz, 1H), 5.49 (d, J=12.0 Hz, 1H), 5.58 (d, J=6.0 Hz, 1H), 6.92 (t, J=8.0 Hz, 2H), 7.38 (m, 6H); MS: 414 (MH+-Boc).

Step C 1-(2,6-Difluorobenzyl-3-[(2R)-tertbutoxycarbonylamino-2-phenyl]ethyl-5-(3-dimethylamino-1-oxypropenyl)-6-methyluracil 1-(2,6-Difluorobenzyl-3-[(2R)-tertbutylcarbonylamino-2-phenyl]ethyl-5-acetyl-6-methyluracil 3 (44 mg) was suspended in DMFDMA (1.0 mL) and heated at 50° C. for 1 hour. The product was purified on silica gel with 1:1 ethyl acetate/hexanes to give compound 4 as a yellow oil; 1H NMR: 1.39 (s, 9H), 2.36 (s, 3H), 2.84 (s, 6H), 4.05 (m, 1H), 4.30 (m, 1H), 4.66 (d, J=12.0 Hz, 1H), 5.03 (m, 1H), 5.20 (d, J=12 Hz, 1H), 5.46 (d, J=12 Hz, 1H), 5.84 (d, J=7 Hz, 1H), 6.64 (d, J=12.0 Hz, 1H), 6.87 (t, J=8.0 Hz, 2H), 7.20–7.40 (m, 6H); MS: 596 (MH+).

Step D 1-(2,6-Difluorobenzyl-3-[(2R)-amino-2-phenyl]ethyl-5-(isoxazol-5-yl)-6-methyluracil A mixture of 1-(2,6-difluorobenzyl-3-[(2R)-tertbutoxycarbonylamino-2-phenyl]ethyl-5-(3-dimethylamino-1-oxopropenyl)-6-methyluracil 4 (95 mg), hydroxylamine hydrochloride (150 mg), sodium carbonate (18 mg) in methanol (5 mL) was acidified with acetic acid to pH ~4. The mixture was then heated at 120° C. for 1.5 hours, cooled down to r.t., filtered, and concentrated in vacuo to give the protected product. MS: 539 (MH+). The protected product was dissolved in dichloromethane (2 mL), treated with TFA (1 mL), and stirred at r.t. for 1 hour. Concentration in vacuo followed by purification on silica gel eluting with 1% aq. NH$_4$OH in ethyl acetate gave product 5; MS: 439 (MH+); 1H NMR (CD$_3$OD): 3.05 (s, 3H), 4.70 (m, 1H), 4.55 (m, 2H), 5.48 (d, J=12.0 Hz, 1H), 5.60 (d, J=12.0 Hz, 1H), 7.00 (t, J=8.0 Hz, 2H), 7.30–7.65 (m, 7H), 8.50 (d, J=6.0 Hz, 1H).

EXAMPLE 12

Synthesis of Representative Compounds

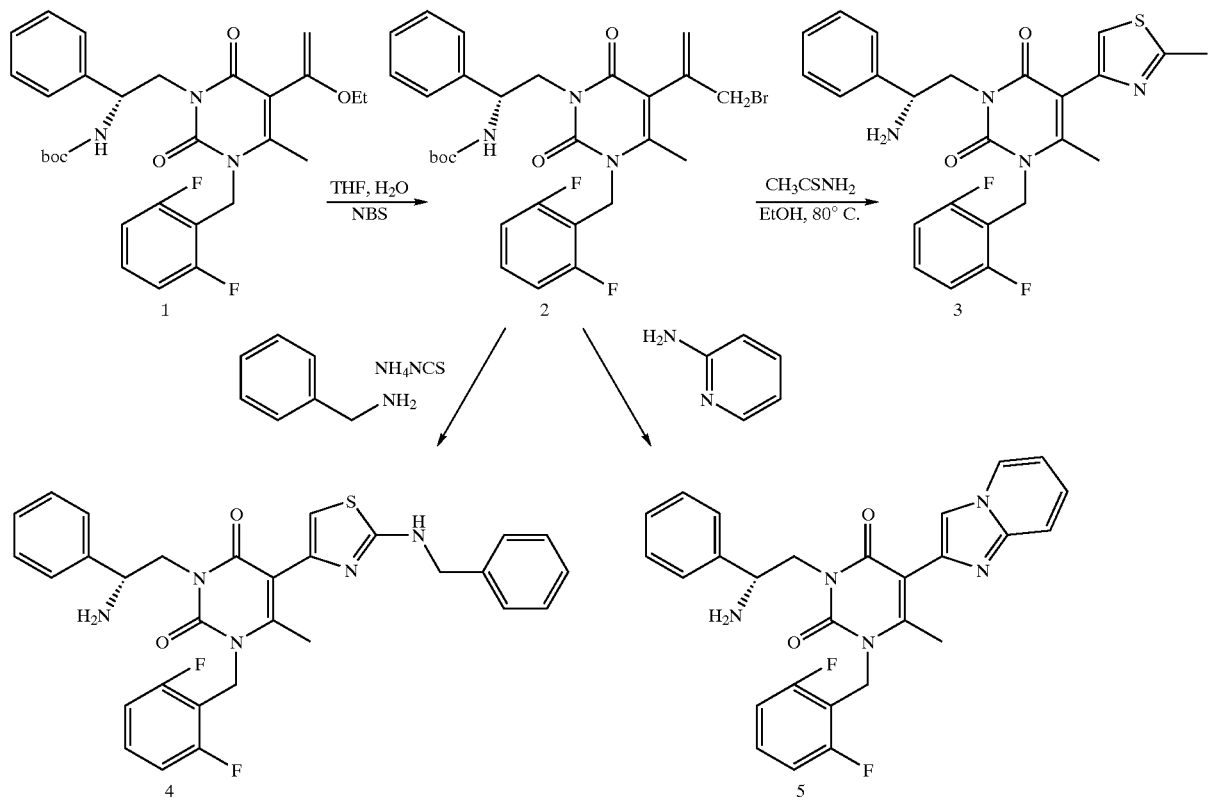

Step A 1-(2,6-Difluorobenzyl-3-[(2R)-tertbutylcarbonylamino-2-phenyl]ethyl-5-bromoacetyl-6-methyluracil A solution of 1-(2,6-difluorobenzyl-3-[(2R)-tertbutylcarbonylamino-2-phenyl]ethyl-5-(1-ethoxyvinyl)-6-methyluracil 1 (3.68 g, 6.8 mmol) in THF (120 mL) and water (120 mL) was treated with N-bromosuccinimide (2.3 g) at r.t. and the mixture was stirred for 4 hours. THF was removed in vacuo and the product which precipitated on standing was collected by filtration and was washed with ether to give white solid 2 (1.6 g, 40%); 1H NMR: 1.39 (s, 9H), 2.40 (s, 3H), 4.04 (dd, J=2.0, 7.0 Hz, 1H), 4.36 (d, J=7.0 Hz, 1H), 4.10 (d, J=5.5 Hz, 1H), 4.56 (d, J=5.5 Hz, 1H), 55.50 (m, 1H), 5.24 (d, J=12.0 Hz, 1H), 5.40 (brs, 1H), 5.50 (d, J=12.0 Hz, 1H), 6.94 (t, J=8.0 Hz, 1H), 7.36 (m, 6H); MS: 492 (MH+).

Step B 1-(2,6-Difluorobenzyl-3-[(2R)-amino-2-phenyl]ethyl-5-(5-methylthiazol-4-yl)-6-methyluracil A solution of 1-(2,6-difluorobenzyl-3-[(2R)-tertbutylcarbonylamino-2-phenyl]ethyl-5-bromoacetyl-6-methyluracil (100 mg, 0.17 mmol) and thioacetamide (30 mg, 0.4 mmol) in ethanol (2 mL) was heated at 80° C. in a sealed reaction vessel for 3 hours. The reaction mixture was then concentrated in vacuo to give an oil and LCMS indicated protected product; MS: 569 (MH+). The protected product was dissolved in dichloromethane (2 mL) and treated with TFA (1 mL) at r.t. for 1 hour, and concentrated in vacuo. The product was purified on silica gel eluting with 5% aq. NH$_4$OH in ethyl acetate to give yellow solid 3; 1H NMR: 2.12 (s, 3H), 2.71 (s, 3H), 4.15–4.70 (m, 3H), 5.66 (s, 2H), 7.00 (t, J=8.0 Hz, 2H), 7.30 (m, 7H); MS: 469 (MH+).

Step C 1-(2,6-Difluorobenzyl-3-[(2R)-amino-2-phenyl] ethyl-5-(5-benzylaminolthiazol-4-yl)-6-methyluracil A solution of 1-(2,6-difluorobenzyl-3-[(2R)-tertbutylcarbonylamino-2-phenyl]ethyl-5-bromoacetyl-6-methyluracil 2 (35 mg) and ammonium thioisocyanate (10 mg) in ethanol (1 mL) was heated at 80° C. in a sealed reaction vessel for 1 hour. Benzylamine (0.2 mL) was added and the mixture was heated at 80° C. overnight. The reaction mixture was then concentrated in vacuo, and the protected product was dissolved in dichloromethane (1 mL) and treated with TFA (1 mL) at r.t. for 1 hour. The mixture was concentrated in vacuo and the residue was purified on silica gel with 5% aq. NH$_4$OH in ethyl acetate to give product 4 as a yellow solid; $^1$H NMR: 2.25 (s, 3H), 4.05 (dd, J=3.0, 7.5 Hz, 1H), 4.28 (dd, J=6.5, 7.5 Hz, 1H), 4.42 (m, 1H), 4.44 (s, 2H), 5.32 (d, J=12.0 Hz, 1H), 5.36 (d, J=12.0 Hz, 1H), 6.54 (s, 1H), 6.92 (t, J=8.0 Hz, 2H), 7.20–7.50 (m, 11H); MS: 560 (MH$^+$).

Step D 1-(2,6-Difluorobenzyl-3-[(2R)-amino-2-phenyl] ethyl-5-(imidazolo[1,2-a]pyrid-2-yl)-6-methyluracil A mixture of 1-(2,6-difluorobenzyl-3-[(2R)-tertbutylcarbonylamino-2-phenyl]ethyl-5-bromoacetyl-6-methyluracil 2 (35 mg) and 2-aminopyridine (7 mg) in ethanol was heated at 80° C. overnight. The reaction mixture was then concentrated in vacuo, and the protected product was dissolved in dichloromethane (1 mL) and treated with TFA (1 mL) at r.t. for 1 hour. After concentration in vacuo, the product 5 was purified on preparative HPLC; 1H NMR: 2.32 (s, 3H), 4.04 (m, 1H), 4.67 (m, 2H), 5.17 (d, J=16.2 Hz, 1H), 5.41 (d, J=16.2 Hz, 1H), 6.92 (t, J=8.1 Hz, 2H), 7.24–7.40 (m, 7H), 7.73 (m, 1H), 7.80 (m, 1H), 8.03 (s, 1H), 8.30 (brs, 3H), 8.44 (d, J=5.5 Hz, 1H); MS: 488 (MH+).

TABLE 12

| Cpd. No. | —Q—R$_4$ | MW (calc.) | MW (obs.) |
|---|---|---|---|
| 12-1 | (2-methylthiazol-4-yl) | 468.5 | 469.1 |
| 12-2 | (2-aminothiazol-4-yl) | 469.5 | 470.1 |
| 12-3 | (2-ethylaminothiazol-4-yl) | 497.6 | 498.2 |
| 12-4 | (2-phenylthiazol-4-yl) | 530.6 | 531.1 |
| 12-5 | (2-benzylthiazol-4-yl) | 544.6 | 545.2 |
| 12-6 | (2-ethoxycarbonylthiazol-4-yl) | 526.6 | 527.2 |
| 12-7 | (imidazo[1,2-a]pyrimidin-2-yl) | 488.5 | 489.2 |
| 12-8 | (3-methylimidazo[2,1-b]thiazol-6-yl) | 507.6 | 508.2 |
| 12-9 | (2-methyl-[1,3,4]thiadiazolo-imidazol-6-yl) | 508.6 | 509.1 |
| 12-10 | (2-(4-methoxyphenylamino)thiazol-4-yl) | 575.6 | 576.2 |
| 12-11 | (2-phenylaminothiazol-4-yl) | 545.6 | 546.2 |
| 12-12 | (2-(2-fluoro-4-methoxyphenylamino)thiazol-4-yl) | 563.6 | 564.2 |
| 12-13 | (2-(4-nitrophenylamino)thiazol-4-yl) | 590.6 | 591.1 |

TABLE 12-continued

| Cpd. No. | —Q—R4 | MW (calc.) | MW (obs.) |
|---|---|---|---|
| 12-14 | thiazol-4-yl, 2-(N-methyl-N-phenylamino) | 559.6 | 560.2 |
| 12-15 | imidazo[1,2-a]pyridin-2-yl | 487.5 | 488.2 |
| 12-16 | thiazol-4-yl, 2-morpholino | 539.6 | 540.2 |
| 12-17 | thiazol-4-yl, 2-(benzylamino) | 559.6 | 560.2 |
| 12-18 | thiazol-4-yl, 2-(N-methyl-N-benzylamino) | 573.7 | 574.2 |
| 12-19 | 2,4-dimethoxypyrimidin-5-yl | 509.5 | 510 |
| 12-20 | thiazol-4-yl, 2-(4-CF3-phenyl) | 598.6 | 599.2 |
| 12-21 | thiazol-4-yl, 2-(2-Cl-phenyl) | 565.0 | 565.2 |
| 12-22 | thiazol-4-yl, 2-(4-Cl-phenyl) | 565.0 | 565.1 |
| 12-23 | thiazol-4-yl, 2-(3-Cl-4-F-phenyl) | 583.0 | 583.1 |
| 12-24 | thiazol-4-yl, 2-(4-F-phenyl) | 548.6 | 549.2 |
| 12-25 | thiazol-4-yl, 2-(2-methylphenylamino) | 559.6 | 560.2 |
| 12-26 | thiazol-4-yl, 2-(2-methoxyphenylamino) | 575.6 | 576.2 |
| 12-27 | thiazol-4-yl, 2-(3,4-dimethoxyphenylamino) | 605.7 | 606.3 |
| 12-28 | thiazol-4-yl, 2-(2,3-dimethylphenylamino) | 573.7 | 574.2 |

TABLE 12-continued
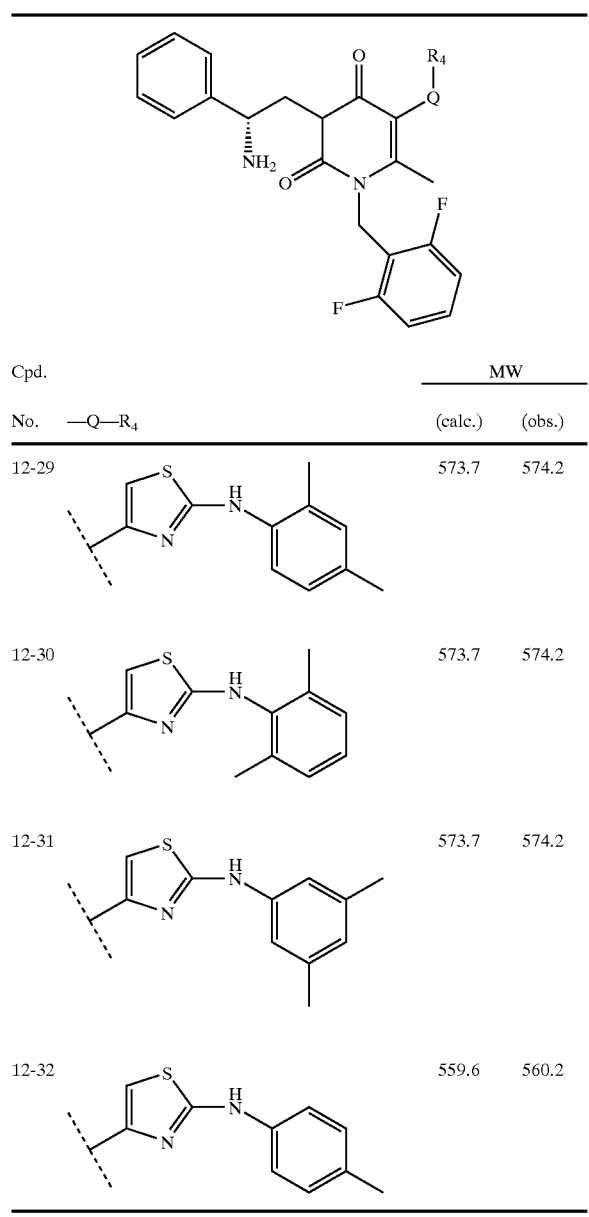
| Cpd. No. | —Q—R4 | MW (calc.) | MW (obs.) |
|---|---|---|---|
| 12-29 | | 573.7 | 574.2 |
| 12-30 | | 573.7 | 574.2 |
| 12-31 | | 573.7 | 574.2 |
| 12-32 | | 559.6 | 560.2 |
EXAMPLE 13
Synthesis of Representative Compounds
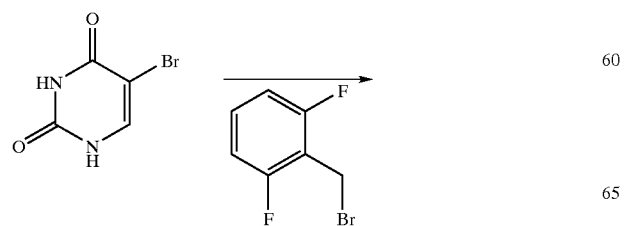
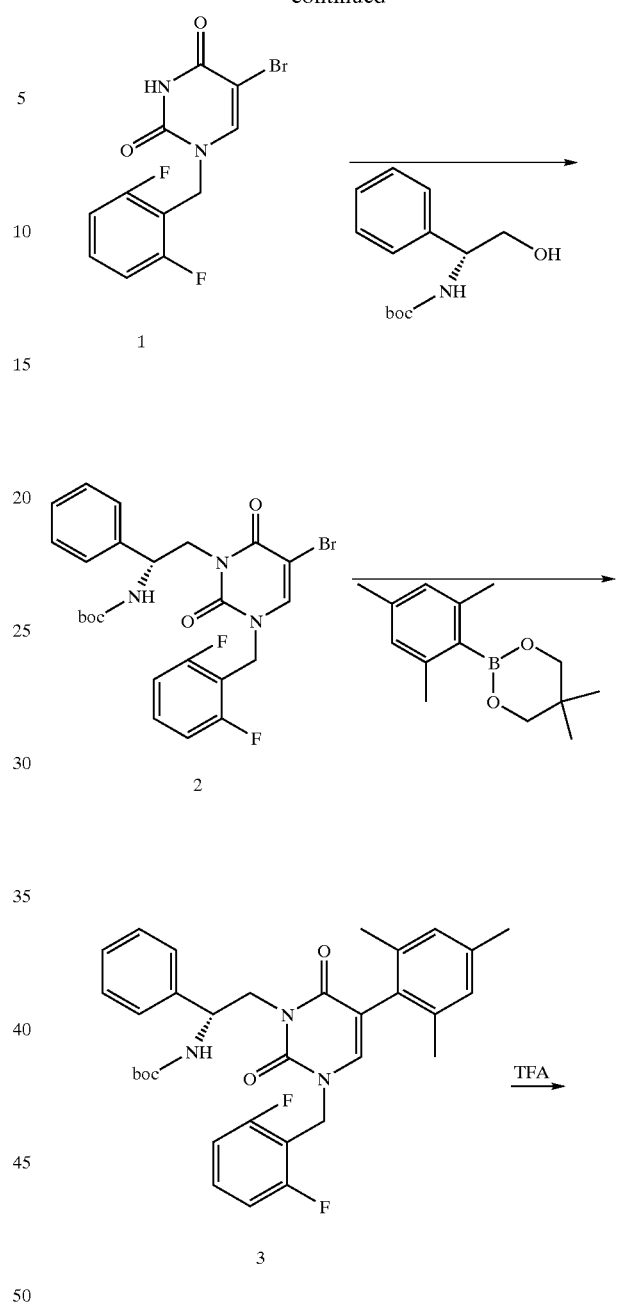
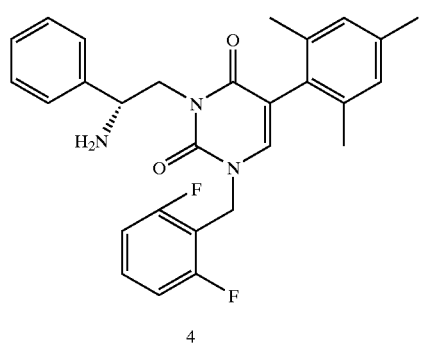

Step A. 5-Bromo-1-(2,6-difluorobenzyl)uracil

A suspension of 5-bromouracil (18.45 g, 96.6 mmol) in 300 mL of dichloroethane was treated with N,O-bis(trimethylsilyl)acetamide (48 mL, 39.5 g, 194 mmol). The reaction mixture was heated at 80° C. for 3 hr under the nitrogen. The solution was cooled down to ambient temperature, 2,6-difluorobenzyl bromide (25 g, 120 mmol) was added and the reaction mixture was heated at 80° C. overnight under the protection of nitrogen. The reaction was cooled down, quenched with MeOH (15 mL), and partitioned between dichloromethane (500 mL) and water (250 mL). The organic layer was washed with brine, dried (sodium sulfate), and evaporated to give a solid. The crude product was triturated with ether, filtered, and washed with ether three times to give compound 1 (15.2 g, 50%) as a white solid; MS (CI) m/z 316.90, 318.90 (MH$^+$).

Step B 1-(2,6-Difluorobenzyl-3-[(2R)-tertbutylcarbonylamino-2-phenyl]ether-5-bromouracil A solution of (R)-N-(tert-butoxycarbonyl)-2-phenylglycinol (14.97 g, 63.1 mmol) in anhydrous THF (300 mL) was treated with 5-bromo-1-(2,6-difluorobenzyl)uracil 1 (20 g, 63.1 mmol) and triphenylphosphine (20.68 g, 78.8 mmol) at ambient temperature, then diisopropylazodicarboxylate (15.52 mL, 15.94 g, 78.8 mmol) in THF (30 mL) was introduced via a dropping funnel. The reaction mixture was stirred at ambient temperature for 16 h and volatiles were evaporated. The residue was purified by flash chromatography (silica, 25% EtOAc/hexanes) to give compound 2 (31.15 g, 92.1%) as a white solid, MS (CI) m/z 436.0, 438.0 (MH$^+$-Boc).

Step C 1-(2,6-Difluorobenzyl-3-[(2R)-tert-butoxycarbonylamino-2-phenyl]ethyl-5-(2,4,6-trimethylphenyl)uracil To compound 2 (134 mg, 0.25 mmol) in toluene/H$_2$O/EtOH (6/3.75/0.75 mL) was added 2,4,6-trimethylphenyl boronic acid ester (87 mg, 1.5 eq), K$_2$CO$_3$ (86 mg, 2.5 eq), and saturated Ba(OH)$_2$/water (0.1 mL). The reaction mixture was deoxygenated with N$_2$ for 10 min, tetrakis(triphenylphosphine) palladium (0) (29 mg, 0.1 eq) was added and the reaction mixture was heated at 100° C. overnight under the protection of N$_2$. The reaction mixture was partitioned between brine and EtOAc. The organic layer was dried (sodium sulfate), evaporated, purified by flash chromatography (silica, 25% EtOAc/hexanes) to give compound 3 (130 mg) as a pale yellow oil.

Step D 1-(2,6-Difluorobenzyl-3-[(2R)-amino-2-phenyl]ethyl-5-(2,4,6-trimethylphenyl)uracil TFA (3 mL) was added to a solution of 3 (130 mg, 0.22 mmol) in dichloromethane (3 mL) and the reaction mixture was stirred at ambient temperature for 2 hours. Volatiles were evaporated and the residue was partitioned between saturated NaHCO$_3$/water and EtOAc. The organic layer was dried (sodium sulfate), evaporated, and purified by prep TLC eluting with 5% MeOH in CH$_2$Cl$_2$ to give compound 4, MS (CI) m/z 476.2 (MH$^+$).

TABLE 13

| Cpd. No. | NR$_1$R$_2$—(CR$_{3a}$CR$_{3b}$)$_n$— | —Q—R$_4$ | MW (calc.) | MW (obs.) |
|---|---|---|---|---|
| 13-1 | (R)-2-amino-2-phenylethyl | 2,4,6-trimethylphenyl | 475.5 | 476.2 |
| 13-2 | (R)-2-amino-2-phenylethyl | 2-fluoro-3-methoxyphenyl | 481.5 | 482 |

TABLE 13-continued
| Cpd. No. | NR₁R₂—(CR₃ₐCR₃ᵦ)ₙ— | —Q—R₄ | MW (calc.) | MW (obs.) |
|---|---|---|---|---|
| 13-3 | benzyl-methylimidazole substituent | 3-methoxyphenyl | 528.6 | 529 |
| 13-4 | (R)-N-methyl isohexylamine substituent | 2-fluoro-3-methoxyphenyl | 475.5 | 476.2 |
EXAMPLE 14
Synthesis of Representative Compounds
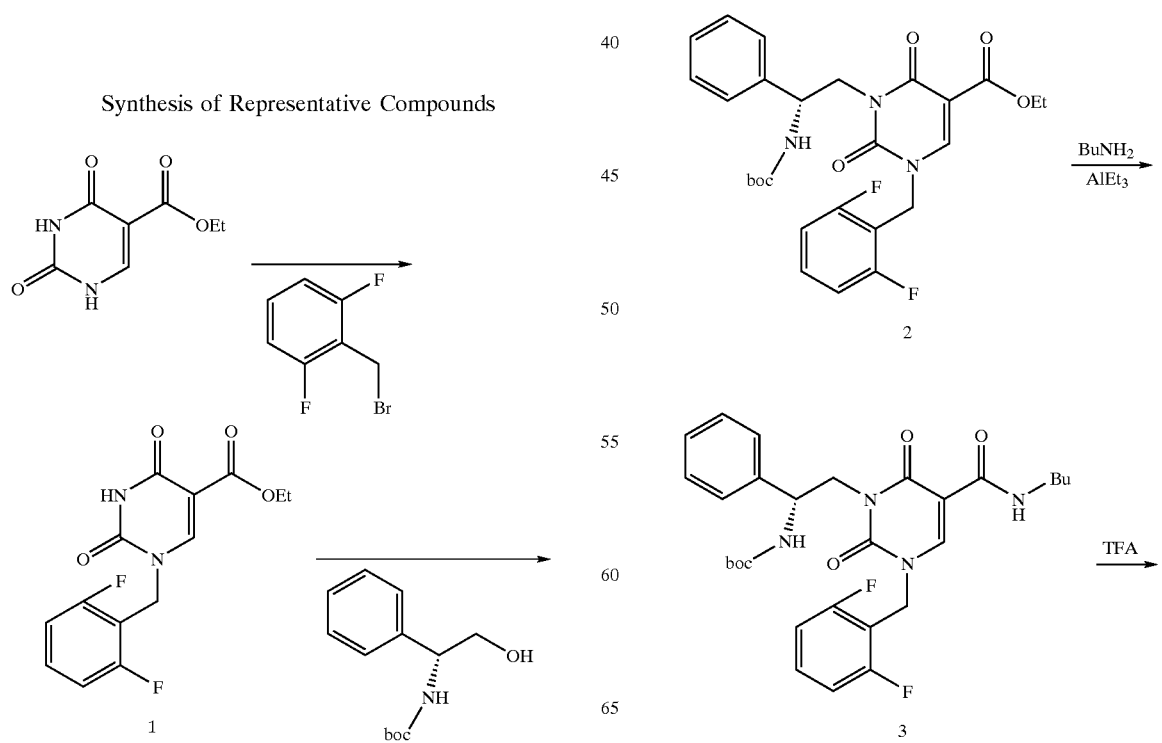

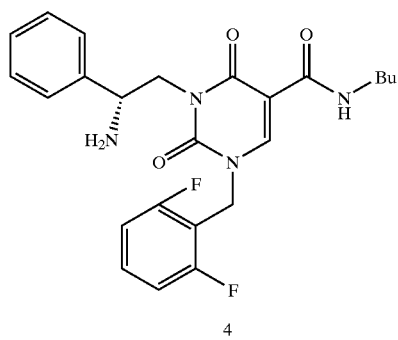

4

Step A 1-(2,6-Difluorobenzyl)-5-carbethoxyuracil

5-Carbethoxyuracil (5 g, 27.15 mmol) and N,O-bis (trimethylsilyl)acetamide (13.4 mL, 2 eq) in dichloroethane (35 mL) were heated at 80° C. for 2 hours. Difluorobenzyl bromide (8.4 g, 1.5 eq) was added and the reaction mixture was heated at 80° C. for 16 hours. The reaction was quenched with methanol and partitioned between methylene chloride and sodium bicarbonate solution. The organic layer was washed with brine, dried and concentrated in vacuo and the residue was triturated with ether to give compound 1 as a white solid (3.26 g).

Step B 1-(2,6-Difluorobenzyl-3-[(2R)-tert-butoxycarbonylamino-2-phenyl]ethyl-5-carbethoxyuracil A solution of (R)-N-(tert-butoxycarbonyl)-2-phenylglycinol (316 mg, 1.33 mmol) in anhydrous THF (30 mL) was treated with 1-(2,6-difluorobenzyl)-5-carbethoxyuracil 1 (413 mg, 1.33 mmol) and triphenylphosphine (525 mg, 2 mmol) at ambient temperature, then diisopropylazodicarboxylate (460 mg, 2 mmol) in THF (5 mL) was introduced via a dropping funnel. The reaction mixture was stirred at ambient temperature for 5 h and volatiles were evaporated. The residue was purified by flash chromatography (silica, 35% EtOAc/hexanes) to give compound 2 (427 mg) as a white foam.

Step C 1-(2,6-Difluorobenzyl-3-[(2R)-tertbutylcarbonylamino-2-phenyl]ethyl-5-n-butylamidouracil A solution of triethylaluminum (1.9 M in toluene, 0.26 mL, 0.5 mmol) was added to n-butylamine (0.1 mL, 1 mmol) in dichloroethane and the reaction mixture was sealed under nitrogen and stirred for ½ hour. 1-(2,6-Difluorobenzyl-3-[(2R)-tertbutylcarbonylamino-2-phenyl]ethyl-5-carbethoxyuracil 2 was added and the mixture was stirred at 70–80° C. for 12 hours to give 3. Trifluoroacetic acid (1 mL) was added and the reaction mixture was stirred for 1 hour. The mixture was concentrated in vacuo and the residue was partitioned between methylene chloride and sodium carbonate solution. The organic layer was washed with brine, dried and concentrated to give a residue which was purified by prep HPLC to give compound 4 (56 mg, $MH^+$ 457).

TABLE 14

| Cpd. No. | $NR_1R_2$—$(CR_{3a}CR_{3b})_n$— | —Q—$R_4$ | MW (calc.) | MW (obs.) |
|---|---|---|---|---|
| 14-1 | (R)-PhCH(NH$_2$)CH$_2$- | -C(O)NHBu | 456.5 | 457.2 |
| 14-2 | (R)-PhCH(NH$_2$)CH$_2$- | -C(O)NHCH$_2$CH(CH$_3$)$_2$ | 456.5 | 457.2 |

TABLE 14-continued

| Cpd. No. | NR₁R₂—(CR₃ₐCR₃ᵦ)ₙ— | —Q—R₄ | MW (calc.) | MW (obs.) |
|---|---|---|---|---|
| 14-3 | (S)-1-phenyl-2-aminoethyl | N-sec-butyl amide | 456.5 | 457.2 |
| 14-4 | (S)-1-phenyl-2-aminoethyl | acetyl | 413.4 | 414.1 |
| 14-5 | N-Boc-N-methyl-leucinyl | ethyl ester | 523.6 | 424.2 |
| 14-6 | N-methyl-leucinyl | ethyl ester | 423.5 | 424.2 |

EXAMPLE 15

Synthesis of Representative Compounds

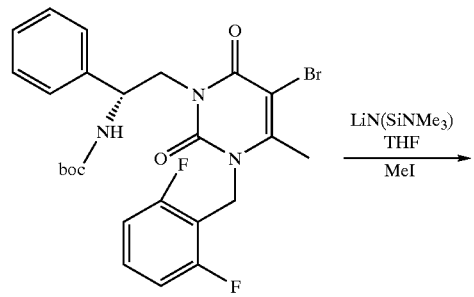

LiN(SiNMe₃)
THF
MeI
→

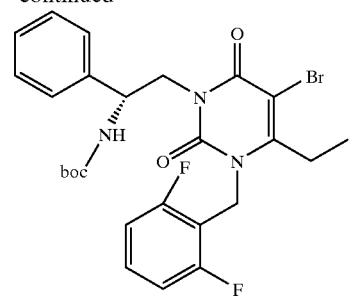

Step A 1-(2,6-Difluorobenzyl-3-[(2R)-tert-butoxycarbonylamino-2-phenyl]ethyl-5-bromo-6-ethyluracil 1-(2,6-Difluorobenzyl-3-[(2R)-tert-butoxycarbonylamino-2-phenyl]ethyl-5-bromo-6-methyluracil 1 (550 mg, 1 mmol) was dissolved in THF (10 mL) and the solution was cooled to 0° C. Lithium bis(trimethylsilyl)amide (1.0 M in THF, 1.3 mL, 1.3 mmol) was added dropwise and the reaction was stirred for 40 minutes at 0° C. Iodomethane (0.093 mL, 1.5 mmol) was added dropwise and after 30 minutes, water was added and the mixture extracted with ethyl acetate. Concentration in vacuo gave compound 2 as a yellow foam.

TABLE 15

| Cpd. No. | $NR_1R_2$—$(CR_{3a}CR_{3b})_n$— | —Q—$R_4$ | MW (calc.) | MW (obs.) |
|---|---|---|---|---|
| 15-1 | phenyl-CH(NH$_2$)-CH$_2$- | 2-F-3-OMe-phenyl-O- | 509.5 | 510.2 |
| 15-2 | phenyl-CH(NH$_2$)-CH$_2$- | 3-OMe-phenyl-O- | 491.5 | 492 |
| 15-3 | (2-pyridyl)-CH$_2$CH$_2$-N(Me)-CH$_2$CH$_2$CH$_2$- | 3-OMe-phenyl-O- | 534.6 | 535 |
| 15-4 | (2-pyridyl)-CH$_2$CH$_2$-N(Me)-CH$_2$CH$_2$CH$_2$- | H | 428.5 | 429 |
| 15-5 | (2-pyridyl)-CH$_2$CH$_2$-N(Me)-CH$_2$CH$_2$CH$_2$- | phenyl-O- | 504.6 | 505 |
| 15-6 | (2-pyridyl)-CH$_2$CH$_2$-N(Me)-CH$_2$CH$_2$CH$_2$- | 4-iPr-phenyl-O- | 546.65 | |
| 15-7 | (2-pyridyl)-CH$_2$CH$_2$-N(Me)-CH$_2$CH$_2$CH$_2$- | 3,4-methylenedioxyphenyl-O- | 548.58 | 549.2 |

TABLE 15-continued

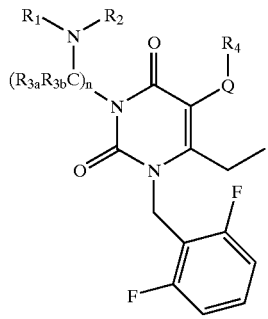

| Cpd. No. | NR₁R₂—(CR₃ₐCR₃ᵦ)ₙ— | —Q—R₄ | MW (calc.) | (obs.) |
|---|---|---|---|---|
| 15-8 | (isobutyl-CH₂-CH(NHMe)-CH₂-) | (2-F-3-OMe-phenyl) | 503.6 | 504.3 |
| 15-9 | (phenyl-CH(NHMe)-CH₂-) | (2-F-3-OMe-phenyl) | 523.6 | 524 |

EXAMPLE 16

Synthesis of Representative Compounds

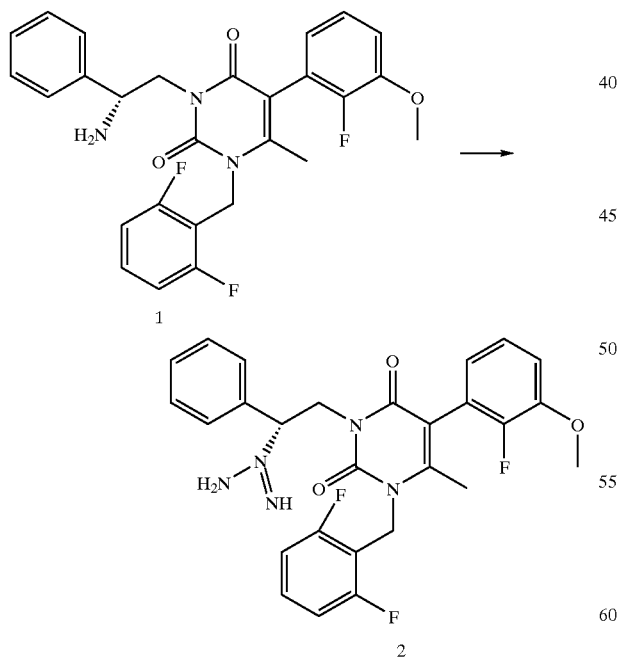

Step A 1-(2,6-Difluorobenzyl)-3-(4-methyl-2R-guanidopentyl)-5-(2-fluoro-3-methoxyphenyl)-6-methyluracil A solution of 1-(2,6-difluorobenzyl)-3-(4-methyl-2R-aminopentyl)-5-(2-fluoro-3-methoxyphenyl)-6-methyluracil 1 (75 mg), (1H)-pyrazole-1-carboxamidine hydrochloride (23 mg) diisopropylethylamine (21 mg) in anhydrous DMF was heated at 40–50° C. overnight (0.5 mL). The reaction mixture was treated with water and the product was extracted with ethyl acetate. The extract was dried over $MgSO_4$, filtered and concentrated in vacuo and the residue was purified on silica gel ($Et_3N/MeOH/CHCl_3$ (2:5:93) as elutant) to give white solid 2. MS: 518 ($MH^+$).

It will be appreciated that, although specific embodiments of the invention have been described herein for purposes of illustration, various modifications may be made without departing from the spirit and scope of the invention. Accordingly, the invention is not limited except as by the appended claims.

We claim:

1. A compound having the following structure:

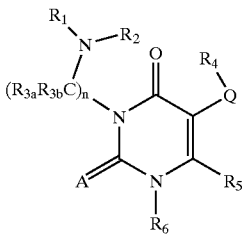

or a stereoisomer or pharmaceutically acceptable salt thereof, wherein:

Q is a direct bond;

A is O;

n is 2, 3 or 4;

R$_1$ and R$_2$ are the same or different and independently hydrogen, alkyl, substituted alkyl, aryl, substituted aryl, arylalkyl, substituted arylalkyl, heterocycle, substituted heterocycle, heterocyclealkyl, substituted heterocyclealkyl, —C(R$_{1a}$)(=NR$_{1b}$), or —C(NR$_{1a}$R$_{1c}$)(=NR$_{1b}$);

or R$_1$ and R$_2$ taken together with the nitrogen atom to which they are attached form a heterocyclic ring or a substituted heterocyclic ring;

R$_{3a}$ and R$_{3b}$ are the same or different and, at each occurrence, independently hydrogen, alkyl, substituted alkyl, alkoxy, alkylthio, alkylamino, aryl, substituted aryl, arylalkyl, substituted arylalkyl, heterocycle, substituted heterocycle, heterocyclealkyl, substituted heterocyclealkyl, —COOR$_{14}$ or —CONR$_{14}$R$_{15}$;

or R$_{3a}$ and R$_{3b}$ taken together with the carbon atom to which they are attached form a homocyclic ring, substituted homocyclic ring, heterocyclic ring or substituted heterocyclic ring;

or R$_{3a}$ and R$_{3b}$ taken together form =NR$_{3c}$;

or R$_{3a}$ and the carbon to which it is attached taken together with R$_1$ and the nitrogen to which it is attached form a heterocyclic ring or substituted heterocyclic ring;

R$_4$ is aryl, substituted aryl, heteroaryl or substituted heteroaryl;

R$_5$ is hydrogen, halogen, lower alkyl, substituted lower alkyl, aryl, substituted aryl, arylalkyl, substituted arylalkyl, alkoxy, alkylthio, alkylamino, cyano or nitro;

R$_6$ is higher alkyl, substituted alkyl, aryl, substituted aryl, arylalkyl, substituted arylalkyl, heteroaryl, substituted heteroaryl, heteroarylalkyl or substituted heteroarylalkyl;

R$_7$ is hydrogen, —SO$_2$R$_{11}$, cyano, alkyl, substituted alkyl, aryl, substituted aryl, arylalkyl, substituted arylalkyl, heteroaryl, substituted heteroaryl, heteroalkyl or substituted heteroarylalkyl; and R$_{1a}$, R$_{1b}$, R$_{1c}$, R$_{3c}$, R$_{11}$, R$_{12}$, R$_{13}$, R$_{14}$ and R$_{15}$ are the same or different and, at each occurrence, independently hydrogen, acyl, alkyl, substituted alkyl, aryl, substituted aryl, arylalkyl, substituted arylalkyl, heterocycle, substituted heterocycle, heterocyclealkyl or substituted heterocyclealkyl;

or R$_{1a}$ and R$_{1b}$, R$_{12}$ and R$_{13}$, or R$_{14}$ and R$_{15}$ taken together with the atom or atoms to which they are attached form a homocyclic ring, substituted homocyclic ring, heterocyclic ring or substituted heterocyclic ring;

with the provisos that:
(a) R$_1$ and R$_2$ is not (1) cyclobutyl, cyclopentyl, cyclohexyl or cycloheptyl substituted with phenyl, pyridyl or thienyl, or (2) a 4-, 5-, 6-, or 7-membered nonaromatic heterocyclic ring containing one ring nitrogen atom and 3, 4, 5, or 6 ring carbon atoms substituted with phenyl, pyridyl or thienyl; and
(b) when R$_1$ and R$_2$ taken together with the nitrogen atom to which they are attached form a substituted heterocyclic ring, said substituted heterocyclic ring is not (1) a 4-, 5-, 6- or 7-membered nonaromatic heterocyclic ring containing one ring nitrogen atom and 3, 4, 5, or 6 ring carbon atoms substituted with phenyl, pyridyl or thienyl, or (2) piperazin-1-yl substituted at the 4 position with phenyl.

2. The compound of claim 1 wherein R$_1$ is aryl, substituted aryl, arylalkyl, substituted arylalkyl, heterocycle, substituted heterocycle, heterocyclealkyl or substituted heterocyclealkyl.

3. The compound of claim 2 wherein as applied to R$_1$ heterocycle is heteroaryl, substituted heterocycle is substituted heteroaryl, heterocyclealkyl is heteroarylalkyl, and substituted heterocyclealkyl is substituted heteroarylalkyl.

4. The compound of claim 3 wherein R$_1$ is heteroarylalkyl or substituted heteroarylalkyl.

5. The compound of claim 1 wherein R$_1$ is phenylalkyl or substituted phenylalkyl.

6. The compound of claim 1 wherein R$_1$ is benzyl.

7. The compound of claim 1 wherein R$_1$ is hydrogen or lower alkyl.

8. The compound of claim 1 wherein R$_2$ is hydrogen, alkyl or substituted alkyl.

9. The compound of claim 1 wherein R$_2$ is hydrogen or methyl.

10. The compound of claim 1 wherein R$_{3a}$ and R$_{3b}$ are, at each occurrence, hydrogen.

11. The compound of claim 1 wherein R$_{3a}$ is hydrogen, alkyl, aryl or arylalkyl.

12. The compound of claim 1 wherein R$_{3a}$ is hydrogen, methyl, isobutyl, cyclohexyl, phenyl or benzyl.

13. The compound of claim 1 wherein R$_{3b}$ is, at each occurrence, hydrogen.

14. The compound of claim 1 wherein n is 3.

15. The compound of claim 1 wherein n is 2.

16. The compound of claim 15 wherein —(R$_{3a}$R$_{3b}$C)$_n$— has the structure —C(R$_{3a}$)(R$_{3b}$)CH$_2$—.

17. The compound of claim 16 wherein R$_{3a}$ is benzyl.

18. The compound of claim 16 wherein R$_{3a}$ is alkyl.

19. The compound of claim 18 wherein R$_{3a}$ is isobutyl or cyclohexyl.

20. The compound of claim 16 wherein R$_{3b}$ is hydrogen or methyl.

21. The compound of claim 1 wherein R$_4$ is substituted aryl or substituted heteroaryl.

22. The compound of claim 1 wherein R$_4$ is substituted phenyl.

23. The compound of claim 22 wherein R$_4$ is phenyl substituted with halogen, alkoxy, or both halogen and alkoxy.

24. The compound of claim 1 wherein R$_5$ is H, lower alkyl or substituted lower alkyl.

25. The compound of claim 1 wherein R$_5$ is hydrogen or methyl.

26. The compound of claim 1 wherein R$_6$ is aryl, substituted aryl, arylalkyl, substituted arylalkyl, heteroaryl, substituted heteroaryl, heteroarylalkyl or substituted heteroarylalkyl.

27. The compound of claim 1 wherein R$_6$ is arylalkyl, substituted arylalkyl, heteroarylalkyl or substituted heteroarylalkyl.

28. The compounds of claim 1 wherein R$_6$ is benzyl or substituted benzyl.

29. The compound of claim 1 wherein R$_6$ is benzyl substituted with two halogens.

30. The compound of claim 1 wherein R$_1$ is —CH$_2$(heteroaryl) or —CH$_2$CH$_2$(heteroaryl).

31. The compound of claim 1 wherein R$_1$ and R$_2$ taken together with the nitrogen atom to which they are attached form a heterocyclic ring or substituted heterocyclic ring.

32. The compound of claim 8 wherein R$_1$ is hydrogen.

33. The compound of claim 32 wherein R$_6$ is arylalkyl, substituted arylalkyl, heteroarylalkyl or substituted heteroarylalkyl.

34. The compound of claim 33 wherein R$_6$ is substituted arylalkyl.

35. The compound of claim 34 wherein R$_6$ is substituted benzyl.

36. The compound of claim 35 wherein $R_4$ is substituted aryl.

37. The compound of claim 36 wherein $R_5$ is hydrogen or methyl.

38. The compound of claim 37 wherein n is 2.

39. The compound of claim 38 wherein —$(R_{3a}R_{3b}C)_n$— has the structure —$C(R_{3a})(R_{3b})CH_2$—.

40. The compound of claim 39 wherein $R_{3a}$ is hydrogen, alkyl or aryl.

41. The compound of claim 40 wherein $R_{3a}$ is phenyl.

42. The compound of claim 39 wherein $R_{3b}$ is hydrogen.

43. A compound having the following structure:

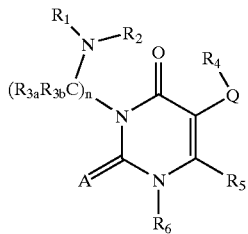

or a stereoisomer or pharmaceutically acceptable salt thereof,
wherein:
Q is a direct bond;
A is O;
n is 2, 3 or 4;
$R_1$ and $R_2$ are the same or different and independently hydrogen, straight chain or branched alkyl, substituted straight chain or branched alkyl, aryl, substituted aryl, arylalkyl, substituted arylalkyl, heteroaryl, substituted heteroaryl, heterocyclealkyl, substituted heterocyclealkyl, —$C(R_{1a})(=NR_{1b})$, or —$C(NR_{1a}R_{1c})(=NR_{1b})$;
or $R_1$ and $R_2$ taken together with the nitrogen atom to which they are attached form heteroaryl or substituted heteroaryl;
$R_{3a}$ and $R_{3b}$ are the same or different and, at each occurrence, independently hydrogen, alkyl, substituted alkyl, alkoxy, alkylthio, alkylamino, aryl, substituted aryl, arylalkyl, substituted arylalkyl, heterocycle, substituted heterocycle, heterocyclealkyl, substituted heterocyclealkyl, —$COOR_{14}$ or —$CONR_{14}R_{15}$;
or $R_{3a}$ and $R_{3b}$ taken together with the carbon atom to which they are attached form a homocyclic ring, substituted homocyclic ring, heterocyclic ring or substituted heterocyclic ring;
or $R_{3a}$ and $R_{3b}$ taken together form =$NR_{3c}$;
or $R_{3a}$ and the carbon to which it is attached taken together with $R_1$ and the nitrogen to which it is attached form a heterocyclic ring or substituted heterocyclic ring;
$R_4$ is aryl, substituted aryl, heteroaryl or substituted heteroaryl;
$R_5$ is hydrogen, halogen, lower alkyl, substituted lower alkyl, aryl, substituted aryl, arylalkyl, substituted arylalkyl, alkoxy, alkylthio, alkylamino, cyano or nitro;
$R_6$ is higher alkyl, substituted alkyl, aryl, substituted aryl, arylalkyl, substituted arylalkyl, heteroaryl, substituted heteroaryl, heteroarylalkyl or substituted heteroarylalkyl;
$R_7$ is hydrogen, —$SO_2R_{11}$, cyano, alkyl, substituted alkyl, aryl, substituted aryl, arylalkyl, substituted arylalkyl, heteroaryl, substituted heteroaryl, heteroalkyl or substituted heteroarylalkyl; and $R_{1a}$, $R_{1b}$, $R_{1c}$, $R_{3c}$, $R_{11}$, $R_{12}$, $R_{13}$, $R_{14}$ and $R_{15}$ are the same or different and, at each occurrence, independently hydrogen, acyl, alkyl, substituted alkyl, aryl, substituted aryl, arylalkyl, substituted arylalkyl, heterocycle, substituted heterocycle, heterocyclealkyl or substituted heterocyclealkyl;
or $R_{1a}$ and $R_{1b}$, $R_{12}$ and $R_{13}$, or $R_{14}$ and $R_{15}$ taken together with the atom or atoms to which they are attached form a homocyclic ring, substituted homocyclic ring, heterocyclic ring or substituted heterocyclic ring.

44. The compound of claim 43 wherein, as applied to $R_1$ and $R_2$, the straight chain or branched portion of the alkyl moiety is saturated.

45. The compound of claim 43 wherein, as applied to $R_1$ and $R_2$, the straight chain or branched portion of the alkyl moiety is unsaturated.

46. The compound of claim 43 wherein $R_1$ is aryl or substituted aryl.

47. The compound of claim 43 wherein $R_1$ is hydrogen.

48. The compound of claim 43 wherein $R_1$ is heteroarylalkyl or substituted heteroarylalkyl.

49. The compound of claim 48 wherein $R_1$ is phenylalkyl or substituted phenylalkyl.

50. The compound of claim 49 wherein $R_1$ is benzyl.

51. The compound of claim 43 wherein $R_1$ is hydrogen, straight chain or branched alkyl or substituted straight chain or branched alkyl.

52. The compound of claim 43 wherein $R_2$ is hydrogen, straight chain or branched alkyl or substituted straight chain or branched alkyl.

53. The compound of claim 43 wherein $R_2$ is hydrogen or methyl.

54. The compound of claim 43 wherein $R_{3a}$ and $R_{3b}$ are, at each occurrence, hydrogen.

55. The compound of claim 43 wherein $R_{3a}$ is hydrogen, alkyl, aryl or arylalkyl.

56. The compound of claim 43 wherein $R_{3a}$ is hydrogen, methyl, isobutyl, cyclohexyl, phenyl or benzyl.

57. The compound of claim 43 wherein $R_{3b}$ is, at each occurrence, hydrogen.

58. The compound of claim 43 wherein n is 3.

59. The compound of claim 43 wherein n is 2.

60. The compound of claim 59 wherein —$(R_{3a}R_{3b}C)_n$— has the structure —$C(R_{3a})(R_{3b})CH_2$—.

61. The compound of claim 60 wherein $R_{3a}$ is benzyl.

62. The compound of claim 60 wherein $R_{3a}$ is alkyl.

63. The compound of claim 60 wherein $R_{3a}$ is isobutyl or cyclohexyl.

64. The compound of claim 60 wherein $R_{3b}$ is hydrogen or methyl.

65. The compound of claim 43 wherein $R_4$ is substituted aryl or substituted heteroaryl.

66. The compound of claim 43 wherein $R_4$ is substituted phenyl.

67. The compound of claim 43 wherein $R_4$ is phenyl substituted with halogen, alkoxy, or both halogen and alkoxy.

68. The compound of claim 43 wherein $R_5$ is hydrogen, lower alkyl or substituted lower alkyl.

69. The compound of claim 43 wherein $R_5$ is hydrogen or methyl.

70. The compound of claim 43 wherein $R_6$ is aryl, substituted aryl, arylalkyl, substituted arylalkyl, heteroaryl, substituted heteroaryl, heteroarylalkyl or substituted heteroarylalkyl.

71. The compound of claim 43 wherein $R_6$ is arylalkyl, substituted arylalkyl, heteroarylalkyl or substituted heteroarylalkyl.

72. The compounds of claim 43 wherein $R_6$ is benzyl or substituted benzyl.

73. The compound of claim 43 wherein $R_6$ is benzyl substituted with two halogens.

74. The compound of claim 43 wherein $R_1$ is —$CH_2$(heteroaryl) or —$CH_2CH_2$(heteroaryl).

75. The compound of claim 43 wherein $R_6$ is arylalkyl, substituted arylalkyl, heteroarylalkyl or substituted heteroarylalkyl.

76. The compound of claim 75 wherein $R_6$ is substituted arylalkyl.

77. The compound of claim 76 wherein $R_6$ is substituted benzyl.

78. The compound of claim 77 wherein $R_4$ is substituted aryl.

79. The compound of claim 78 wherein $R_5$ is hydrogen or methyl.

80. The compound of claim 79 wherein n is 2.

81. The compound of claim 80 wherein —$(R_{3a}R_{3b}C)_n$— has the structure —$C(R_{3a})(R_{3b})CH_2$—.

82. The compound of claim 81 wherein $R_{3a}$ is hydrogen, alkyl or aryl.

83. The compound of claim 82 wherein $R_{3b}$ is hydrogen.

84. The compound of claim 83 wherein $R_1$ is hydrogen, straight chain or branched alkyl, or substituted straight chain or branched alkyl.

85. The compound of claim 84 wherein $R_2$ is hydrogen.

86. A pharmaceutical composition comprising a compound of any one of claim 1 or 43 and a pharmaceutically acceptable carrier or diluent.

* * * * *

UNITED STATES PATENT AND TRADEMARK OFFICE
CERTIFICATE OF CORRECTION

PATENT NO. : 6,872,728 B2 Page 1 of 1
DATED : March 29, 2005
INVENTOR(S) : Yun-Fei Zhu et al.

It is certified that error appears in the above-identified patent and that said Letters Patent is hereby corrected as shown below:

<u>Column 327,</u>
Line 36, "heteroalkyl" should read as -- heteroarylalkyl --.

<u>Column 330,</u>
Line 1, "heteroalkyl" should read as -- heteroarylalkyl --.

Signed and Sealed this

Sixth Day of September, 2005

JON W. DUDAS
*Director of the United States Patent and Trademark Office*